US009331288B2

(12) United States Patent
Park et al.

(10) Patent No.: US 9,331,288 B2
(45) Date of Patent: May 3, 2016

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicants: DUK SAN NEOLUX CO., LTD., Cheonan-si, Chungcheongnam-do (KR); SAMSUNG DISPLAY CO., LTD., Yongin-si, Gyeonggi-do (KR)

(72) Inventors: Junghwan Park, Hwaseong-si (KR); Wonsam Kim, Hwaseong-si (KR); Jihun Byun, Cheonan-si (KR); Jeongkeun Park, Seoul (KR); Hwasoon Jung, Anseong-si (KR); Yeonhee Choi, Cheonan-si (KR); Seokhyun Kim, Seongnam-si (KR); Kwanhee Lee, Yongin-si (KR); Mikyung Kim, Yongin-si (KR)

(73) Assignees: SAMSUNG DISPLAY CO., LTD., Yongin-si (KR); DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 14/722,870

(22) Filed: May 27, 2015

(65) Prior Publication Data

US 2015/0349272 A1 Dec. 3, 2015

(30) Foreign Application Priority Data

May 28, 2014 (KR) ........................ 10-2014-0064229

(51) Int. Cl.

| H01L 51/54 | (2006.01) |
| C09K 11/06 | (2006.01) |
| H01L 51/00 | (2006.01) |
| C07D 495/04 | (2006.01) |
| H01L 27/32 | (2006.01) |
| H01L 27/28 | (2006.01) |
| H01L 27/30 | (2006.01) |
| C07D 491/04 | (2006.01) |
| H01L 51/52 | (2006.01) |
| H01L 51/50 | (2006.01) |
| H01L 51/05 | (2006.01) |
| H01L 51/42 | (2006.01) |

(52) U.S. Cl.
CPC .......... *H01L 51/0071* (2013.01); *C07D 491/04* (2013.01); *C07D 495/04* (2013.01); *C09K 11/06* (2013.01); *H01L 27/283* (2013.01); *H01L 27/301* (2013.01); *H01L 27/3244* (2013.01); *H01L 51/0072* (2013.01); *H01L 51/0073* (2013.01); *H01L 51/0074* (2013.01); *C09K 2211/1029* (2013.01); *C09K 2211/1037* (2013.01); *C09K 2211/1048* (2013.01); *C09K 2211/1051* (2013.01); *C09K 2211/1088* (2013.01); *C09K 2211/1092* (2013.01); *C09K 2211/185* (2013.01); *H01L 51/0004* (2013.01); *H01L 51/0005* (2013.01); *H01L 51/0052* (2013.01); *H01L 51/0067* (2013.01); *H01L 51/0508* (2013.01); *H01L 51/42* (2013.01); *H01L 51/5016* (2013.01); *H01L 51/5206* (2013.01); *H01L 51/5221* (2013.01); *H01L 2251/5361* (2013.01)

(58) Field of Classification Search
None
See application file for complete search history.

(56) References Cited

U.S. PATENT DOCUMENTS

2015/0243893 A1* 8/2015 Joseph ................ H01L 51/0032 257/40

FOREIGN PATENT DOCUMENTS

| JP | 2011-84531 A | 4/2011 |
| KR | 10-2010-0099327 A | 9/2010 |
| KR | 2011-066766 * | 6/2011 |
| KR | 10-2011-0110591 A | 10/2011 |
| KR | 10-2013-0050237 A | 5/2013 |
| KR | 10-2013-0076904 A | 7/2013 |
| KR | 10-2013-0105800 A | 9/2013 |
| KR | 10-2013-0135771 A | 12/2013 |
| KR | 10-2014-0000611 A | 1/2014 |
| KR | 10-1355558 B1 | 1/2014 |
| WO | 2013/081416 A1 | 6/2013 |
| WO | 2013/105747 | 7/2013 |
| WO | 2013/108997 A1 | 7/2013 |
| WO | 2013/122402 A1 | 8/2013 |
| WO | 2014/061546 A1 | 4/2014 |

OTHER PUBLICATIONS

Machine translation of KR2011-066766. Date of publication: Jun. 17, 2011.*
Search Report for corresponding Korean Application KR 10-2014-0064229, ten pages, dated May 26, 2015.
Extended European Search Report, mailed Oct. 16, 2015, four pages.
Notice of Allowance received in corresponding Korean patent application No. 10-2014-0064229; six pages; mailed Oct. 8, 2015.

* cited by examiner

*Primary Examiner* — Andrew K Bohaty
(74) *Attorney, Agent, or Firm* — Vorys, Sater, Seymour & Pease LLP; Mih Suhn Koh

(57) ABSTRACT

A compound represented by Formula 1. An organic electric element includes a first electrode, a second electrode, and an organic material layer between the first electrode and the second electrode. The organic material layer includes the compound represented by Formula 1. When the organic electric element includes the compound in the organic material layer, driving voltage, luminous efficiency, color purity, stability, and life span can be improved.

13 Claims, 1 Drawing Sheet

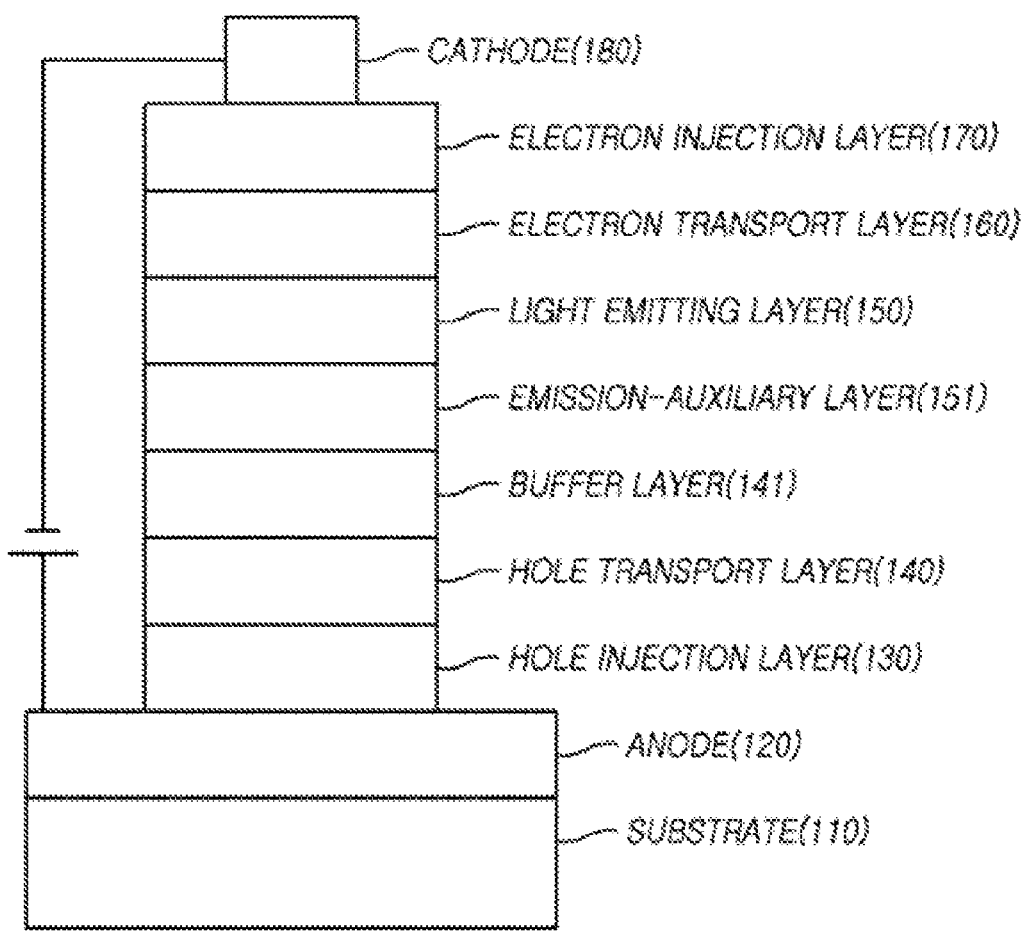

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATION

This application claims priority from and the benefit under 35 U.S.C. §119(a) of Korean Patent Application No. 10-2014-0064229, filed on May 28, 2014, the contents of which are hereby incorporated by reference for all purposes as if fully set forth herein.

BACKGROUND

1. Technical Field

The present invention relates to a compound for an organic electric element, an organic electric element using the same, and an electronic device thereof.

2. Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. Here, in many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, and the like.

A material used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more and more as size of display becomes larger and larger in the portable display market. Therefore, the power consumption is a very important factor in the portable display with a limited power source of the battery, and efficiency and life span issue also be solved.

The most problematic issues in an organic electric element are life span and efficiency, and the situation is such that this life span or efficiency issue must be solved as displays become larger and larger.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Therefore it is required to develop a light emitting material that has high thermal stability and can achieve efficiently a charge balance in the light-emitting layer. In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material. However, such a stable and efficient organic material layer material for an organic electric element has not yet been fully developed. Accordingly, there is a continuous need to develop new host materials for an organic material layer.

SUMMARY

In order to solve one or more of the above-mentioned problems occurring in the prior art, an aspect of the present invention is to provide a compound which allows an organic electric element to have high luminous efficiency, low driving voltage and high heat-resistant and to be improved in color purity and life span, an organic electric element using the same, and an electronic device including the organic electric element.

In accordance with an aspect of the present invention, there is provided a compound represented by Formula below.

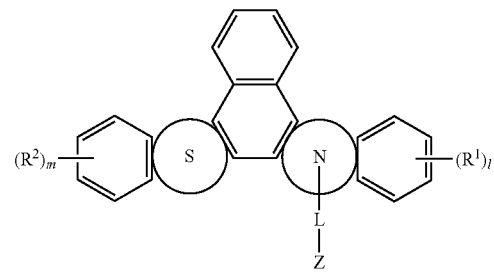

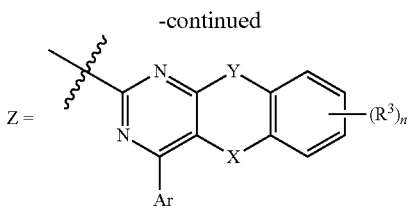

In another aspect of the present invention, there are provided an organic electric element using the compound represented by Formula above and an electronic device including the organic electric element.

By using the compound according to embodiments of the present invention, an organic electric element according to one or more embodiments of the present invention not only has low driving voltage and high heat-resistant and, but can also be significantly improved in color purity, luminous efficiency, and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine, chlorine, bromine, or iodine.

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "alkenyl" or "alkynyl" as used herein has, but not limited to, double or triple bonds of 2 to 60 carbon atoms, and includes a linear alkyl group, or a branched chain alkyl group, Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "aryl group" or "arylene group" as used herein has, but not limited to, 6 to 60 carbon atoms. Herein, the aryl group or arylene group means a monocyclic or polycyclic aromatic group, and may also be formed in conjunction with an adjacent group. Examples of "aryl group" or "arylene group" may include a phenyl group, an indenyl group, a naphthyl group, a biphenylyl group, an anthryl group, a phenanthryl group, a pyrenyl group, a fluoranthenyl group, a terphenylyl group, a naphthacenyl group, a chrysenyl group, a triphenylenyl group, a perylenyl group, a fluorene group, a spirofluorene group or a spirobifluorene group and so on.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "heteroaryl group" or "heteroarylene group" as used herein means, but not limited to, a $C_2$ to $C_{60}$ aryl or arylene group containing one or more heteroatoms, includes both monocyclic and polycyclic rings, and may also be formed in conjunction with an adjacent group. Examples of "heteroaryl group" or "heteroarylene group" may include a triazolyl group, an oxadiazolyl group, a triazinyl group, an imidazolyl group, an oxazolyl group, a pyrrolyl group, a furyl group, a thienyl group, a pyridazinyl group, a pyrimidinyl group, a pyrazinyl group, a pyridyl group, an indolyl group, an isoindolyl group, a quinazolinyl group, a benzofuranyl group, a benzothienyl group, a naphthyridinyl group, a phthalazinyl group, a quinolyl group, an isoquinolyl group, a quinoxanyl group, a carbazolyl group, a dibenzofuranyl group, a dibenzothienyl group, a phenothiazinyl group, a phenoxazinyl group, a phenanthrolinyl group, a phenazinyl group, a phenanthridinyl group or an acridinyl group and so on.

Unless otherwise stated, the term "heterocyclic group" as used herein contains one or more heteroatoms, but not limited to, has 2 to 60 carbon atoms, includes both monocyclic and polycyclic rings, and may include alicyclic and/or aromatic group containing heteroatoms. Also, the heterocyclic group may also be formed in conjunction with an adjacent group. Examples of "heterocyclic group" may include a thiaoxazolidinonyl group, an oxazolidinonyl group, a morpholinyl group, a pyrrolidinyl group, a piperazinyl group, a pyrrolidonyl group, a piperidinyl group, a piperidonyl group, a triazolyl group, an oxadiazolyl group, a triazinyl group, an imidazolyl group, an oxazolyl group, a pyrrolyl group, a furyl group, a thienyl group, a pyridazinyl group, a pyrimidinyl group, a pyrazinyl group, a pyridyl group, an indolyl group, an isoindolyl group, a quinazolinyl group, a benzofuranyl group, a benzothienyl group, a naphthyridinyl group, a phthalazinyl group, a quinolyl group, an isoquinolyl group, a quinoxanyl group, a carbazolyl group, a dibenzofuranyl group, a dibenzothienyl group, a phenothiazinyl group, a phenoxazinyl group, a phenanthrolinyl group, a phenazinyl group, a phenanthridinyl group or an acridinyl group and so on.

Unless otherwise stated, the term "heteroatom" as used herein represents at least one of N, O, S, P, and Si.

Unless otherwise stated, the term "aliphatic" as used herein means an aliphatic hydrocarbon having 1 to 60 carbon atoms, and the term "aliphatic ring" as used herein means an aliphatic hydrocarbon ring having 3 to 60 carbon atoms.

Unless otherwise stated, the term "ring" means an aliphatic ring having 3 to 60 carbon atoms, an aromatic ring having 6 to 60 carbon atoms, a hetero ring having 2 to 60 carbon atoms, or a fused ring formed by the combination of them, and includes a saturated or unsaturated ring.

Hetero compounds or hetero radicals other than the above-mentioned hetero compounds each contain, but not limited to, one or more heteroatoms.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a fluorine group, a $C_6$-$C_{20}$ aryl group substituted by deuterium, a $C_8$-$C_{20}$ arylalkenyl group, a silane group, a boron group, a germanium group, and a $C_5$-$C_{20}$ heterocyclic group.

Otherwise specified, the Formulas used in the present invention are as defined in the index definition of the substituent of the following Formula:

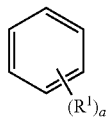

wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows:

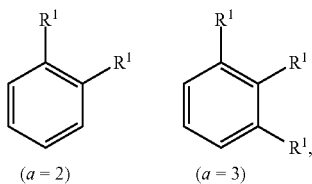

and when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a host material, a dopant material, or a capping layer material in the hole injection layer 130, the hole transport layer 140, the electron transport layer 160, the electron injection layer 170, or the light emitting layer 150.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate 110 to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, screen printing, inkjet printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode (OLED), an organic solar cell, an organic photo conductor (OPC), an organic transistor (organic TFT), and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

The compound according to an aspect of the present invention is represented by Formula 1 below.

[Formula 1]

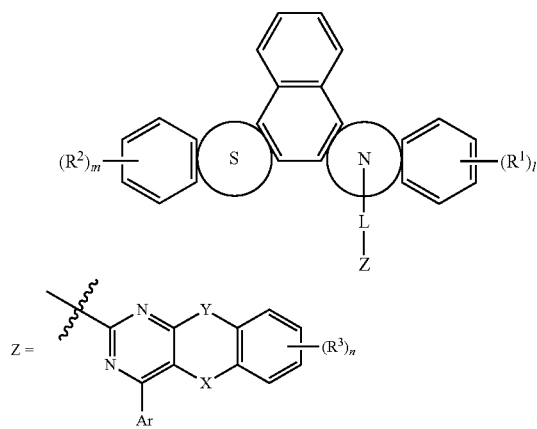

In Formula 1 above,

S ring may be a $C_4$-$C_8$ heterocyclic group containing S (sulfur) and may be a thiophene and so on.

N ring may be a $C_4$-$C_8$ heterocyclic group containing N (nitrogen) and may be a pyrrole and so on.

l, m, and n may be each an integer from 0 to 4.

$R^1$ to $R^3$ may be independently selected from the group consisting of halogen, deuterium, a cyano group, a $C_6$-$C_{60}$ aryl group, a $C_2$-$C_{60}$ heterocyclic group containing at least one heteroatom selected from O, N, S, Si, and P, a $C_1$-$C_{30}$ alkoxy group, a $C_1$-$C_{60}$ alkyl group, a $C_2$-$C_{60}$ alkenyl group, a fluorenyl group, and -$L^1$-N(R')(R''). For example, $R^1$ to $R^3$ may be independently a $C_6$-$C_{24}$ aryl group or a $C_3$-$C_{20}$ heterocyclic group, preferably a $C_6$-$C_{14}$ aryl group or a $C_5$-$C_{12}$ heterocyclic group, and examples of $R^1$ to $R^3$ may be a phenyl group, a phenyl group substituted by deuterium, an indenyl group, a naphthyl group, a biphenylyl group, an anthryl group, a phenanthryl group, a piperidinyl group, a piperidonyl group, a pyridyl group, an indolyl group, an isoindolyl group, a quinazolinyl group, a benzofuranyl group, a benzothienyl group, a naphthyridinyl group, a phthalazinyl group, a quinolyl group, an isoquinolyl group, a quinoxanyl group, a carbazolyl group, a dibenzofuranyl group, a dibenzothienyl group, a phenothiazinyl group, a phenoxazinyl group, a phenanthrolinyl group or a phenazinyl group and so on.

In addition, any two adjacent groups of $R^1$s to $R^3$s can be independently linked together to form at least one fused ring. Here, $R^1$s to $R^3$s don't form a fused ring can be as defined above. For example, when 1 and m are both an integer 2, adjacent $R^1$s can be linked together to form a fused ring but $R^2$s can be independently aryl group or hetero ring.

Of course, when 1 is an integer 2 or more, plural $R^1$s may be the same or different from each other, and the part of the adjacent groups can be linked together to form a fused ring but the rest of the adjacent groups can be selected from the substituent group as defined above. When m or n is an integer 2 or more, it is the same.

The fused ring may be a $C_3$-$C_{60}$ aliphatic ring, a $C_6$-$C_{60}$ aromatic ring, a $C_2$-$C_{60}$ hetero ring containing at least one heteroatom selected from O, N, S, Si, and P, or a fused ring formed by the combination of them, and include monocyclic or polycyclic rings, and include a saturated or unsaturated ring.

L and $L^1$ may be independently selected from the group consisting of a single bond, a $C_6$-$C_{60}$ arylene group, a fluorenylene group, and a $C_2$-$C_{60}$ heteroarylene group containing at least one heteroatom selected from O, N, S, Si, and P. For example, L and $L^1$ may be independently a single bond, $C_6$-$C_{24}$ arylene group or a $C_3$-$C_{20}$ heteroarylene group, and examples of L and $L^1$ may be a phenyl group, a naphthyl group, a biphenylyl group, an anthryl group, a phenanthryl group, a pyrrolyl group, a furyl group, a thienyl group, a pyridazinyl group, a pyrimidinyl group, a pyrazinyl group, a pyridyl group, an indolyl group, an isoindolyl group, a quinazolinyl group, a benzofuranyl group, a benzothienyl group, a naphthyridinyl group, a phthalazinyl group, a quinolyl group, an isoquinolyl group, a quinoxanyl group, a carbazolyl group, a dibenzofuranyl group or a dibenzothienyl group and so on. The arylene group, the fluorenyl group, and the heteroarylene group are optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a fluorenyl group, a $C_2$-$C_{60}$ heterocyclic group containing at least one heteroatom selected from O, N, S, Si, and P, a $C_3$-$C_{20}$ cycloalkyl group, a $C_7$-$C_{20}$ arylalkyl group, and a $C_8$-$C_{20}$ arylalkenyl group.

R' and R'' may be independently selected from the group consisting of a $C_6$-$C_{60}$ aryl group, a $C_2$-$C_{60}$ heterocyclic group containing at least one heteroatom selected from O, N, S, Si, and P, and a fluorenyl group. For example, R' and R'' may be independently a $C_6$-$C_{24}$ aryl group, a $C_3$-$C_{20}$ heterocyclic group or a fluorenyl group, and examples of R' and R'' may be a phenyl group, an indenyl group, a naphthyl group, a biphenylyl group, an anthryl group, a phenanthryl group, a fluorenyl group, a morpholinyl group, a pyrrolidinyl group, a piperazinyl group, a pyrrolidonyl group, a piperidinyl group, a triazinyl group, an imidazolyl group, an oxazolyl group, a pyrrolyl group, a furyl group, a thienyl group, a pyridazinyl group, a pyrimidinyl group, a pyrazinyl group, a pyridyl group, an indolyl group, an isoindolyl group, a quinazolinyl group, a benzofuranyl group, a benzothienyl group, a naphthyridinyl group, a phthalazinyl group, a quinolyl group, an isoquinolyl group, a quinoxanyl group, a carbazolyl group, a dibenzofuranyl group or a dibenzothienyl group and so on.

Ar may be selected from the group consisting of a $C_6$-$C_{60}$ aryl group, a $C_2$-$C_{60}$ heterocyclic group containing at least one heteroatom selected from O, N, S, Si, and P, and a fluorenyl group. For example, Ar may be a $C_6$-$C_{24}$ aryl group, a $C_3$-$C_{20}$ heterocyclic group, or fluorenyl group, preferably a $C_6$-$C_{18}$ aryl group or a $C_5$-$C_{12}$ heterocyclic group, and an example of Ar may be a phenyl group, a phenyl group substituted by deuterium, an indenyl group, a naphthyl group, a biphenylyl group, an anthryl group, a phenanthryl group, a pyrenyl group, a fluoranthenyl group, a terphenylyl group, a naphthacenyl group, a chrysenyl group, a triphenylenyl group, a fluorenyl group, a piperidinyl group, a piperidonyl group, a pyridyl group, an indolyl group, an isoindolyl group, a quinazolinyl group, a benzofuranyl group, a benzothienyl group, a naphthyridinyl group, a phthalazinyl group, a quinolyl group, an isoquinolyl group, a quinoxanyl group, a carbazolyl group, a dibenzofuranyl group or a dibenzothienyl group and so on.

X and Y may be independently selected from the group consisting of a single bond, $C(R^4)(R^5)$, $N(R^4)$, O, S, Se, and $Si(R^4)(R^5)$. In this case, X and Y may not be a sing bond at the same time.

$R^4$ and $R^5$ may be independently selected from the group consisting of hydrogen, deuterium, a $C_6$-$C_{60}$ aryl group, a $C_2$-$C_{60}$ heterocyclic group containing at least one heteroatom selected from O, N, S, Si, and P, a $C_1$-$C_{30}$ alkoxy group, a $C_1$-$C_{60}$ alkyl group, a $C_2$-$C_{60}$ alkenyl group and a fluorenyl group. For example, $R^4$ and $R^5$ may be independently a $C_6$-$C_{24}$ aryl group, a $C_3$-$C_{20}$ heterocyclic group or a fluorenyl group, and examples of $R^4$ and $R^5$ may be a phenyl group, an indenyl group, a naphthyl group, a biphenylyl group, an anthryl group, a phenanthryl group, a fluorenyl group, a morpholinyl group, a pyrrolidinyl group, a piperazinyl group, a pyrrolidonyl group, a piperidinyl group, a triazinyl group, an imidazolyl group, an oxazolyl group, a pyrrolyl group, a furyl group, a thienyl group, a pyridazinyl group, a pyrimidinyl group, a pyrazinyl group, a pyridyl group, an indolyl group, an isoindolyl group, a quinazolinyl group, a benzofuranyl group, a benzothienyl group, a naphthyridinyl group, a phthalazinyl group, a quinolyl group, an isoquinolyl group, a quinoxanyl group, a carbazolyl group, a dibenzofuranyl group or a dibenzothienyl group and so on.

When Ar, $R^1$ to $R^5$, R', and R'' are an aryl group, a fluorenyl group or a heterocyclic group, Ar, $R^1$ to $R^5$, R', and R'' are optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a fluorenyl group, a $C_2$-$C_{60}$ heterocyclic group containing at least one heteroatom selected from O, N, S, Si, and P, a $C_3$-$C_{20}$ cycloalkyl group, a $C_7$-$C_{20}$ arylalkyl group, and a $C_8$-$C_{20}$ arylalkenyl group.

When $R^1$ to $R^5$ are an alkyl group, alkenyl group or alkoxy, $R^1$ to $R^5$ are optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a fluorenyl group, a $C_2$-$C_{60}$ heterocyclic group containing at least one heteroatom selected from O, N, S, Si, and P, a $C_3$-$C_{20}$ cycloalkyl group, a $C_7$-$C_{20}$ arylalkyl group, and a $C_8$-$C_{20}$ arylalkenyl group.

The compound represented by Formula 1 above may be represented by one of Formulas below.

<Formula 1-1>

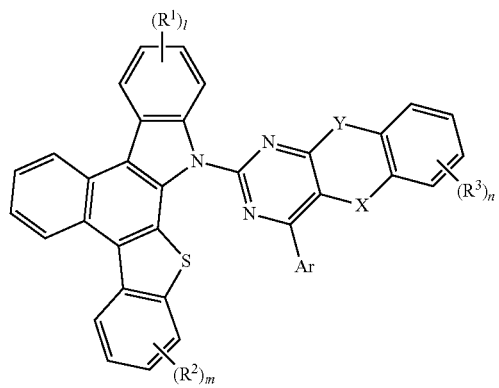

<Formula 1-2>

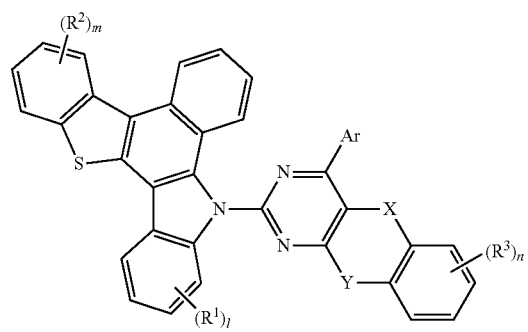

<Formula 1-3>

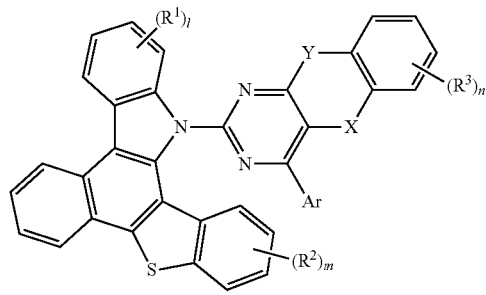

<Formula 1-4>

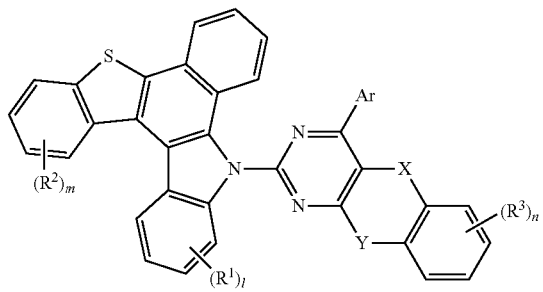

In formulas 1-1 to 1-4 above, Ar, $R^1$ to $R^3$, l, m, n, X, and Y are as defined in Formula 1 above.

Also, in Formula 1 above, Z may be any one of formulas below.
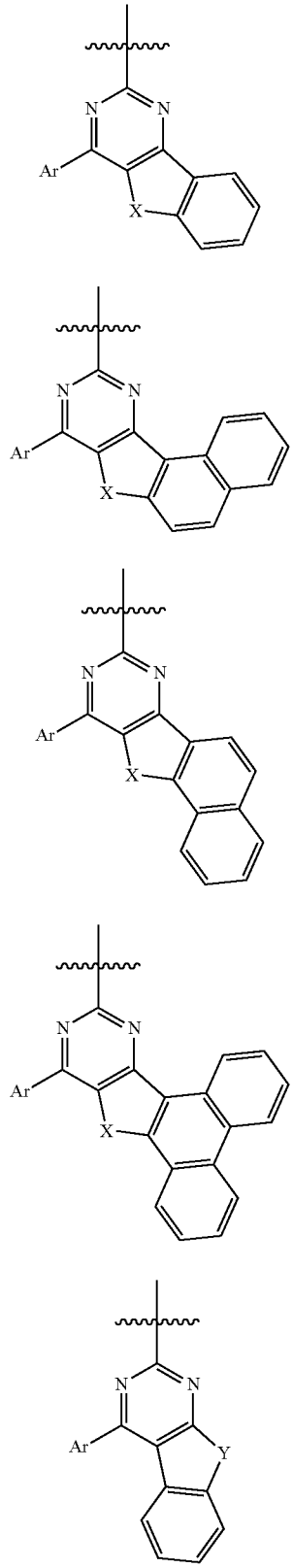
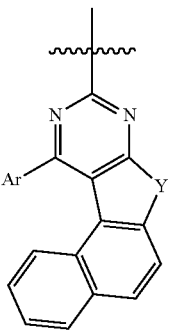
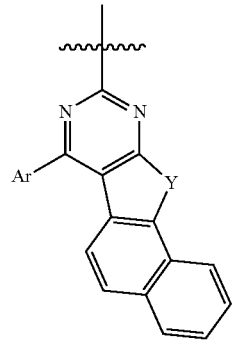
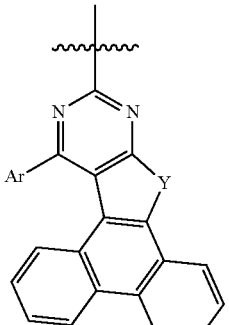
In formulas above, Ar, X, and Y are as defined in Formula 1 above.
Specially, the compound represented by Formula 1 above may be represented by one of Formulas below.
<Formula 1-1-1-O>
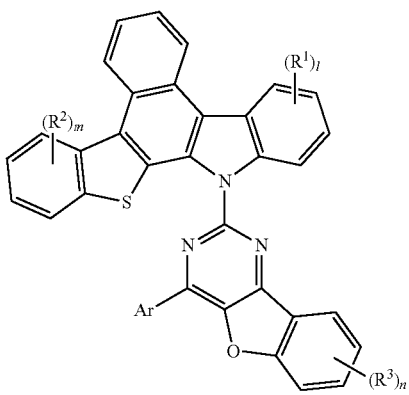

<Formula 1-1-1-S>
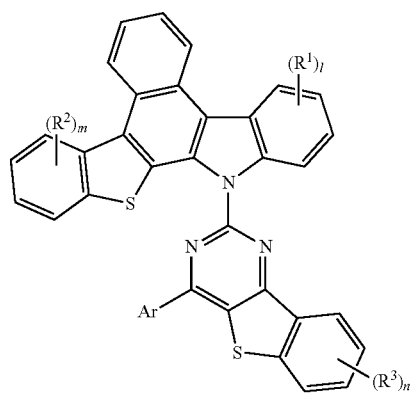
<Formula 1-1-2-O>
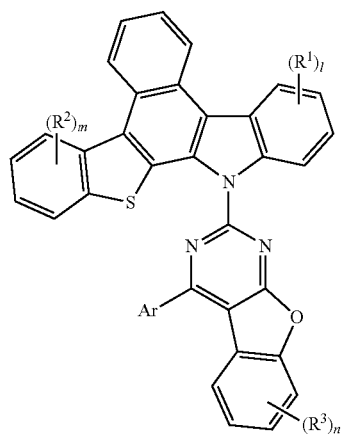
<Formula 1-1-2-S>
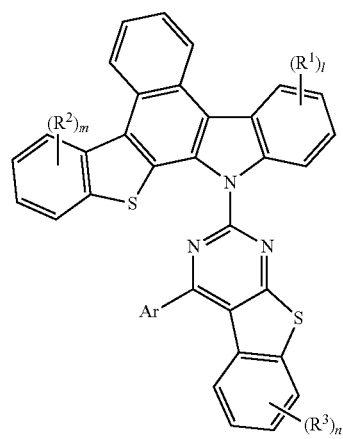
<Formula 1-2-1-O>
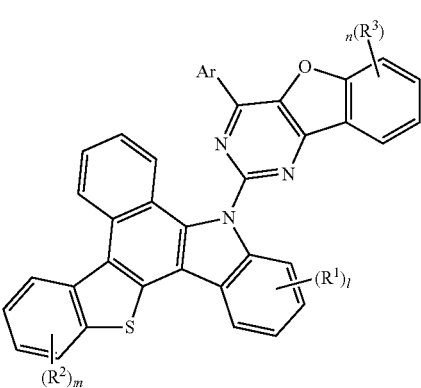
<Formula 1-2-1-S>
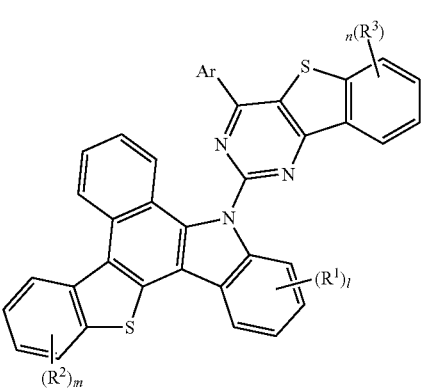
<Formula 1-2-2-O>
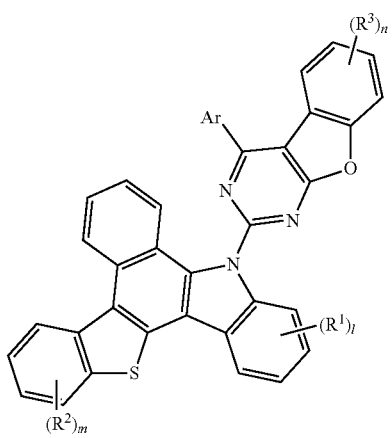

<Formula 1-2-2-S>
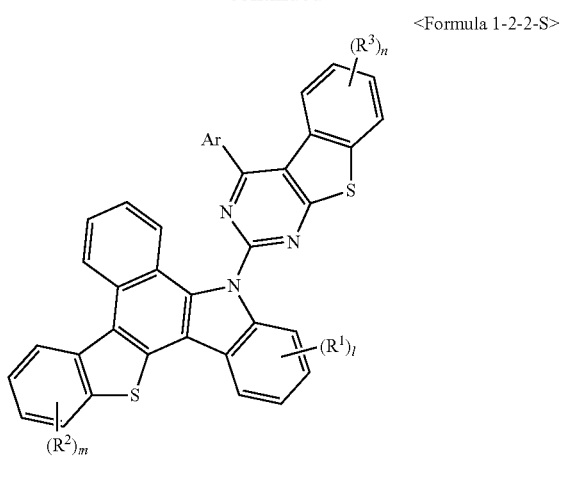
<Formula 1-3-1-O>
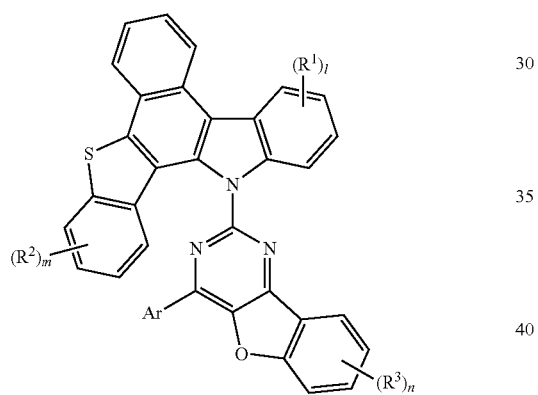
<Formula 1-3-1-S>
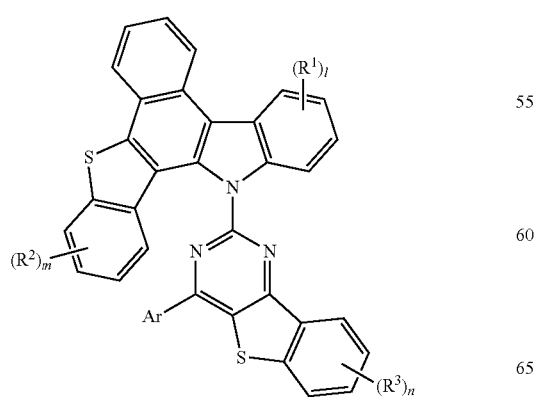
<Formula 1-3-2-O>
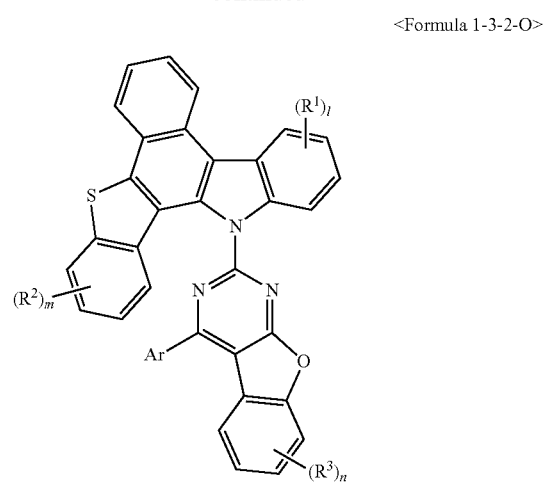
<Formula 1-3-2-S>
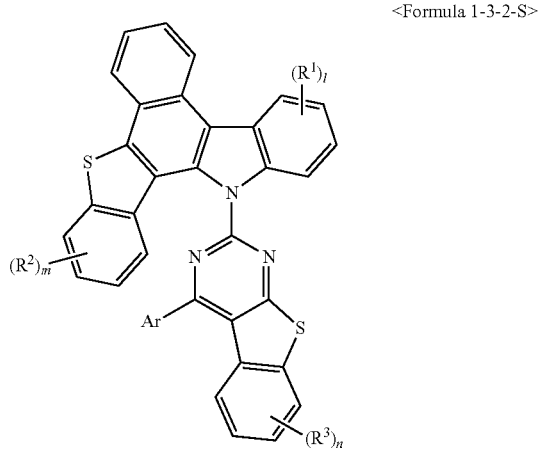
<Formula 1-4-1-O>
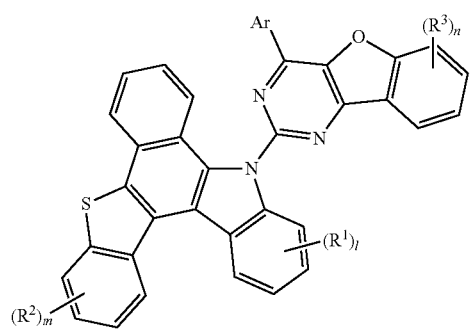
<Formula 1-4-1-S>
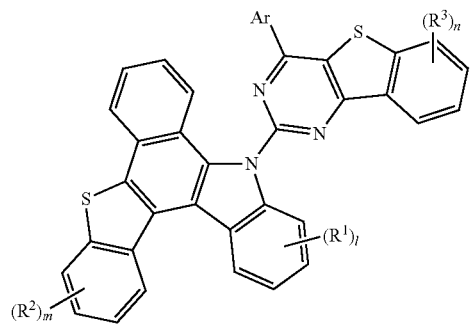

<Formula 1-4-2-O>
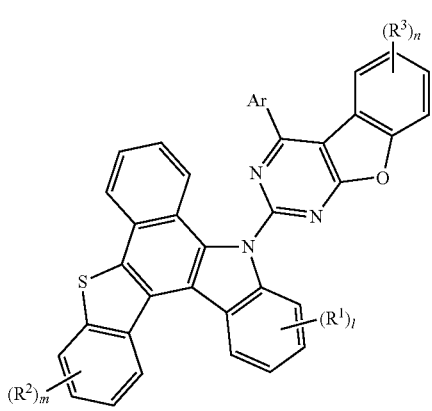
<Formula 1-4-2-S>
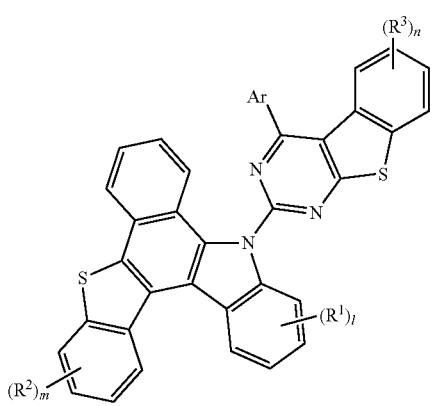
In formulas above, Ar, $R^1$ to $R^3$, l, m, and n are as defined in Formula 1 above.
Also, in Formula 1 above, Ar may be any one of formulas below.
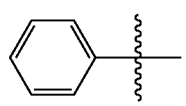
Ar-1
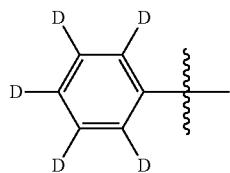
Ar-2
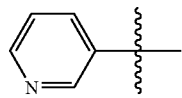
Ar-3
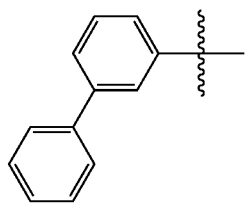
Ar-4
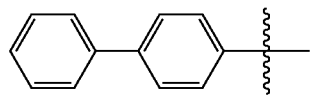
Ar-5
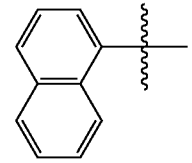
Ar-6
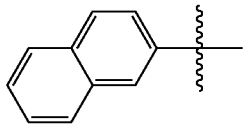
Ar-7
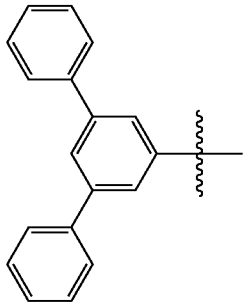
Ar-8
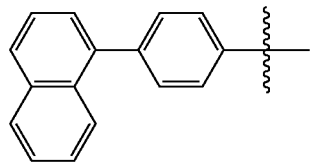
Ar-9
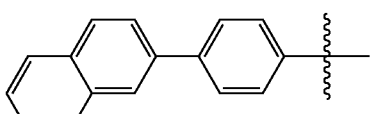
Ar-10
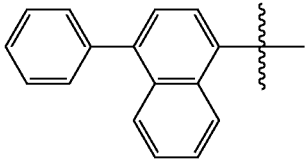
Ar-11
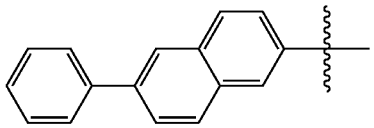
Ar-12
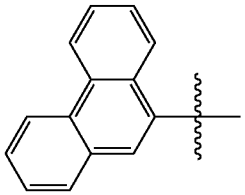
Ar-13

-continued
Ar-14 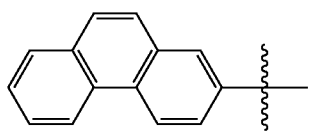
Ar-15 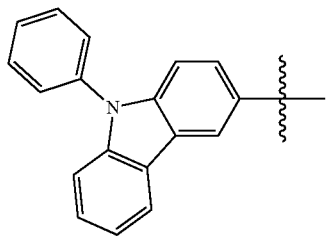
Ar-16 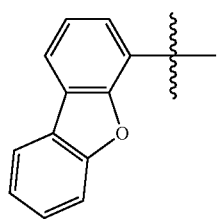
Ar-17 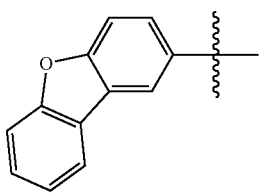
Ar-18 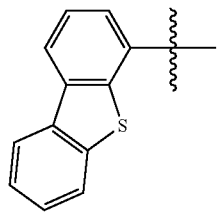
Ar-19 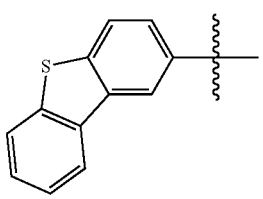
Ar-20 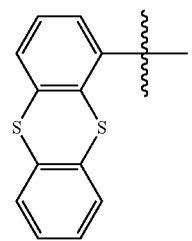
More specially, the compound represented by Formula 1 above may be one of compounds below.
1-1-1-O-(1)
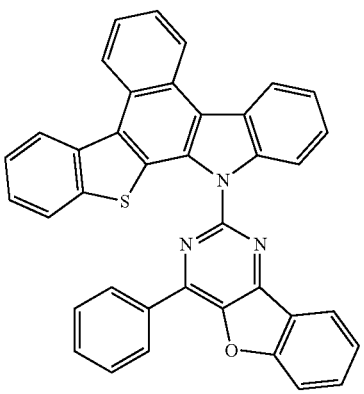
1-1-1-O-(2)
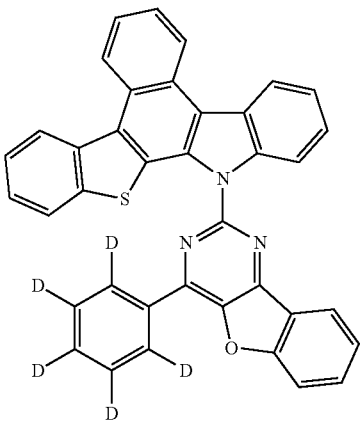
1-1-1-O-(3)
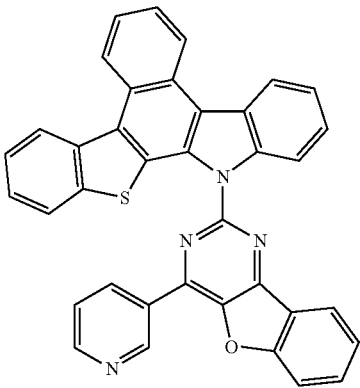

-continued
1-1-1-O-(4)
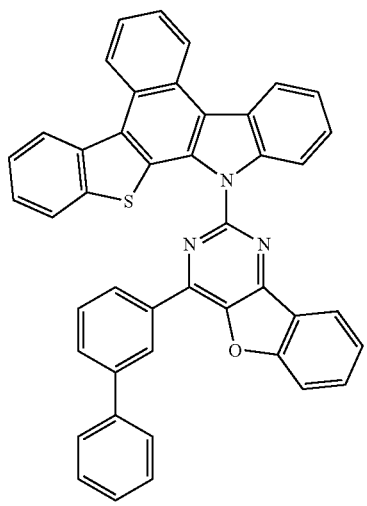
1-1-1-O-(5)
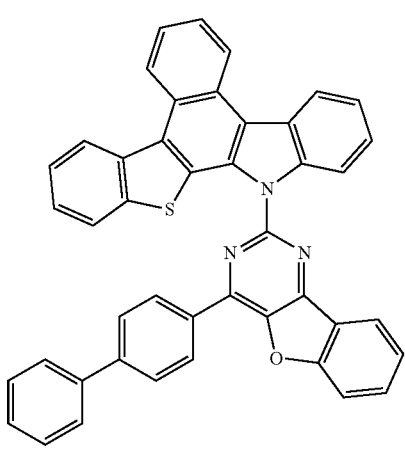
1-1-1-O-(6)
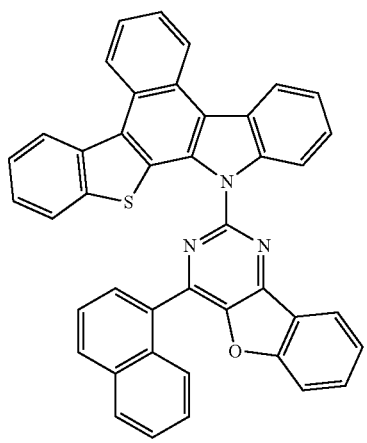
-continued
1-1-1-O-(7)
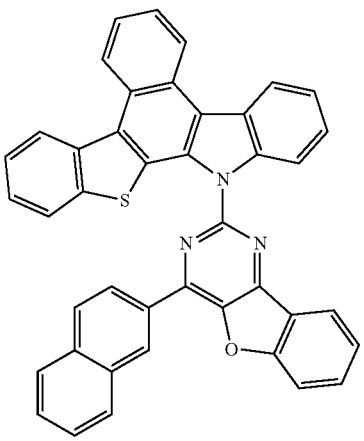
1-1-1-O-(8)
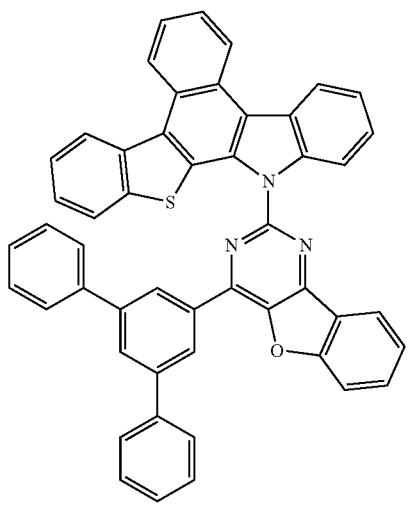
1-1-1-O-(9)
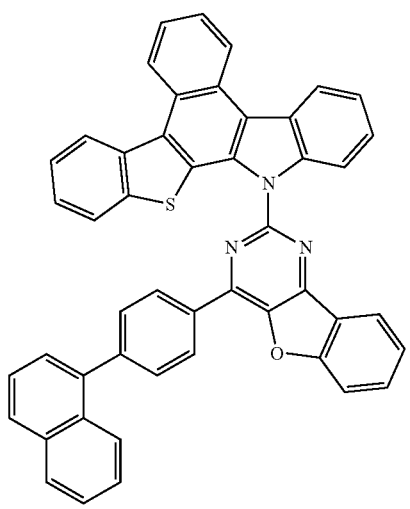

1-1-1-O-(10)
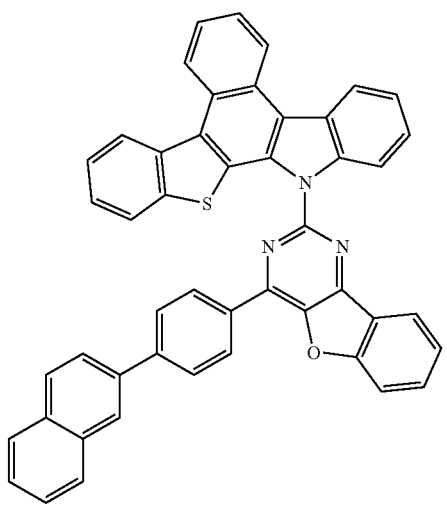
1-1-1-O-(11)
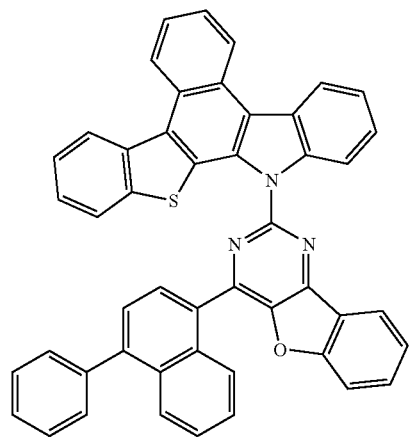
1-1-1-O-(12)
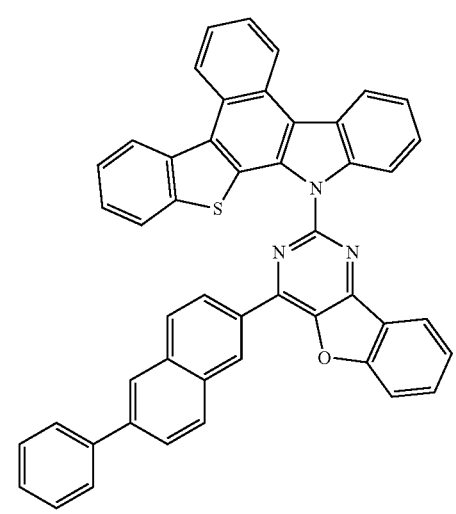
1-1-1-O-(13)
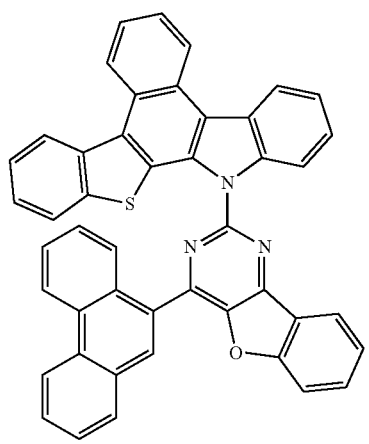
1-1-1-O-(14)
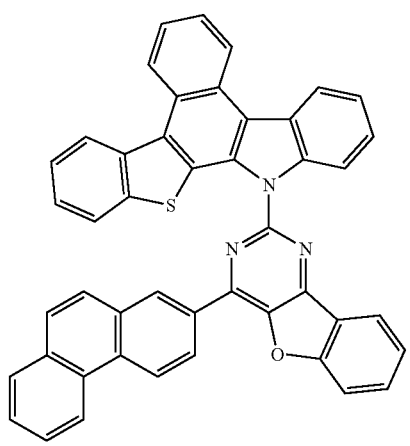
1-1-1-O-(15)
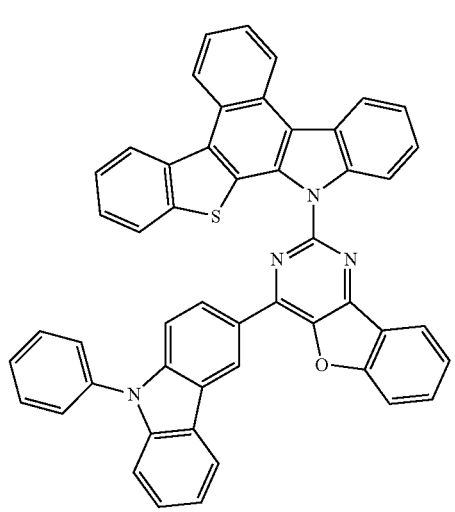

1-1-1-O-(16)
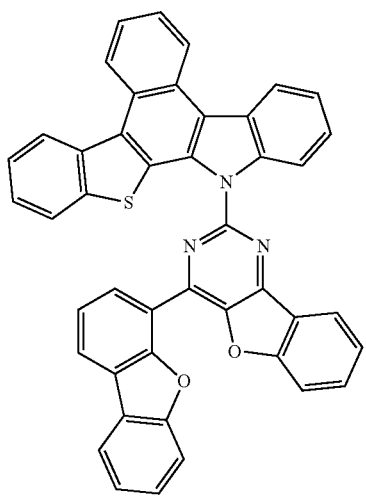
1-1-1-O-(17)
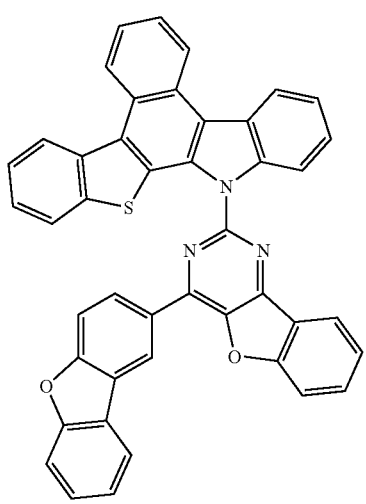
1-1-1-O-(18)
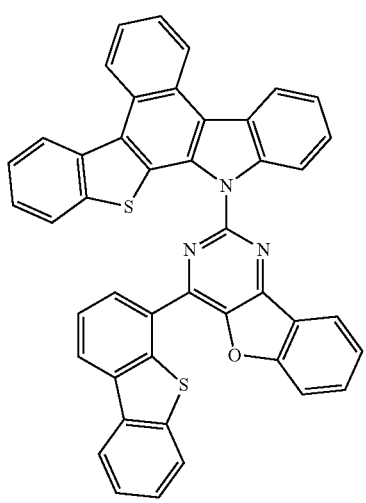
1-1-1-O-(19)
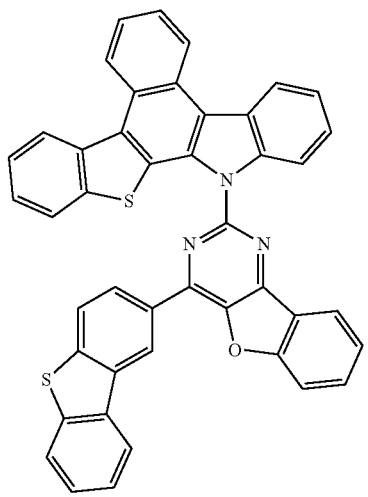
1-1-1-O-(20)
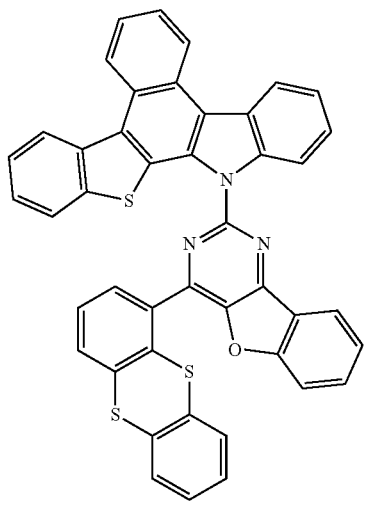
1-1-1-S-(1)
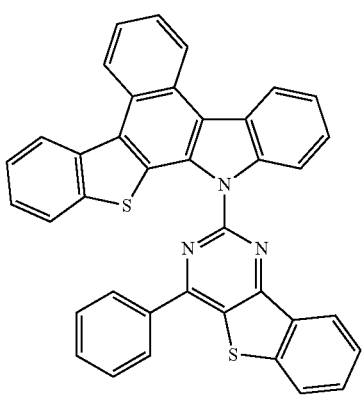

1-1-1-S-(2)
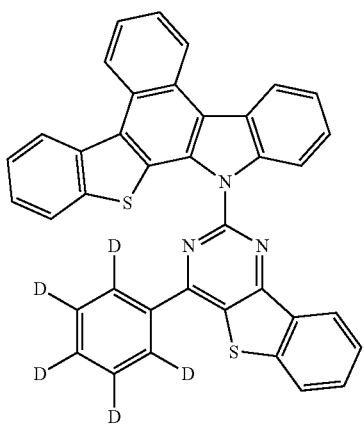
1-1-1-S-(3)
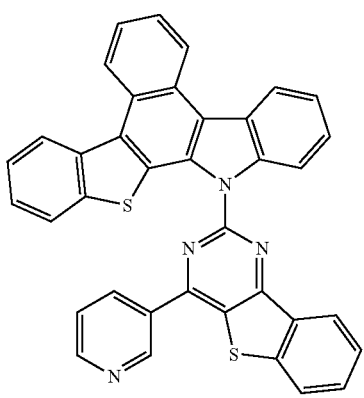
1-1-1-S-(4)
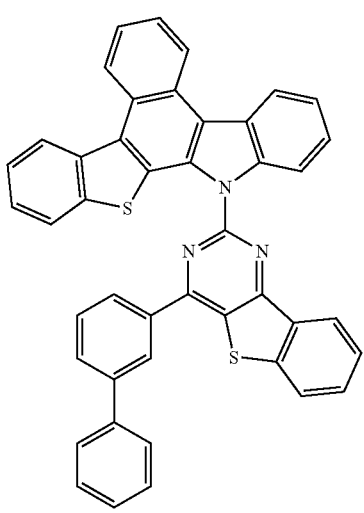
1-1-1-S-(5)
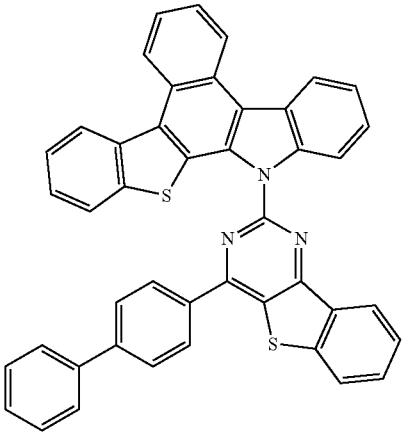
1-1-1-S-(6)
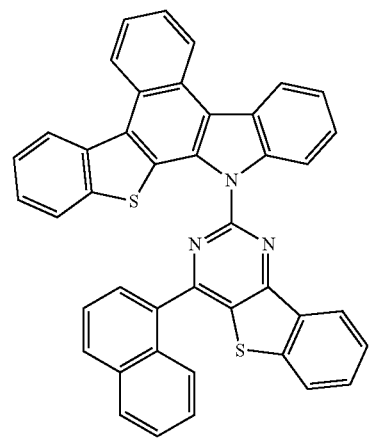
1-1-1-S-(7)
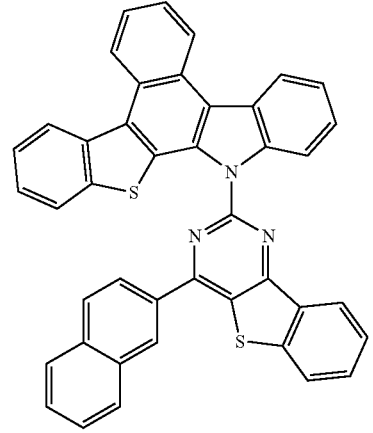

-continued
1-1-1-S-(8)
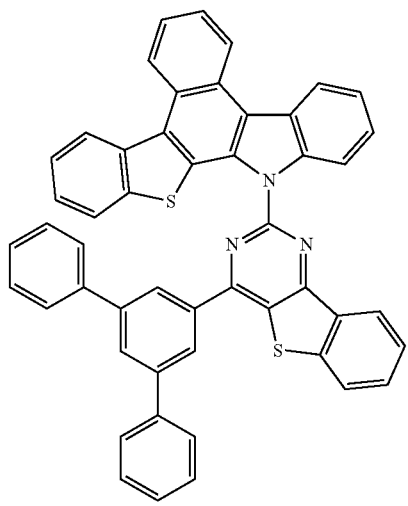
1-1-1-S-(9)
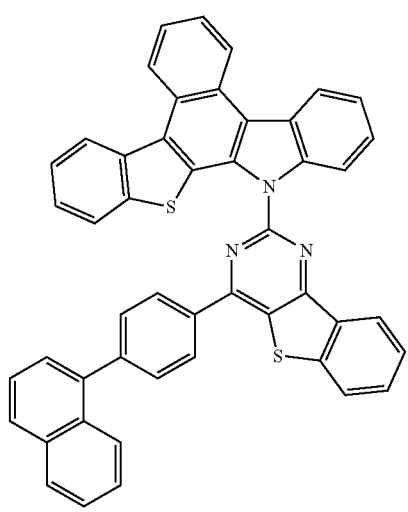
1-1-1-S-(10)
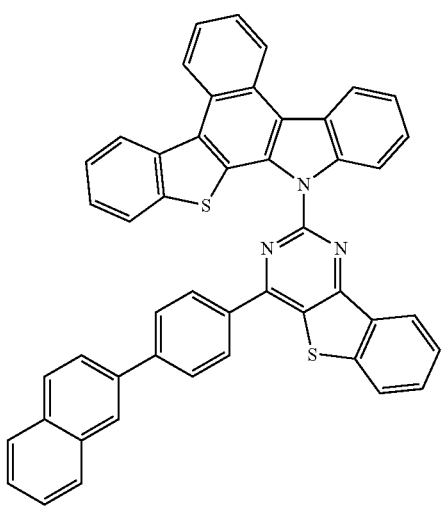
-continued
1-1-1-S-(11)
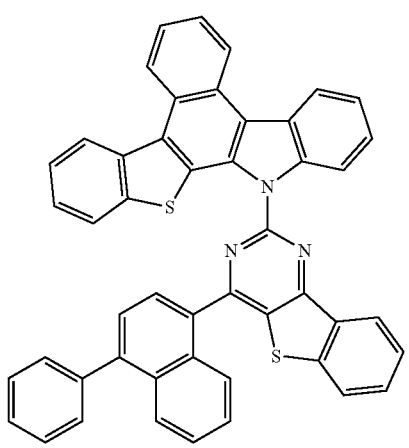
1-1-1-S-(12)
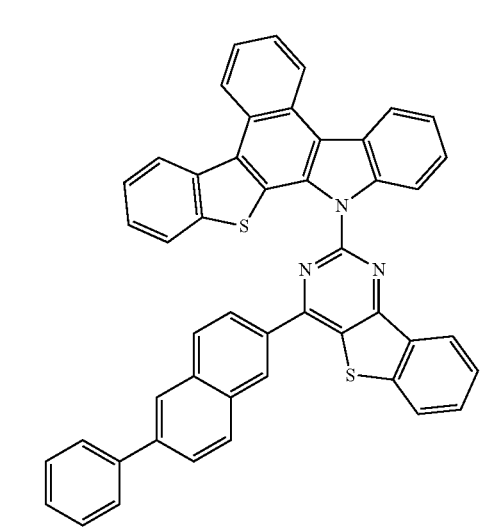
1-1-1-S-(13)
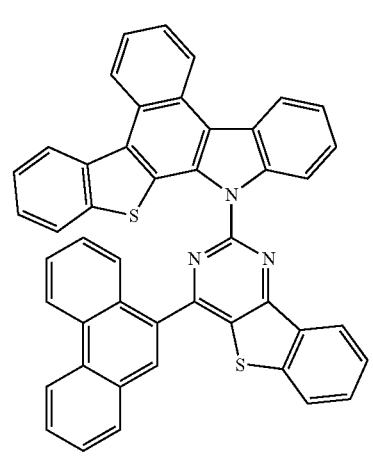

1-1-1-S-(14)
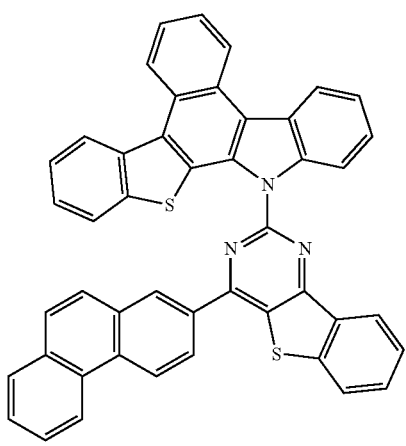
1-1-1-S-(15)
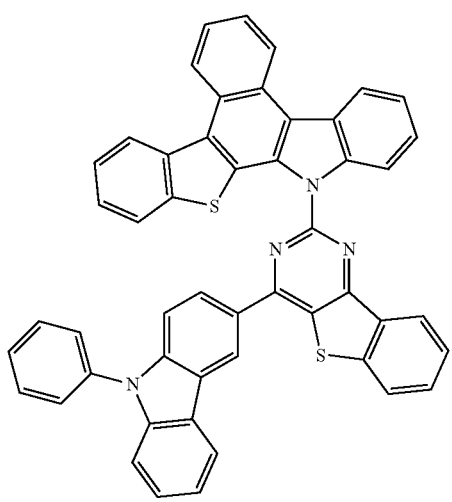
1-1-1-S-(16)
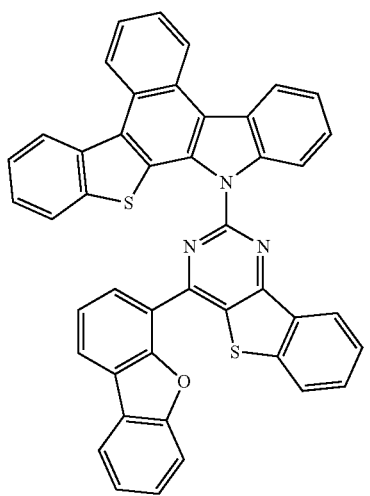
1-1-1-S-(17)
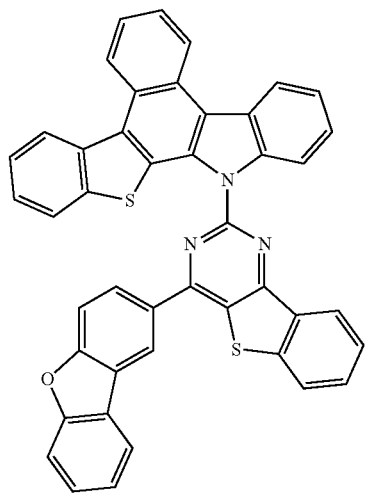
1-1-1-S-(18)
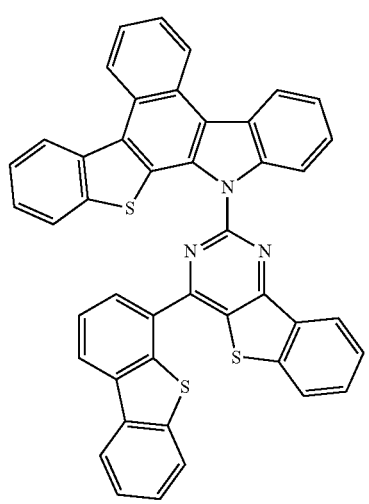
1-1-1-S-(19)
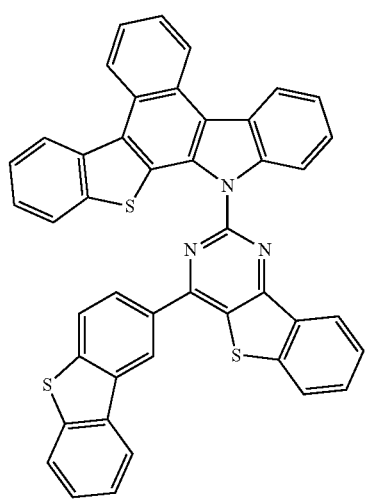

1-1-1-S-(20)
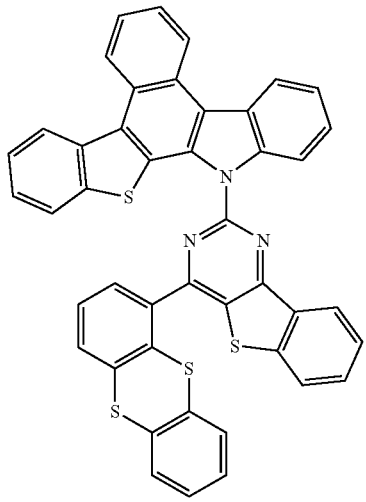
1-1-1-O-(21)
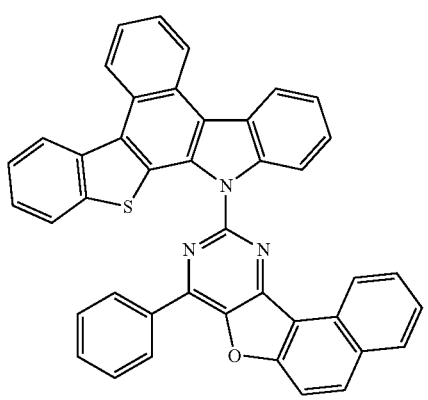
1-1-1-O-(22)
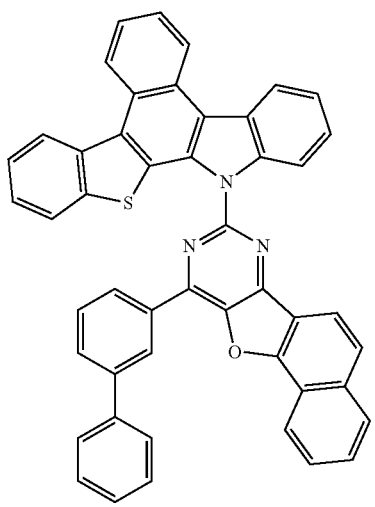
1-1-1-S-(21)
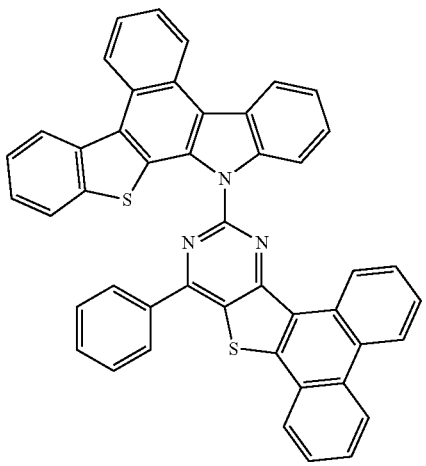
1-1-1-S-(22)
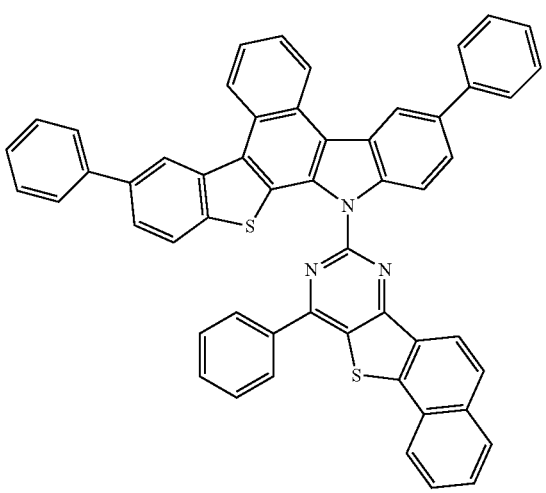
1-1-1-S-(23)
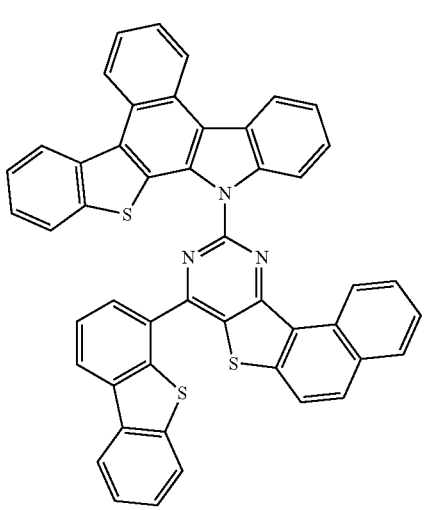

1-1-2-O-(1)
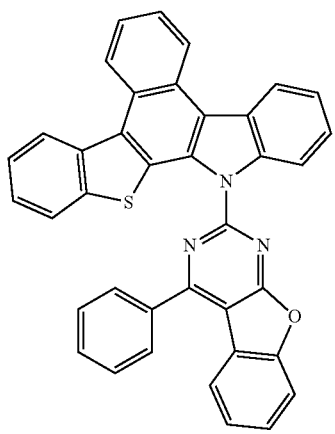
1-1-2-O-(2)
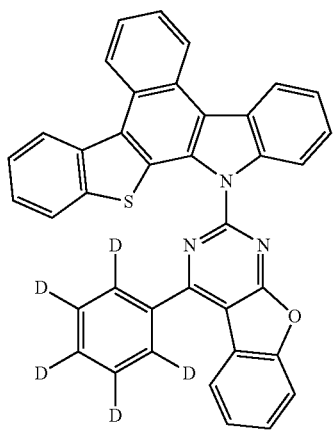
1-1-2-O-(3)
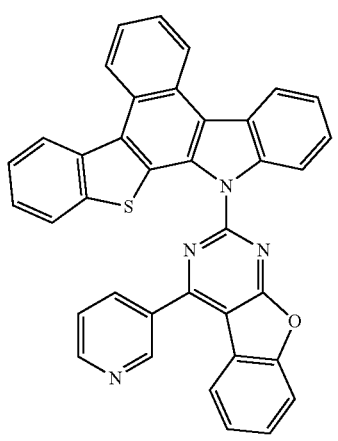
1-1-2-O-(4)
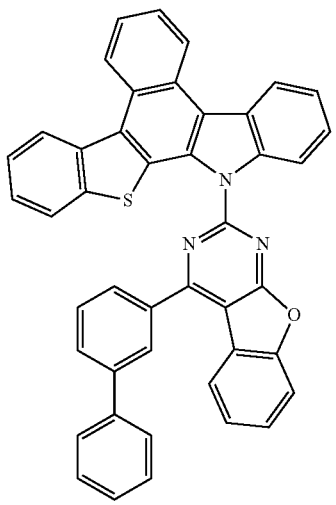
1-1-2-O-(5)
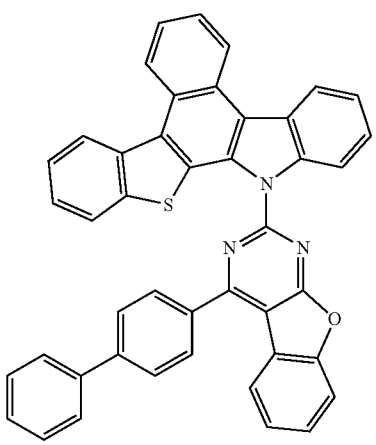
1-1-2-O-(6)
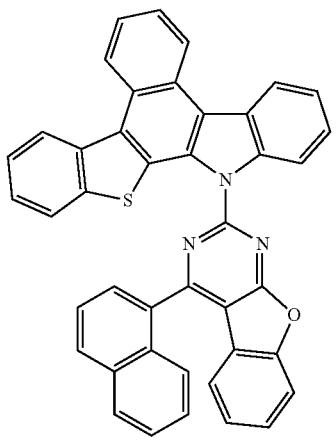

1-1-2-O-(7)
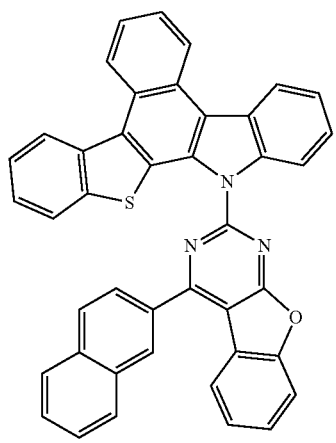
1-1-2-O-(8)
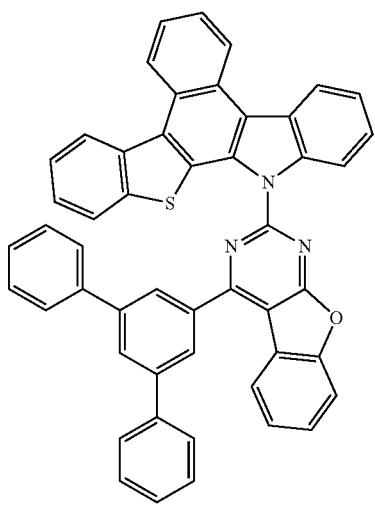
1-1-2-O-(9)
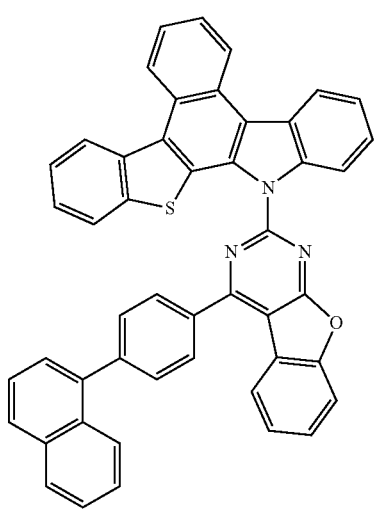
1-1-2-O-(10)
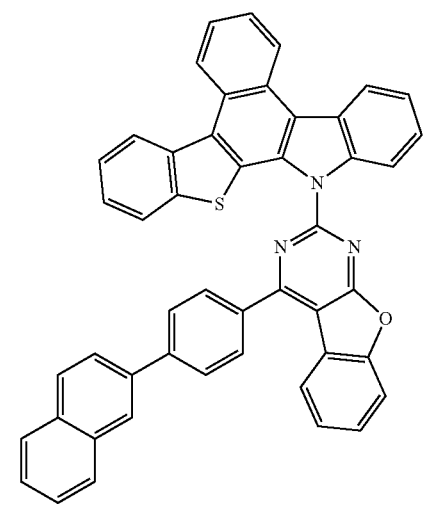
1-1-2-O-(11)
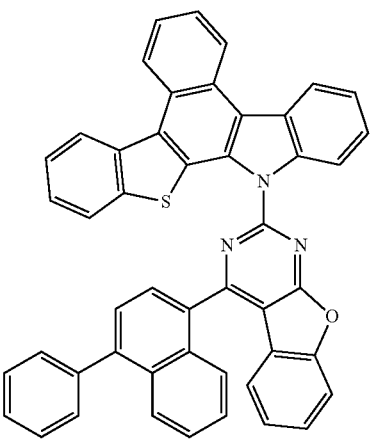
1-1-2-O-(12)
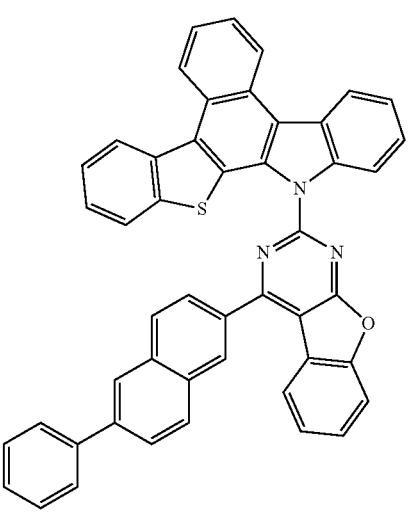

1-1-2-O-(13)
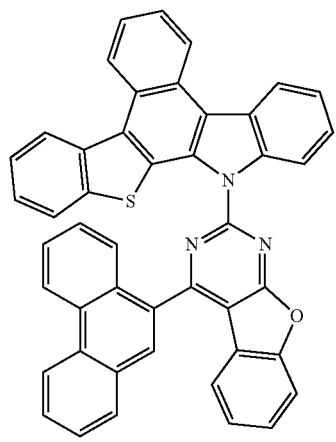
1-1-2-O-(14)
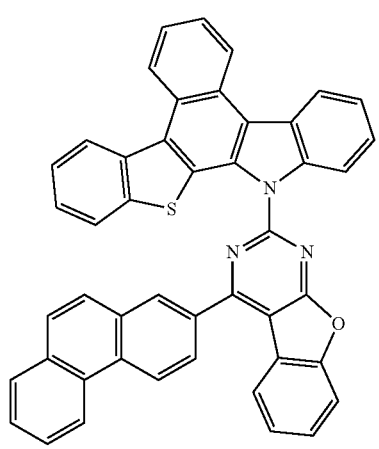
1-1-2-O-(15)
1-1-2-O-(16)
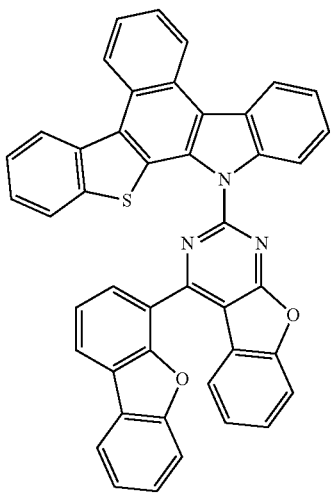
1-1-2-O-(17)
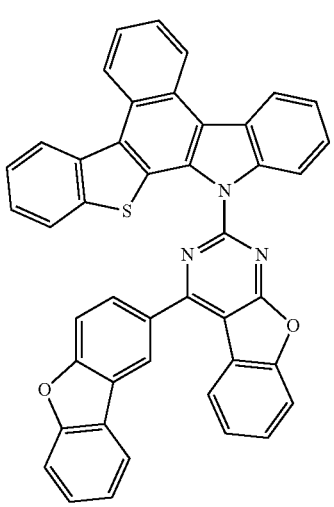
1-1-2-O-(18)
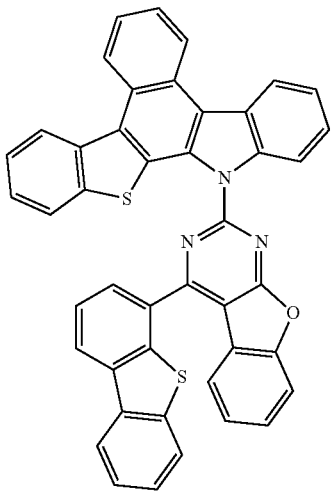

1-1-2-O-(19)
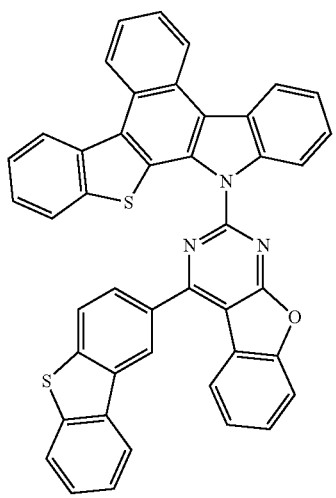
1-1-2-O-(20)
1-1-2-S-(1)
1-1-2-S-(2)
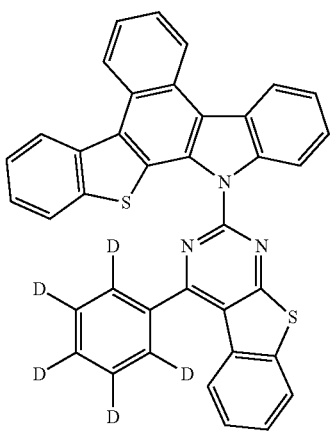
1-1-2-S-(3)
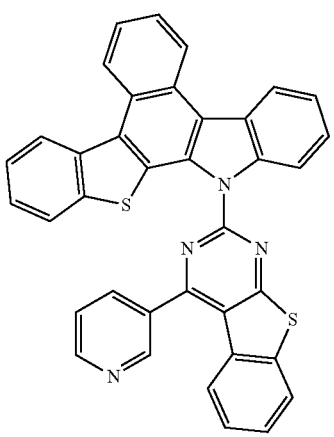
1-1-2-S-(4)
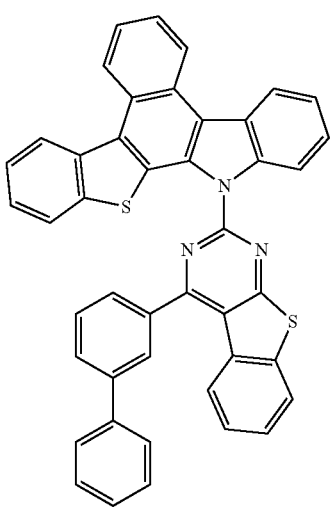

1-1-2-S-(5)
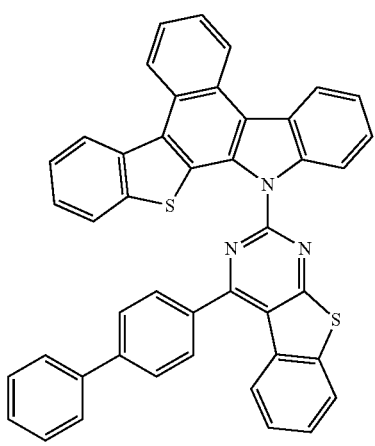
1-1-2-S-(8)
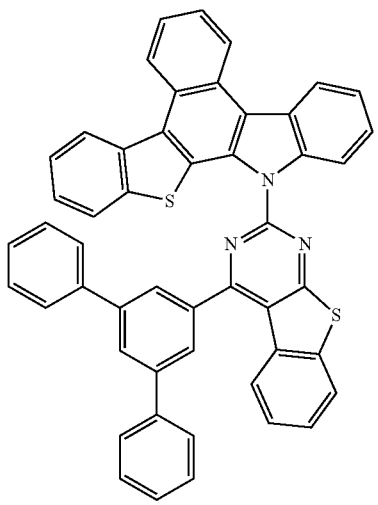
1-1-2-S-(6)
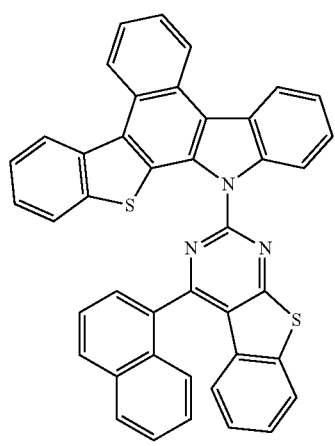
1-1-2-S-(9)
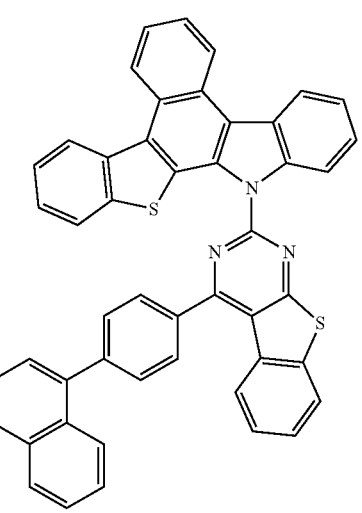
1-1-2-S-(7)
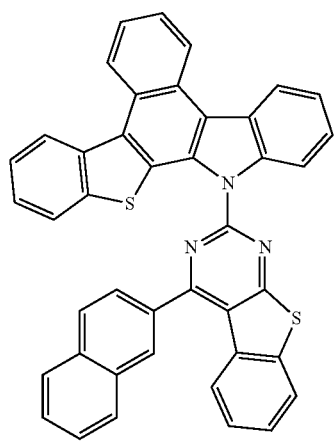
1-1-2-S-(10)
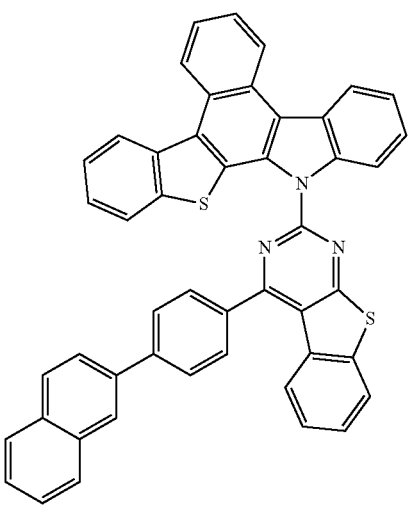

1-1-2-S-(11)
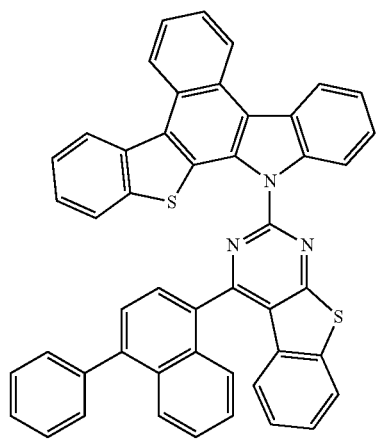
1-1-2-S-(12)
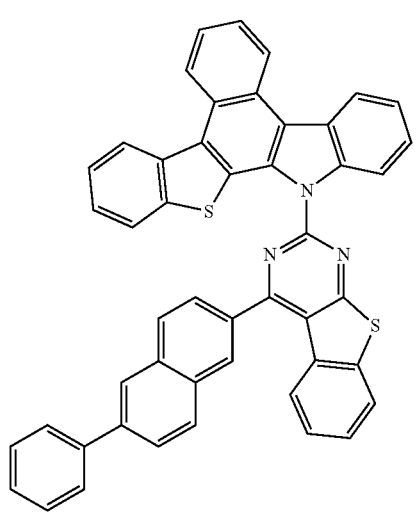
1-1-2-S-(13)
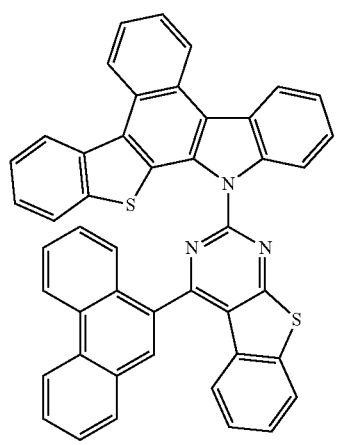
1-1-2-S-(14)
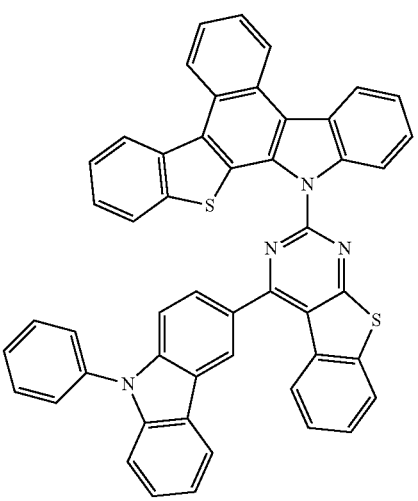
1-1-2-S-(15)
1-1-2-S-(16)
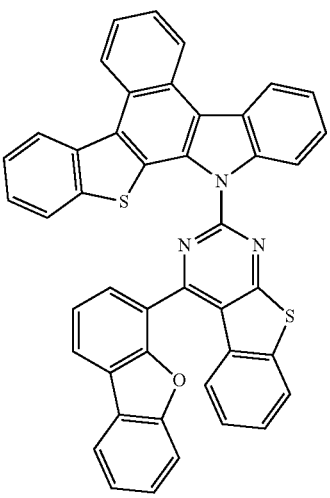

1-1-2-S-(17)
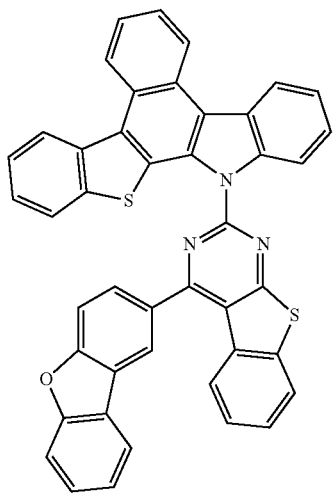
1-1-2-S-(18)
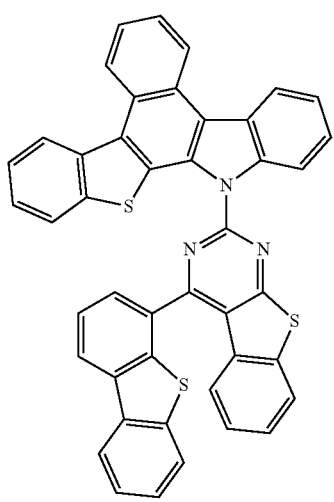
1-1-2-S-(19)
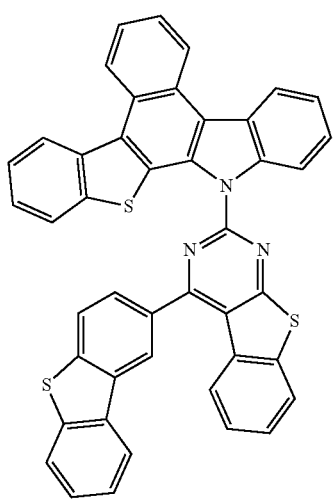
1-1-2-S-(20)
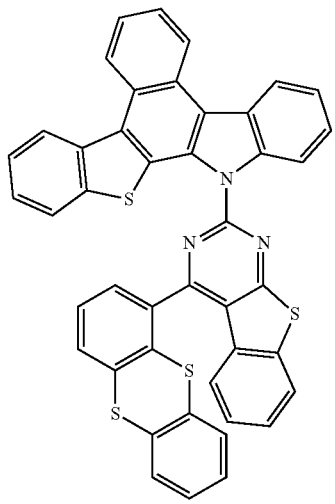
1-1-2-O-(21)
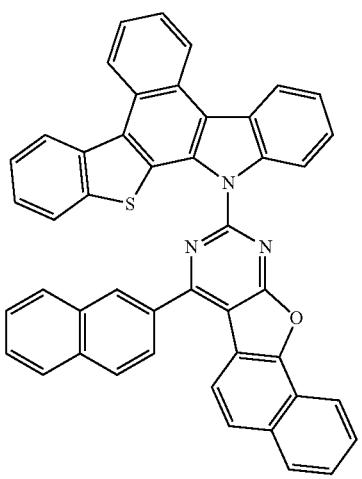
1-1-2-O-(22)
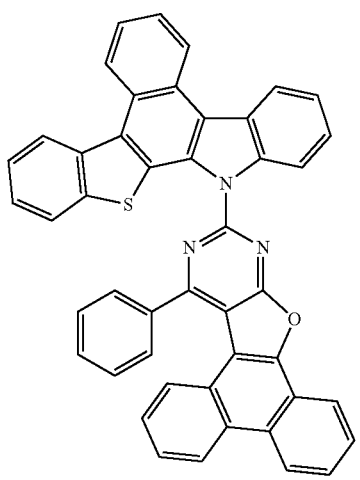

1-1-2-S-(21)
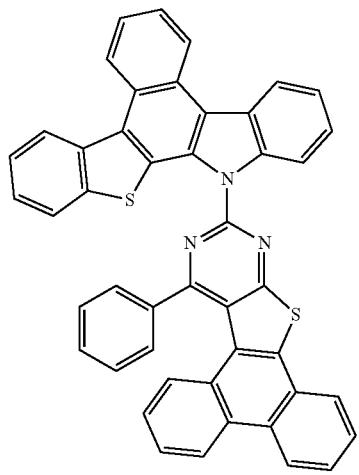
1-1-2-S-(22)
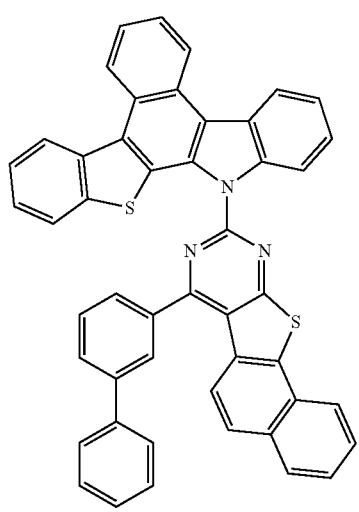
1-1-2-S-(23)
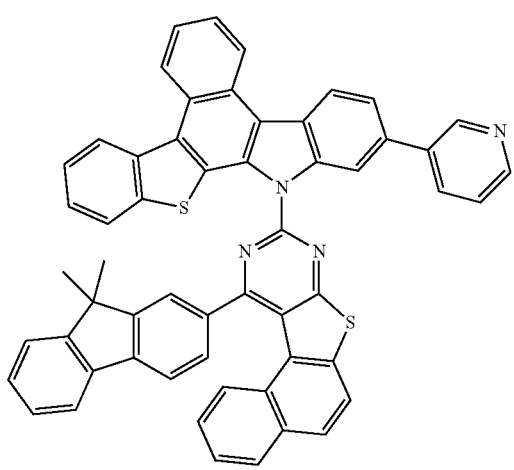
1-2-1-O-(1)
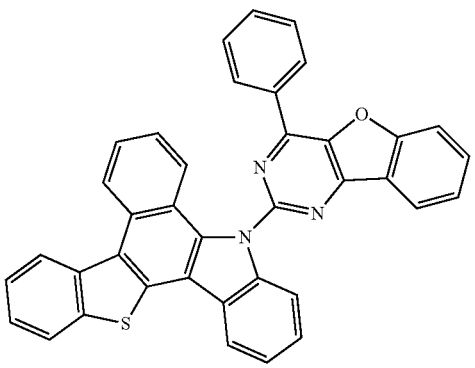
1-2-1-O-(2)
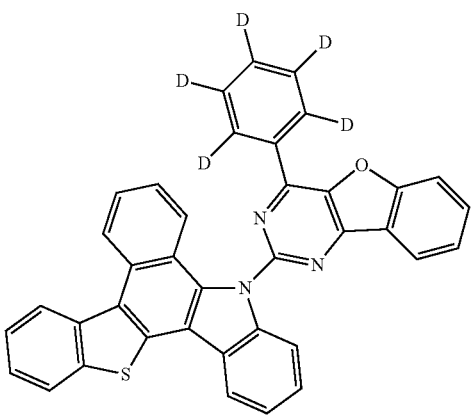
1-2-1-O-(3)
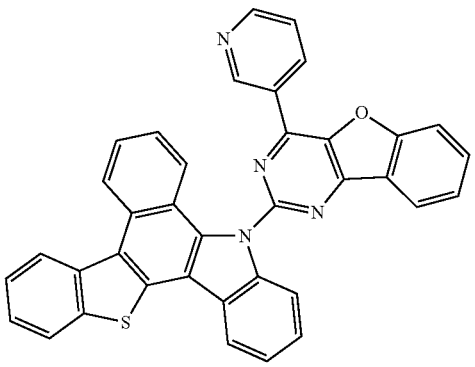
1-2-1-O-(4)
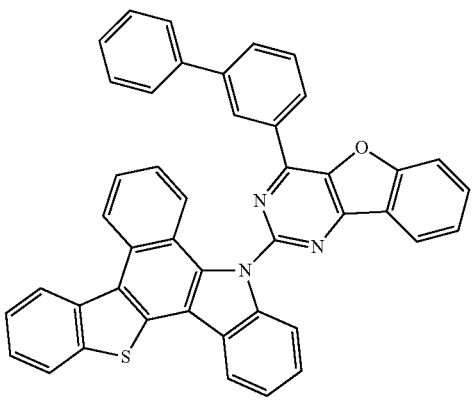

-continued
1-2-1-O-(5)
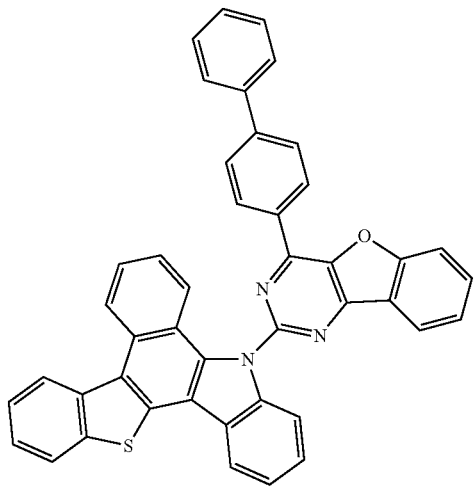
1-2-1-O-(6)
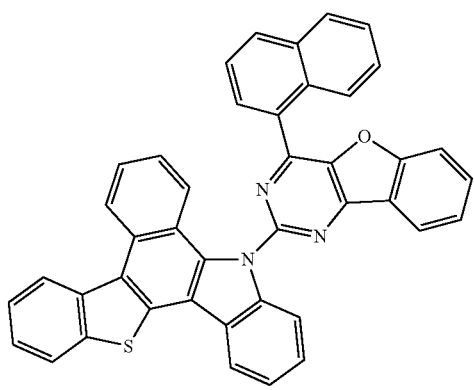
1-2-1-O-(7)
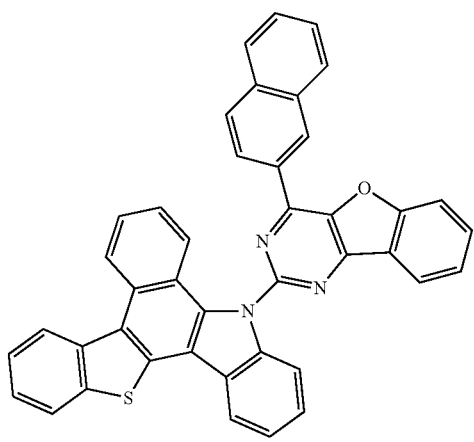
-continued
1-2-1-O-(8)
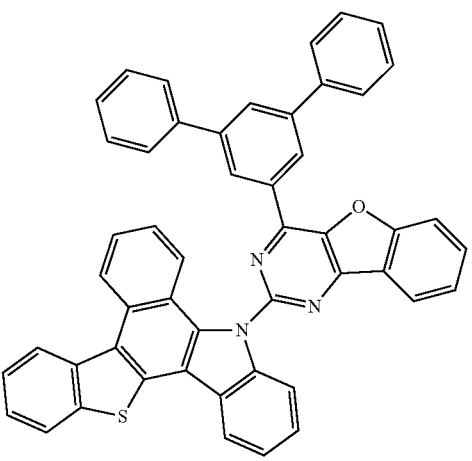
1-2-1-O-(9)
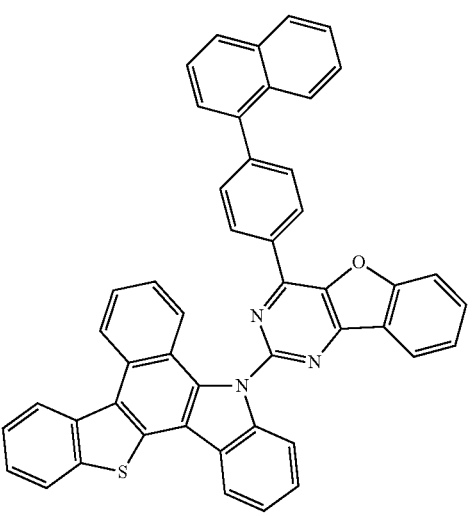
1-2-1-O-(10)
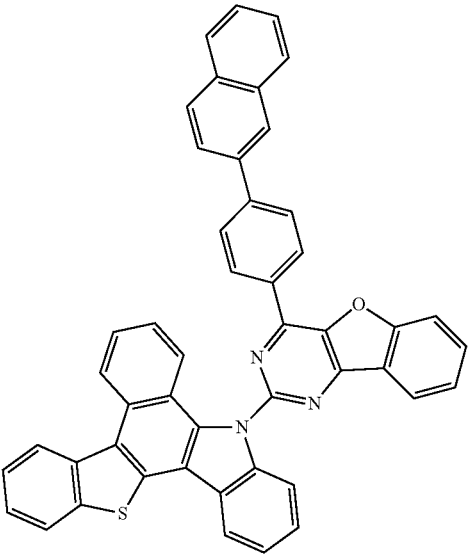

1-2-1-O-(11)
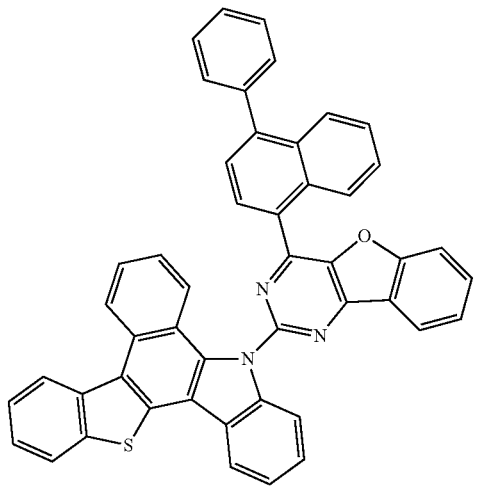
1-2-1-O-(12)
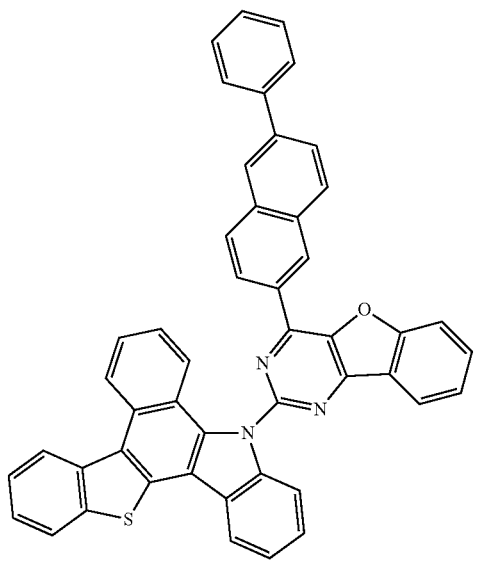
1-2-1-O-(13)
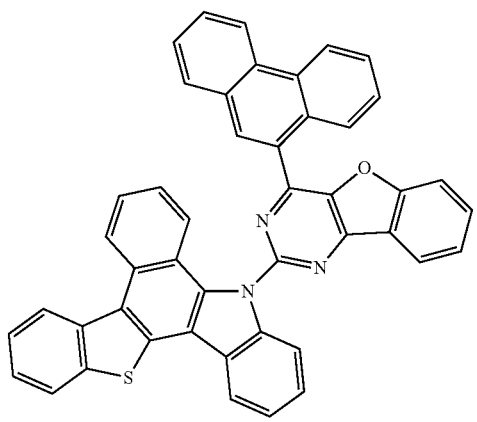
1-2-1-O-(14)
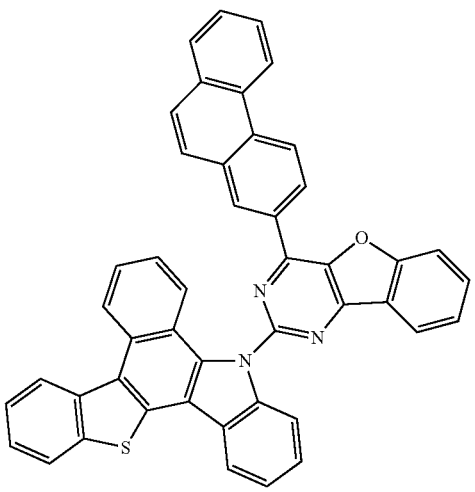
1-2-1-O-(15)
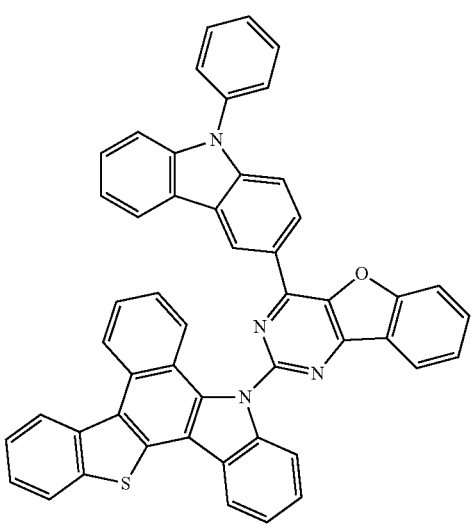
1-2-1-O-(16)
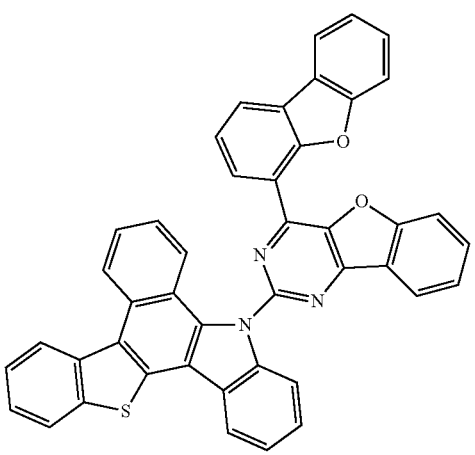

1-2-1-O-(17)
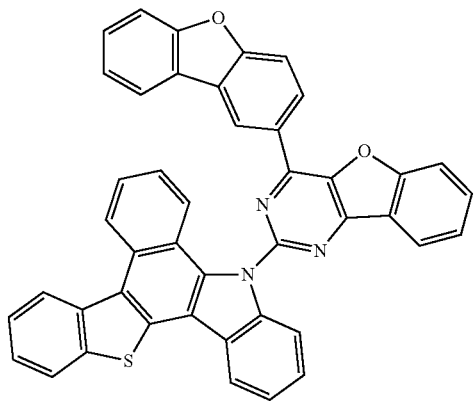
1-2-1-O-(18)
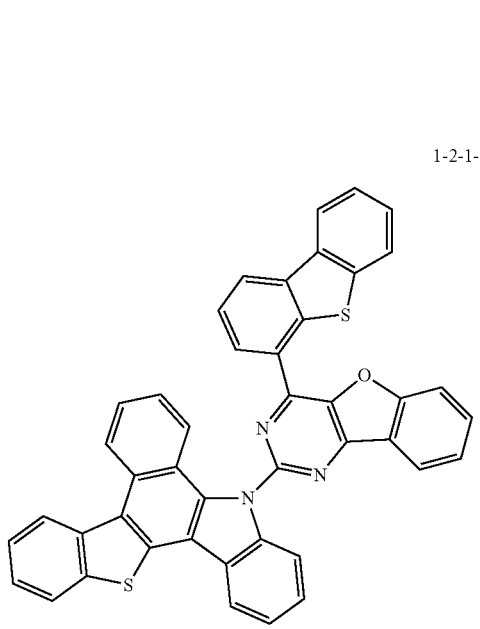
1-2-1-O-(19)
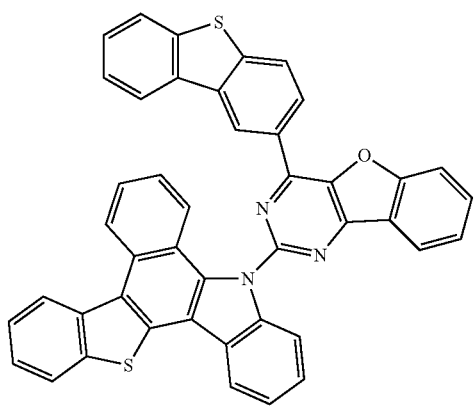
1-2-1-O-(20)
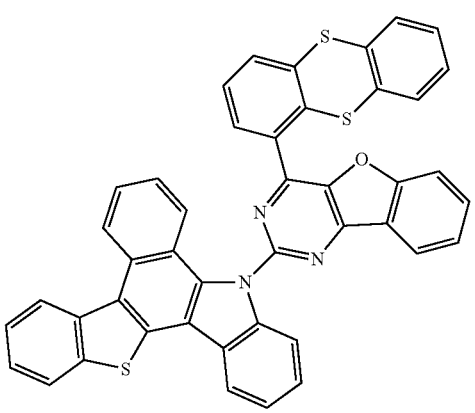
1-2-1-S-(1)
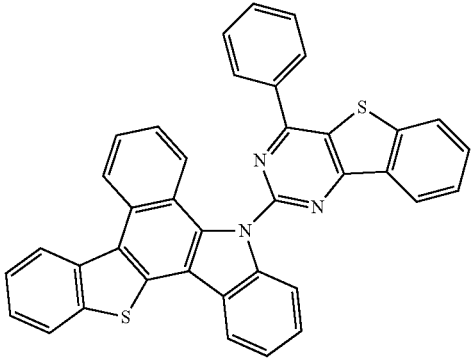
1-2-1-S-(2)
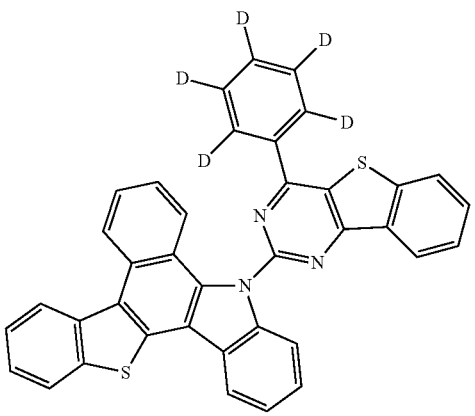
1-2-1-S-(3)
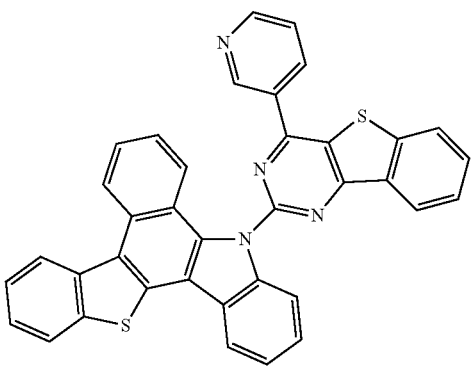

1-2-1-S-(4)
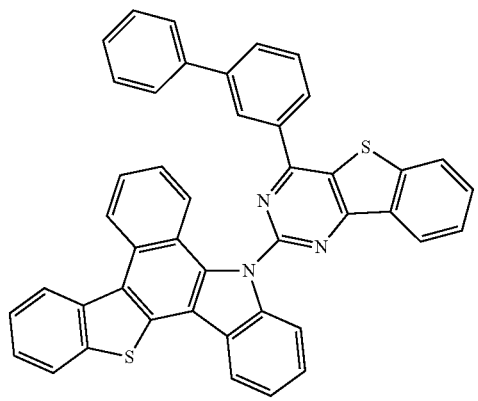
1-2-1-S-(5)
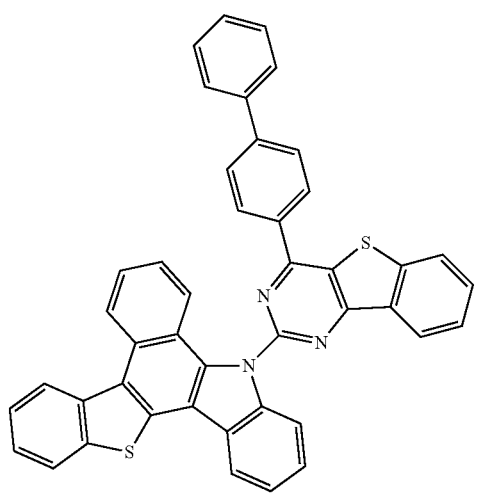
1-2-1-S-(6)
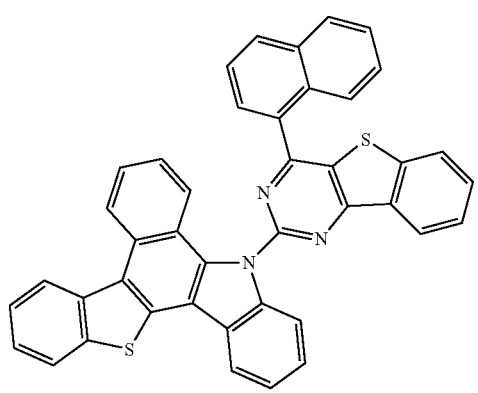
1-2-1-S-(7)
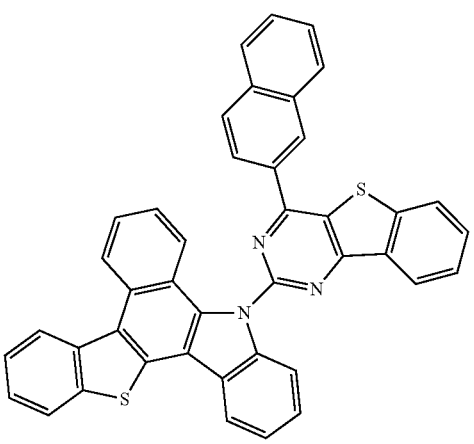
1-2-1-S-(8)
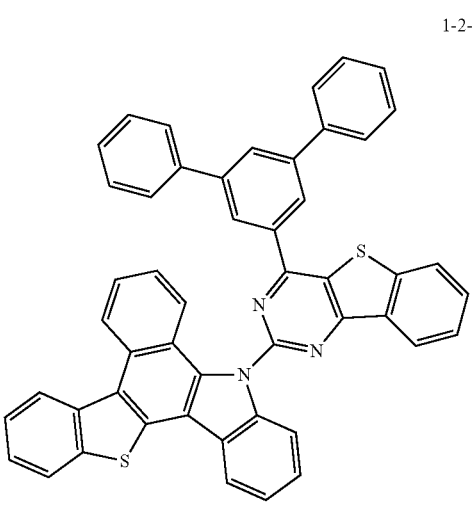
1-2-1-S-(9)
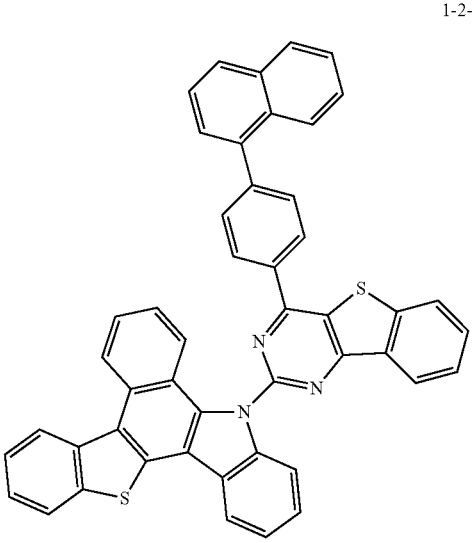

-continued
1-2-1-S-(10)
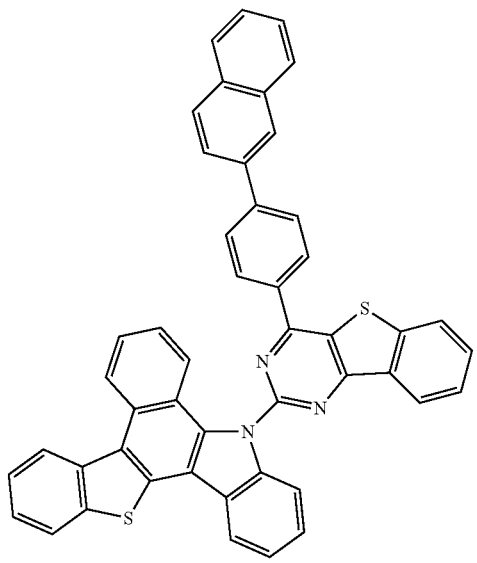
1-2-1-S-(11)
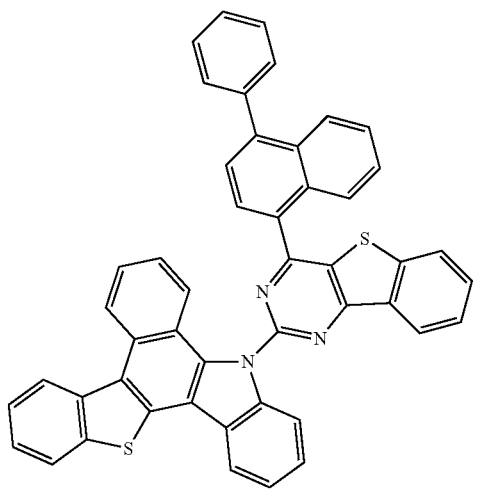
1-2-1-S-(12)
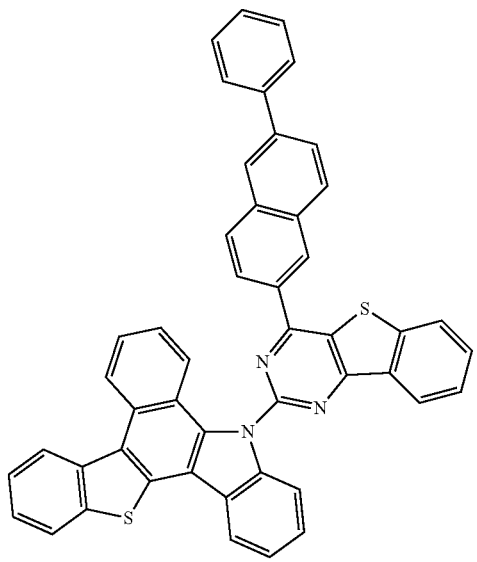
-continued
1-2-1-S-(13)
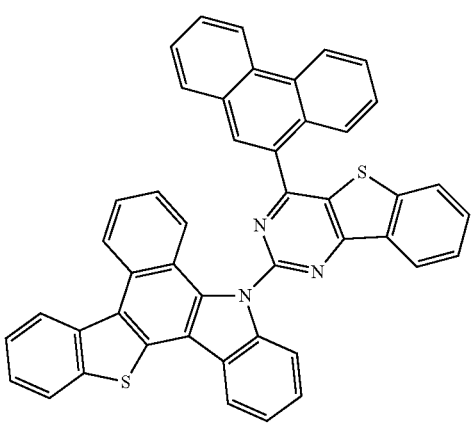
1-2-1-S-(14)
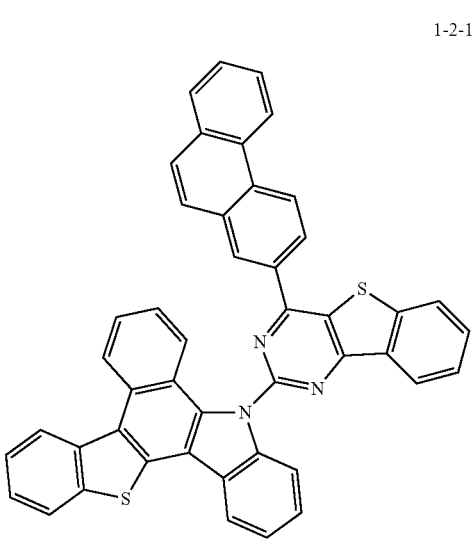
1-2-1-S-(15)
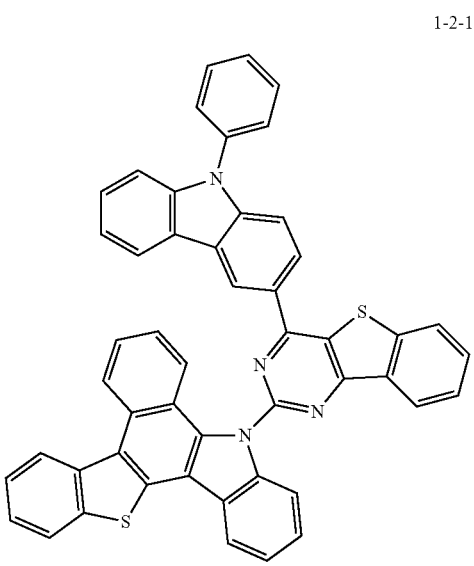

1-2-1-S-(16)
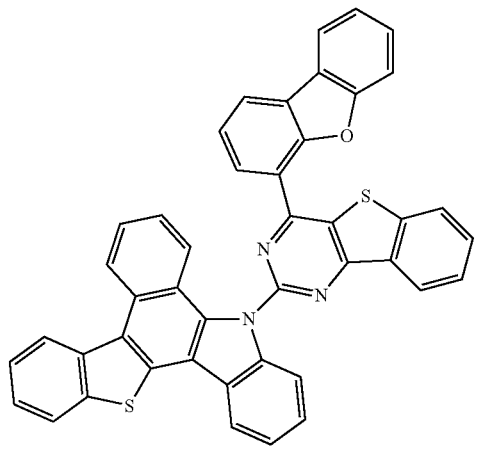
1-2-1-S-(17)
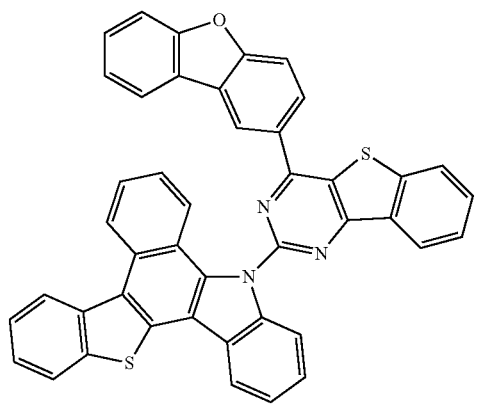
1-2-1-S-(18)
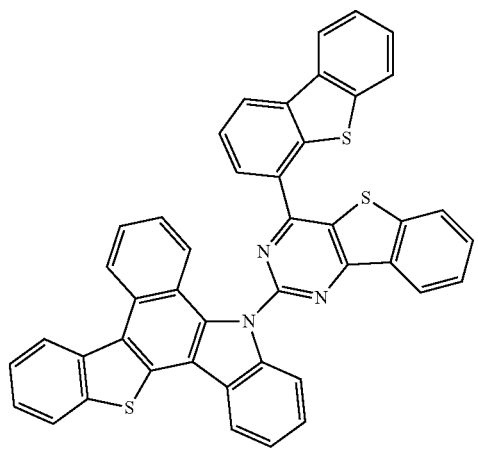
1-2-1-S-(19)
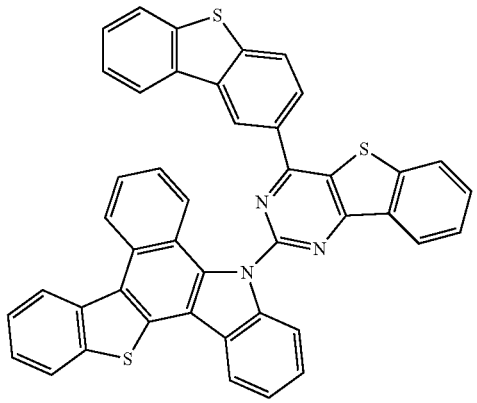
1-2-1-S-(20)
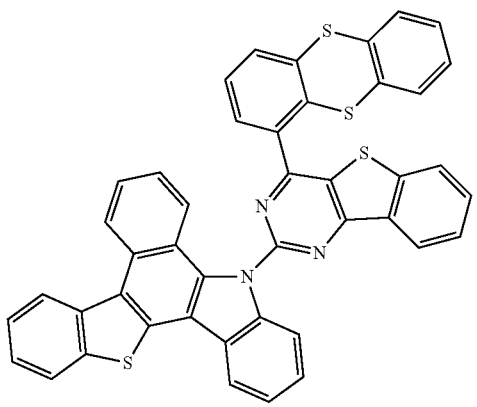
1-2-1-O-(21)
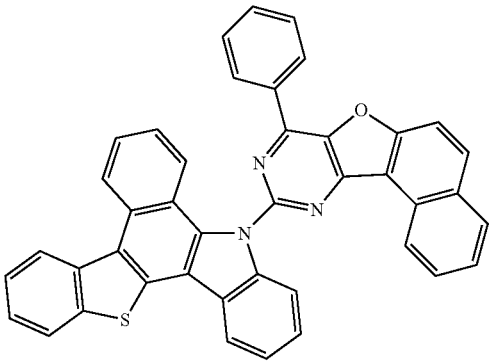
1-2-1-O-(22)
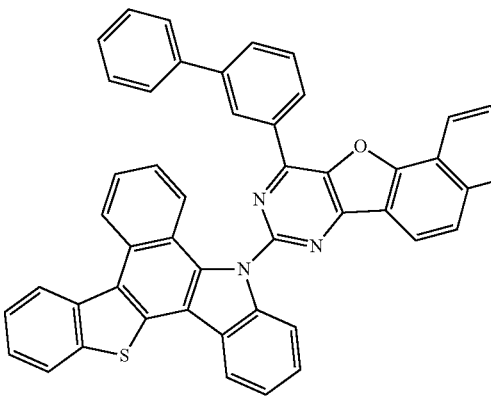

63
-continued
1-2-1-S-(21)
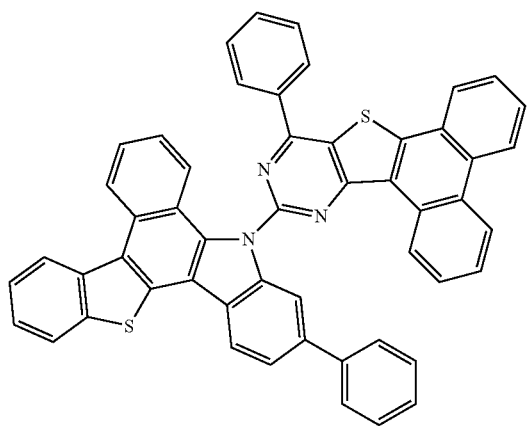
1-2-1-S-(22)
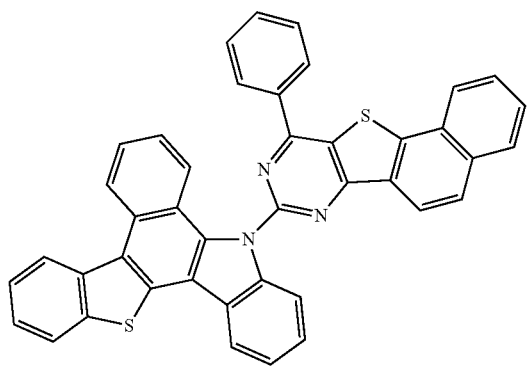
1-2-1-S-(23)
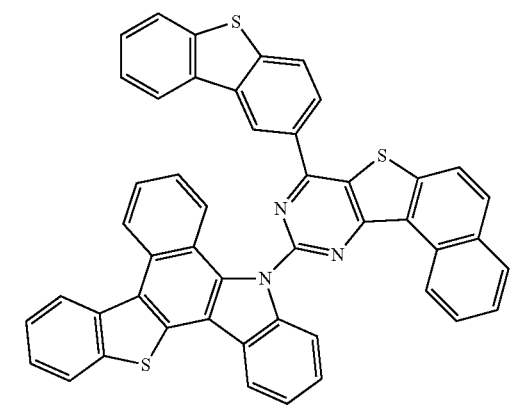
1-2-2-O-(1)
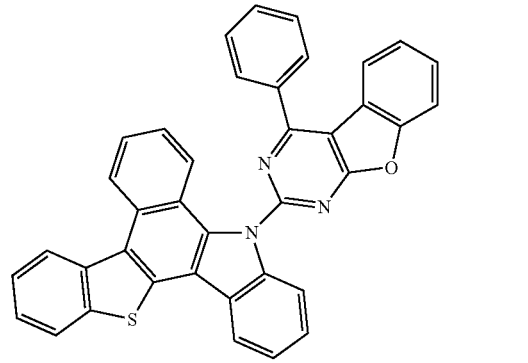
64
-continued
1-2-2-O-(2)
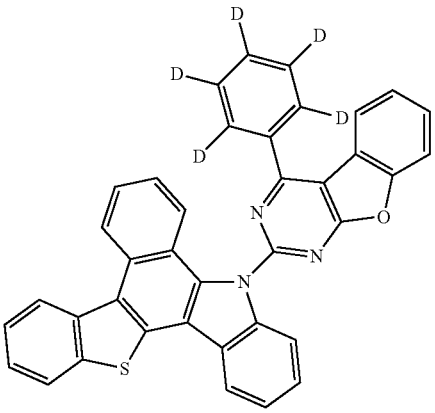
1-2-2-O-(3)
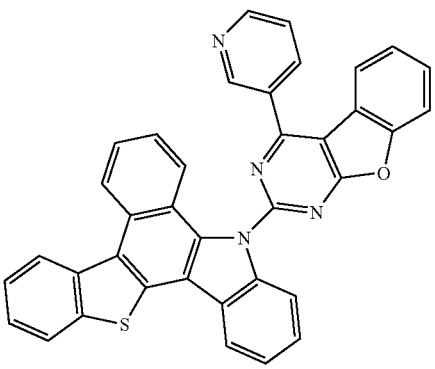
1-2-2-O-(4)
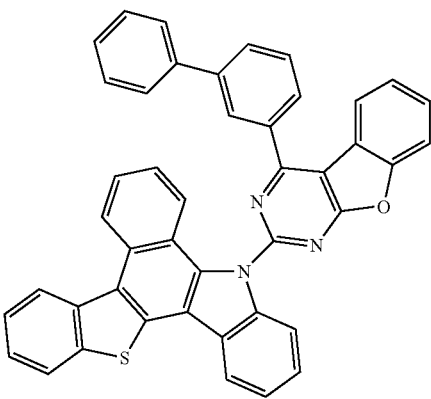

65
-continued
1-2-2-O-(5)
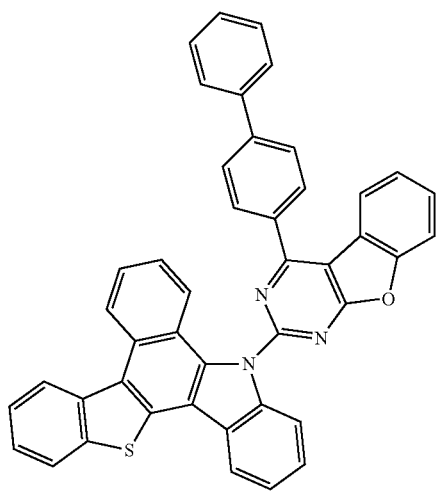
1-2-2-O-(6)
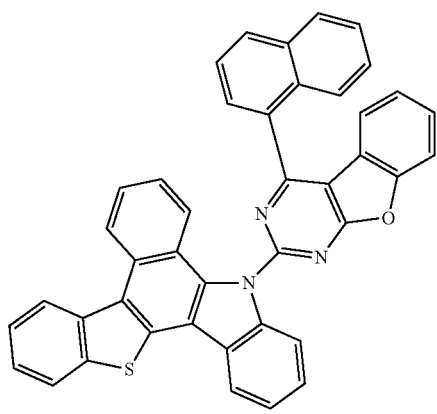
1-2-2-O-(7)
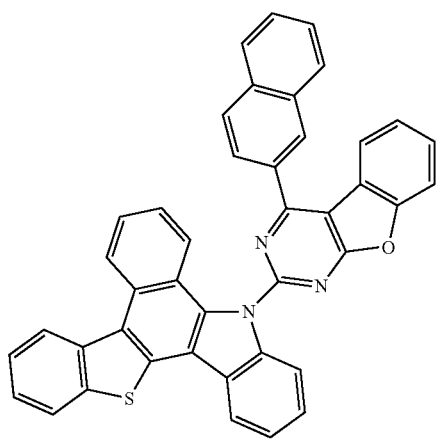
66
-continued
1-2-2-O-(8)
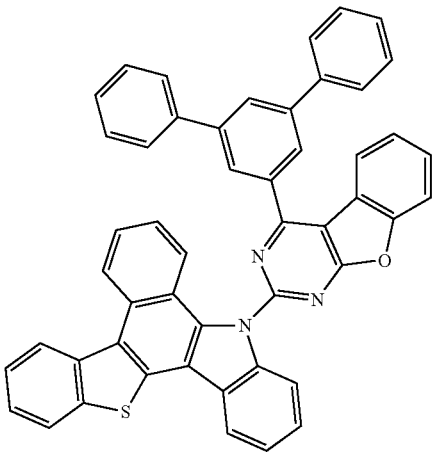
1-2-2-O-(9)
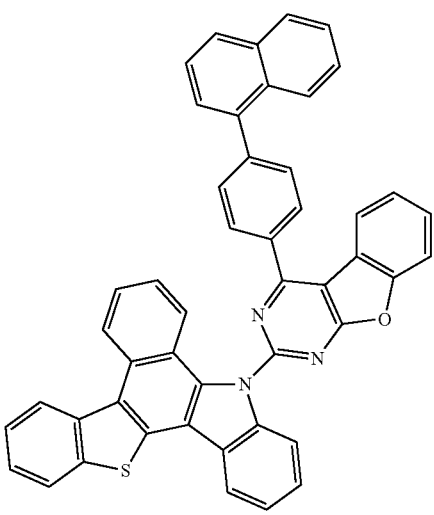
1-2-2-O-(10)
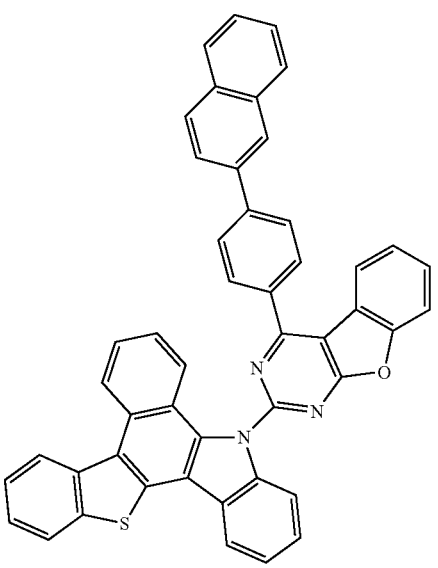

1-2-2-O-(11)
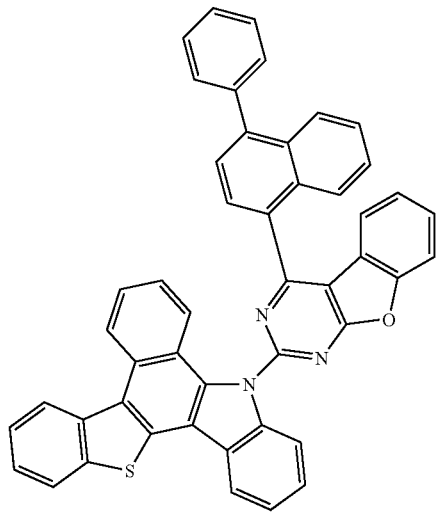
1-2-2-O-(12)
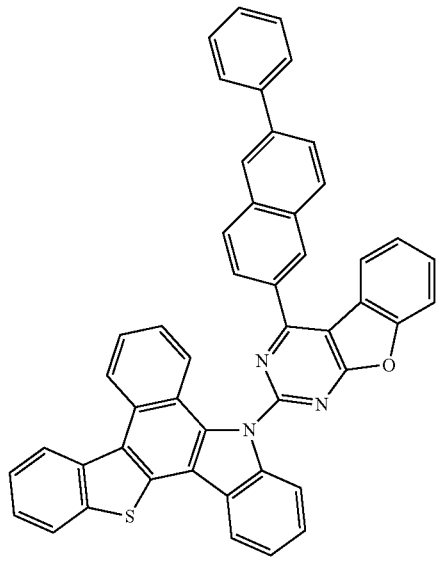
1-2-2-O-(13)
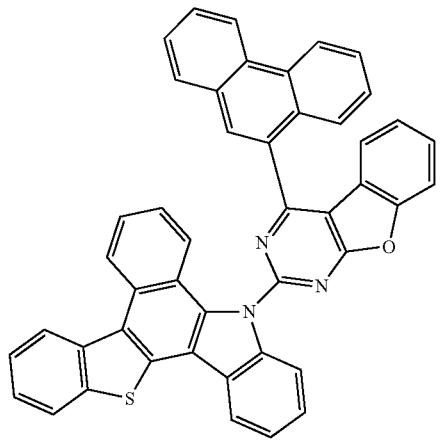
1-2-2-O-(14)
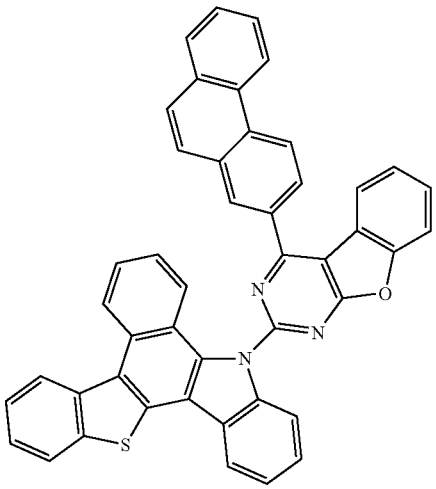
1-2-2-O-(15)
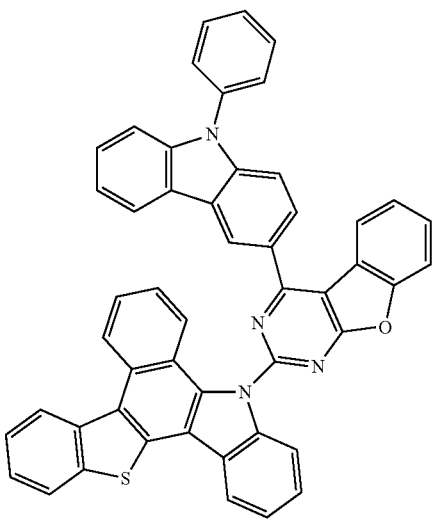
1-2-2-O-(16)
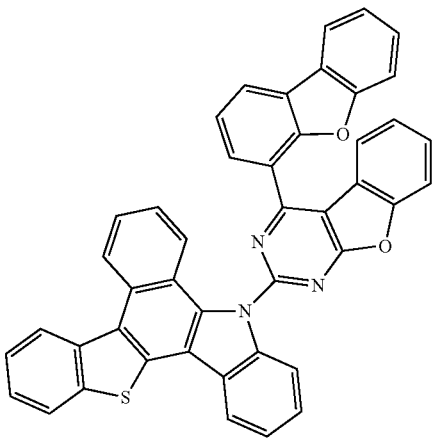

1-2-2-O-(17)
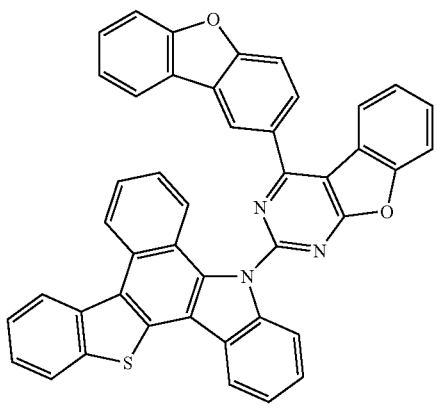
1-2-2-O-(18)
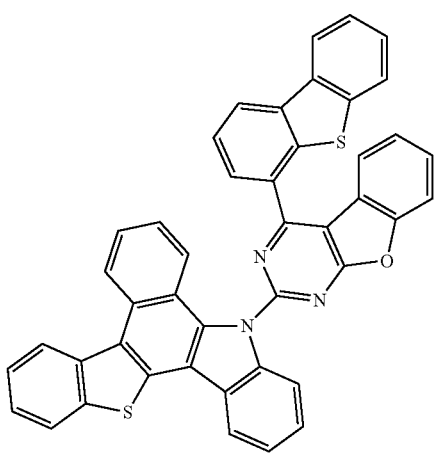
1-2-2-O-(19)
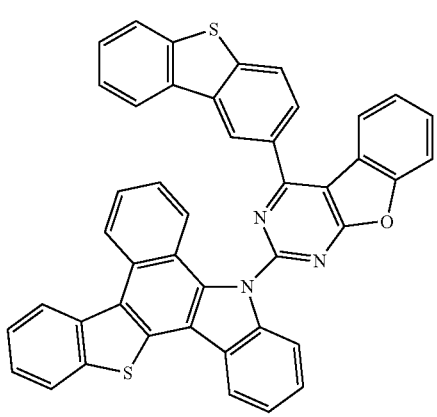
1-2-2-O-(20)
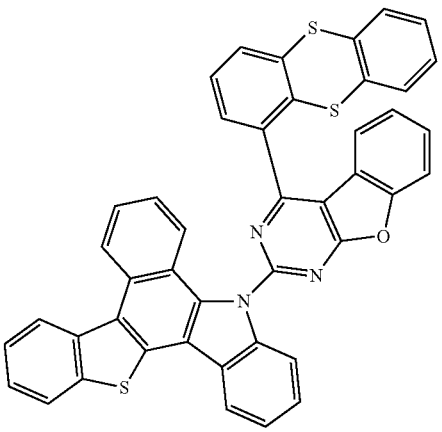
1-2-2-S-(1)
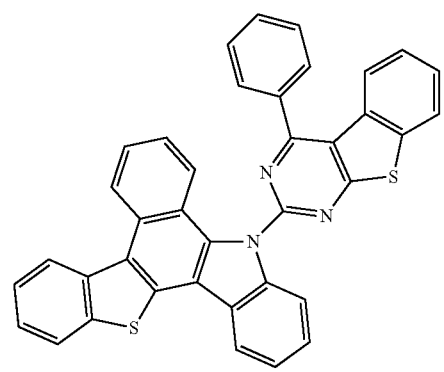
1-2-2-S-(2)
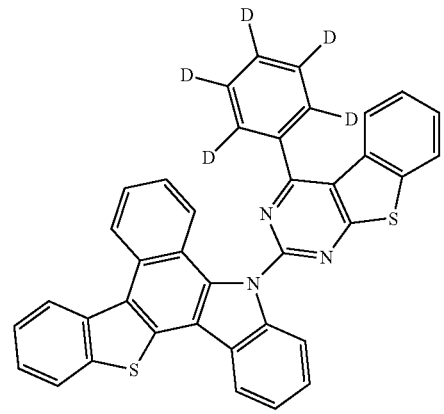
1-2-2-S-(3)
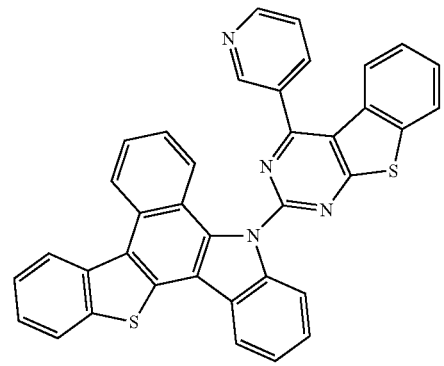

1-2-2-S-(4)
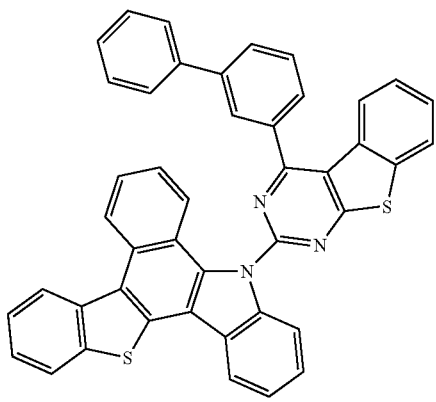
1-2-2-S-(5)
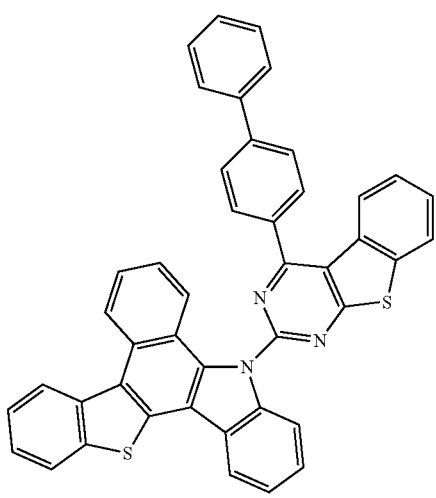
1-2-2-S-(6)
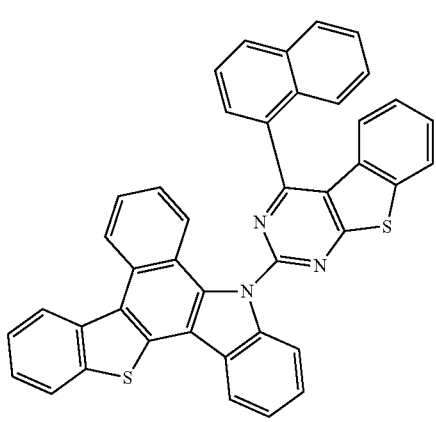
1-2-2-S-(7)
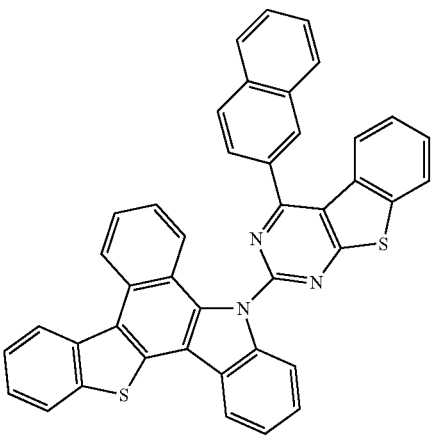
1-2-2-S-(8)
1-2-2-S-(9)
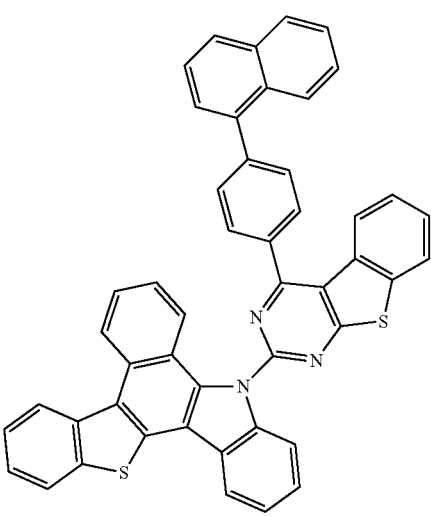

1-2-2-S-(10)
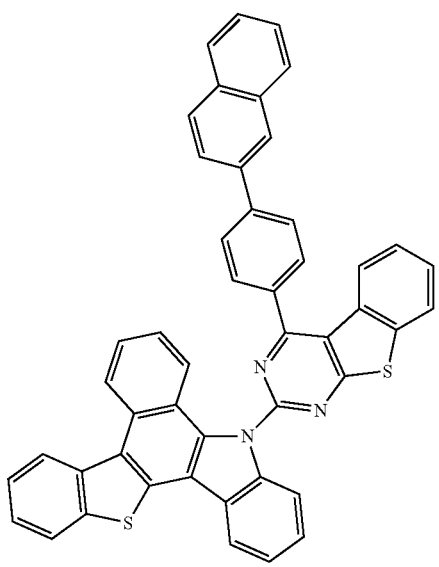
1-2-2-S-(11)
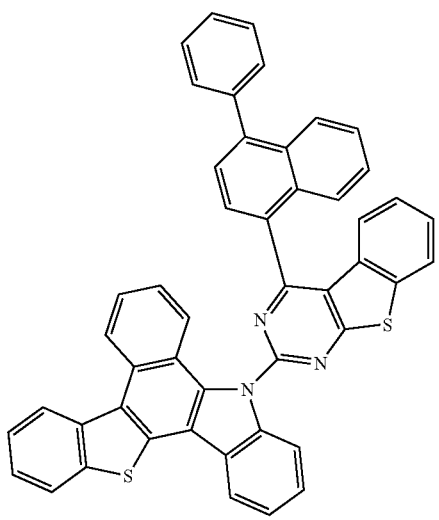
1-2-2-S-(12)
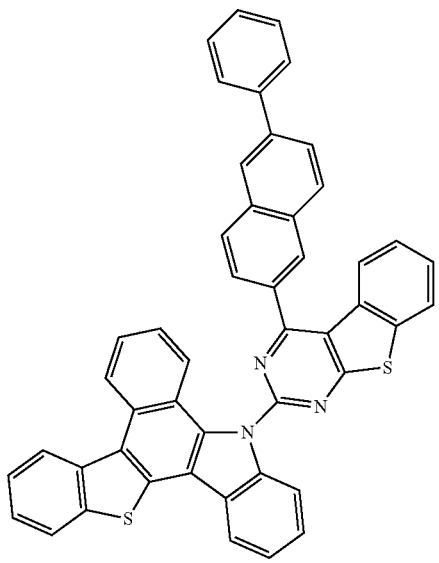
1-2-2-S-(13)
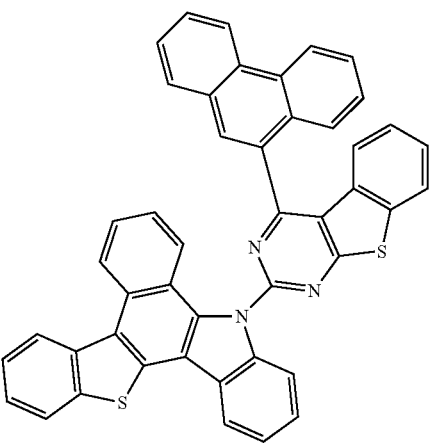
1-2-2-S-(14)
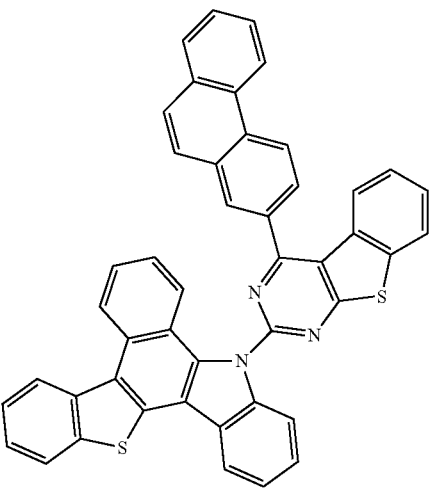
1-2-2-S-(15)
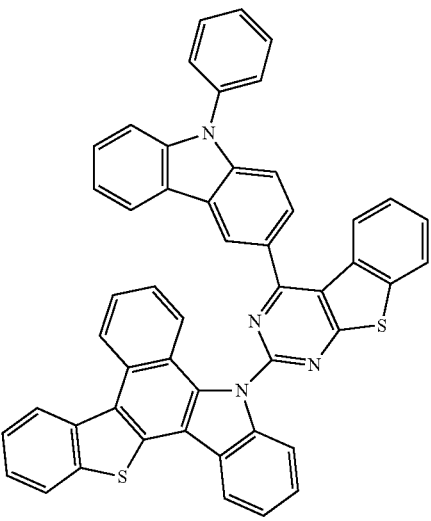

-continued
1-2-2-S-(16)
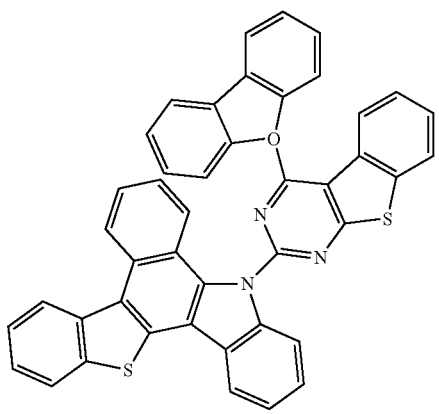
1-2-2-S-(19)
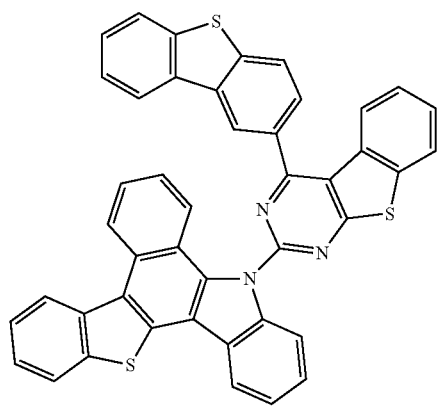
1-2-2-S-(17)
1-2-2-S-(20)
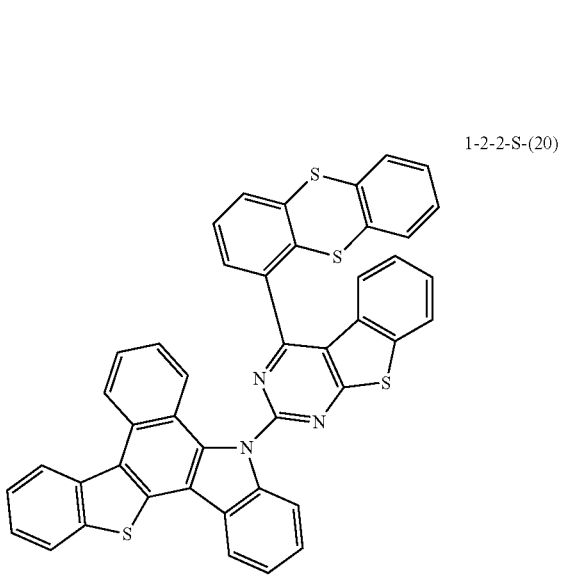
1-2-2-S-(18)
1-2-2-O-(21)
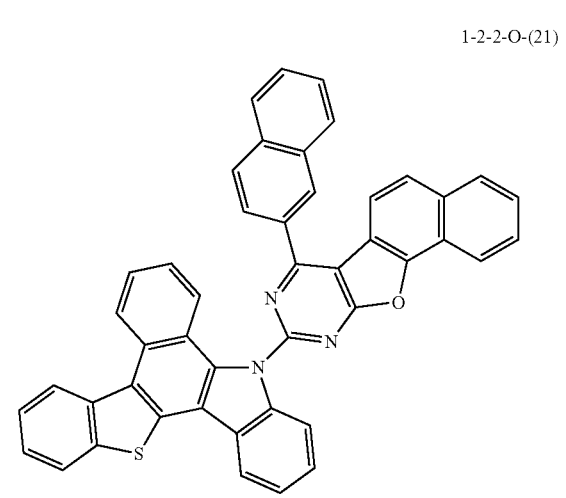

-continued
1-2-2-O-(22)
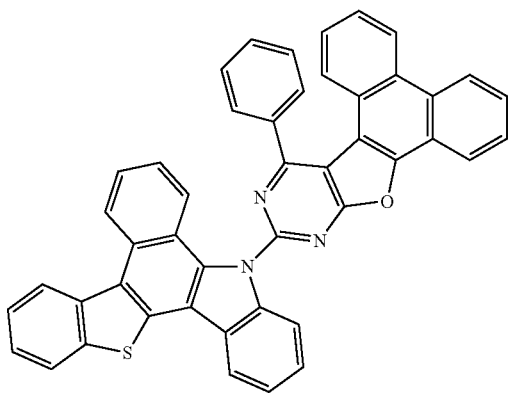
1-2-2-S-(21)
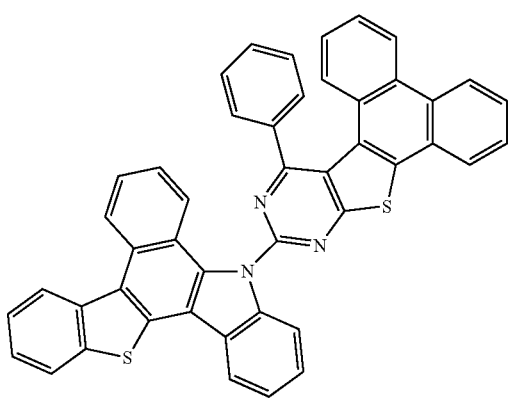
1-2-2-S-(22)
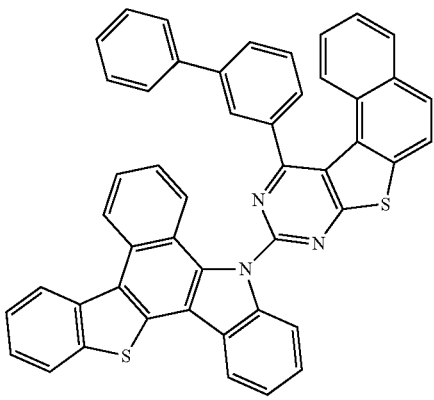
-continued
1-2-2-S-(23)
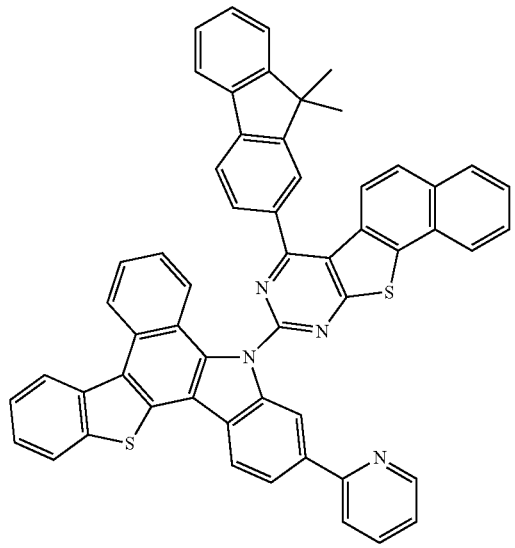
1-3-1-O-(1)
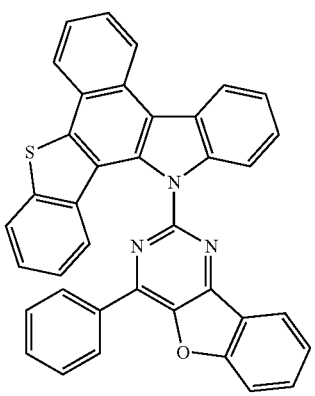
1-3-1-O-(2)
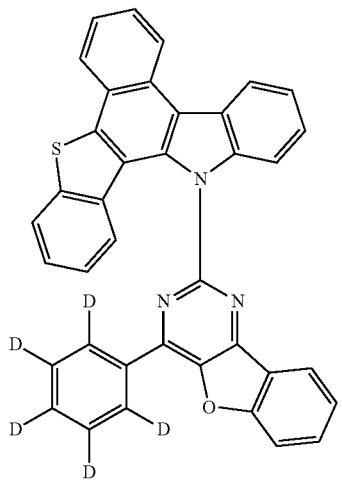

1-3-1-O-(3)
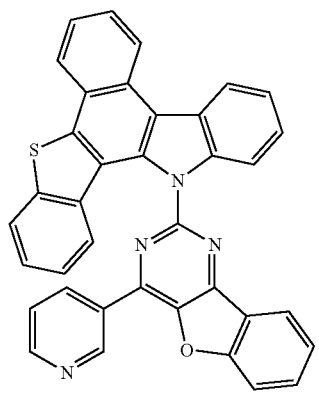
1-3-1-O-(4)
1-3-1-O-(5)
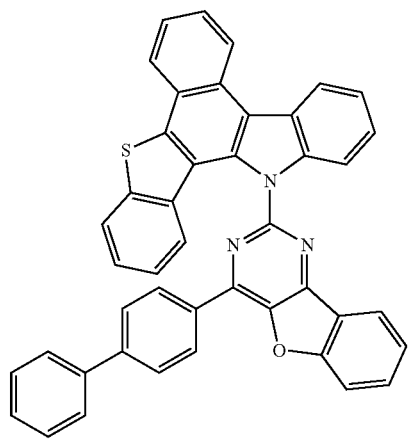
1-3-1-O-(6)
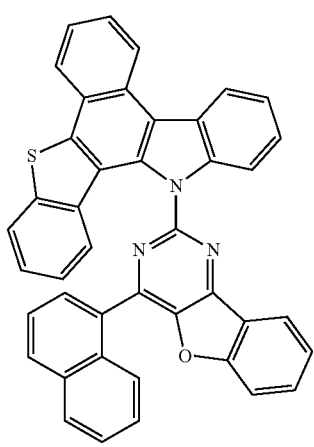
1-3-1-O-(7)
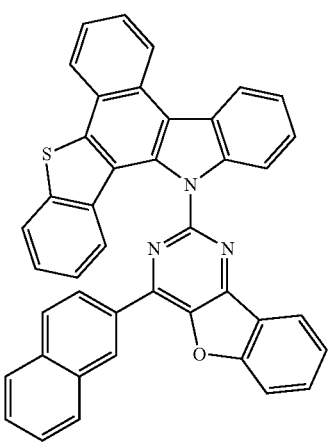
1-3-1-O-(8)
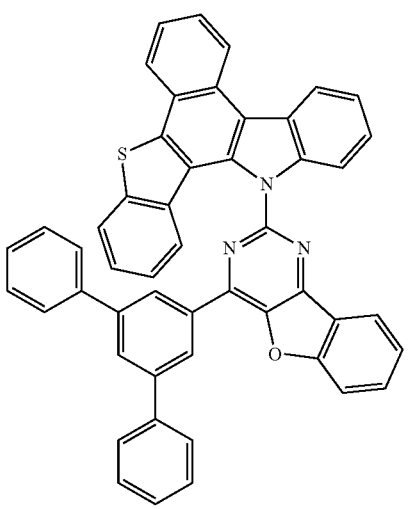

-continued
1-3-1-O-(9)
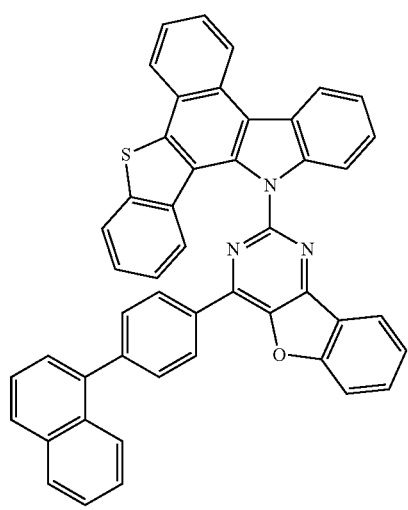
1-3-1-O-(10)
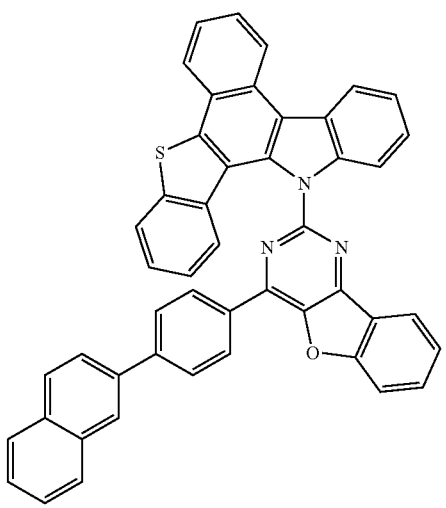
1-3-1-O-(11)
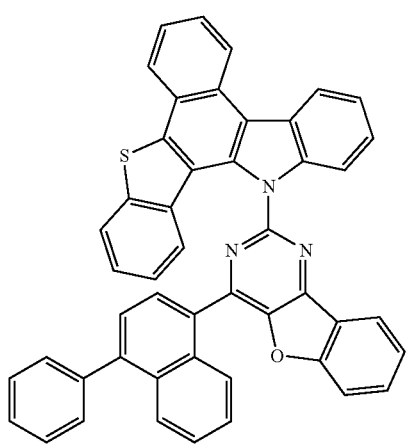
-continued
1-3-1-O-(12)
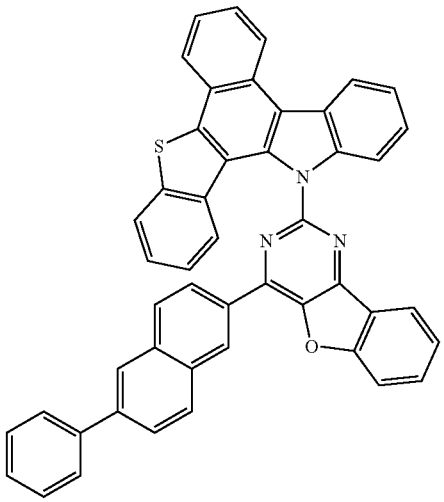
1-3-1-O-(13)
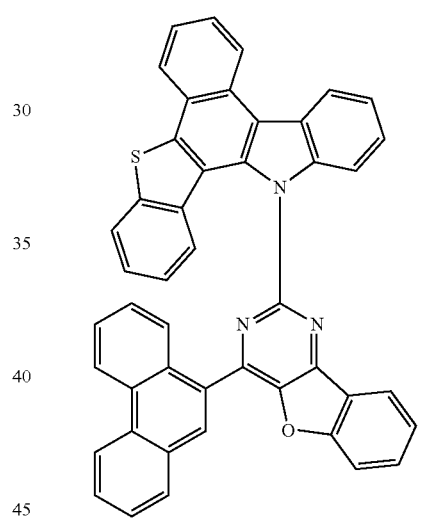
1-3-1-O-(14)
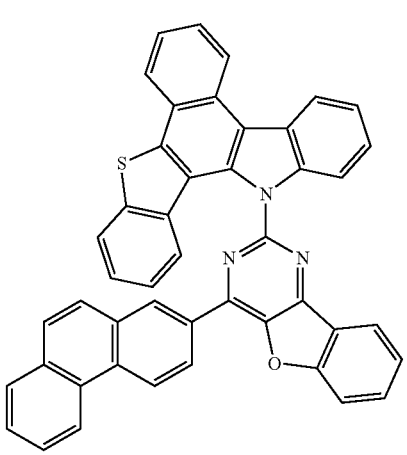

1-3-1-O-(15)
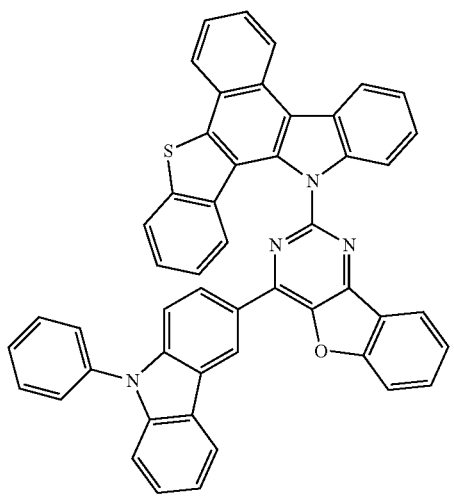
1-3-1-O-(18)
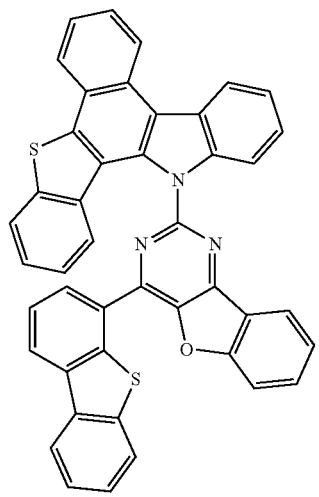
1-3-1-O-(16)
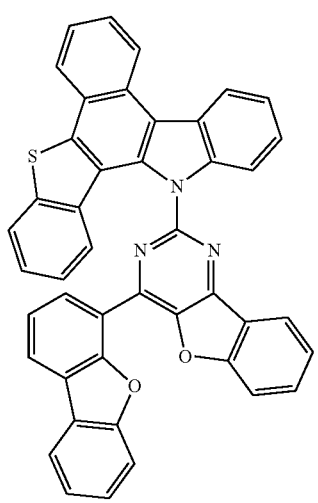
1-3-1-O-(19)
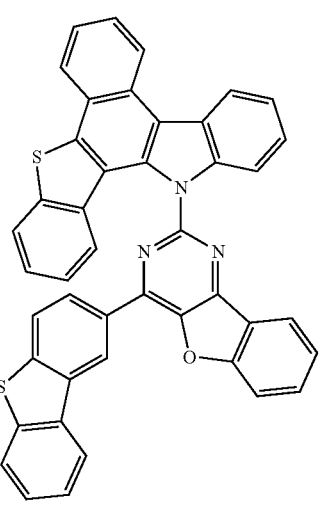
1-3-1-O-(17)
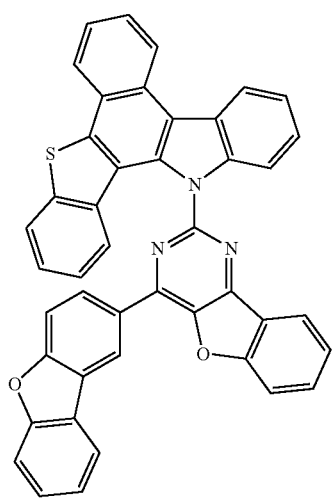
1-3-1-O-(20)
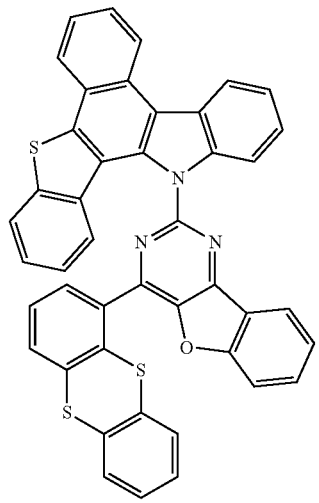

1-3-1-S-(1)
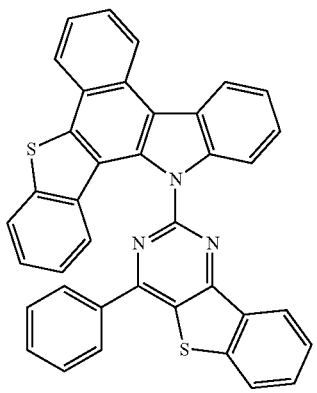
1-3-1-S-(2)
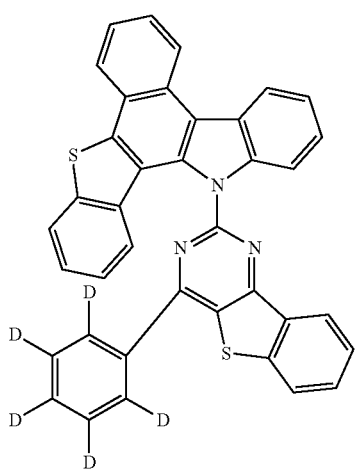
1-3-1-S-(3)
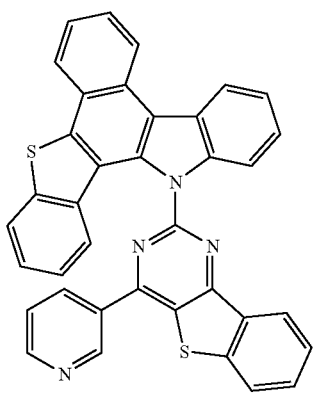
1-3-1-S-(4)
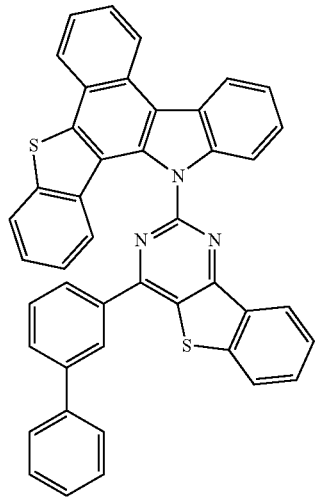
1-3-1-S-(5)
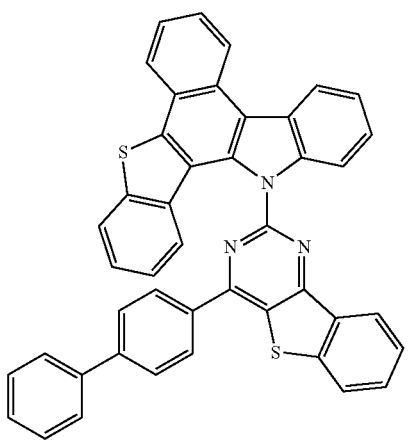
1-3-1-S-(6)
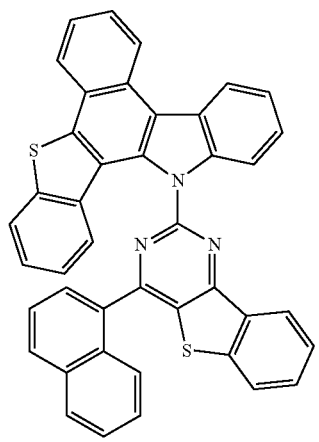

1-3-1-S-(7)
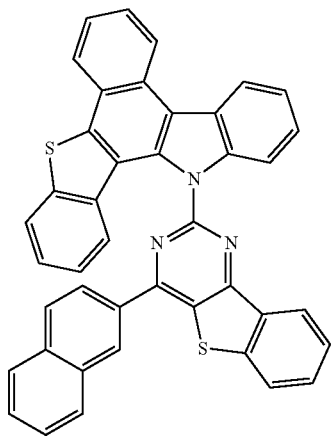
1-3-1-S-(8)
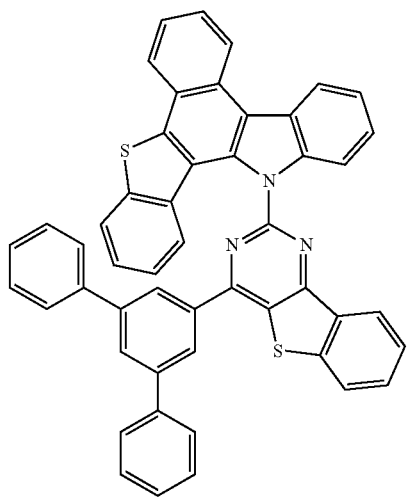
1-3-1-S-(9)
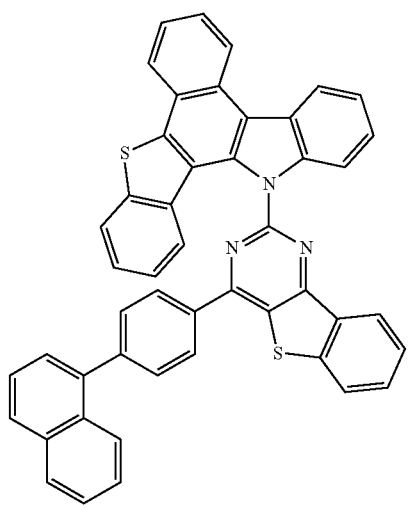
1-3-1-S-(10)
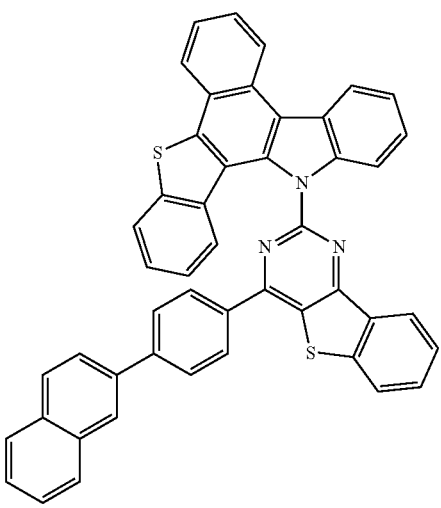
1-3-1-S-(11)
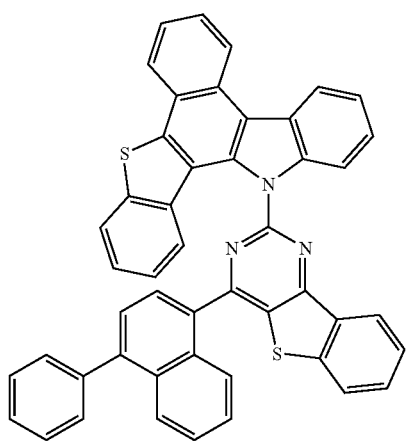
1-3-1-S-(12)
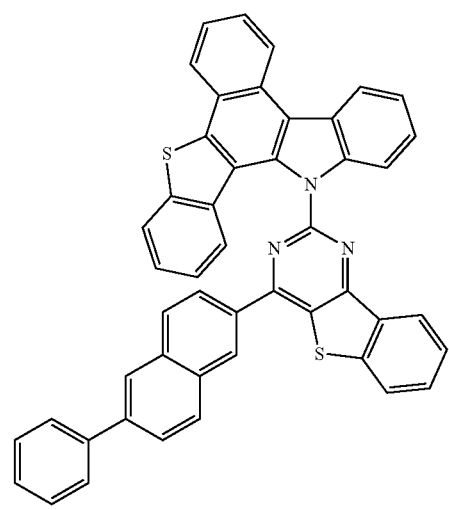

1-3-1-S-(13)
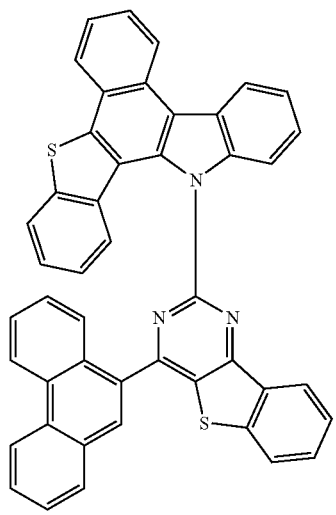
1-3-1-S-(14)
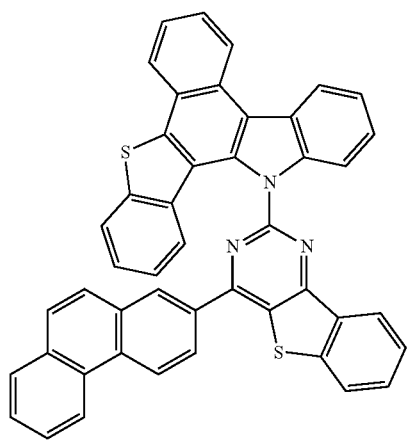
1-3-1-S-(15)
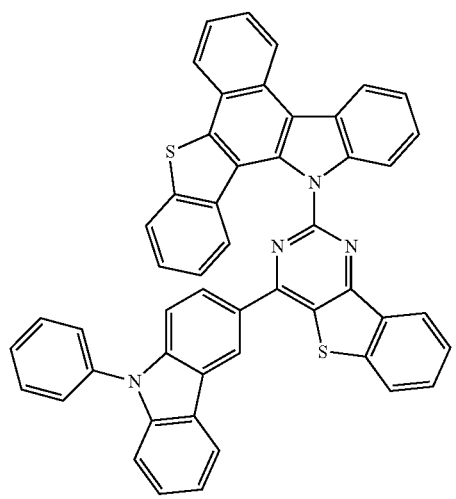
1-3-1-S-(16)
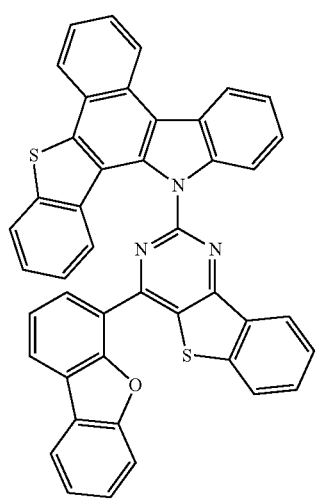
1-3-1-S-(17)
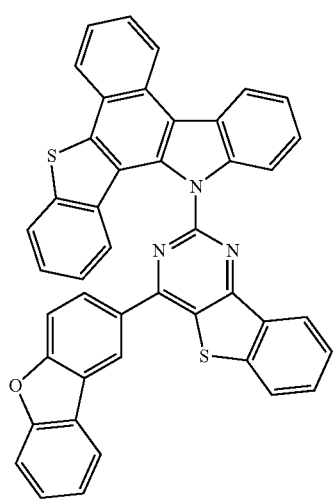
1-3-1-S-(18)
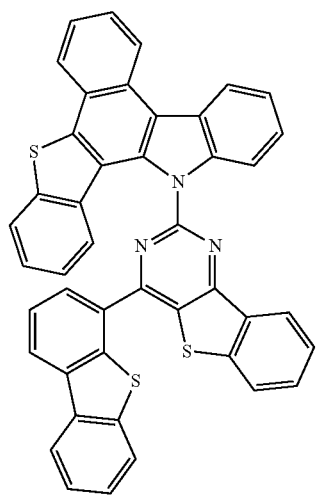

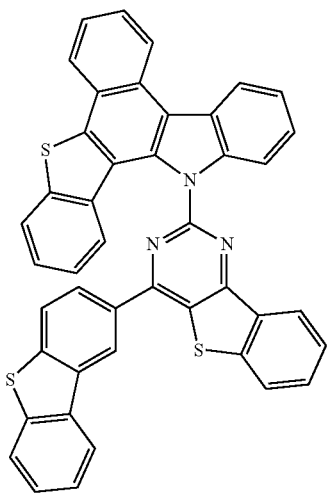
1-3-1-S-(19)
1-3-1-S-(20)
1-3-1-O-(21)
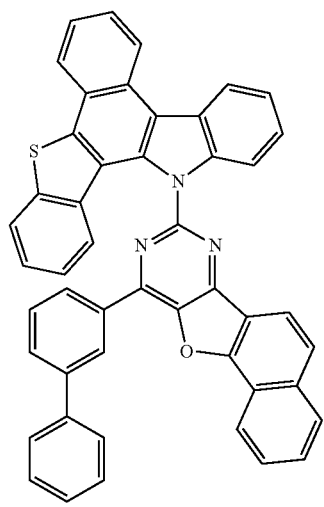
1-3-1-O-(22)
1-3-1-S-(21)
1-3-1-S-(22)

1-3-1-S-(23)
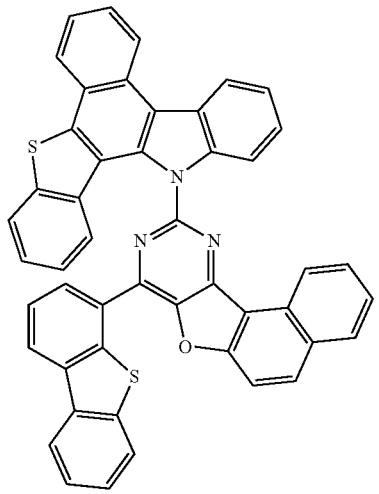
1-3-2-O-(3)
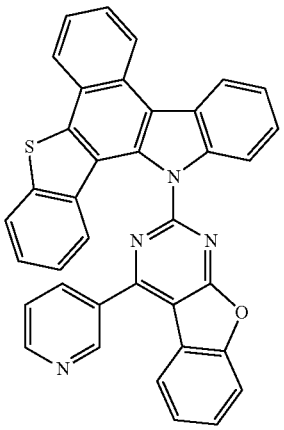
1-3-2-O-(1)
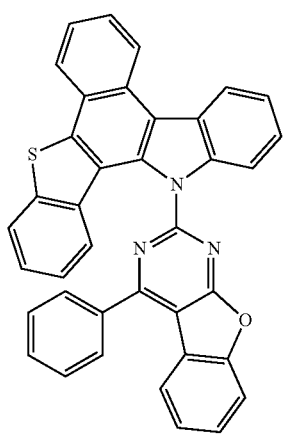
1-3-2-O-(4)
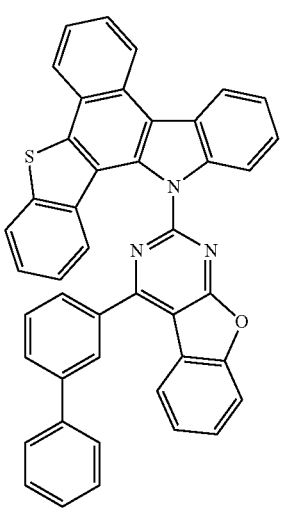
1-3-2-O-(2)
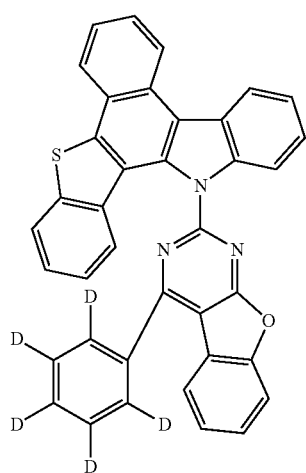
1-3-2-O-(5)
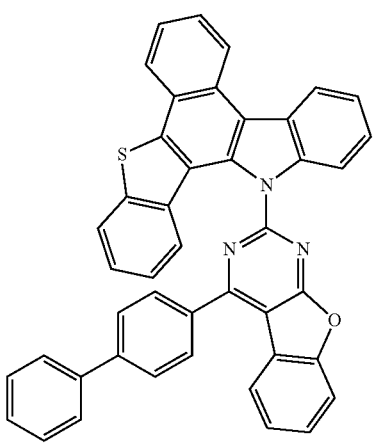

1-3-2-O-(6)
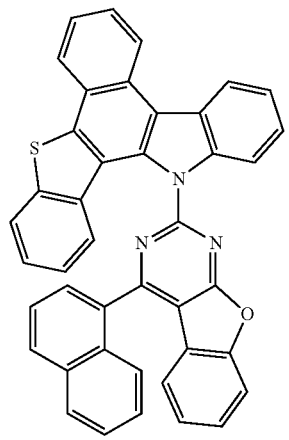
1-3-2-O-(9)
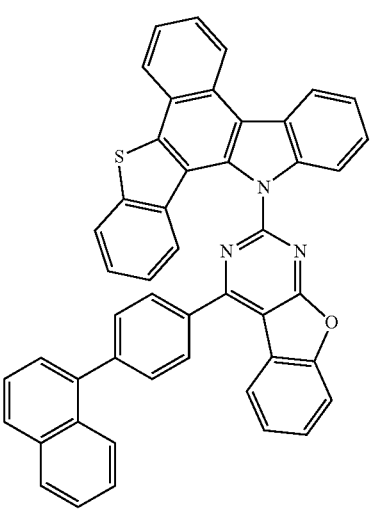
1-3-2-O-(7)
1-3-2-O-(10)
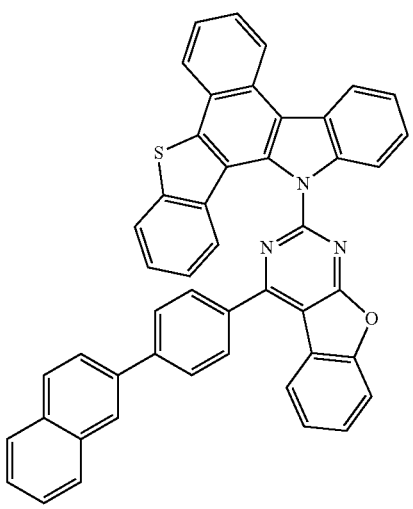
1-3-2-O-(8)
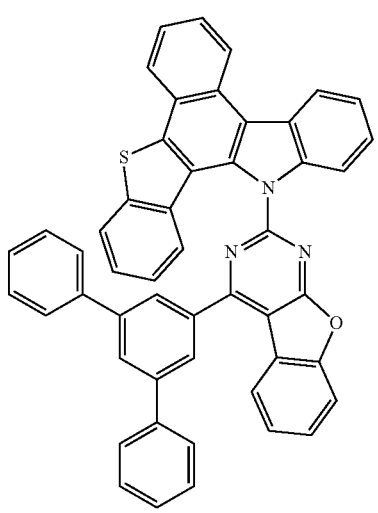
1-3-2-O-(11)
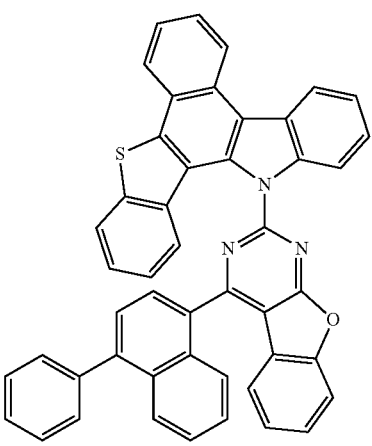

1-3-2-O-(12)
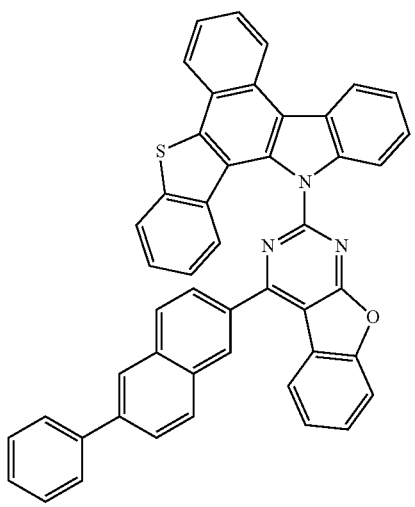
1-3-2-O-(15)
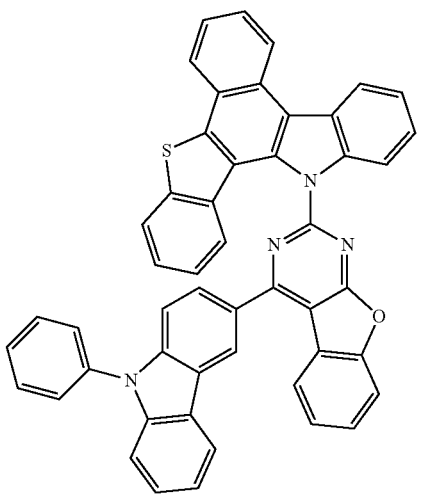
1-3-2-O-(13)
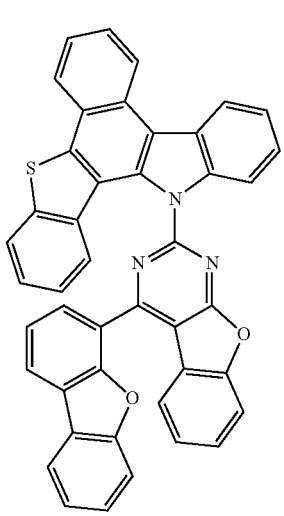
1-3-2-O-(16)
1-3-2-O-(14)
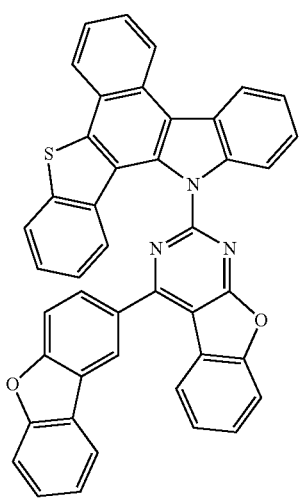
1-3-2-O-(17)

1-3-2-O-(18)
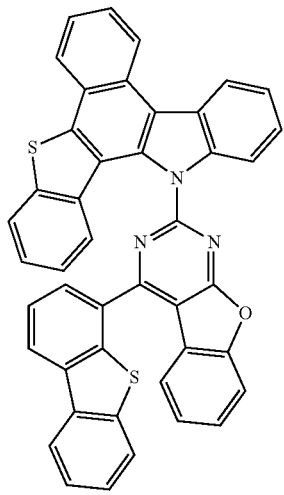
1-3-2-S-(1)
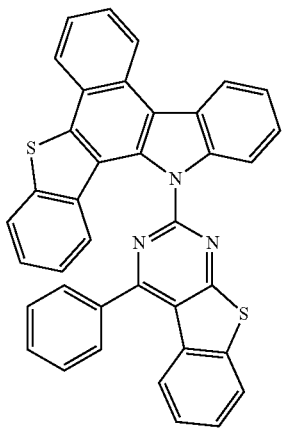
1-3-2-O-(19)
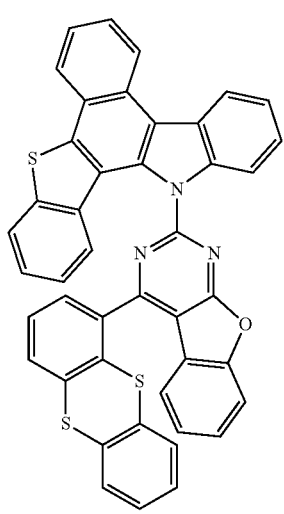
1-3-2-S-(2)
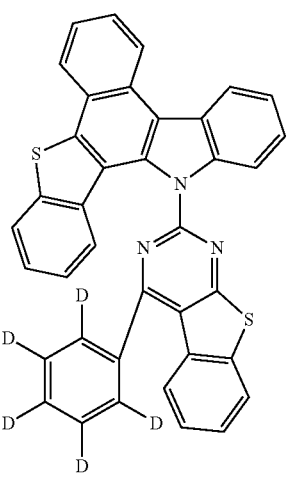
1-3-2-O-(20)
1-3-2-S-(3)
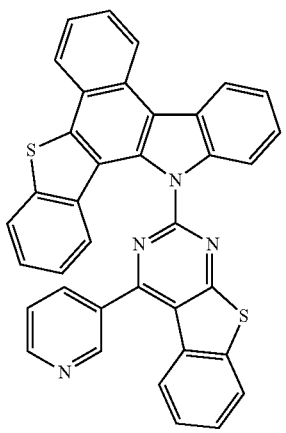

101
-continued
1-3-2-S-(4)
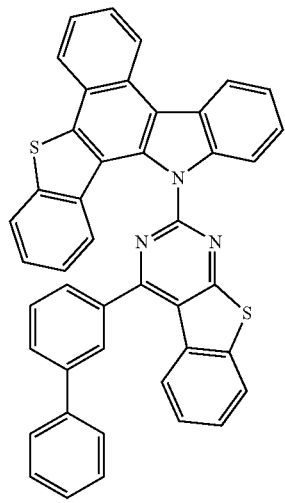
1-3-2-S-(5)
1-3-2-S-(6)
102
-continued
1-3-2-S-(7)
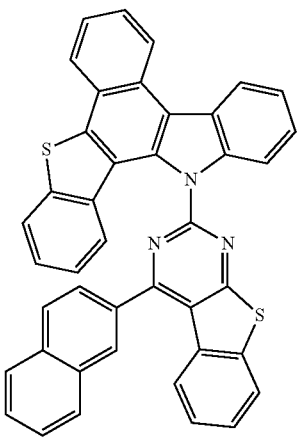
1-3-2-S-(8)
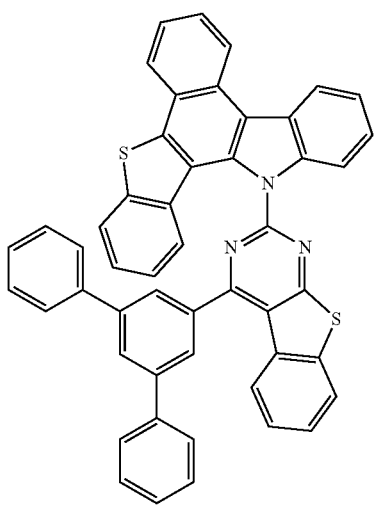
1-3-2-S-(9)
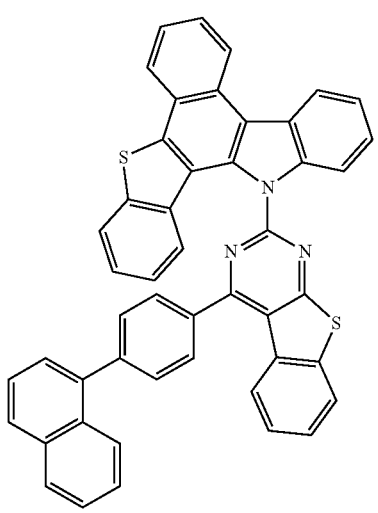

1-3-2-S-(10)
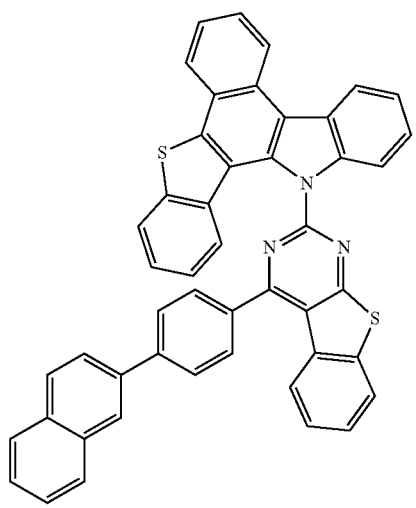
1-3-2-S-(11)
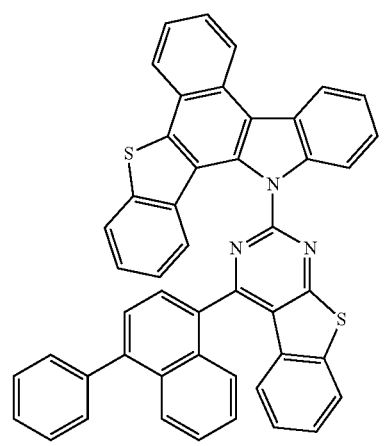
1-3-2-S-(12)
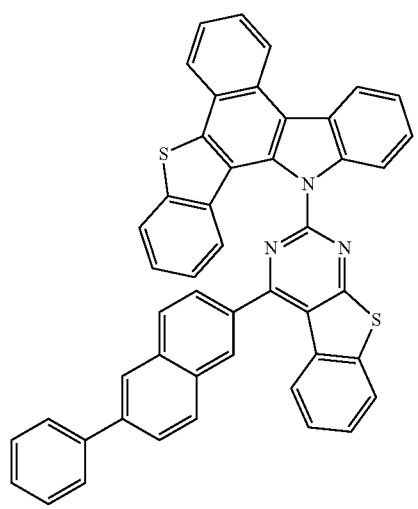
1-3-2-S-(13)
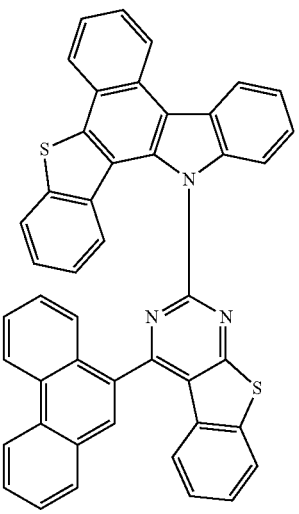
1-3-2-S-(14)
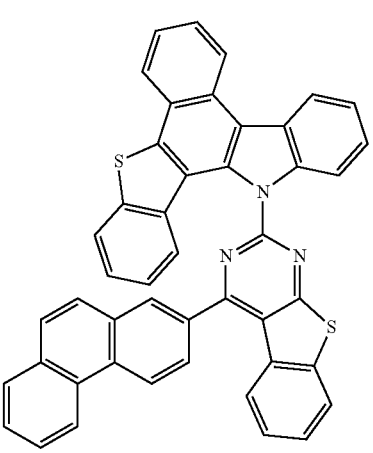
1-3-2-S-(15)
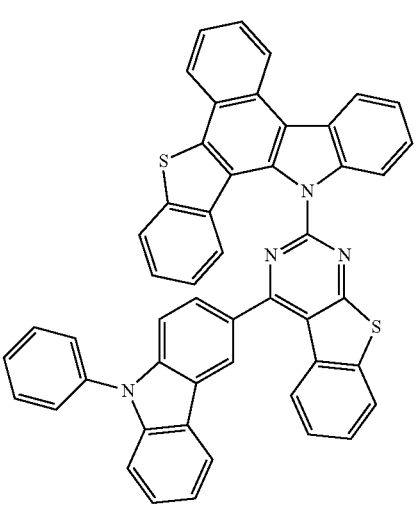

| 105 -continued | 106 -continued |
|---|---|
| 1-3-2-S-(16) 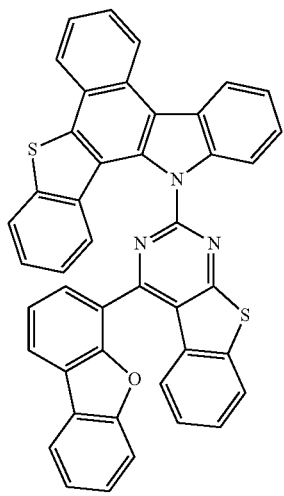 | 1-3-2-S-(19) 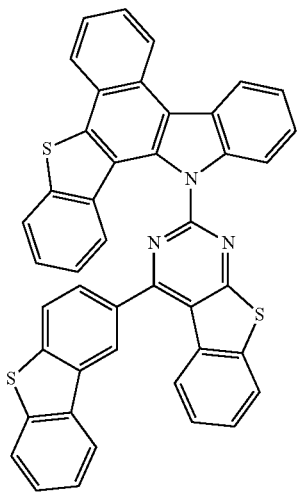 |
| 1-3-2-S-(17) 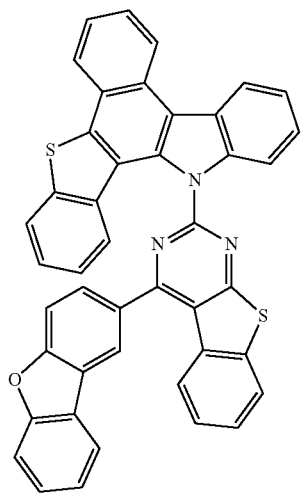 | 1-3-2-S-(20) 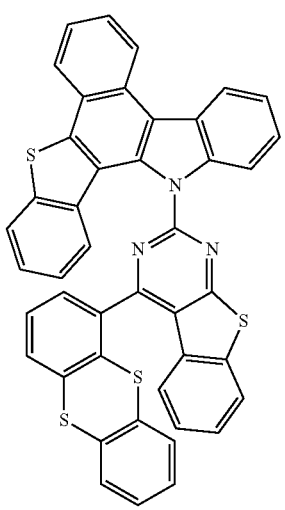 |
| 1-3-2-S-(18) 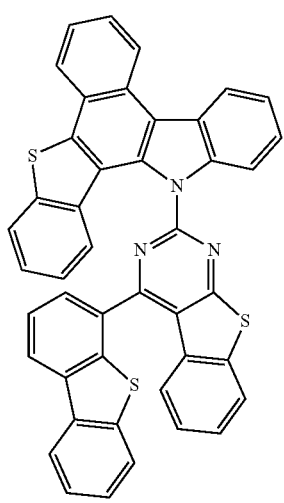 | 1-3-2-O-(21) 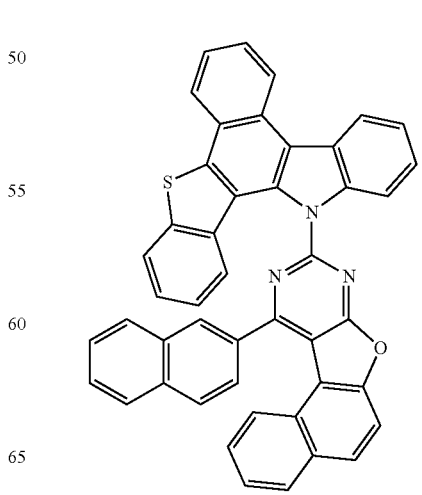 |

107
-continued
1-3-2-O-(22)
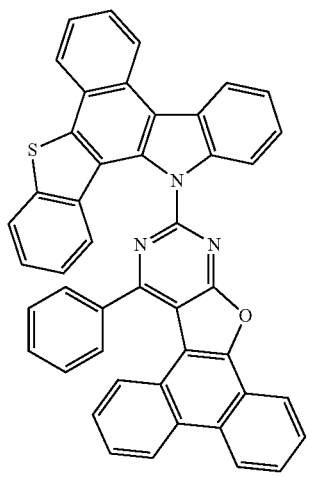
1-3-2-S-(21)
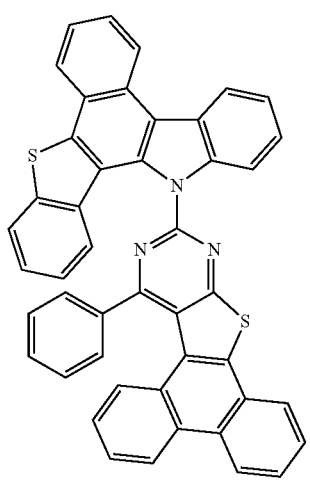
1-3-2-S-(22)
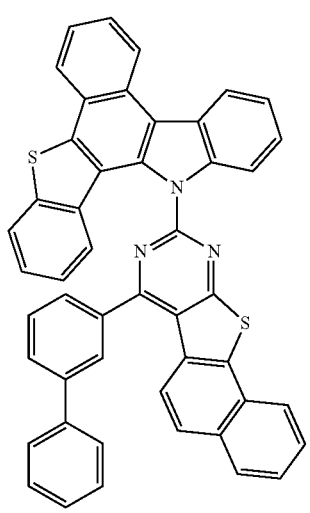
108
-continued
1-3-2-S-(23)
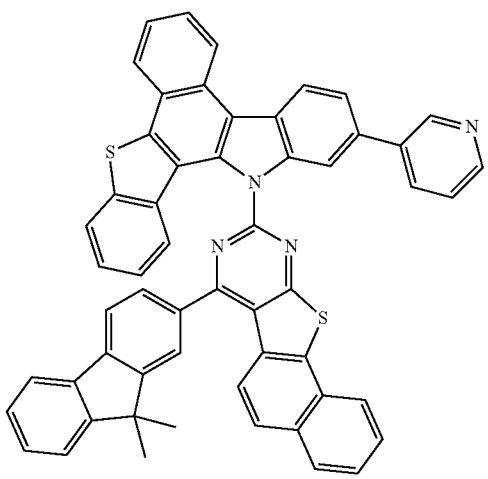
1-4-1-O-(1)
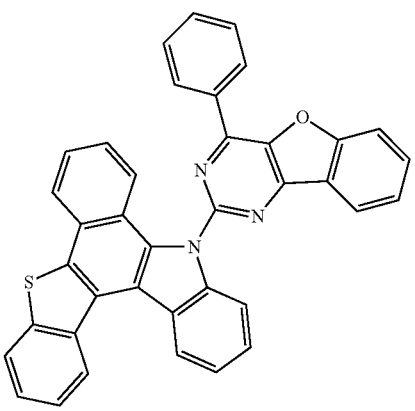
1-4-1-O-(2)
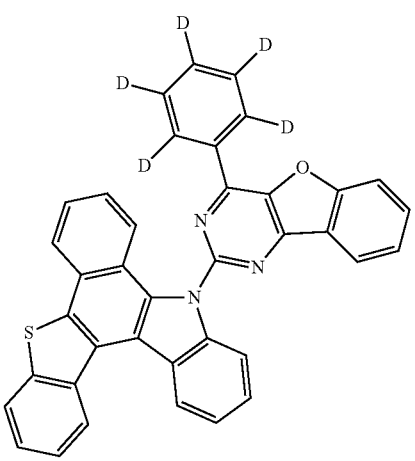

109
-continued
1-4-1-O-(3)
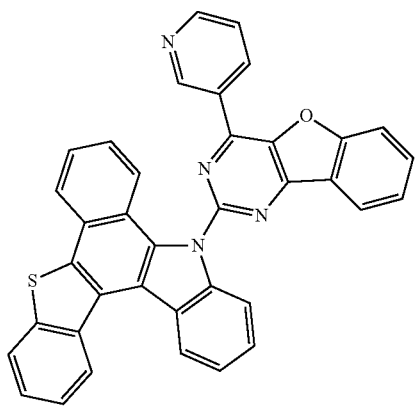
1-4-1-O-(4)
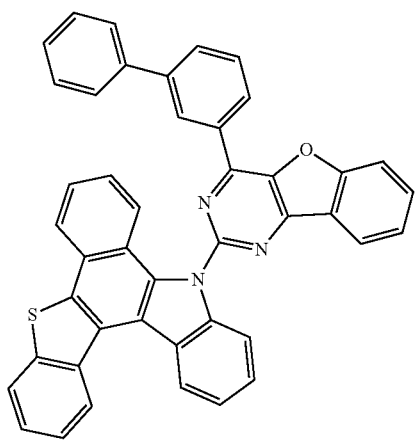
1-4-1-O-(5)
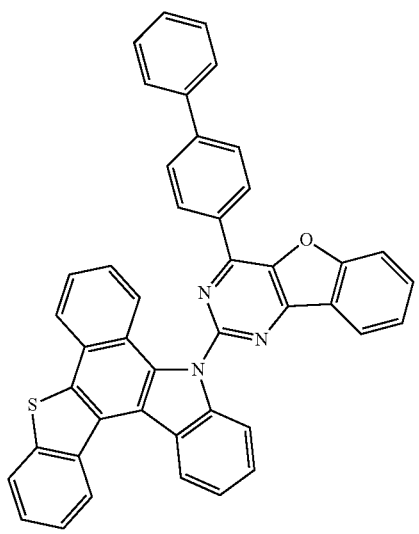
110
-continued
1-4-1-O-(6)
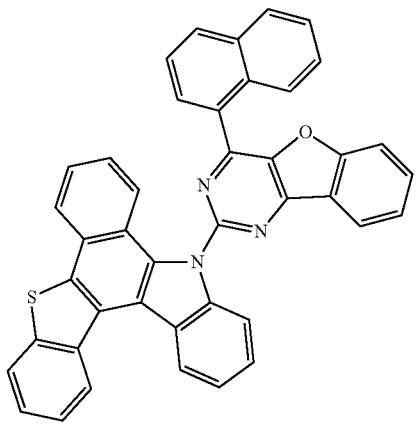
1-4-1-O-(7)
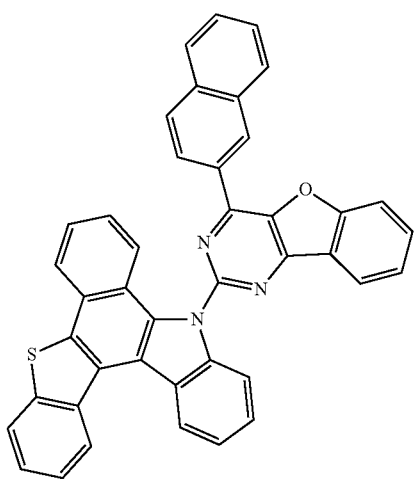
1-4-1-O-(8)
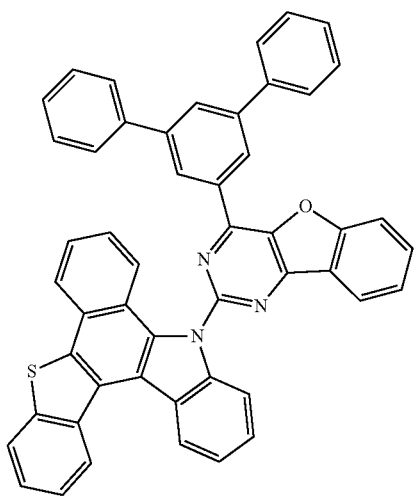

111
-continued
1-4-1-O-(9)
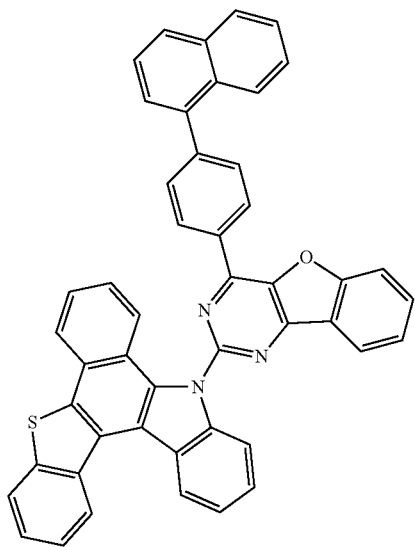
1-4-1-O-(10)
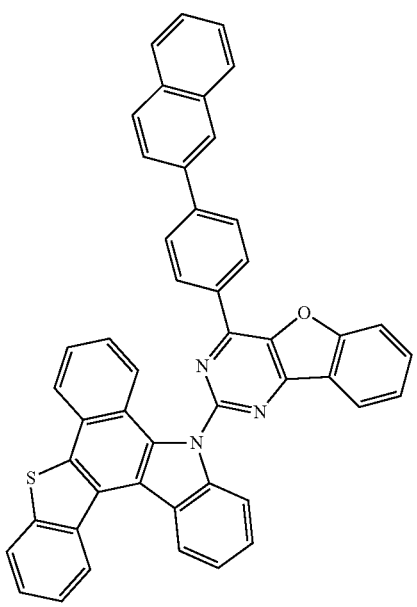
112
-continued
1-4-1-O-(11)
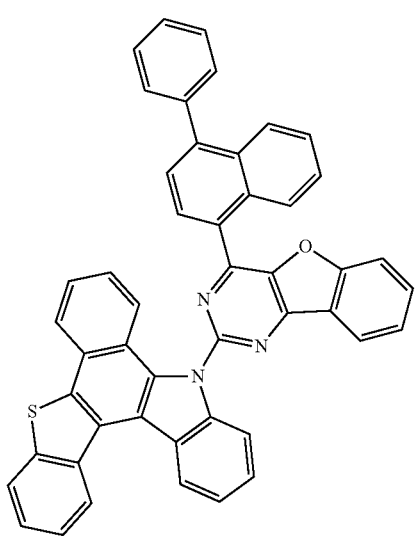
1-4-1-O-(12)
1-4-1-O-(13)
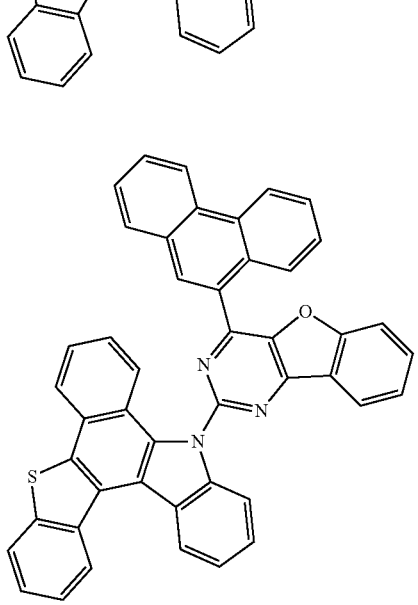

1-4-1-O-(14)
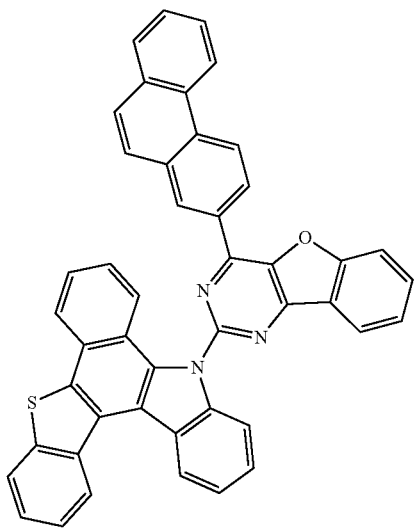
1-4-1-O-(17)
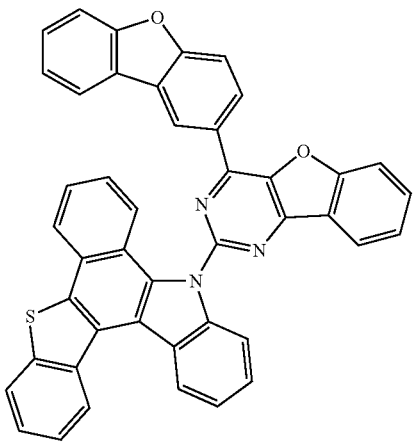
1-4-1-O-(15)
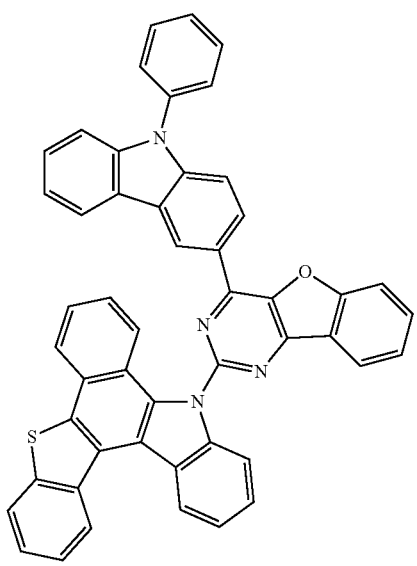
1-4-1-O-(18)
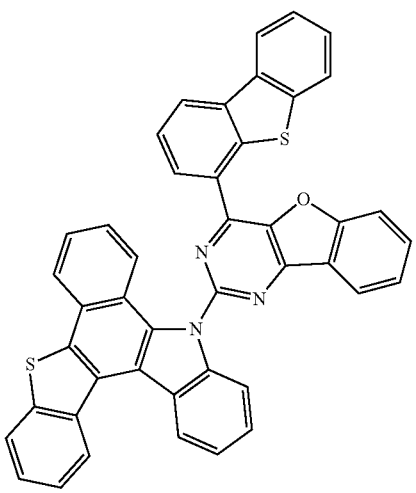
1-4-1-O-(16)
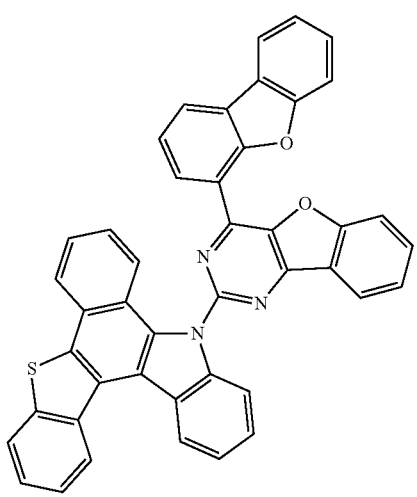
1-4-1-O-(19)
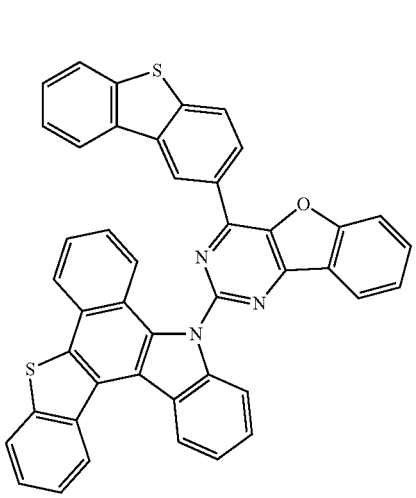

115
-continued
1-4-1-O-(20)
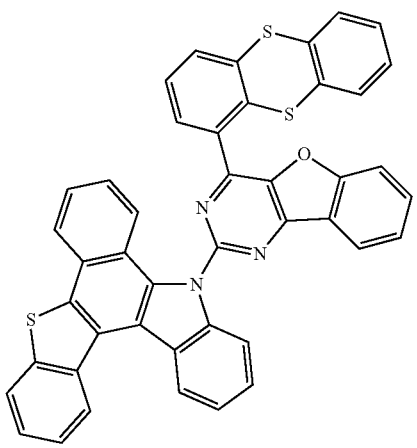
1-4-1-S-(1)
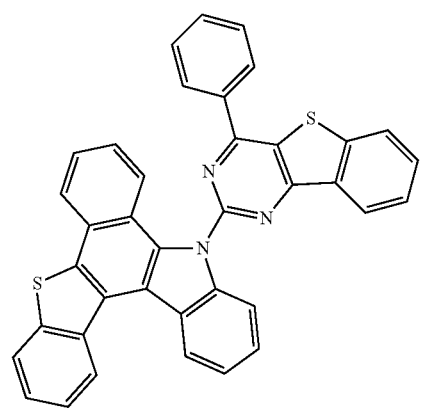
1-4-1-S-(2)
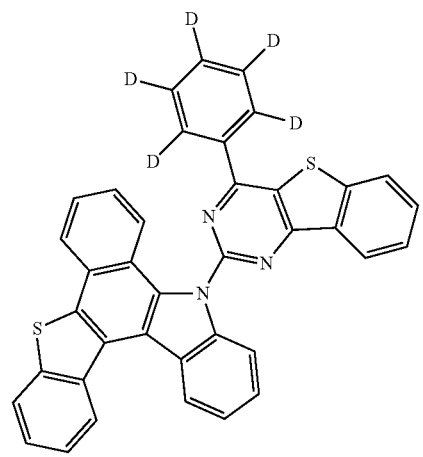
116
-continued
1-4-1-S-(3)
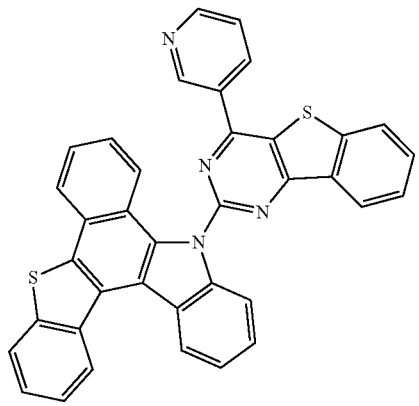
1-4-1-S-(4)
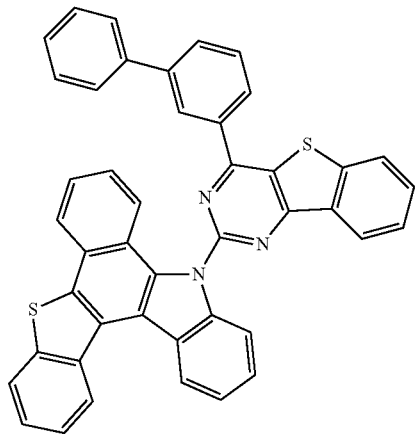
1-4-1-S-(5)
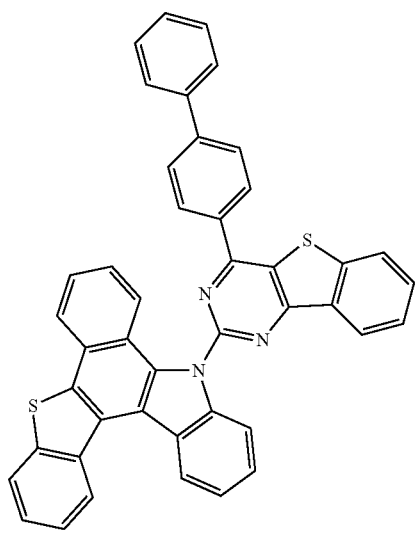

1-4-1-S-(6)
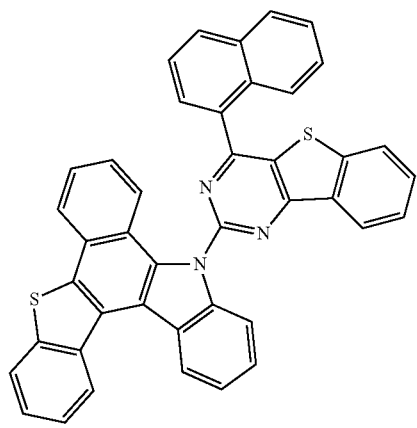
1-4-1-S-(7)
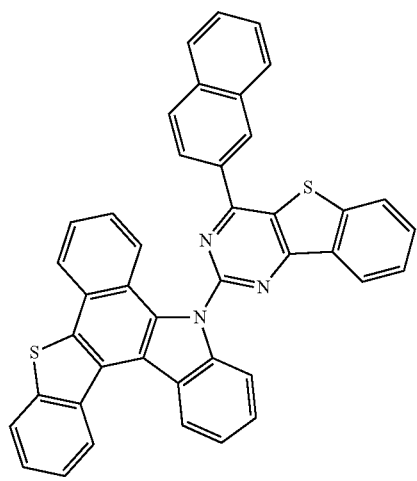
1-4-1-S-(8)
1-4-1-S-(9)
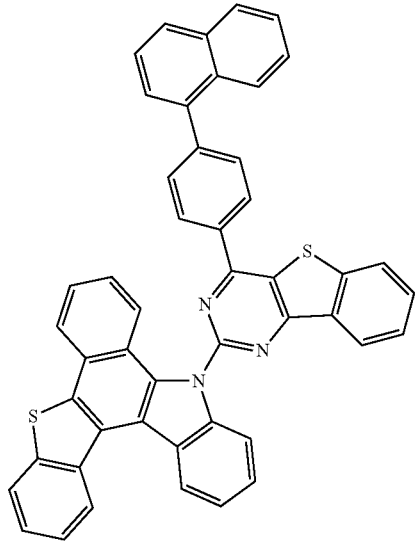
1-4-1-S-(10)
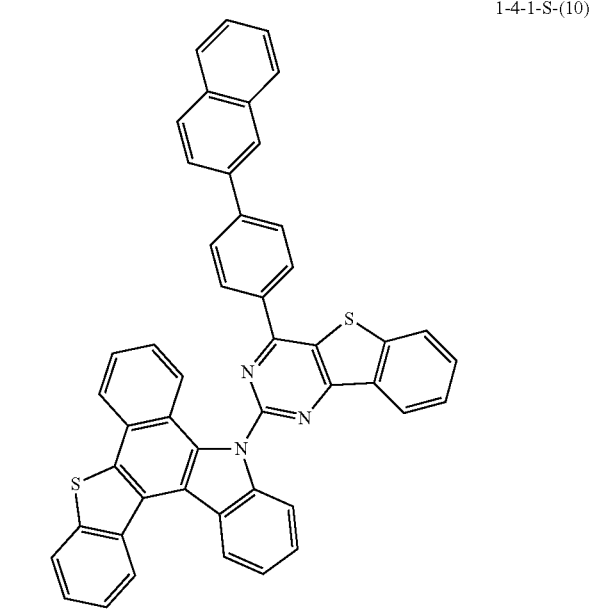

1-4-1-S-(11)
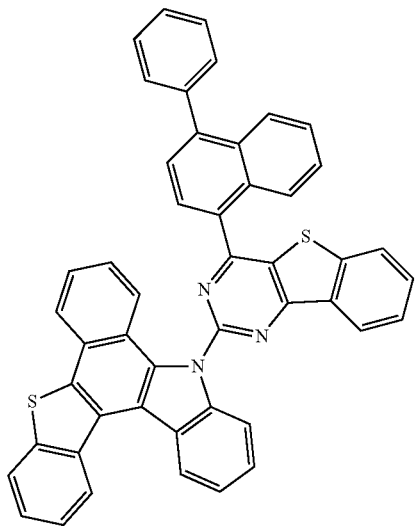
1-4-1-S-(12)
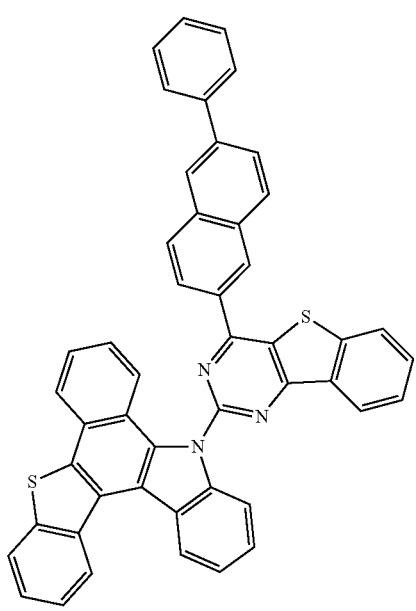
1-4-1-S-(13)
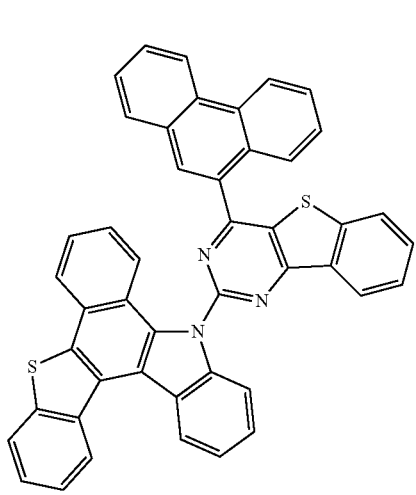
1-4-1-S-(14)
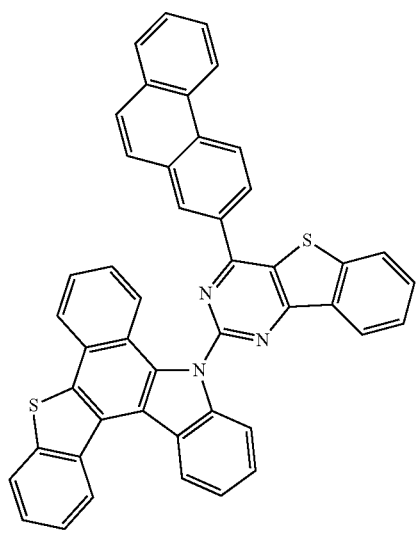
1-4-1-S-(15)
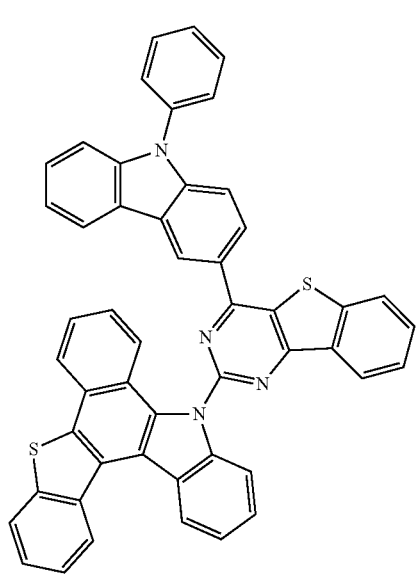
1-4-1-S-(16)
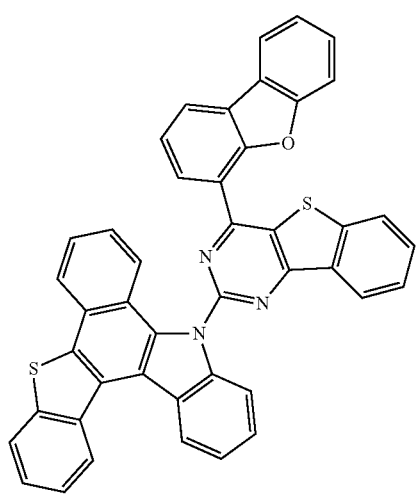

121
-continued
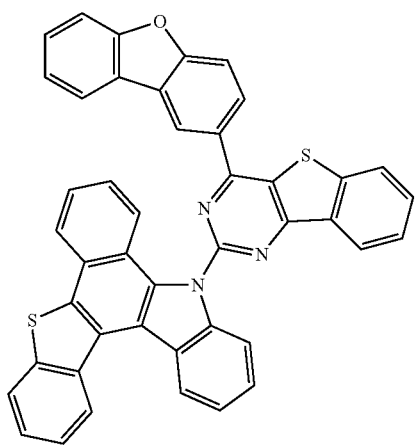
1-4-1-S-(17)
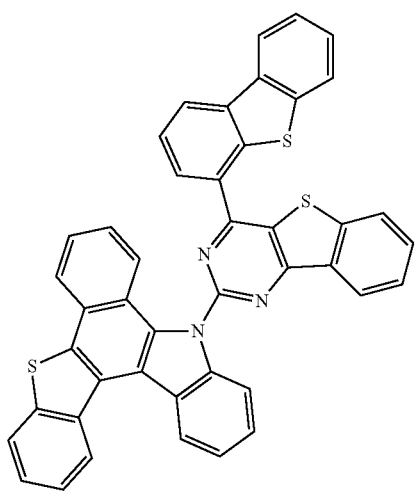
1-4-1-S-(18)
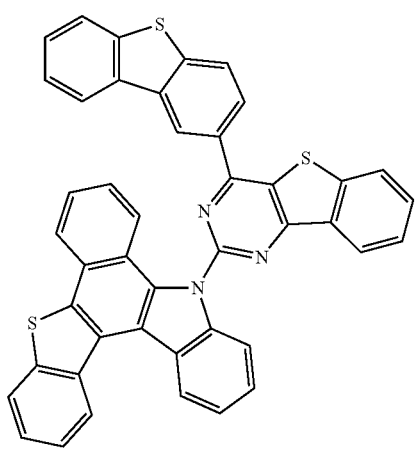
1-4-1-S-(19)
122
-continued
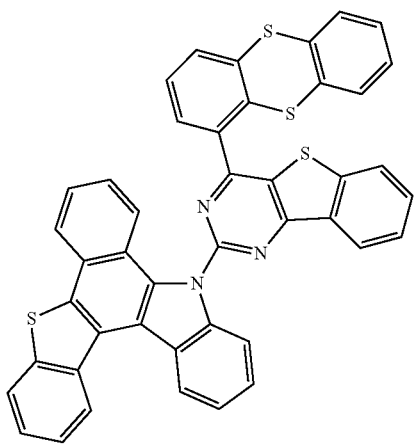
1-4-1-S-(20)
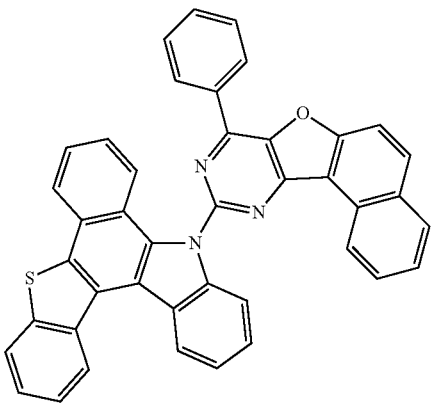
1-4-1-O-(21)
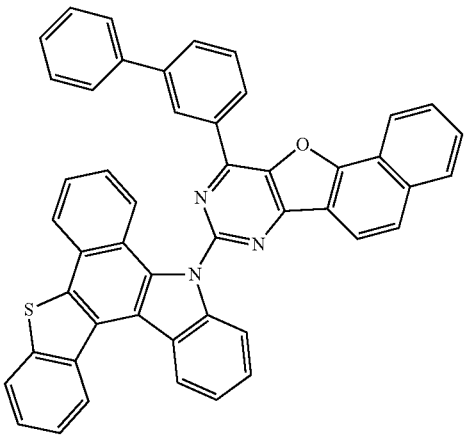
1-4-1-O-(22)

1-4-1-S-(21)
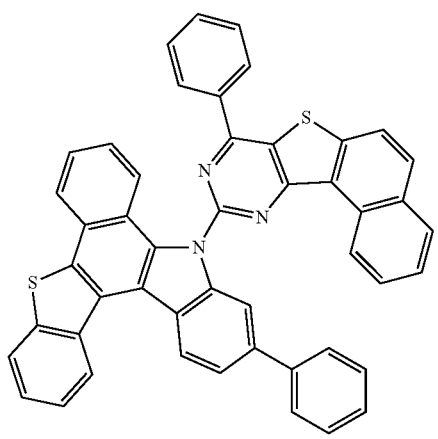
1-4-2-O-(1)
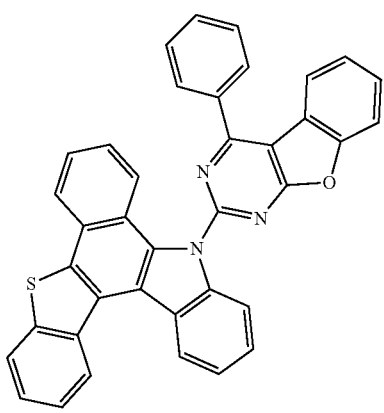
1-4-1-S-(22)
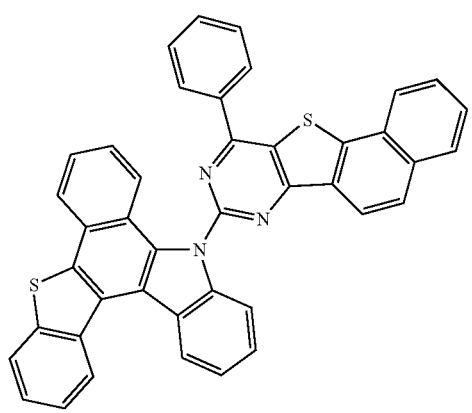
1-4-2-O-(2)
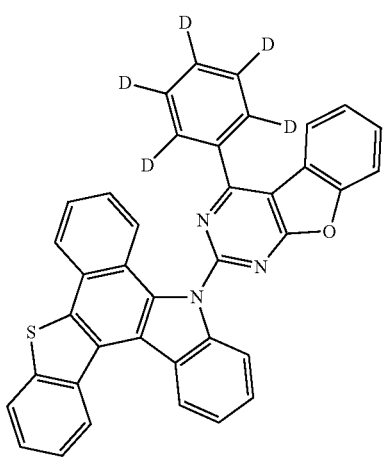
1-4-1-S-(23)
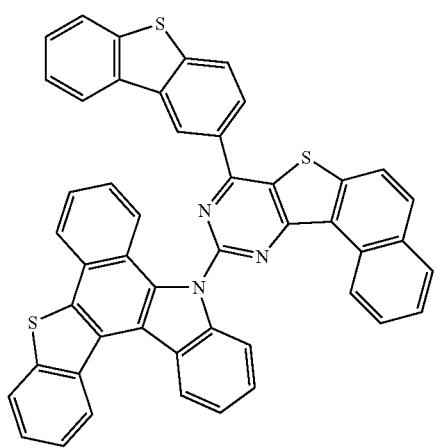
1-4-2-O-(3)
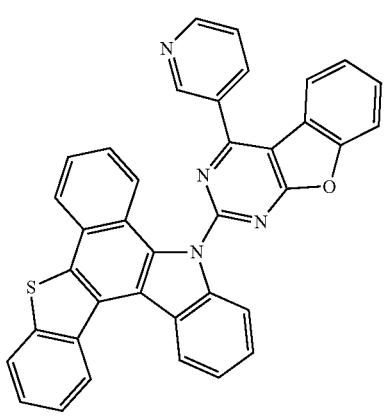

125
-continued
1-4-2-O-(4)
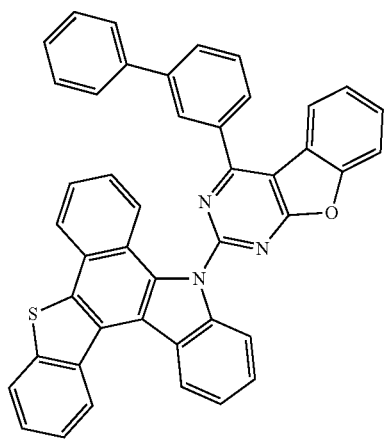
1-4-2-O-(5)
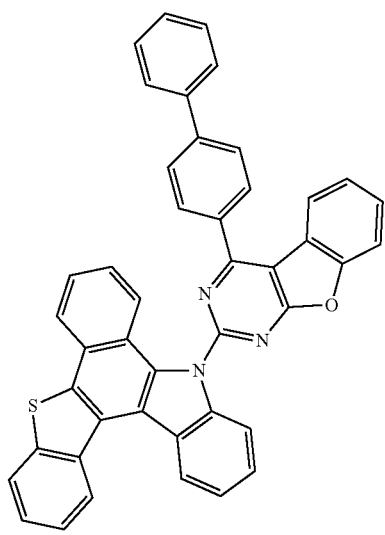
1-4-2-O-(6)
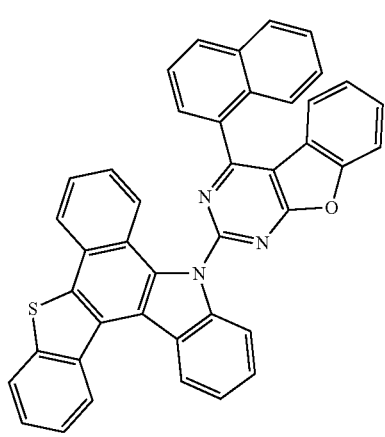
126
-continued
1-4-2-O-(7)
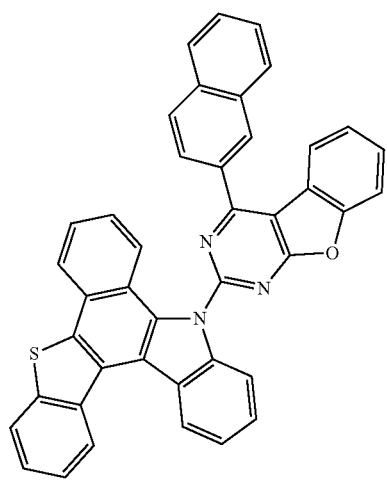
1-4-2-O-(8)
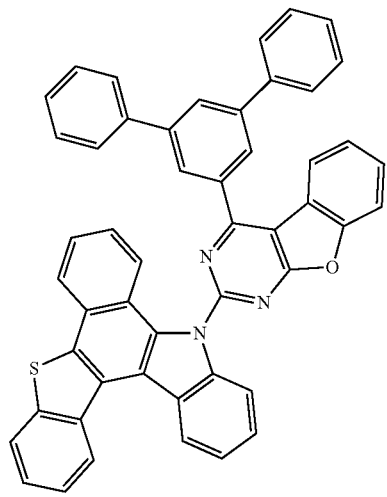
1-4-2-O-(9)
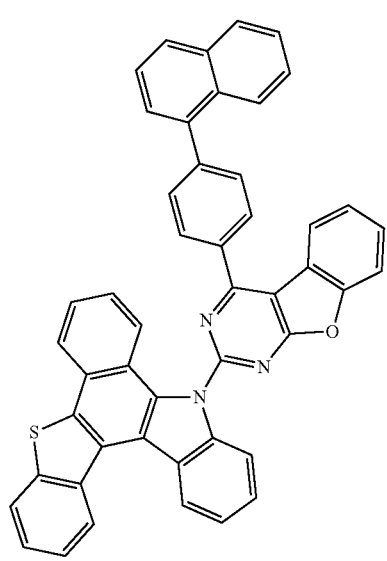

1-4-2-O-(10)
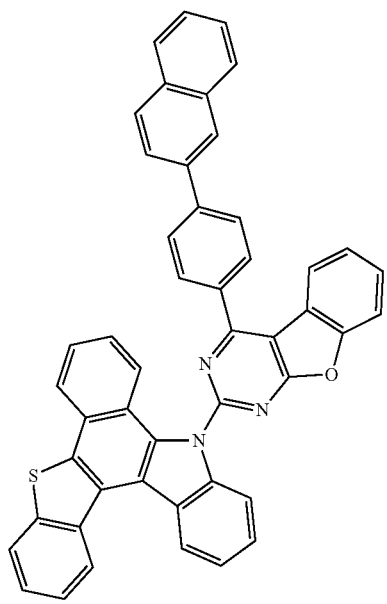
1-4-2-O-(11)
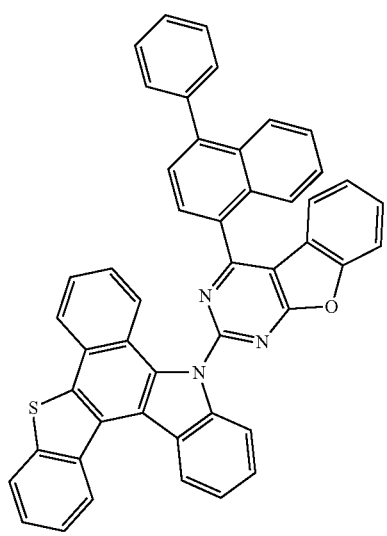
1-4-2-O-(12)
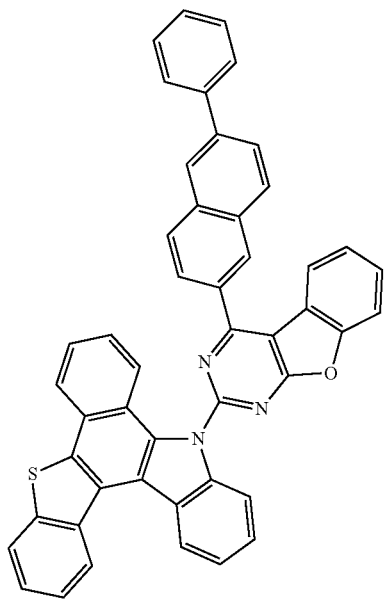
1-4-2-O-(13)
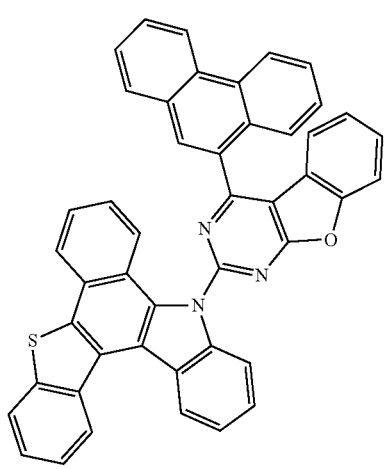
1-4-2-O-(14)
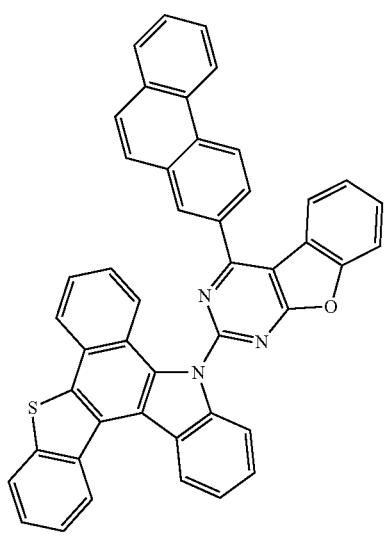

129
-continued
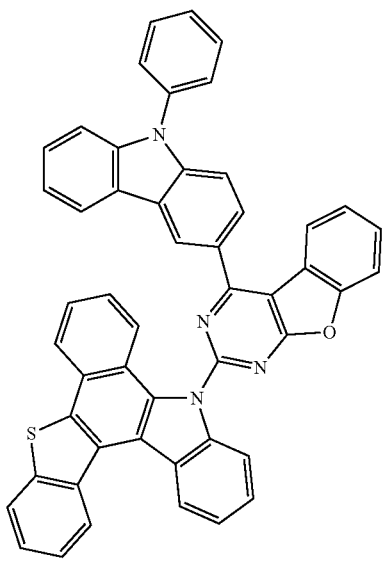
1-4-2-O-(15)
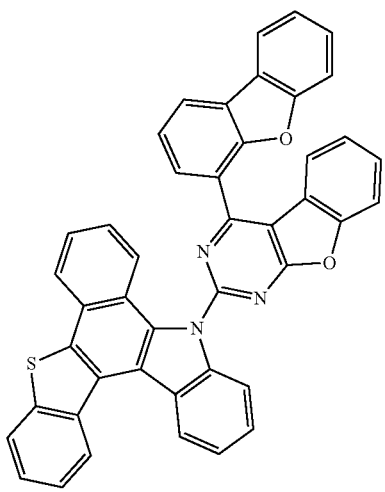
1-4-2-O-(16)
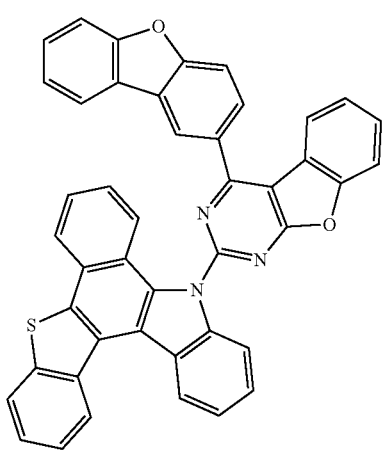
1-4-2-O-(17)
130
-continued
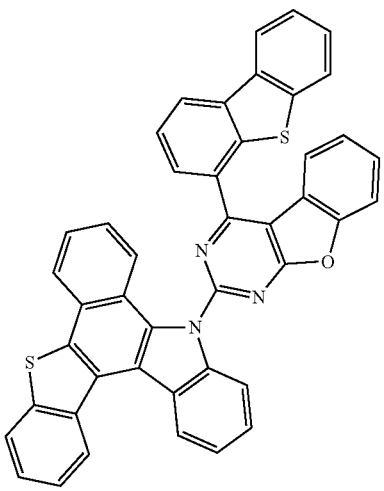
1-4-2-O-(18)
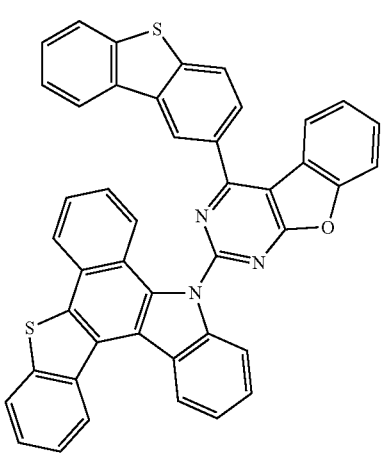
1-4-2-O-(19)
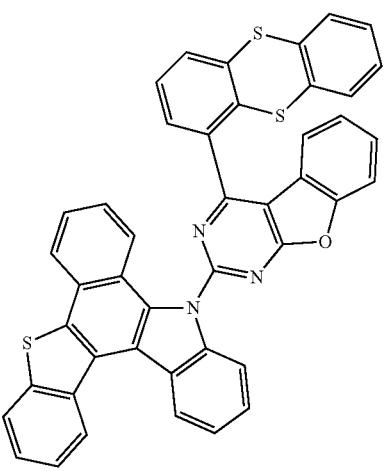
1-4-2-O-(20)

-continued
1-4-2-S-(1)
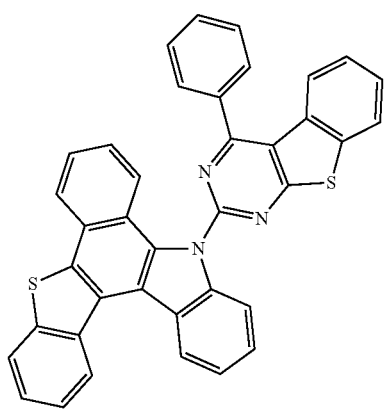
1-4-2-S-(2)
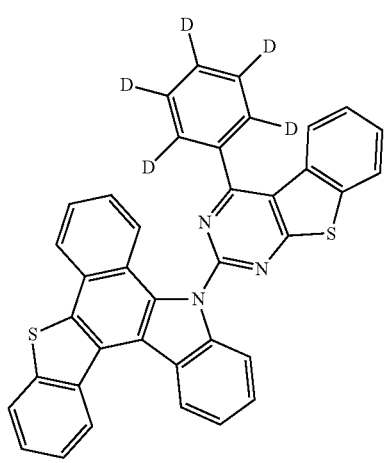
1-4-2-S-(3)
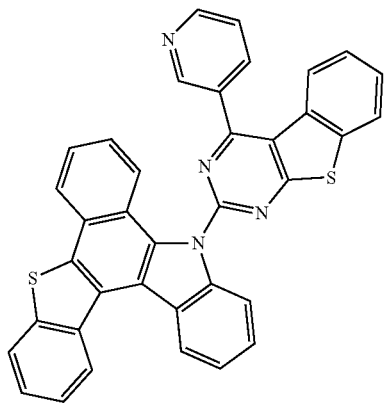
-continued
1-4-2-S-(4)
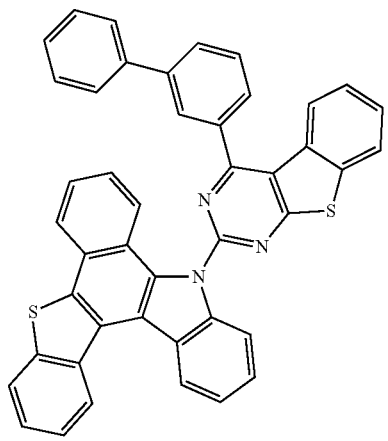
1-4-2-S-(5)
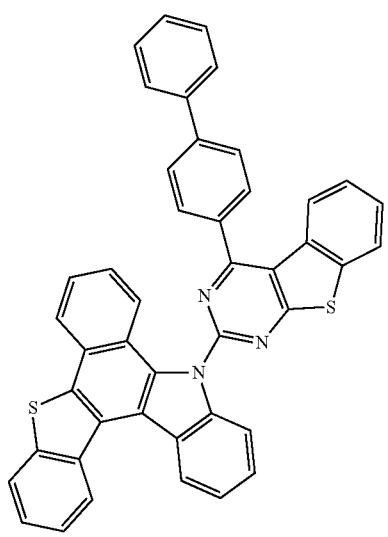
1-4-2-S-(6)
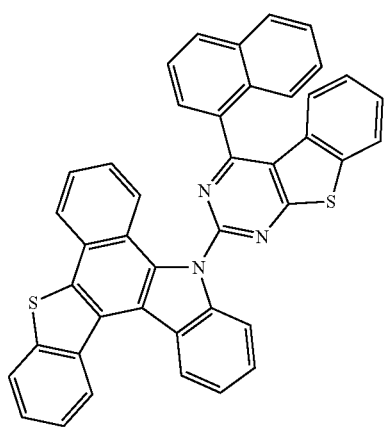

1-4-2-S-(7)
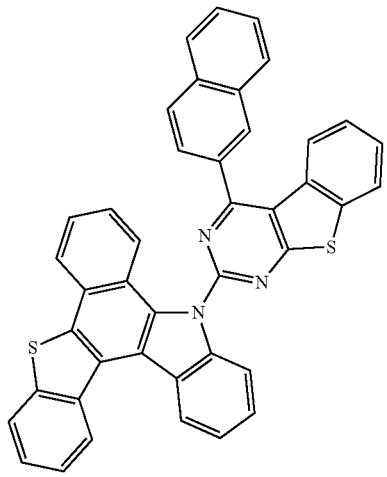
1-4-2-S-(8)
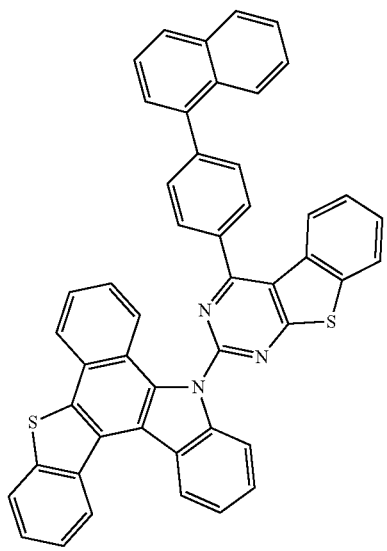
1-4-2-S-(9)
1-4-2-S-(10)
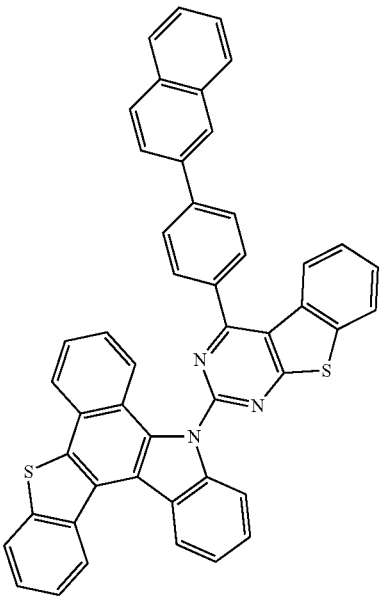
1-4-2-S-(11)
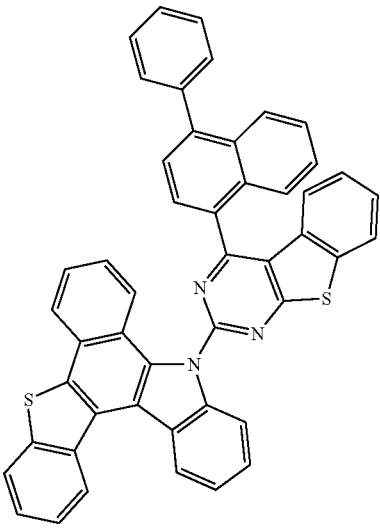

1-4-2-S-(12)
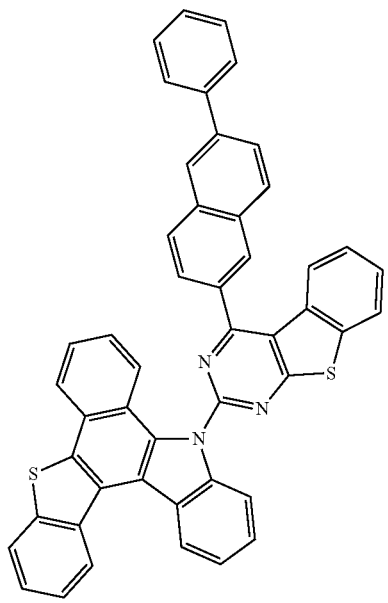
1-4-2-S-(13)
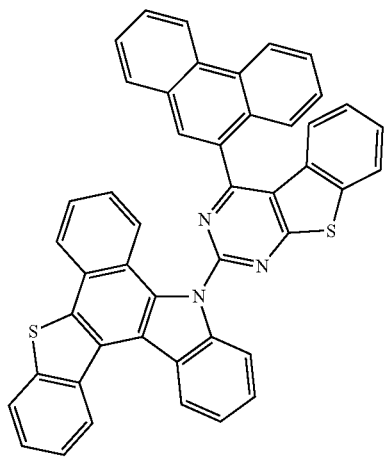
1-4-2-S-(14)
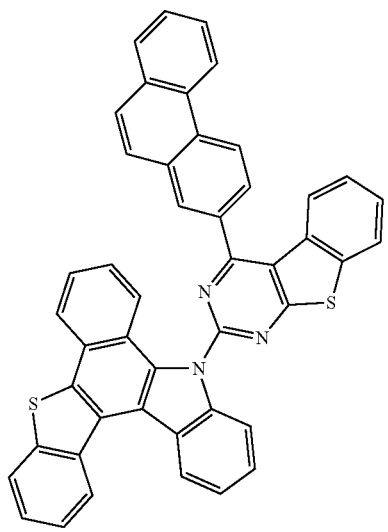
1-4-2-S-(15)
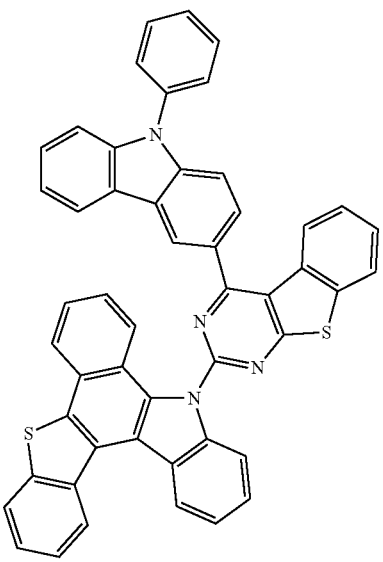
1-4-2-S-(16)
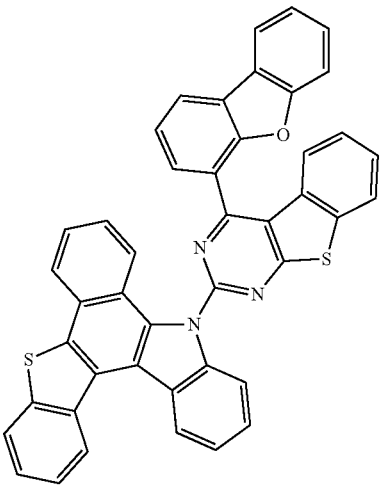
1-4-2-S-(17)
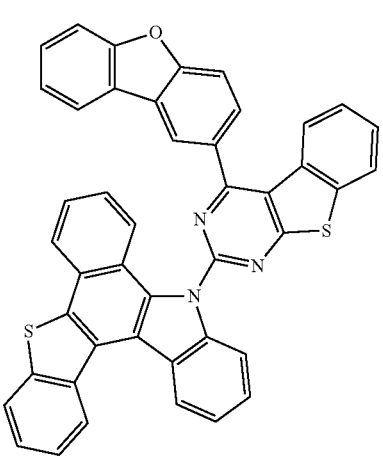

1-4-2-S-(18)
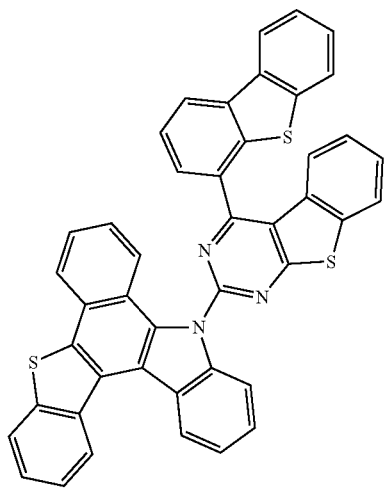
1-4-2-O-(21)
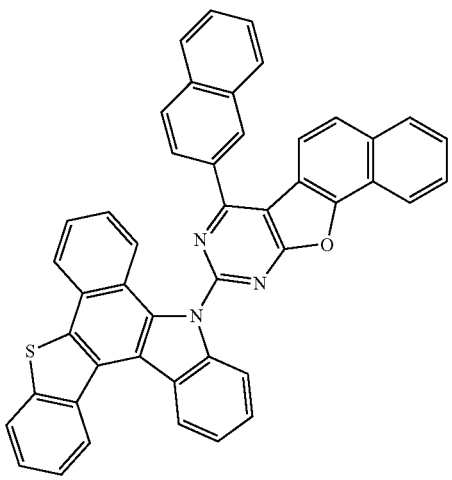
1-4-2-S-(19)
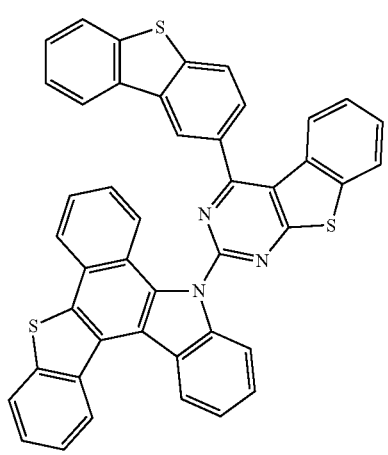
1-4-2-O-(22)
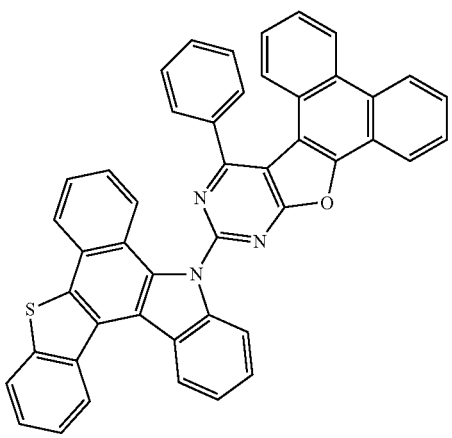
1-4-2-S-(20)
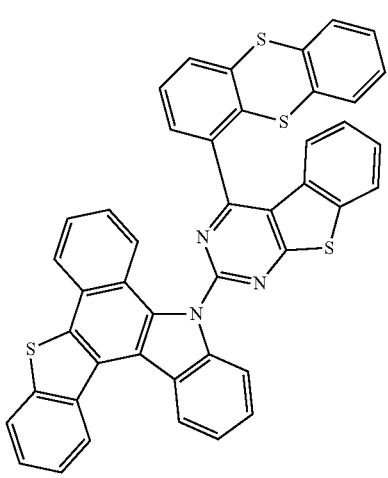
1-4-2-S-(21)
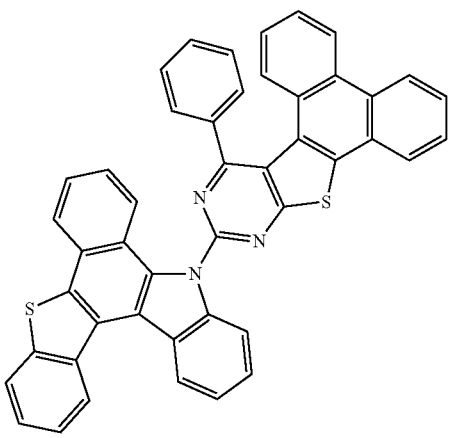

1-4-2-S-(22)

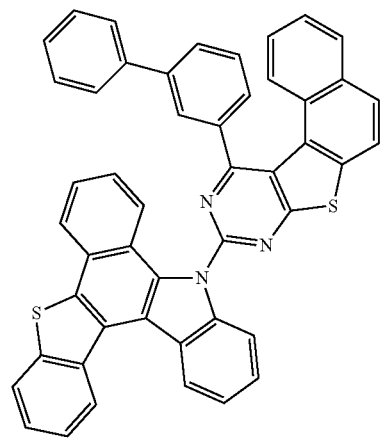

1-4-2-S-(23)

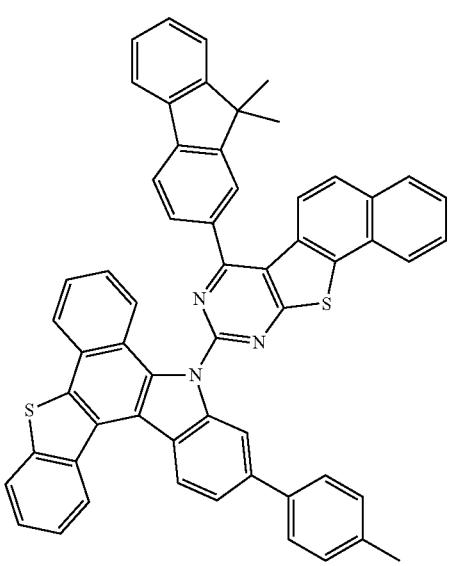

In another aspect of the present invention, there is provided a compound for an organic electric element represented by Formula 1 above.

In another aspect of the present invention, there is provided an organic electric element comprising the compound represented by Formula 1 above.

The organic electric element can comprise a first electrode, a second electrode, and an organic material layer disposed between the first electrode and the second electrode. The organic material layer can comprise the compound represented by Formula 1. The compound by represented Formula 1 can be contained in at least one layer of a hole injection layer, a hole transport layer, an emission-auxiliary layer, or a light emitting layer of the organic material layer. The compound represented by Formula 1 may be used a material in the hole injection layer, a material in the hole transport layer, a material in the emission-auxiliary layer, or a material in the light emitting layer. In addition, the compound represented by Formula 1 may be used as a phosphorescent host material of the light emitting layer.

There is provided the organic electric element comprising the organic material layer comprising at least one of the compounds represented by Formula 1-1 to Formula 1-4. Specially, there is provided the organic electric element comprising the organic material layer comprising at least one of the compounds represented by Formula 1-1-1-O to Formula 1-4-2-S. More specially, there is provided and the organic electric element comprising the organic material layer comprising at least one of the compounds represented by Formula 1-1-1-O-(1) to Formula 1-4-2-S-(23).

In another aspect of the present invention, the present invention provides an organic electric element further including at least a layer to improve luminous efficiency which is formed on at least one of the sides the first and second electrodes, which is opposite to the organic material layer.

In addition, the compounds contained in the organic layer can be comprised a same compound, but can be comprised two or more different compounds. But, the compounds contained in the organic layer can be comprised a same compound, but can be comprised two or more different compounds. For example, the phosphorescent host material of the light emitting layer according to embodiments of the present invention can comprise two different compounds like compound 1-1-1-O-(1) and 1-1-1-S(1), or three different compounds like compound 1-1-1-O-(1), 1-1-1-S(1) and 1-2-1-S(1).

Hereinafter, Synthesis Examples of the inventive compound represented by Formula 1 above and Preparation Examples of an organic electric element will be described in detail by way of example. However, the following examples are only for illustrative purposes and are not intended to limit the scope of the invention.

Synthesis Example

The final product according to the present invention can be synthesized by reaction between Sub 1 and Sub 2 as illustrated in, but not limited to, the following Reaction Scheme 1.

<Reaction Scheme 1>

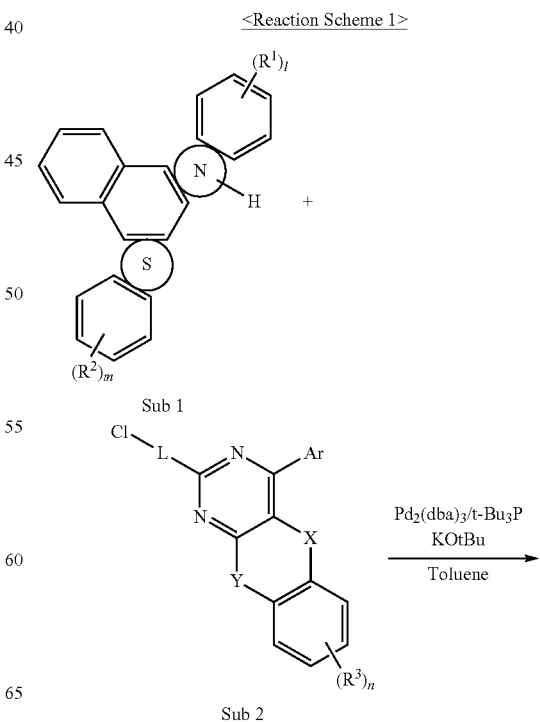

141
-continued

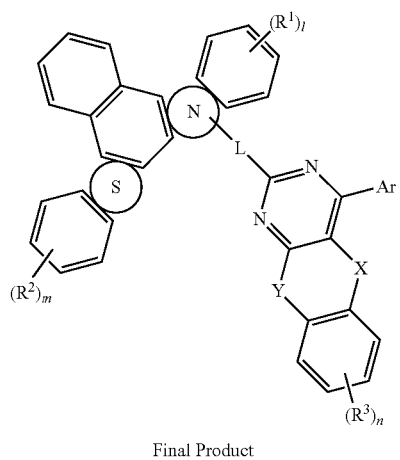

Final Product

I. Synthesis of Sub 1

Sub 1 of Reaction Scheme 1 can be synthesized according to, but not limited to, the following Reaction Scheme 2.

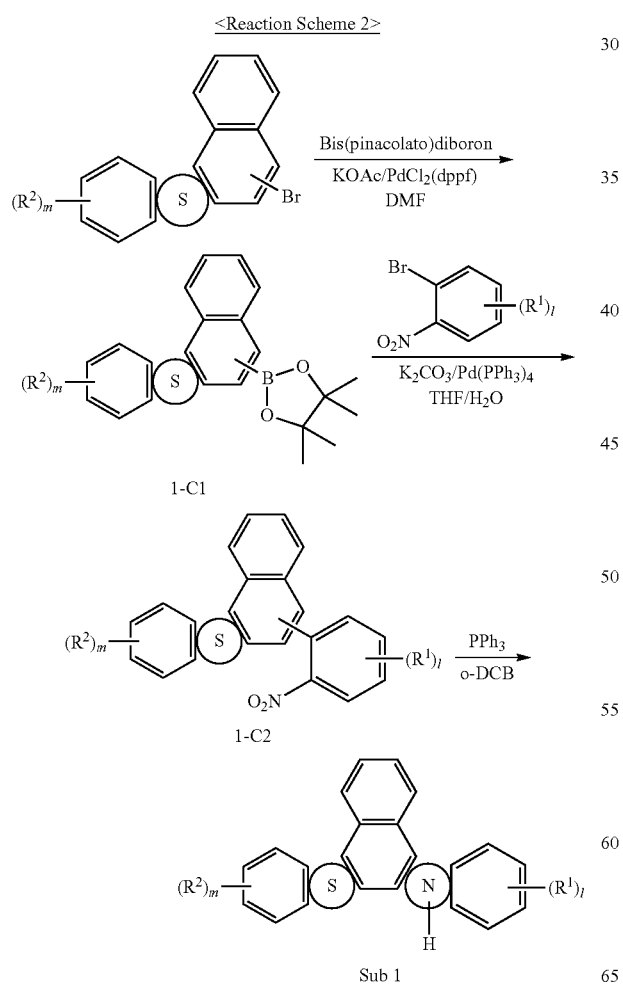

142

Synthesis Examples of the compounds of Sub 1 will be described in detail.

1. Sub 1-1 Synthesis

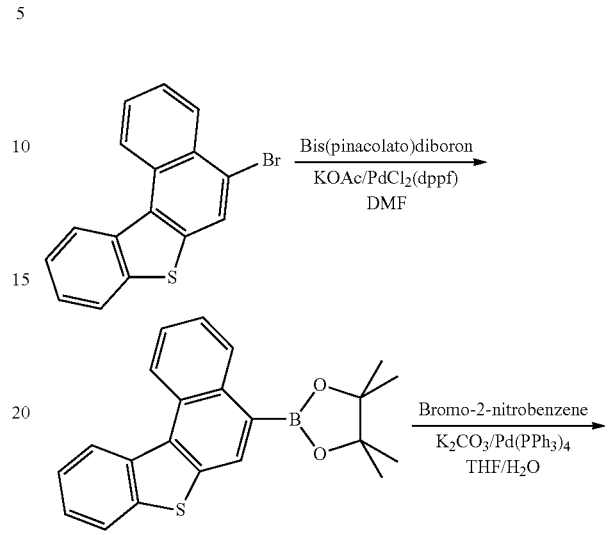

(1) 1-1-C1 Synthesis

To a solution of the starting material 5-bromobenzo[b]naphtha[1,2-d]thiophene (50 g, 0.16 mol), bis(pinacolato)diboron (48.65 g, 0.19 mol), KOAc (47 g, 0.48 mol) and $PdCl_2$(dppf) (5.21 g, 4 mol %) were dissolved in DMF, followed by reflux at 100° C. for 12 hours. Upon completion of the reaction, the temperature of the reaction product was lowered to room temperature, the reaction product was extracted with $CH_2Cl_2$, and was washed with water. The extracted organic layer was dried with $MgSO_4$ and concentrated, and then the produced organic material was recrystallized by $CH_2Cl_2$ and methanol to obtain desired 1-1-C1 (46 g, yield 80%).

(2) 1-1-C2 Synthesis

To a solution of the obtained 1-1-C1 (40 g, 0.11 mol), bromo-2-nitrobenzene (26.91 g, 0.13 mol), $K_2CO_3$ (46.03 g, 0.33 mol) and Pd(PPh$_3$)$_4$ (5.13 g, 4 mol %) were dissolved in anhydrous THF and a small amount of water, followed by reflux at 80° C. for 12 hours. Upon completion of the reaction, the temperature of the reaction product was lowered to room temperature, the reaction product was extracted with $CH_2Cl_2$, and was washed with water. The extracted organic layer was dried with $MgSO_4$ and concentrated, and then the produced organic material was separated by a silica gel column chromatography to obtain desired 1-1-C2 (27.62 g, yield 70%)

(3) Sub 1-1 Synthesis

To a solution of the obtained 1-1-C2 (20 g, 0.05 mol) and triphenylphosphine (44.28 g, 0.17 mol) were dissolved in o-dichlorobenzene, followed by reflux for 24 hours. Upon completion of the reaction, the solvent was removed using vacuum distillation, and then the concentrated product was separated by a silica gel column chromatography and recrystallized to obtain desired Sub 1-1 (13.65 g, yield 75%).

2. Sub 1-2 Synthesis (1) 1-2-C1 Synthesis

Except for using 6-bromobenzo[b]naphtha[1,2-d]thiophene (50 g, 0.16 mol) as a starting material plus bis(pinacolato)diboron (48.65 g, 0.19 mol), KOAc (47 g, 0.48 mol), $PdCl_2$(dppf) (5.21 g, 4 mol %) and DMF, the same procedure as described in Synthesis Method of 1-1-C1 was carried out to obtain desired 1-2-C1 (42 g, yield 73%).

(2) 1-2-C2 Synthesis

Except for using the obtained 1-2-C1 (40 g, 0.11 mol) plus bromo-2-nitrobenzene (26.91 g, 0.13 mol), $K_2CO_3$ (46.03 g, 0.33 mol), $Pd(PPh_3)_4$ (5.13 g, 4 mol %), anhydrous THF and water, the same procedure as described in Synthesis Method of 1-1-C2 was carried out to obtain desired 1-2-C2 (25.52 g, yield 65%).

(3) Sub 1-2 Synthesis

Except for using the obtained 1-2-C2 (20 g, 0.05 mol) plus triphenylphosphine (44.28 g, 0.17 mol) and o-dichlorobenzene, the same procedure as described in Synthesis Method of Sub 1-1 was carried out to obtain desired Sub 1-2 (12.4 g, yield 68%).

3. Sub 1-3 Synthesis

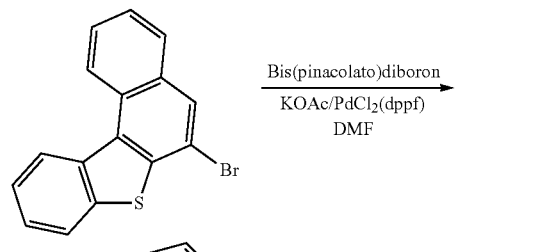

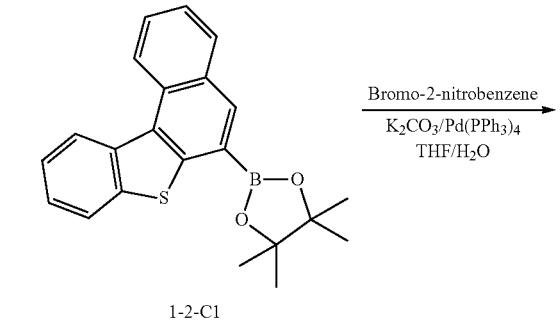

1-2-C1

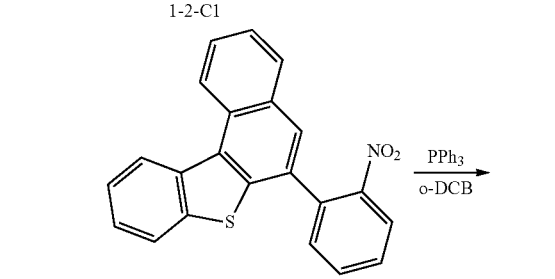

1-2-C2

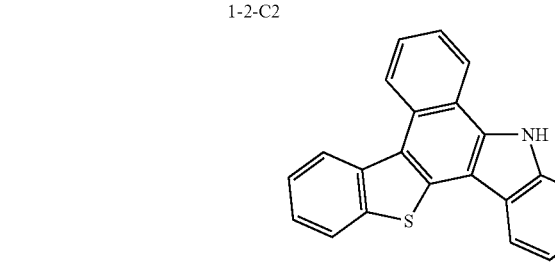

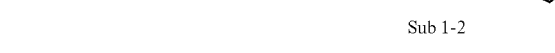
Sub 1-2

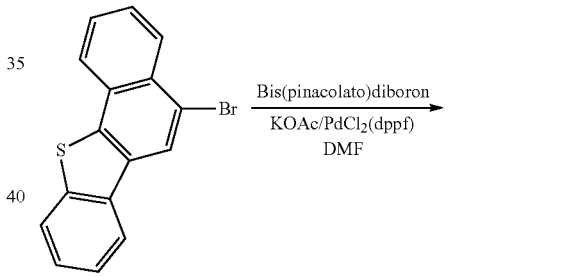

1-3-C1

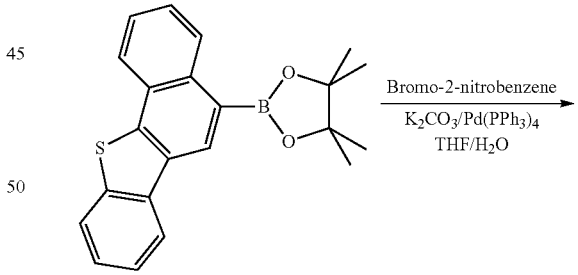

1-3-C2

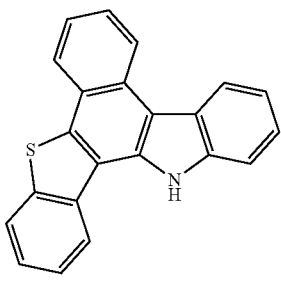

Sub 1-3

(1) 1-3-C1 Synthesis

Except for using 5-bromobenzo[b]naphtha[2,1-d]thiophene (50 g, 0.16 mol) as a starting material plus bis(pinacolato)diboron (48.65 g, 0.19 mol), KOAc (47 g, 0.48 mol), $PdCl_2$(dppf) (5.21 g, 4 mol %) and DMF, the same procedure as described in Synthesis Method of 1-1-C1 was carried out to obtain desired 1-3-C1 (49.5 g, yield 86%).

(2) 1-3-C2 Synthesis

Except for using the obtained 1-3-C1 (40 g, 0.11 mol) plus bromo-2-nitrobenzene (26.91 g, 0.13 mol), $K_2CO_3$ (46.03 g, 0.33 mol), $Pd(PPh_3)_4$ (5.13 g, 4 mol %), anhydrous THF and water, the same procedure as described in Synthesis Method of 1-1-C2 was carried out to obtain desired 1-3-C2 (30 g, yield 76%).

(3) Sub 1-3 Synthesis

Except for using the obtained 1-3-C2 (20 g, 0.05 mol) plus triphenylphosphine (44.28 g, 0.17 mol) and o-dichlorobenzene, the same procedure as described in Synthesis Method of Sub 1-1 was carried out to obtain desired Sub 1-3 (12.43 g, yield 68%).

4. Sub 1-4 Synthesis

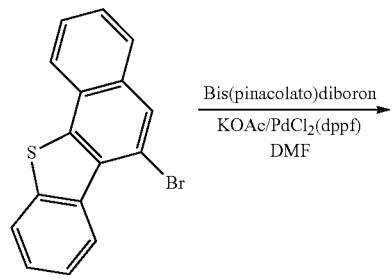

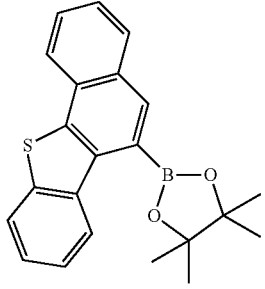 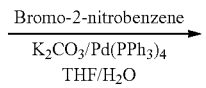

1-4-C1

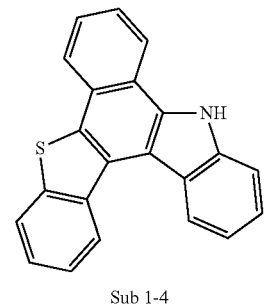

1-4-C2

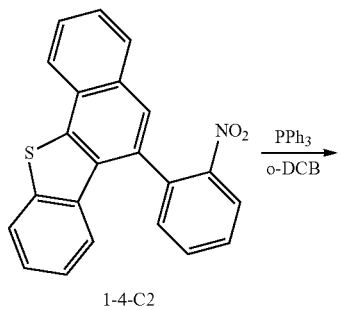

Sub 1-4

(1) 1-4-C1 Synthesis

Except for using 6-bromobenzo[b]naphtha[2,1-d]thiophene (50 g, 0.16 mol) as a starting material plus bis(pinacolato)diboron (48.65 g, 0.19 mol), KOAc (47 g, 0.48 mol), $PdCl_2$(dppf) (5.21 g, 4 mol %) and DMF, the same procedure as described in Synthesis Method of 1-1-C1 was carried out to obtain desired 1-4-C1 (43.5 g, yield 75%).

(2) 1-4-C2 Synthesis

Except for using the obtained 1-4-C1 (40 g, 0.11 mol) plus bromo-2-nitrobenzene (26.91 g, 0.13 mol), $K_2CO_3$ (46.03 g, 0.33 mol), $Pd(PPh_3)_4$ (5.13 g, 4 mol %), anhydrous THF and water, the same procedure as described in Synthesis Method of 1-1-C2 was carried out to obtain desired 1-4-C2 (22 g, yield 56%).

(3) Sub 1-4 Synthesis

Except for using the obtained 1-4-C2 (20 g, 0.05 mol) plus triphenylphosphine (44.28 g, 0.17 mol) and o-dichlorobenzene, the same procedure as described in Synthesis Method of Sub 1-1 was carried out to obtain desired Sub 1-4 (10.5 g, yield 58%).

Meanwhile, examples of Sub 1 compounds include, but are not limited to, the following compounds:

-continued
| | |
|---|---|
| Sub 1-1 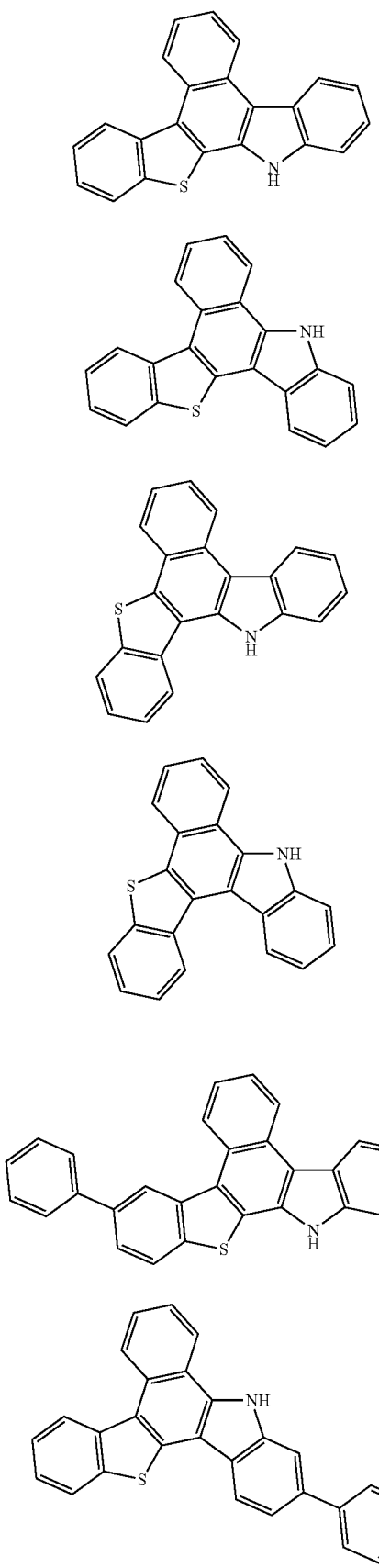 | Sub 1-7 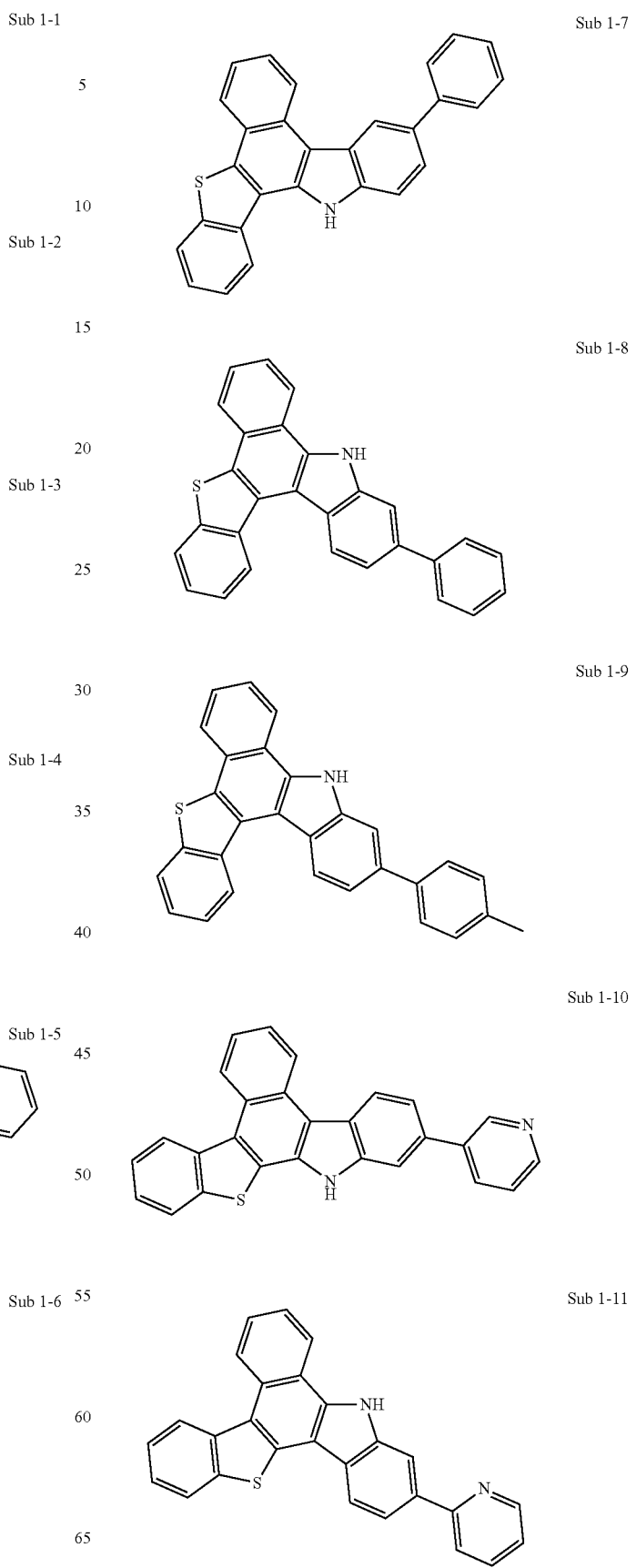 |
| Sub 1-2 | |
| Sub 1-3 | Sub 1-8 |
| Sub 1-4 | Sub 1-9 |
| Sub 1-5 | Sub 1-10 |
| Sub 1-6 | Sub 1-11 |

Sub 1-12

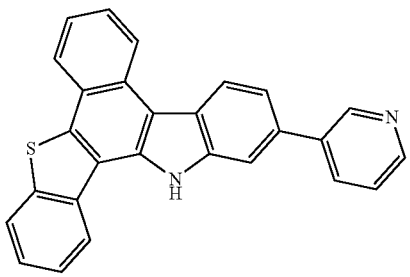

Field desorption mass spectrometry (FD-MS) data of the Sub 1 compounds are given in Table 1 below.

TABLE 1

| Compound | FD-MS | Compound | FD-MS |
|---|---|---|---|
| Sub 1-1 | m/z = 323.08($C_{22}H_{13}NS$ = 323.41) | Sub 1-2 | m/z = 323.08($C_{22}H_{13}NS$ = 323.41) |
| Sub 1-3 | m/z = 323.08($C_{22}H_{13}NS$ = 323.41) | Sub 1-4 | m/z = 323.08($C_{22}H_{13}NS$ = 323.41) |
| Sub 1-5 | m/z = 475.14($C_{34}H_{21}NS$ = 475.60) | Sub 1-6 | m/z = 399.11($C_{28}H_{17}NS$ = 399.51) |
| Sub 1-7 | m/z = 399.11($C_{28}H_{17}NS$ = 399.51) | Sub 1-8 | m/z = 399.11($C_{28}H_{17}NS$ = 399.51) |
| Sub 1-9 | m/z = 413.12($C_{29}H_{19}NS$ = 413.53) | Sub 1-10 | m/z = 400.10($C_{27}H_{16}N_2S$ = 400.49) |
| Sub 1-11 | m/z = 400.10($C_{27}H_{16}N2S$ = 400.49) | Sub 1-12 | m/z = 400.10($C_{27}H_{16}N_2S$ = 400.49) |

II. Synthesis of Sub 2

Sub 2 in Reaction Scheme 1 may be synthesized according to, but not limited to, the following Reaction Scheme 3.

<Reaction Scheme 3>

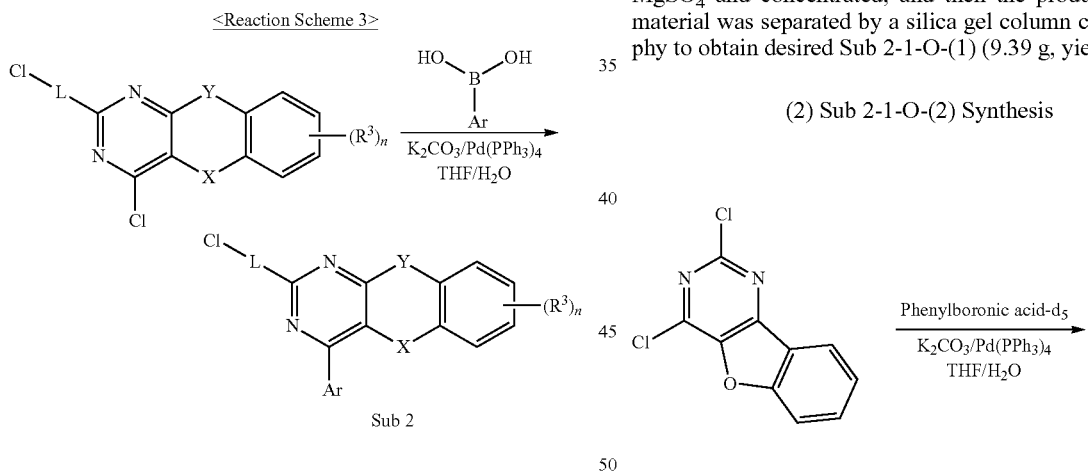

Sub 2

1. Sub 2-1-O Synthesis (1) Sub 2-1-O-(1) Synthesis

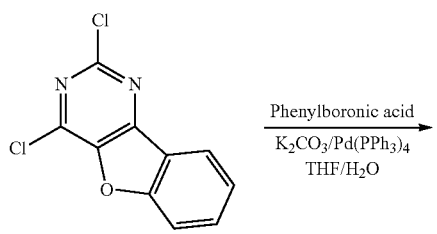

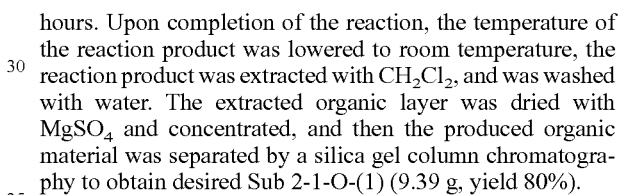

To a solution of the starting material 2,4-Dichlorobenzofuro[3,2-d]pyrimidine (10 g, 0.04 mol), phenylboronic acid (5.1 g, 0.04 mol), $K_2CO_3$ (17.34 g, 0.12 mol) and $Pd(PPh_3)_4$ (1.93 g, 4 mol %) were dissolved in anhydrous THF and a small amount of water, followed by reflux at 80° C. for 12 hours. Upon completion of the reaction, the temperature of the reaction product was lowered to room temperature, the reaction product was extracted with $CH_2Cl_2$, and was washed with water. The extracted organic layer was dried with $MgSO_4$ and concentrated, and then the produced organic material was separated by a silica gel column chromatography to obtain desired Sub 2-1-O-(1) (9.39 g, yield 80%).

(2) Sub 2-1-O-(2) Synthesis

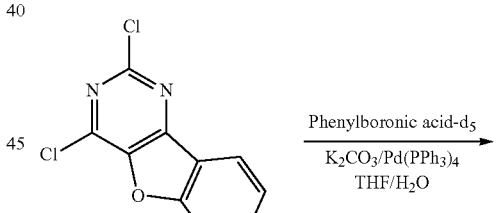

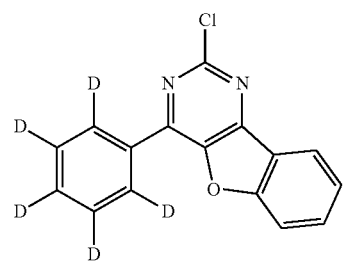

Except for using 2,4-Dichlorobenzofuro[3,2-d]pyrimidine (10 g, 0.04 mol) as a starting material plus phenylboronic acid-$d_5$ (5.31 g, 0.04 mol), $K_2CO_3$ (17.34 g, 0.12 mol), $Pd(PPh_3)_4$ (1.93 g, 4 mol %), anhydrous THF and water, the same procedure as described in Synthesis Method of Sub 2-1-O-(1) was carried out to obtain desired Sub 2-1-O-(2) (9.80 g, yield 82%).

(3) Sub 2-1-O-(3) Synthesis

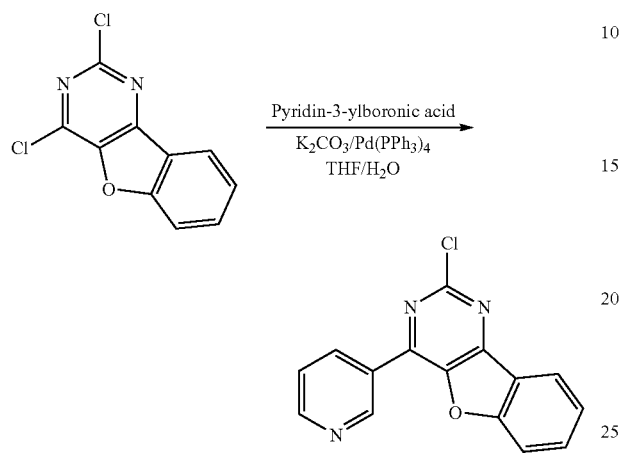

Except for using 2,4-Dichlorobenzofuro[3,2-d]pyrimidine (10 g, 0.04 mol) as a starting material plus pyridine-3-ylboronic acid (5.14 g, 0.04 mol), $K_2CO_3$ (17.34 g, 0.12 mol), Pd(PPh$_3$)$_4$ (1.93 g, 4 mol %), anhydrous THF and water, the same procedure as described in Synthesis Method of Sub 2-1-O-(1) was carried out to obtain desired Sub 2-1-O-(3) (11.78 g, yield 73%).

(4) Sub 2-1-O-(4) Synthesis

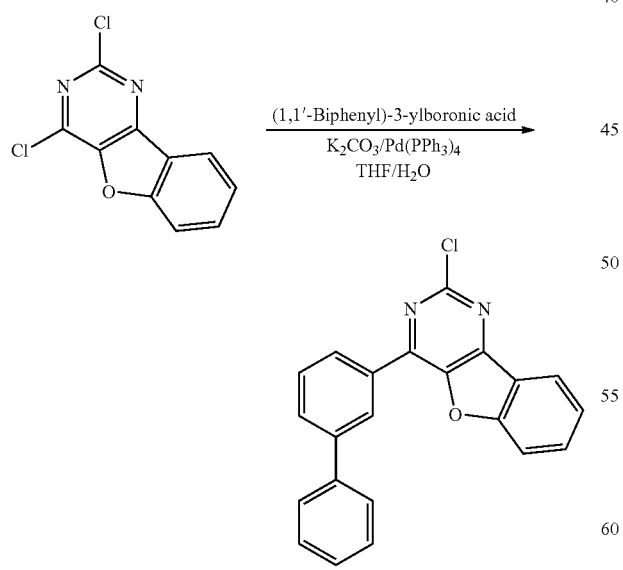

Except for using 2,4-Dichlorobenzofuro[3,2-d]pyrimidine (10 g, 0.04 mol) as a starting material plus (1,1'-biphenyl)-3-ylboronic acid (8.28 g, 0.04 mol), $K_2CO_3$ (17.34 g, 0.12 mol), Pd(PPh$_3$)$_4$ (1.93 g, 4 mol %), anhydrous THF and water, the same procedure as described in Synthesis Method of Sub 2-1-O-(1) was carried out to obtain desired Sub 2-1-O-(4) (11.19 g, yield 75%).

(5) Sub 2-1-O-(5) Synthesis

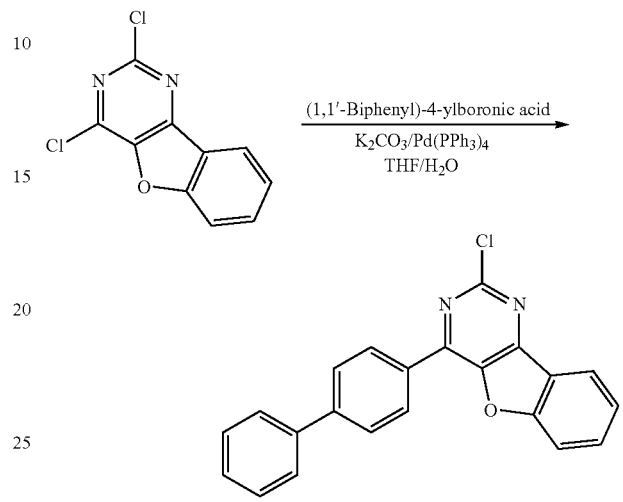

Except for using 2,4-Dichlorobenzofuro[3,2-d]pyrimidine (10 g, 0.04 mol) as a starting material plus (1,1'-biphenyl)-4-ylboronic acid (8.28 g, 0.04 mol), $K_2CO_3$ (17.34 g, 0.12 mol), Pd(PPh$_3$)$_4$ (1.93 g, 4 mol %), anhydrous THF and water, the same procedure as described in Synthesis Method of Sub 2-1-O-(1) was carried out to obtain desired Sub 2-1-O-(5) (11.93 g, yield 80%).

2. Sub 2-1-S Synthesis (1) Sub 2-1-S-(6) Synthesis

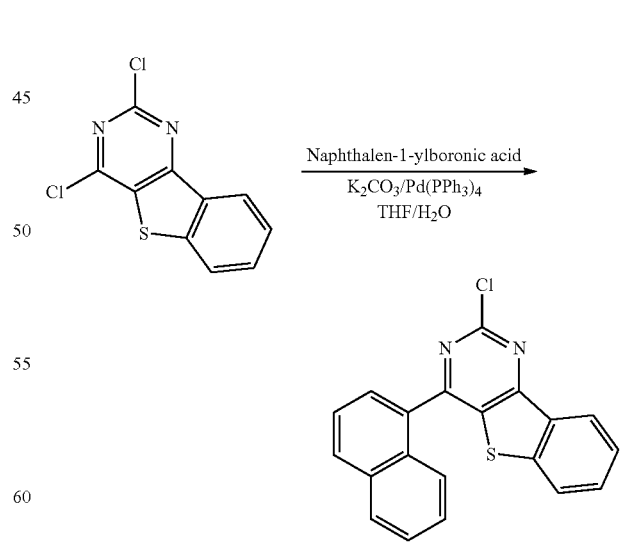

Except for using 2,4-Dichlorobenzo[4,5]thieno[3,2-d]pyrimidine (10 g, 0.04 mol) as a starting material plus naphthalene-1-ylboronic acid (6.74 g, 0.04 mol), $K_2CO_3$ (16.25 g, 0.12 mol), Pd(PPh$_3$)$_4$ (1.81 g, 4 mol %), anhydrous THF and water, the same procedure as described in Synthesis Method of Sub 2-1-O-(1) was carried out to obtain desired Sub 2-1-S-(6) (11.55 g, yield 85%).

(2) Sub 2-1-S-(7) Synthesis

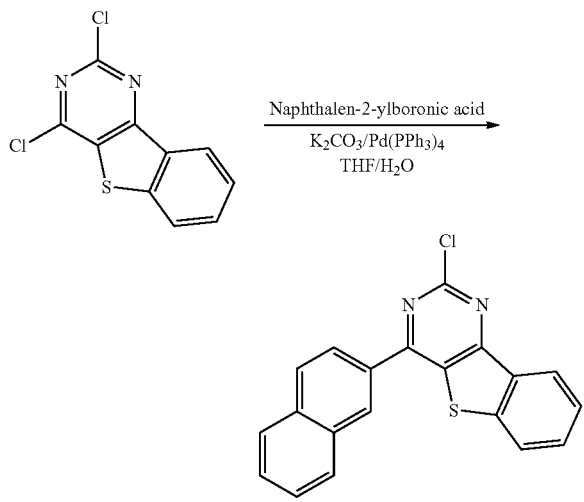

Except for using 2,4-Dichlorobenzo[4,5]thieno[3,2-d]pyrimidine (10 g, 0.04 mol) as a starting material plus naphthalene-2-ylboronic acid (6.74 g, 0.04 mol), $K_2CO_3$ (16.25 g, 0.12 mol), $Pd(PPh_3)_4$ (1.81 g, 4 mol %), anhydrous THF and water, the same procedure as described in Synthesis Method of Sub 2-1-O-(1) was carried out to obtain desired Sub 2-1-S-(7) (11.23 g, yield 83%).

(3) Sub 2-1-S-(8) Synthesis

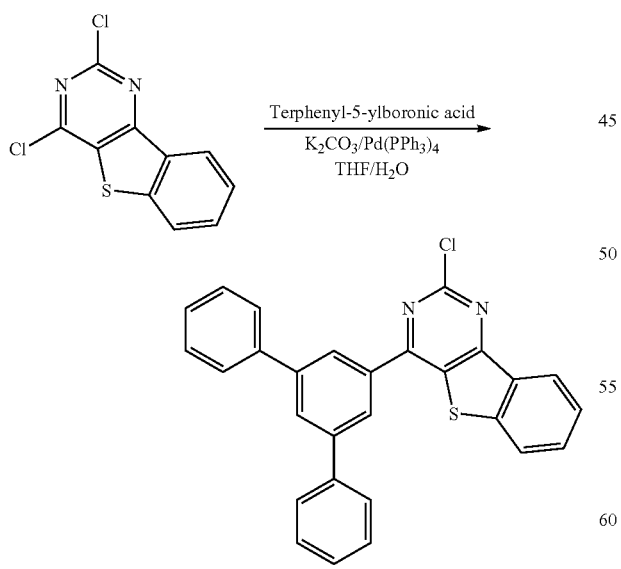

Except for using 2,4-Dichlorobenzo[4,5]thieno[3,2-d]pyrimidine (10 g, 0.04 mol) as a starting material plus terphenyl-5-ylboronic acid (10.74 g, 0.04 mol), $K_2CO_3$ (16.25 g, 0.12 mol), $Pd(PPh_3)_4$ (1.81 g, 4 mol %), anhydrous THF and water, the same procedure as described in Synthesis Method of Sub 2-1-O-(1) was carried out to obtain desired Sub 2-1-S-(8) (12.14 g, yield 69%).

(4) Sub 2-1-S-(9) Synthesis

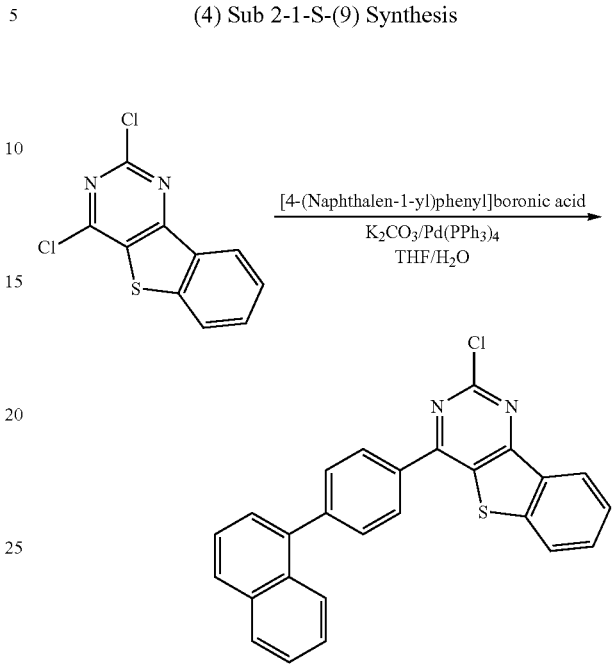

Except for using 2,4-Dichlorobenzo[4,5]thieno[3,2-d]pyrimidine (10 g, 0.04 mol) as a starting material plus [4-(naphthalene-1-yl)phenyl]-boronic acid (9.72 g, 0.04 mol), $K_2CO_3$ (16.25 g, 0.12 mol), $Pd(PPh_3)_4$ (1.81 g, 4 mol %), anhydrous THF and water, the same procedure as described in Synthesis Method of Sub 2-1-O-(1) was carried out to obtain desired Sub 2-1-S-(9) (12.76 g, yield 77%).

(5) Sub 2-1-S-(10) Synthesis

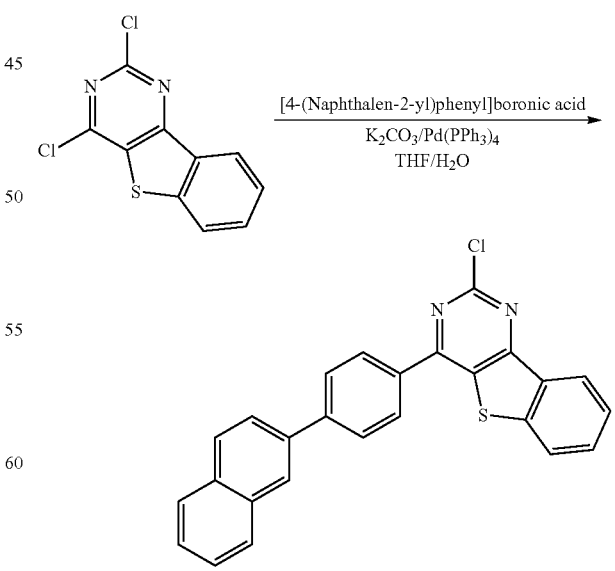

Except for using 2,4-Dichlorobenzo[4,5]thieno[3,2-d]pyrimidine (10 g, 0.04 mol) as a starting material plus [4-(naphthalene-2-yl)phenyl]-boronic acid (9.72 g, 0.04 mol), K₂CO₃ (16.25 g, 0.12 mol), Pd(PPh₃)₄ (1.81 g, 4 mol %), anhydrous THF and water, the same procedure as described in Synthesis Method of Sub 2-1-O-(1) was carried out to obtain desired Sub 2-1-S-(10) (12.93 g, yield 78%).

3. Sub 2-2-O Synthesis (1) Sub 2-2-O-(11) Synthesis

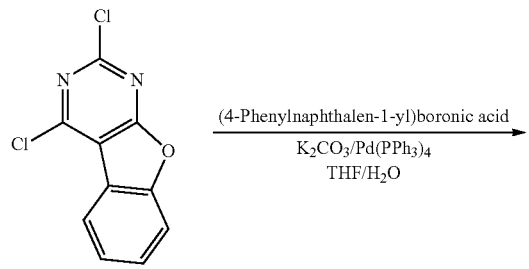

Except for using 2,4-Dichlorobenzofuro[2,3-d]pyrimidine (10 g, 0.04 mol) as a starting material plus (4-phenylnaphthalen-1-yl)boronic acid (10.37 g, 0.04 mol), K₂CO₃ (17.34 g, 0.12 mol), Pd(PPh₃)₄ (1.93 g, 4 mol %), anhydrous THF and water, the same procedure as described in Synthesis Method of Sub 2-1-O-(1) was carried out to obtain desired Sub 2-2-O-(11) (10.89 g, yield 64%).

(2) Sub 2-2-O-(12) Synthesis

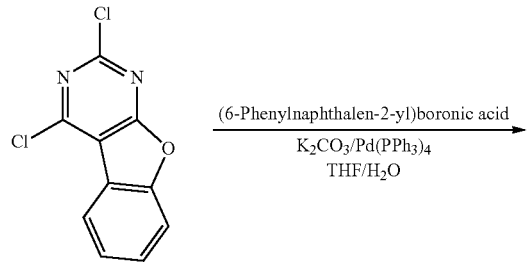

Except for using 2,4-Dichlorobenzofuro[2,3-d]pyrimidine (10 g, 0.04 mol) as a starting material plus (6-phenylnaphtha-len-2-yl)boronic acid (10.37 g, 0.04 mol), K₂CO₃ (17.34 g, 0.12 mol), Pd(PPh₃)₄ (1.93 g, 4 mol %), anhydrous THF and water, the same procedure as described in Synthesis Method of Sub 2-1-O-(1) was carried out to obtain desired Sub 2-2-O-(12) (11.23 g, yield 66%).

(3) Sub 2-2-O-(13) Synthesis

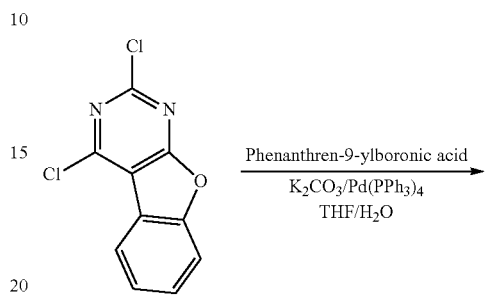

Except for using 2,4-Dichlorobenzofuro[2,3-d]pyrimidine (10 g, 0.04 mol) as a starting material plus phenanthren-9-ylboronic acid (9.28 g, 0.04 mol), K₂CO₃ (17.34 g, 0.12 mol), Pd(PPh₃)₄ (1.93 g, 4 mol %), anhydrous THF and water, the same procedure as described in Synthesis Method of Sub 2-1-O-(1) was carried out to obtain desired Sub 2-2-O-(13) (12.9 g, yield 81%).

(4) Sub 2-2-O-(14) Synthesis

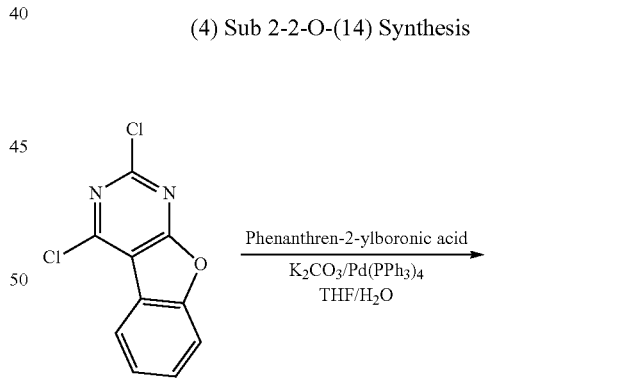

Except for using 2,4-Dichlorobenzofuro[2,3-d]pyrimidine (10 g, 0.04 mol) as a starting material plus phenanthren-2- ylboronic acid (9.28 g, 0.04 mol), K₂CO₃ (17.34 g, 0.12 mol), Pd(PPh₃)₄ (1.93 g, 4 mol %), anhydrous THF and water, the same procedure as described in Synthesis Method of Sub 2-1-O-(1) was carried out to obtain desired Sub 2-2-O-(14) (12.74 g, yield 80%).

(5) Sub 2-2-O-(15) Synthesis

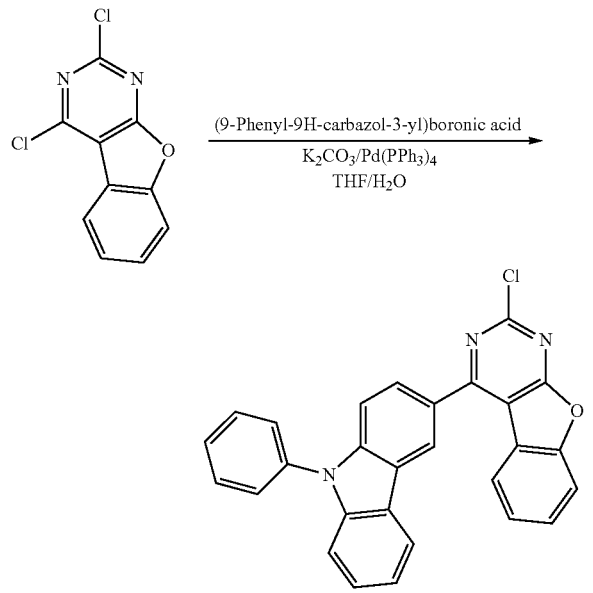

Except for using 2,4-Dichlorobenzofuro[2,3-d]pyrimidine (10 g, 0.04 mol) as a starting material plus (9-phenyl-9H-carbazol-3-yl)boronic acid (12.01 g, 0.04 mol), K₂CO₃ (17.34 g, 0.12 mol), Pd(PPh₃)₄ (1.93 g, 4 mol %), anhydrous THF and water, the same procedure as described in Synthesis Method of Sub 2-1-O-(1) was carried out to obtain desired Sub 2-2-O-(15) (11.56 g, yield 62%).

4. Sub 2-2-S Synthesis (1) Sub 2-2-S-(16) Synthesis

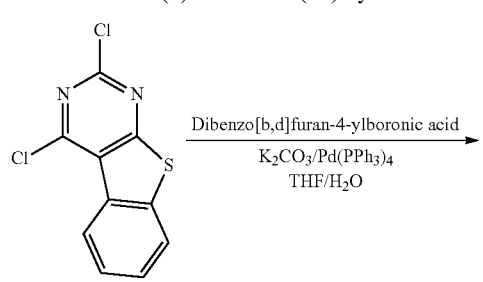

Except for using 2,4-Dichlorobenzo[4,5]thieno[2,3-d]pyrimidine (10 g, 0.04 mol) as a starting material plus dibenzo[b,d]furan-4-ylboronic acid (8.31 g, 0.04 mol), K₂CO₃ (16.25 g, 0.12 mol), Pd(PPh₃)₄ (1.81 g, 4 mol %), anhydrous THF and water, the same procedure as described in Synthesis Method of Sub 2-1-O-(1) was carried out to obtain desired Sub 2-2-S-(16) (8.79 g, yield 58%).

(2) Sub 2-2-S-(17) Synthesis

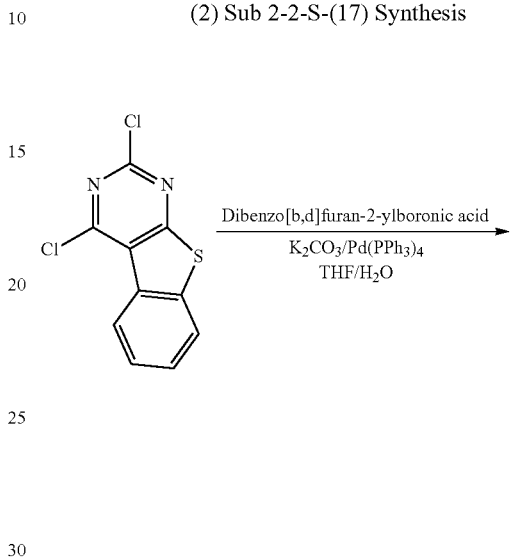

Except for using 2,4-Dichlorobenzo[4,5]thieno[2,3-d]pyrimidine (10 g, 0.04 mol) as a starting material plus dibenzo[b,d]furan-2-ylboronic acid (8.31 g, 0.04 mol), K₂CO₃ (16.25 g, 0.12 mol), Pd(PPh₃)₄ (1.81 g, 4 mol %), anhydrous THF and water, the same procedure as described in Synthesis Method of Sub 2-1-O-(1) was carried out to obtain desired Sub 2-2-S-(17) (9.09 g, yield 60%).

(3) Sub 2-2-S-(18) Synthesis

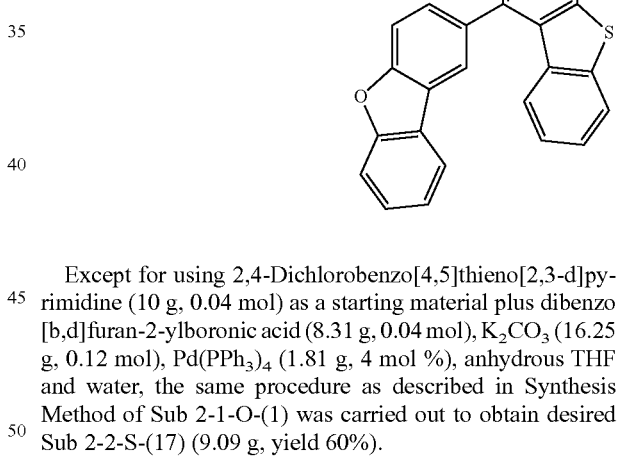

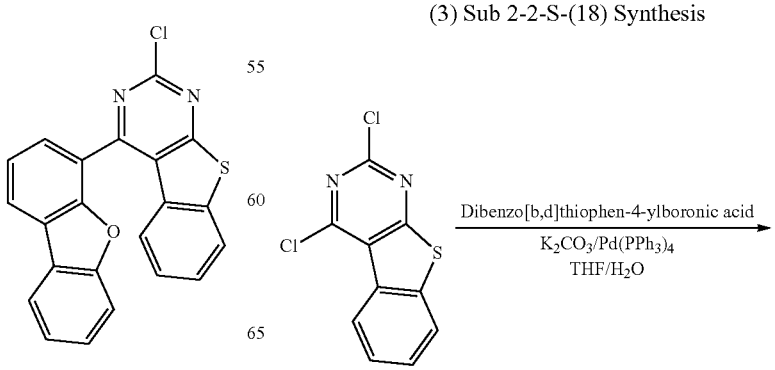

(5) Sub 2-2-S-(20) Synthesis

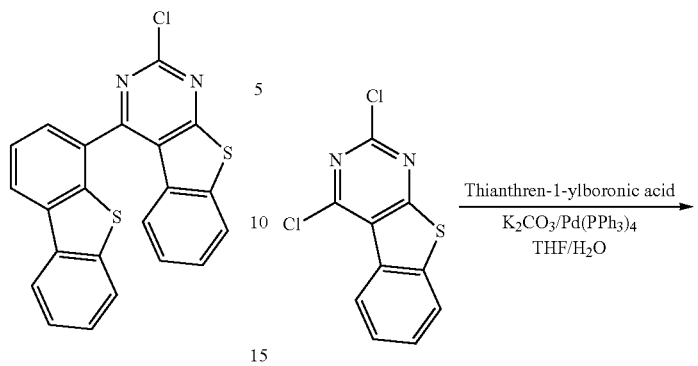

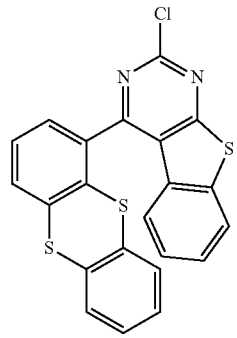

Except for using 2,4-Dichlorobenzo[4,5]thieno[2,3-d]pyrimidine (10 g, 0.04 mol) as a starting material plus dibenzo[b,d]thiophen-4-ylboronic acid (8.93 g, 0.04 mol), K$_2$CO$_3$ (16.25 g, 0.12 mol), Pd(PPh$_3$)$_4$ (1.81 g, 4 mol %), anhydrous THF and water, the same procedure as described in Synthesis Method of Sub 2-1-O-(1) was carried out to obtain desired Sub 2-2-S-(18) (10.73 g, yield 68%).

(4) Sub 2-2-S-(19) Synthesis

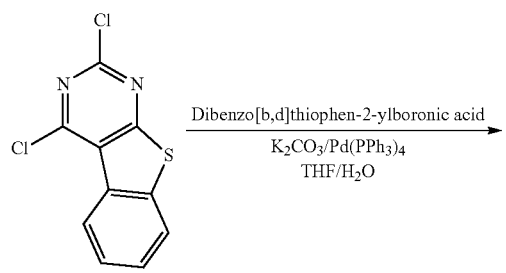

Except for using 2,4-Dichlorobenzo[4,5]thieno[2,3-d]pyrimidine (10 g, 0.04 mol) as a starting material plus thianthren-1-ylboronic acid (10.19 g, 0.04 mol), K$_2$CO$_3$ (16.25 g, 0.12 mol), Pd(PPh$_3$)$_4$ (1.81 g, 4 mol %), anhydrous THF and water, the same procedure as described in Synthesis Method of Sub 2-1-O-(1) was carried out to obtain desired Sub 2-2-S-(20) (13.98 g, yield 82%).

Meanwhile, examples of Sub 2 compounds include, but are not limited to, the following compounds:

Sub 2-1-O-(1)

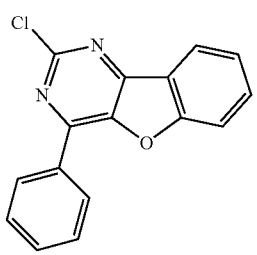

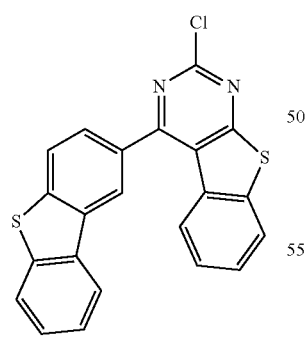

Sub 2-1-O-(2)

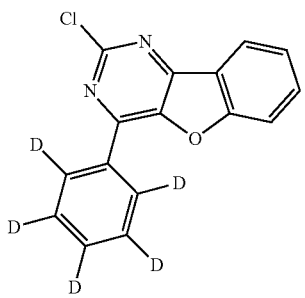

Except for using 2,4-Dichlorobenzo[4,5]thieno[2,3-d]pyrimidine (10 g, 0.04 mol) as a starting material plus dibenzo[b,d]thiophen-2-ylboronic acid (8.93 g, 0.04 mol), K$_2$CO$_3$ (16.25 g, 0.12 mol), Pd(PPh$_3$)$_4$ (1.81 g, 4 mol %), anhydrous THF and water, the same procedure as described in Synthesis Method of Sub 2-1-O-(1) was carried out to obtain desired Sub 2-2-S-(19) (11.21 g, yield 71%).

-continued
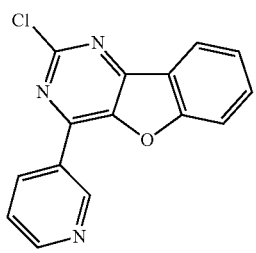
Sub 2-1-O-(3)
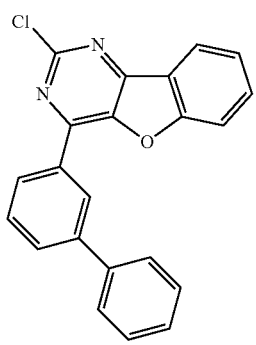
Sub 2-1-O-(4)
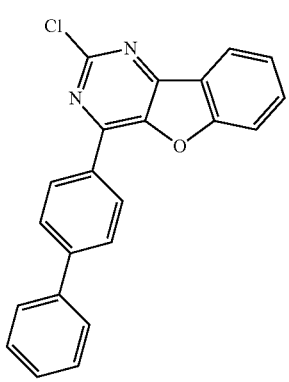
Sub 2-1-O-(5)
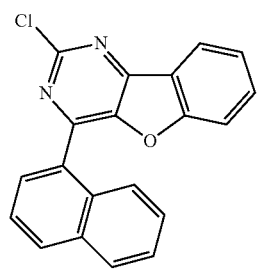
Sub 2-1-O-(6)
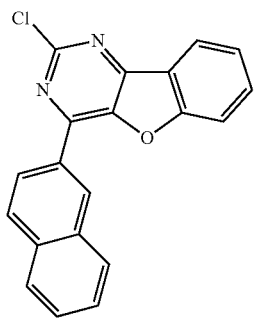
Sub 2-1-O-(7)
-continued
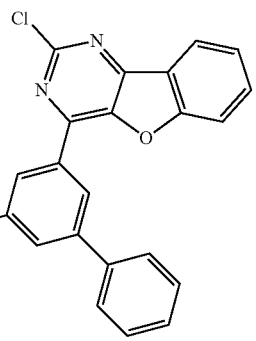
Sub 2-1-O-(8)
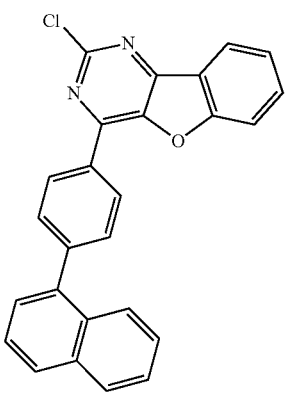
Sub 2-1-O-(9)
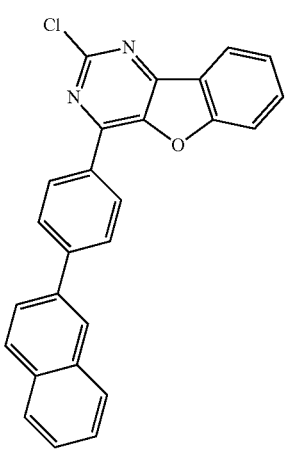
Sub 2-1-O-(10)
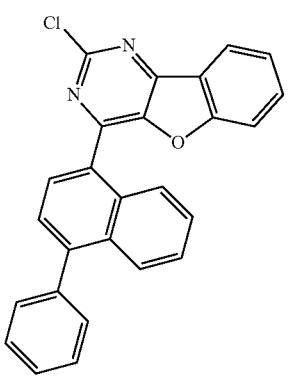
Sub 2-1-O-(11)

Sub 2-1-O-(12)
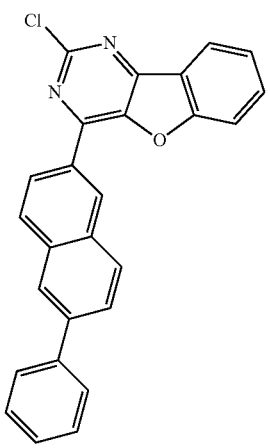
Sub 2-1-O-(13)
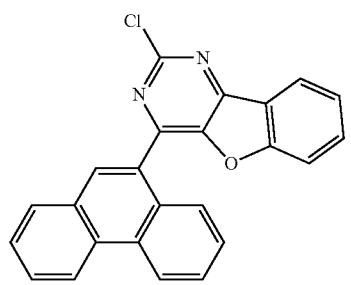
Sub 2-1-O-(14)
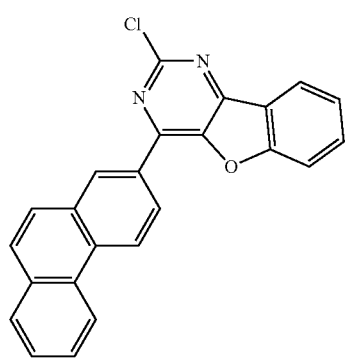
Sub 2-1-O-(15)
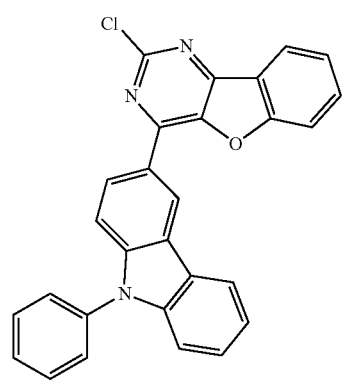
Sub 2-1-O-(16)
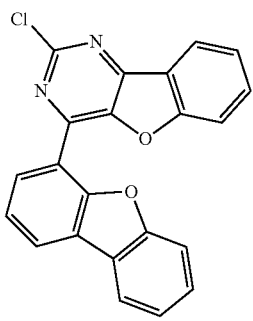
Sub 2-1-O-(17)
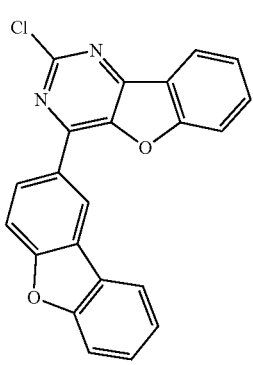
Sub 2-1-O-(18)
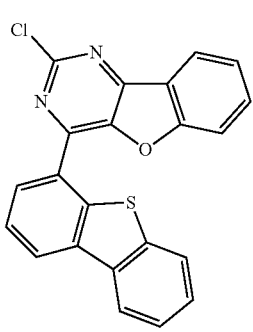
Sub 2-1-O-(19)
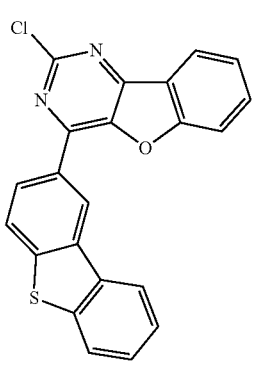
Sub 2-1-O-(20)
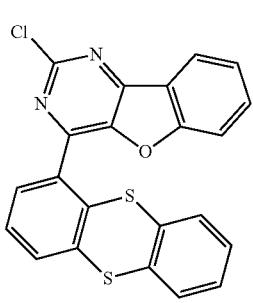

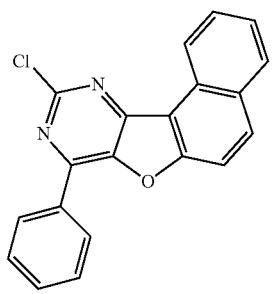
Sub 2-1-O-(21)
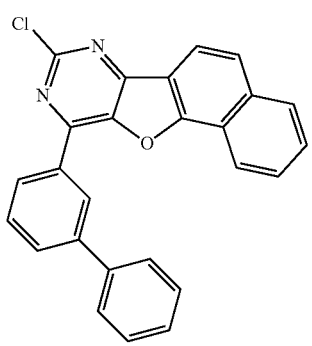
Sub 2-1-O-(22)
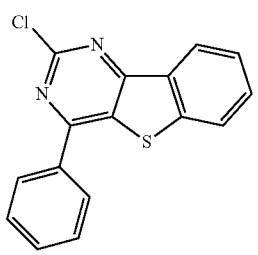
Sub 2-1-S-(1)
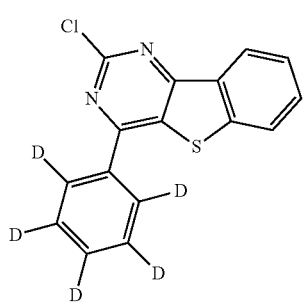
Sub 2-1-S-(2)
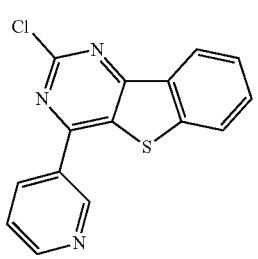
Sub 2-1-S-(3)
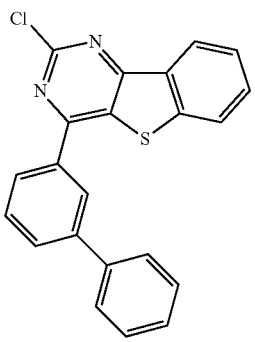
Sub 2-1-S-(4)
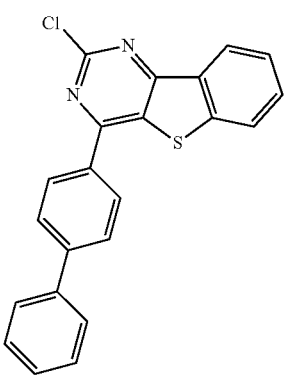
Sub 2-1-S-(5)
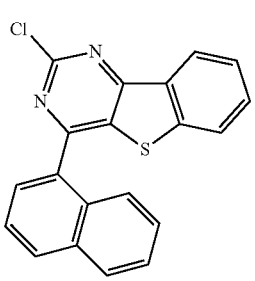
Sub 2-1-S-(6)
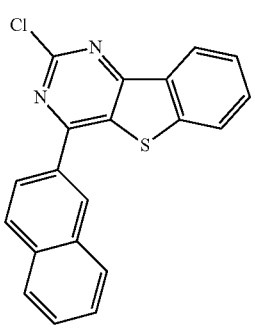
Sub 2-1-S-(7)
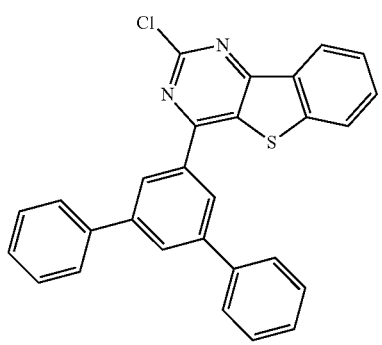
Sub 2-1-S-(8)

-continued
Sub 2-1-S-(9)
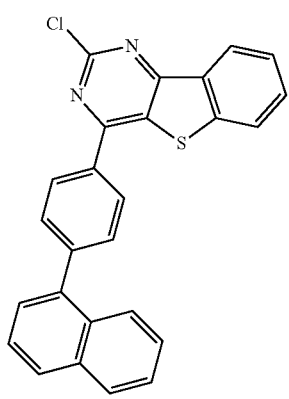
Sub 2-1-S-(10)
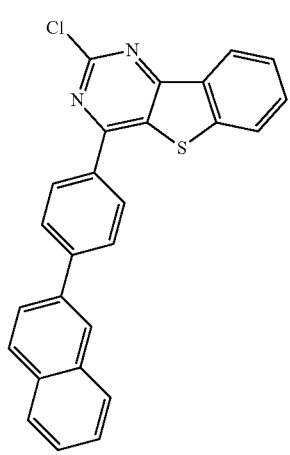
Sub 2-1-S-(11)
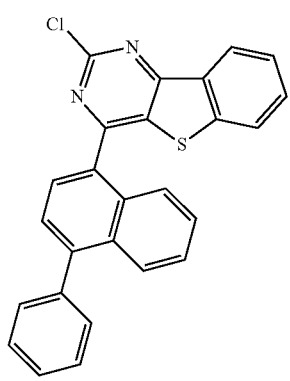
Sub 2-1-S-(12)
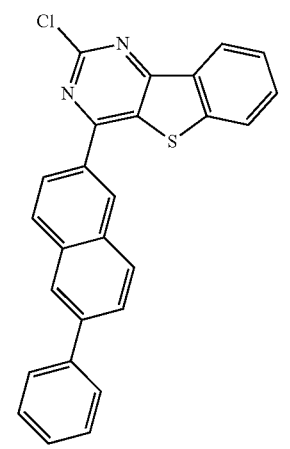
-continued
Sub 2-1-S-(13)
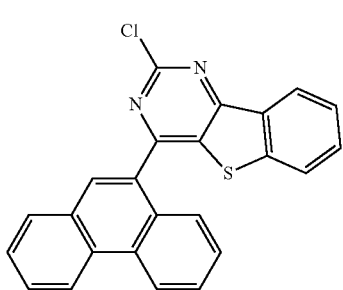
Sub 2-1-S-(14)
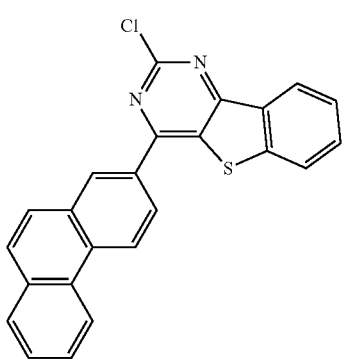
Sub 2-1-S-(15)
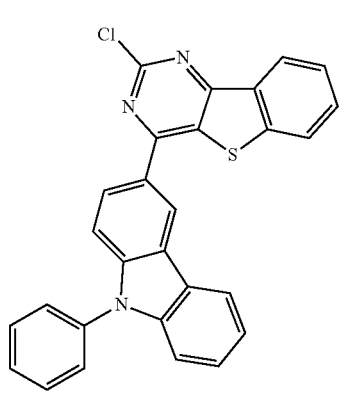
Sub 2-1-S-(16)
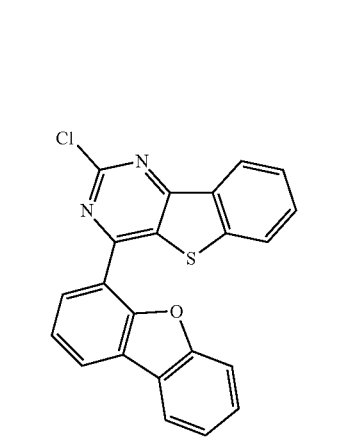

Sub 2-1-S-(17)
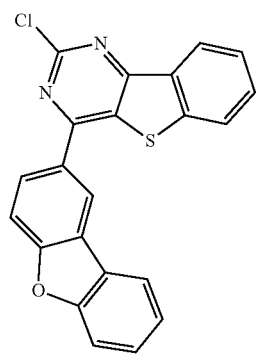
Sub 2-1-S-(18)
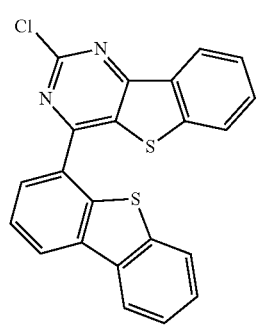
Sub 2-1-S-(19)
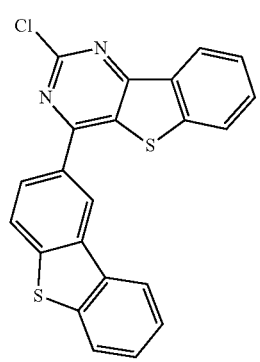
Sub 2-1-S-(20)
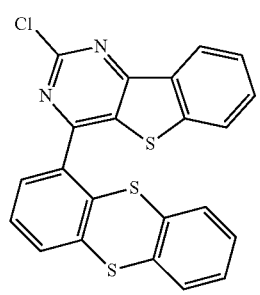
Sub 2-1-S-(21)
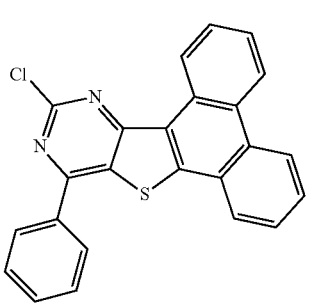
Sub 2-1-S-(22)
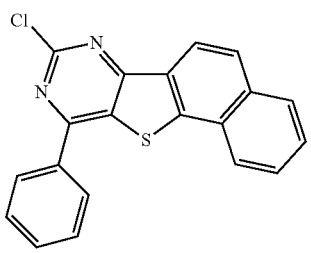
Sub 2-1-S-(23)
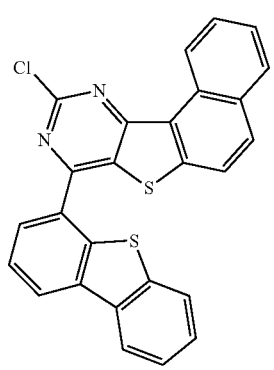
Sub 2-1-S-(24)
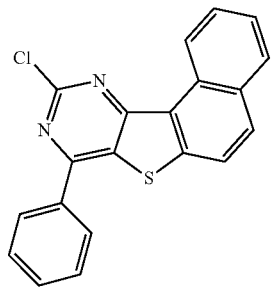
Sub 2-1-S-(25)
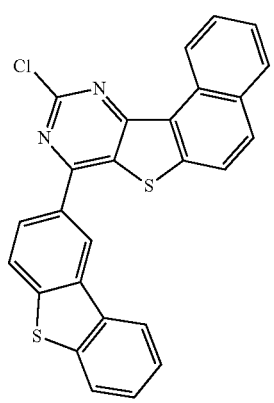
Sub 2-2-O-(1)
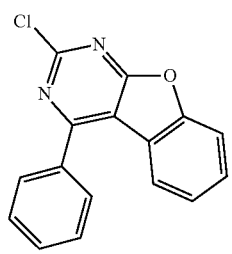

Sub 2-2-O-(2)
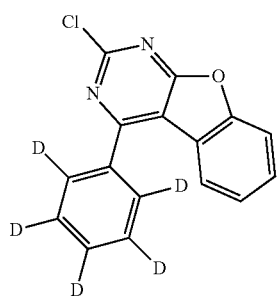
Sub 2-2-O-(3)
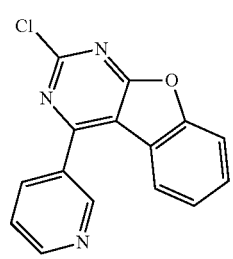
Sub 2-2-O-(4)
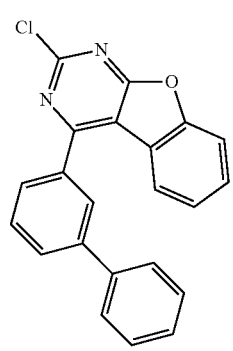
Sub 2-2-O-(5)
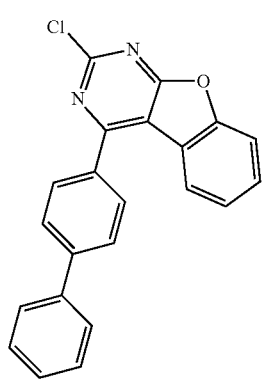
Sub 2-2-O-(6)
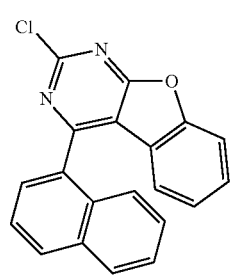
Sub 2-2-O-(7)
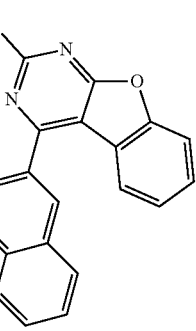
Sub 2-2-O-(8)
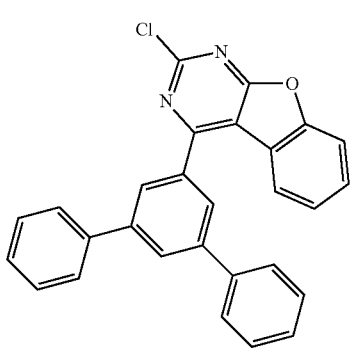
Sub 2-2-O-(9)
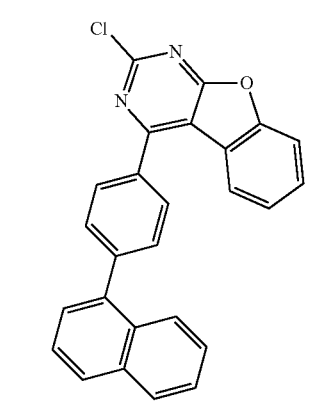
Sub 2-2-O-(10)
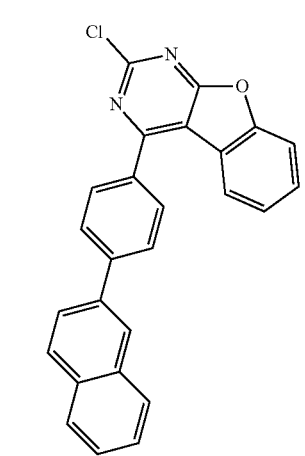

Sub 2-2-O-(11)
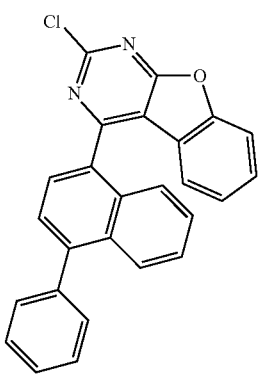
Sub 2-2-O-(12)
Sub 2-2-O-(13)
Sub 2-2-O-(14)
Sub 2-2-O-(15)
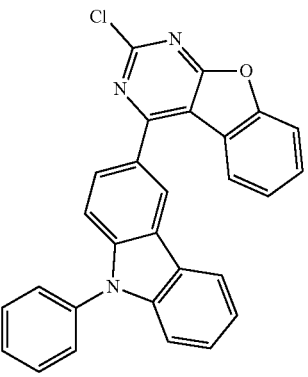
Sub 2-2-O-(16)
Sub 2-2-O-(17)
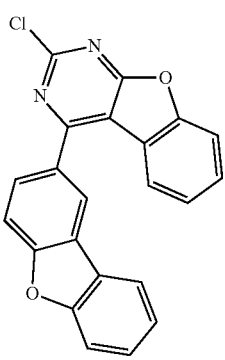
Sub 2-2-O-(18)
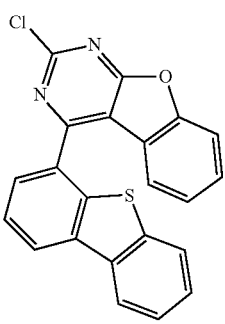

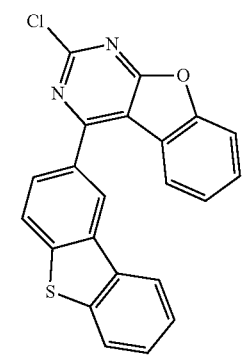
Sub 2-2-O-(19)
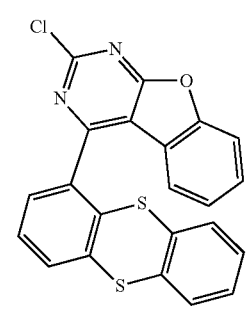
Sub 2-2-O-(20)
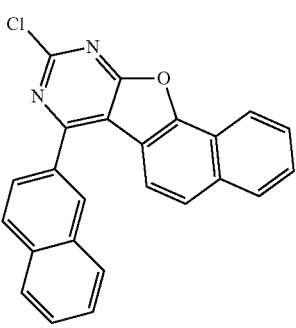
Sub 2-2-O-(21)
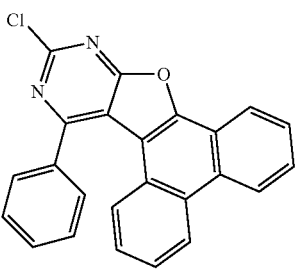
Sub 2-2-O-(22)
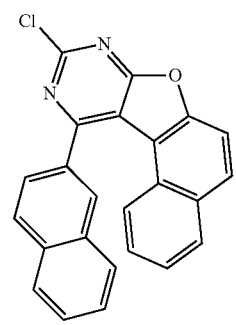
Sub 2-2-O-(23)
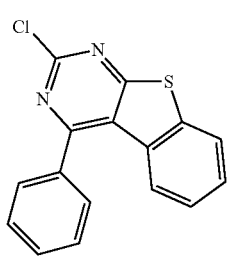
Sub 2-2-S-(1)
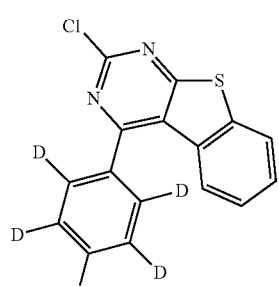
Sub 2-2-S-(2)
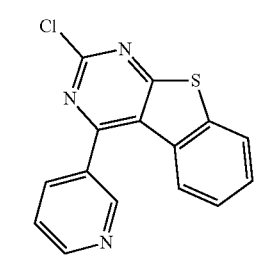
Sub 2-2-S-(3)
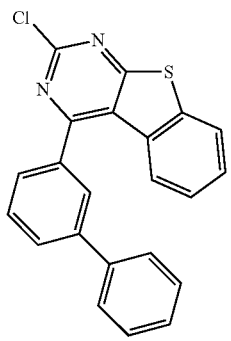
Sub 2-2-S-(4)
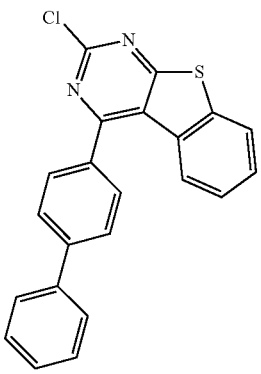
Sub 2-2-S-(5)

Sub 2-2-S-(6)
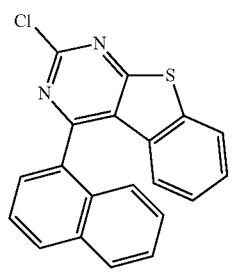
Sub 2-2-S-(7)
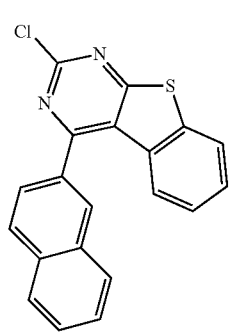
Sub 2-2-S-(8)
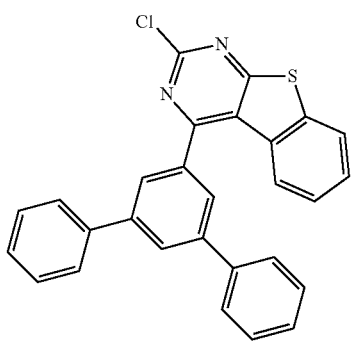
Sub 2-2-S-(9)
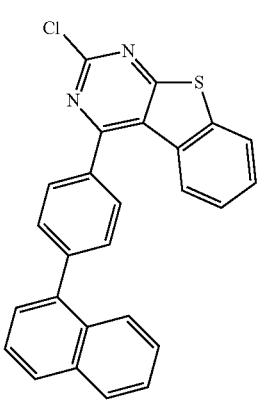
Sub 2-2-S-(10)
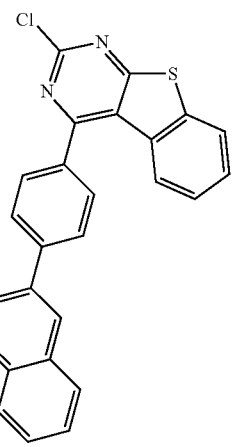
Sub 2-2-S-(11)
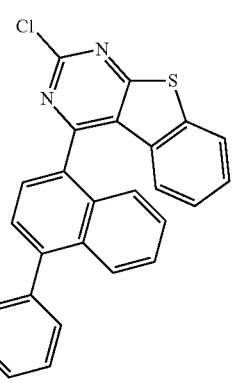
Sub 2-2-S-(12)
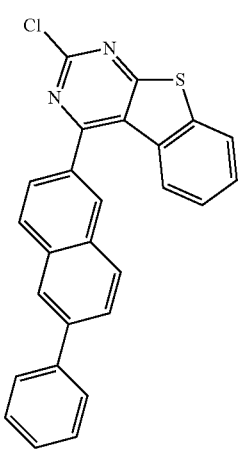
Sub 2-2-S-(13)
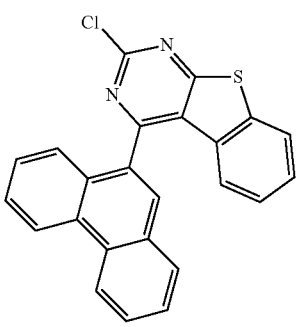

Sub 2-2-S-(14)
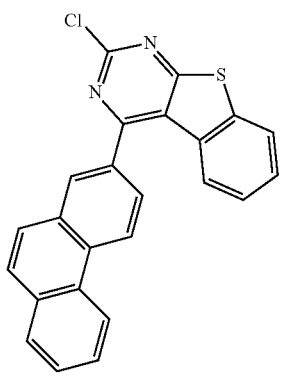
Sub 2-2-S-(15)
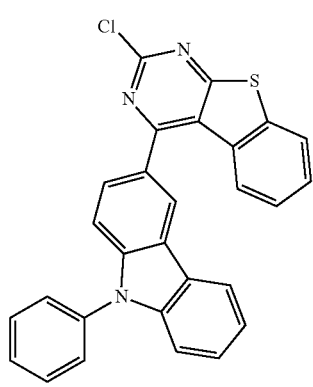
Sub 2-2-S-(16)
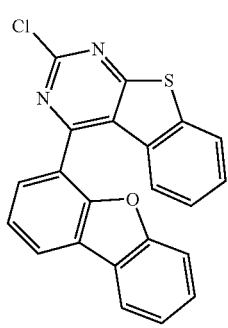
Sub 2-2-S-(17)
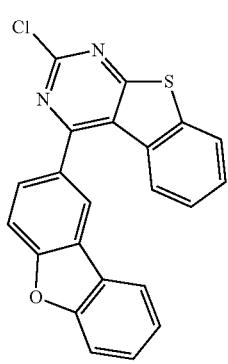
Sub 2-2-S-(18)
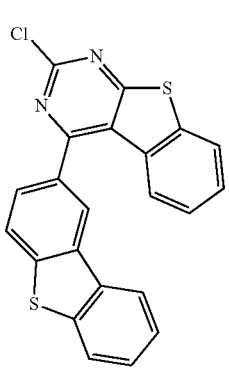
Sub 2-2-S-(19)
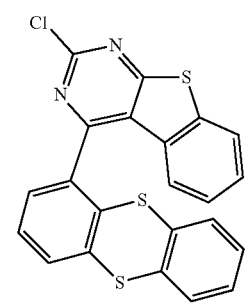
Sub 2-2-S-(20)
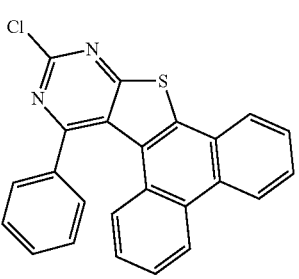
Sub 2-2-S-(21)

-continued

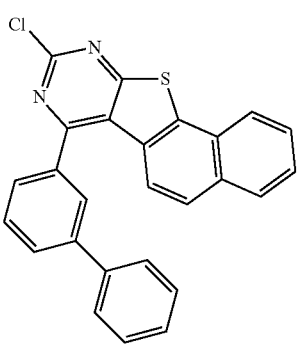

Sub 2-2-S-(22)

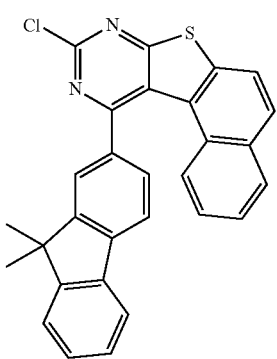

Sub 2-2-S-(23)

-continued

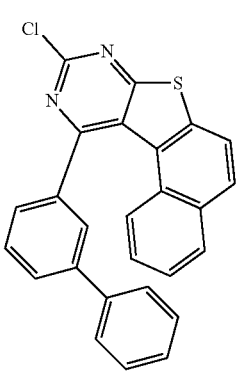

Sub 2-2-S-(24)

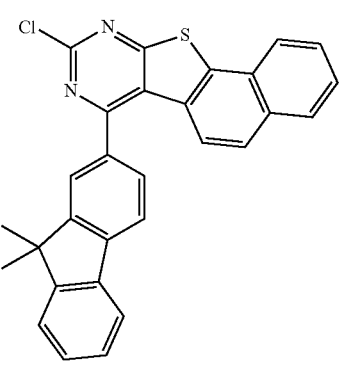

Sub 2-2-S-(25)

FD-MS data of the Sub 2 compounds are given in Table 2 below.

TABLE 2

| Compound | FD-MS | Compound | FD-MS |
| --- | --- | --- | --- |
| Sub 2-1-O-(1) | m/z = 280.04($C_{16}H_9ClN_2O$ = 280.71) | Sub 2-1-O-(2) | m/z = 285.07($C_{16}H_4D_5ClN_2O$ = 285.74) |
| Sub 2-1-O-(3) | m/z = 281.04($C_{15}H_8ClN_3O$ = 281.70) | Sub 2-1-O-(4) | m/z = 356.07($C_{22}H_{13}ClN_2O$ = 356.80) |
| Sub 2-1-O-(5) | m/z = 356.07($C_{22}H_{13}ClN_2O$ = 356.80) | Sub 2-1-O-(6) | m/z = 330.06($C_{20}H_{11}ClN_2O$ = 330.77) |
| Sub 2-1-O-(7) | m/z = 330.06($C_{20}H_{11}ClN_2O$ = 330.77) | Sub 2-1-O-(8) | m/z = 432.10($C_{28}H_{17}ClN_2O$ = 432.90) |
| Sub 2-1-O-(9) | m/z = 406.09($C_{26}H_{15}ClN_2O$ = 406.86) | Sub 2-1-O-(10) | m/z = 406.09($C_{26}H_{15}ClN_2O$ = 406.86) |
| Sub 2-1-O-(11) | m/z = 406.09($C_{26}H_{15}ClN_2O$ = 406.86) | Sub 2-1-O-(12) | m/z = 406.09($C_{26}H_{15}ClN_2O$ = 406.86) |
| Sub 2-1-O-(13) | m/z = 380.07($C_{24}H_{13}ClN_2O$ = 380.83) | Sub 2-1-O-(14) | m/z = 380.07($C_{24}H_{13}ClN_2O$ = 380.83) |
| Sub 2-1-O-(15) | m/z = 445.10($C_{28}H_{16}ClN_3O$ = 445.90) | Sub 2-1-O-(16) | m/z = 370.05($C_{22}H_{11}ClN_2O_2$ = 370.79) |
| Sub 2-1-O-(17) | m/z = 370.05($C_{22}H_{11}ClN_2O_2$ = 370.79) | Sub 2-1-O-(18) | m/z = 386.03($C_{22}H_{11}ClN_2OS$ = 386.85) |
| Sub 2-1-O-(19) | m/z = 386.03($C_{22}H_{11}ClN_2OS$ = 386.85) | Sub 2-1-O-(20) | m/z = 418.00($C_{22}H_{11}ClN_2OS_2$ = 418.92) |
| Sub 2-1-O-(21) | m/z = 330.06($C_{20}H_{11}ClN_2O$ = 330.77) | Sub 2-1-O-(22) | m/z = 406.09($C_{26}H_{15}ClN_2O$ = 406.86) |
| Sub 2-1-S-(1) | m/z = 296.02($C_{16}H_9ClN_2S$ = 296.77) | Sub 2-1-S-(2) | m/z = 301.05($C_{16}H_4D_5ClN_2S$ = 301.80) |
| Sub 2-1-S-(3) | m/z = 297.01($C_{15}H_8ClN_3S$ = 297.76) | Sub 2-1-S-(4) | m/z = 372.05($C_{22}H_{13}ClN_2S$ = 372.87) |
| Sub 2-1-S-(5) | m/z = 372.05($C_{22}H_{13}ClN_2S$ = 372.87) | Sub 2-1-S-(6) | m/z = 346.03($C_{20}H_{11}ClN_2S$ = 346.83) |
| Sub 2-1-S-(7) | m/z = 346.03($C_{20}H_{11}ClN_2S$ = 346.83) | Sub 2-1-S-(8) | m/z = 448.08($C_{28}H_{17}ClN_2S$ = 448.97) |
| Sub 2-1-S-(9) | m/z = 422.06($C_{26}H_{15}ClN_2S$ = 422.93) | Sub 2-1-S-(10) | m/z = 422.06($C_{26}H_{15}ClN_2S$ = 422.93) |
| Sub 2-1-S-(11) | m/z = 346.03($C_{20}H_{11}ClN_2S$ = 346.83) | Sub 2-1-S-(12) | m/z = 346.03($C_{20}H_{11}ClN_2S$ = 346.83) |
| Sub 2-1-S-(13) | m/z = 396.05($C_{24}H_{13}ClN_2S$ = 396.89) | Sub 2-1-S-(14) | m/z = 396.05($C_{24}H_{13}ClN_2S$ = 396.89) |
| Sub 2-1-S-(15) | m/z = 461.08($C_{28}H_{16}ClN_3S$ = 461.96) | Sub 2-1-S-(16) | m/z = 386.03($C_{22}H_{11}ClN_2OS$ = 386.85) |
| Sub 2-1-S-(17) | m/z = 386.03($C_{22}H_{11}ClN_2OS$ = 386.85) | Sub 2-1-S-(18) | m/z = 402.01($C_{22}H_{11}ClN_2S_2$ = 402.92) |
| Sub 2-1-S-(19) | m/z = 402.01($C_{22}H_{11}ClN_2S_2$ = 402.92) | Sub 2-1-S-(20) | m/z = 433.98($C_{22}H_{11}ClN_2S_3$ = 434.98) |
| Sub 2-1-S-(21) | m/z = 396.05($C_{24}H_{13}ClN_2S$ = 396.89) | Sub 2-1-S-(22) | m/z = 346.03($C_{20}H_{11}ClN_2S$ = 346.83) |
| Sub 2-1-S-(23) | m/z = 452.02($C_{26}H_{13}ClN_2S_2$ = 452.98) | Sub 2-1-S-(24) | m/z = 346.03($C_{20}H_{11}ClN_2S$ = 346.83) |
| Sub 2-1-S-(25) | m/z = 452.02($C_{26}H_{13}ClN_2S_2$ = 452.98) | | |
| Sub 2-2-O-(1) | m/z = 280.04($C_{16}H_9ClN_2O$ = 280.71) | Sub 2-2-O-(2) | m/z = 285.07($C_{16}H_4D_5ClN_2O$ = 285.74) |
| Sub 2-2-O-(3) | m/z = 281.04($C_{15}H_8ClN_3O$ = 281.70) | Sub 2-2-O-(4) | m/z = 356.07($C_{22}H_{13}ClN_2O$ = 356.80) |
| Sub 2-2-O-(5) | m/z = 356.07($C_{22}H_{13}ClN_2O$ = 356.80) | Sub 2-2-O-(6) | m/z = 330.06($C_{20}H_{11}ClN_2O$ = 330.77) |
| Sub 2-2-O-(7) | m/z = 330.06($C_{20}H_{11}ClN_2O$ = 330.77) | Sub 2-2-O-(8) | m/z = 432.10($C_{28}H_{17}ClN_2O$ = 432.90) |
| Sub 2-2-O-(9) | m/z = 406.09($C_{26}H_{15}ClN_2O$ = 406.86) | Sub 2-2-O-(10) | m/z = 406.09($C_{26}H_{15}ClN_2O$ = 406.86) |
| Sub 2-2-O-(11) | m/z = 406.09($C_{26}H_{15}ClN_2O$ = 406.86) | Sub 2-2-O-(12) | m/z = 406.09($C_{26}H_{15}ClN_2O$ = 406.86) |
| Sub 2-2-O-(13) | m/z = 380.07($C_{24}H_{13}ClN_2O$ = 380.83) | Sub 2-2-O-(14) | m/z = 380.07($C_{24}H_{13}ClN_2O$ = 380.83) |
| Sub 2-2-O-(15) | m/z = 445.10($C_{28}H_{16}ClN_3O$ = 445.90) | Sub 2-2-O-(16) | m/z = 370.05($C_{22}H_{11}ClN_2O_2$ = 370.79) |
| Sub 2-2-O-(17) | m/z = 370.05($C_{22}H_{11}ClN_2O_2$ = 370.79) | Sub 2-2-O-(18) | m/z = 386.03($C_{22}H_{11}ClN_2OS$ = 386.85) |
| Sub 2-2-O-(19) | m/z = 386.03($C_{22}H_{11}ClN_2OS$ = 386.85) | Sub 2-2-O-(20) | m/z = 418.00($C_{22}H_{11}ClN_2OS_2$ = 418.92) |
| Sub 2-2-O-(21) | m/z = 380.07($C_{24}H_{13}ClN_2O$ = 380.83) | Sub 2-2-O-(22) | m/z = 380.07($C_{24}H_{13}ClN_2O$ = 380.83) |
| Sub 2-2-O-(23) | m/z = 380.07($C_{24}H_{13}ClN_2O$ = 380.83) | | |

TABLE 2-continued

| Compound | FD-MS | Compound | FD-MS |
|---|---|---|---|
| Sub 2-2-S-(1) | m/z = 296.02($C_{16}H_9ClN_2S$ = 296.77) | Sub 2-2-S-(2) | m/z = 301.05($C_{16}H_4D_5ClN_2S$ = 301.80) |
| Sub 2-2-S-(3) | m/z = 297.01($C_{15}H_8ClN_3S$ = 297.76) | Sub 2-2-S-(4) | m/z = 372.05($C_{22}H_{13}ClN_2S$ = 372.87) |
| Sub 2-2-S-(5) | m/z = 372.05($C_{22}H_{13}ClN_2S$ = 372.87) | Sub 2-2-S-(6) | m/z = 346.03($C_{20}H_{11}ClN_2S$ = 346.83) |
| Sub 2-2-S-(7) | m/z = 346.03($C_{20}H_{11}ClN_2S$ = 346.83) | Sub 2-2-S-(8) | m/z = 448.08($C_{28}H_{17}ClN_2S$ = 448.97) |
| Sub 2-2-S-(9) | m/z = 422.06($C_{26}H_{15}ClN_2S$ = 422.93) | Sub 2-2-S-(10) | m/z = 422.06($C_{26}H_{15}ClN_2S$ = 422.93) |
| Sub 2-2-S-(11) | m/z = 346.03($C_{20}H_{11}ClN_2S$ = 346.83) | Sub 2-2-S-(12) | m/z = 346.03($C_{20}H_{11}ClN_2S$ = 346.83) |
| Sub 2-2-S-(13) | m/z = 396.05($C_{24}H_{13}ClN_2S$ = 396.89) | Sub 2-2-S-(14) | m/z = 396.05($C_{24}H_{13}ClN_2S$ = 396.89) |
| Sub 2-2-S-(15) | m/z = 461.08($C_{28}H_{16}ClN_3S$ = 461.96) | Sub 2-2-S-(16) | m/z = 386.03($C_{22}H_{11}ClN_2OS$ = 386.85) |
| Sub 2-2-S-(17) | m/z = 386.03($C_{22}H_{11}ClN_2OS$ = 386.85) | Sub 2-2-S-(18) | m/z = 402.01($C_{22}H_{11}ClN_2S_2$ = 402.92) |
| Sub 2-2-S-(19) | m/z = 402.01($C_{22}H_{11}ClN_2S_2$ = 402.92) | Sub 2-2-S-(20) | m/z = 433.98($C_{22}H_{11}ClN_2S_3$ = 434.98) |
| Sub 2-2-S-(21) | m/z = 396.05($C_{24}H_{13}ClN_2S$ = 396.89) | Sub 2-2-S-(22) | m/z = 422.06($C_{26}H_{15}ClN_2S$ = 422.93) |
| Sub 2-2-S-(23) | m/z = 462.10($C_{29}H_{19}ClN_2S$ = 462.99) | Sub 2-2-S-(24) | m/z = 422.06($C_{26}H_{15}ClN_2S$ = 422.93) |
| Sub 2-2-S-(25) | m/z = 462.10($C_{29}H_{19}ClN_2S$ = 462.99) | | |

III. Synthesis of Final Product

To a solution of Sub 1 (1 eq.), Sub 2 (1.2 eq.), $Pd_2(dba)_3$ (4 mol %), t-$Bu_3P$ (8 mol %), and KOtBu (3 eq.) were dissolved in toluene, followed by reflux at 100° C. for 12 hours. Upon completion of the reaction, the temperature of the reaction product was lowered to room temperature, the reaction product was extracted with $CH_2Cl_2$, and was washed with water. The extracted organic layer was dried with $MgSO_4$ and concentrated, and then the produced organic material was separated by a silica gel column chromatography, and recrystallized to obtain the final product.

1. Final Product 1 Synthesis (1) 1-1-1-O-(1) Synthesis

To a solution of Sub 1-1 (5 g, 15.46 mmol), Sub 2-1-O-(1) (5.2 g, 18.55 mmol), $Pd_2(dba)_3$ (0.56 g, 4 mol %), t-$Bu_3P$ (0.25 g, 8 mol %) and KOtBu (5.2 g, 46.38 mmol) were dissolved in toluene, followed by reflux at 100° C. for 12 hours. Upon completion of the reaction, the temperature of the reaction product was lowered to room temperature, the reaction product was extracted with $CH_2Cl_2$, and was washed with water. The extracted organic layer was dried with $MgSO_4$ and concentrated, and then the produced organic material was separated by a silica gel column chromatography, and recrystallized to obtain Compound 1-1-1-O-(1) (7.28 g, yield 83%).

(2) 1-1-1-O-(2) Synthesis

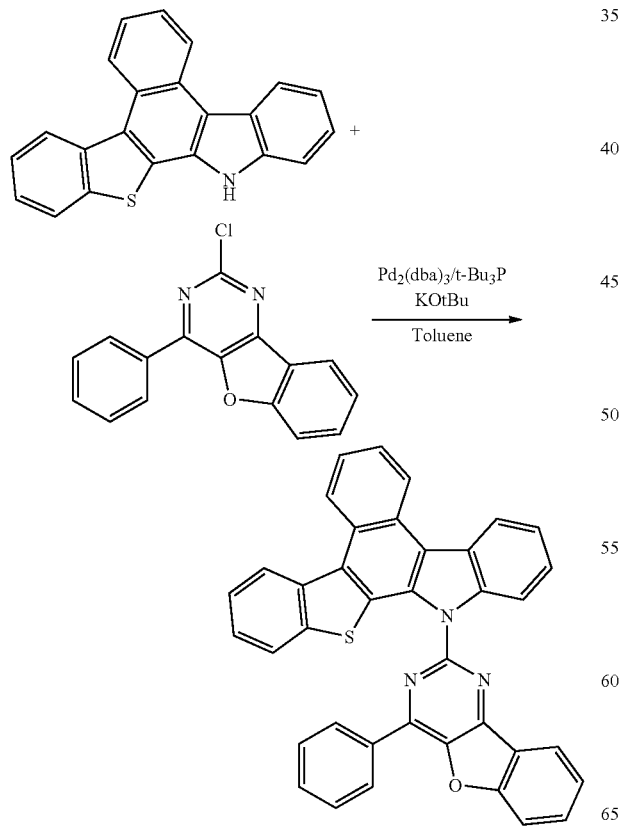

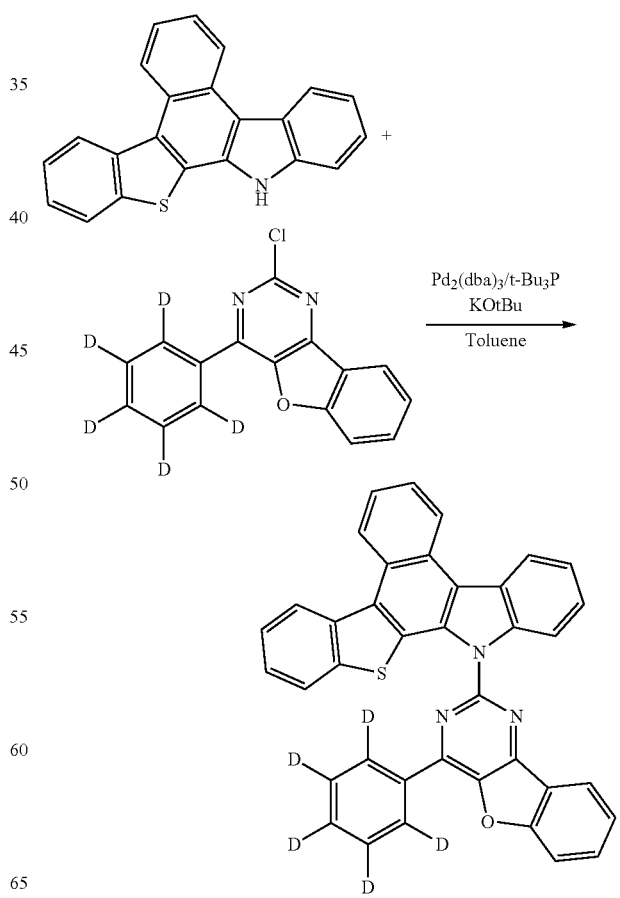

Except for using Sub 1-1 (5 g, 15.46 mmol), Sub 2-1-O-(2) (5.3 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-O-(2) (7.52 g, yield 85%).

(3) 1-1-1-O-(3) Synthesis

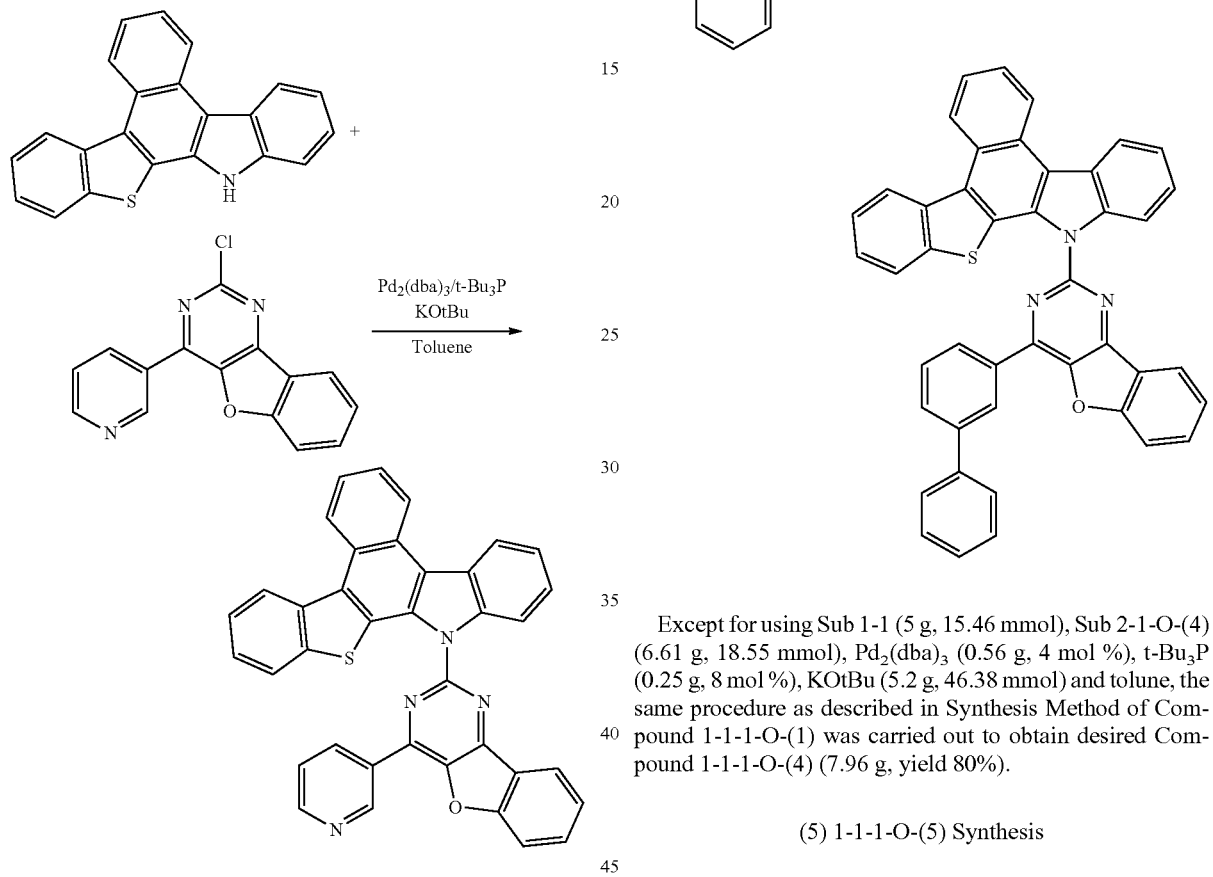

Except for using Sub 1-1 (5 g, 15.46 mmol), Sub 2-1-O-(3) (5.3 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-O-(3) (7.12 g, yield 81%).

(4) 1-1-1-O-(4) Synthesis

Except for using Sub 1-1 (5 g, 15.46 mmol), Sub 2-1-O-(4) (6.61 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-O-(4) (7.96 g, yield 80%).

(5) 1-1-1-O-(5) Synthesis

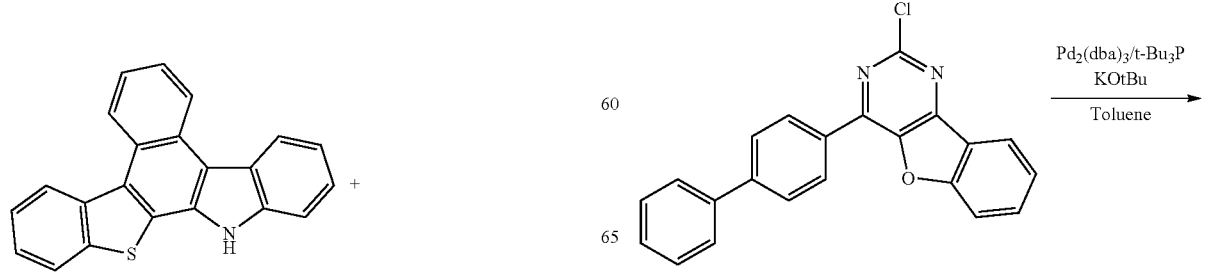

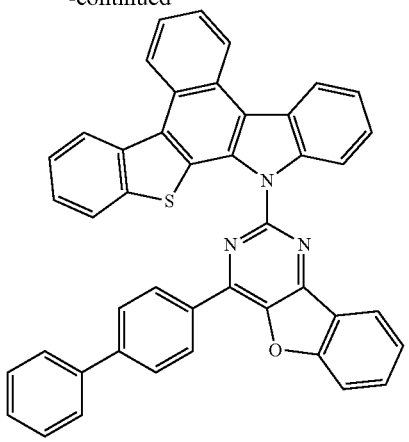

Except for using Sub 1-1 (5 g, 15.46 mmol), Sub 2-1-O-(5) (6.61 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-O-(5) (8.26 g, yield 83%).

(6) 1-1-1-S-(6) Synthesis

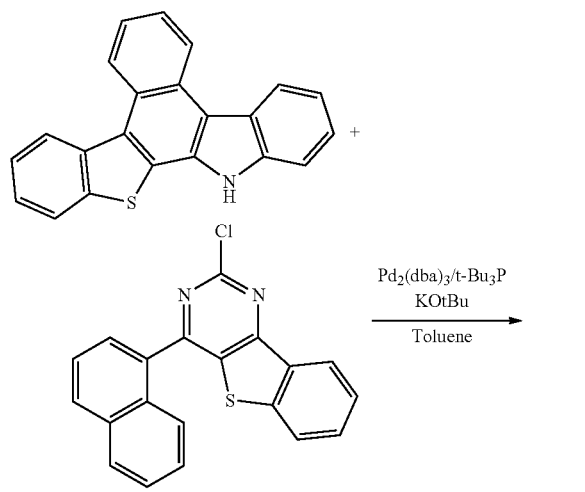

Except for using Sub 1-1 (5 g, 15.46 mmol), Sub 2-1-S-(6) (6.43 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-S-(6) (7.34 g, yield 75%).

(7) 1-1-1-S-(7) Synthesis

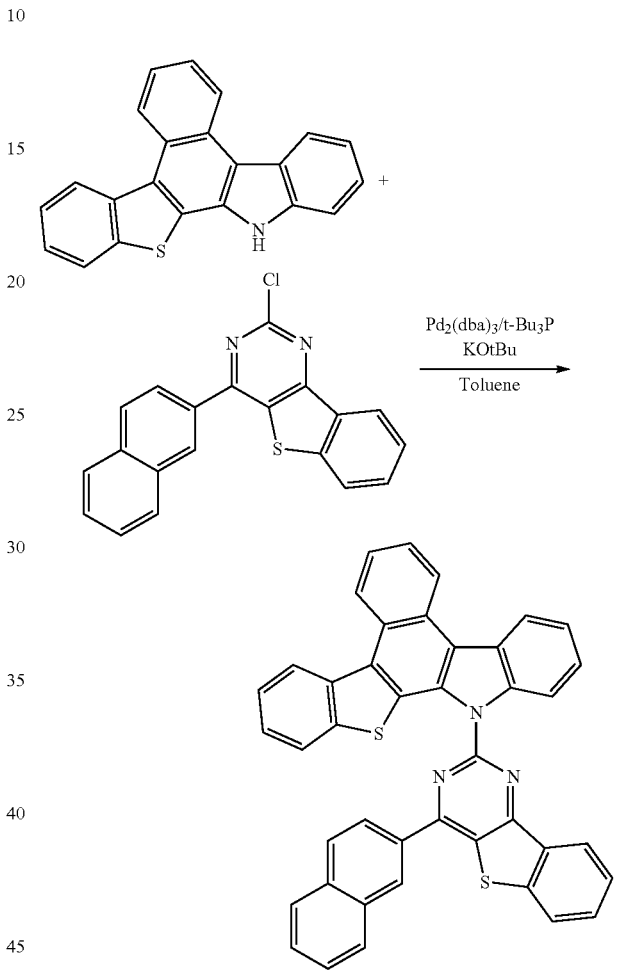

Except for using Sub 1-1 (5 g, 15.46 mmol), Sub 2-1-S-(7) (6.43 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-S-(7) (7.05 g, yield 72%).

(8) 1-1-1-S-(8) Synthesis

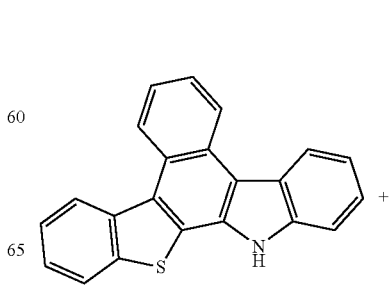

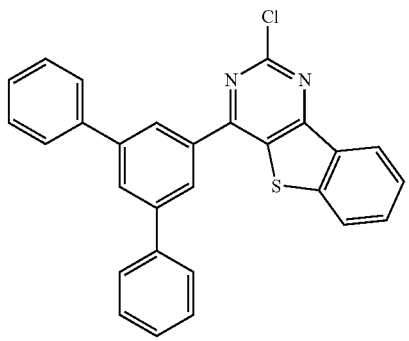

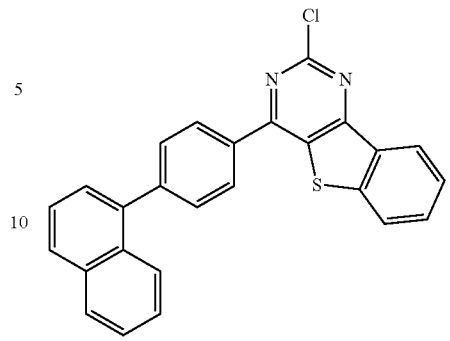

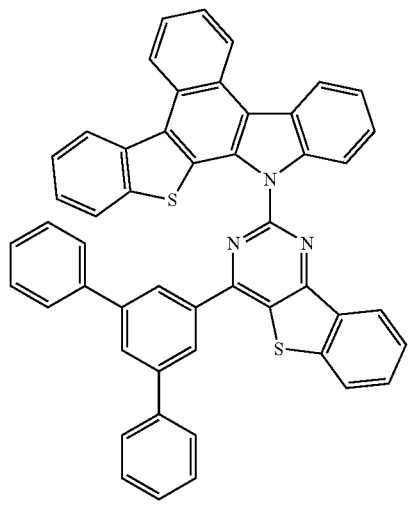

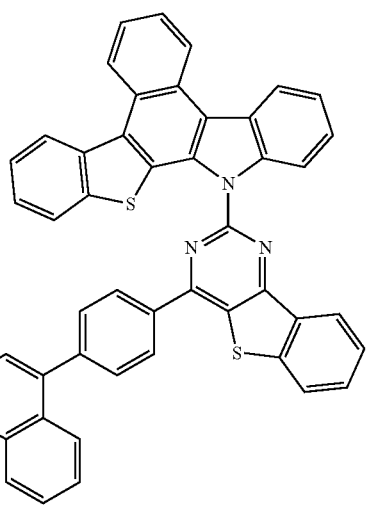

Except for using Sub 1-1 (5 g, 15.46 mmol), Sub 2-1-S-(9) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-S-(9) (8.45 g, yield 77%).

(10) 1-1-1-S-(10) Synthesis

Except for using Sub 1-1 (5 g, 15.46 mmol), Sub 2-1-S-(8) (8.32 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-S-(8) (9.1 g, yield 80%).

(9) 1-1-1-S-(9) Synthesis

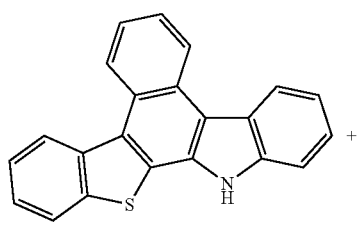

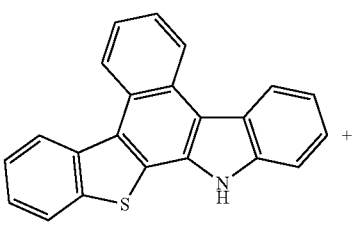

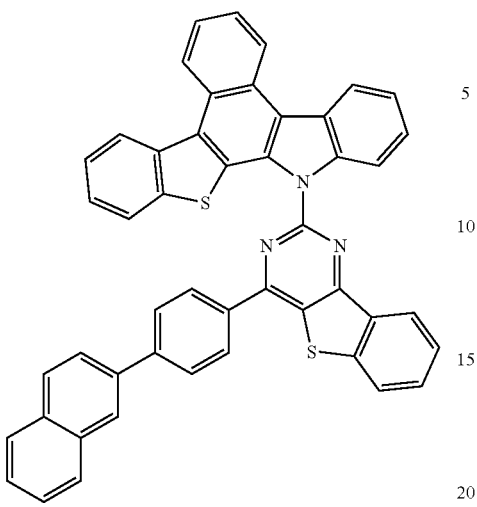

Except for using Sub 1-1 (5 g, 15.46 mmol), Sub 2-1-S-(10) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-1-S-(10) (8.88 g, yield 81%).

(11) 1-1-2-O-(11) Synthesis

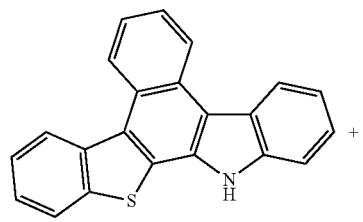

Except for using Sub 1-1 (5 g, 15.46 mmol), Sub 2-2-O-(11) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-O-(11) (8.58 g, yield 80%).

(12) 1-1-2-O-(12) Synthesis

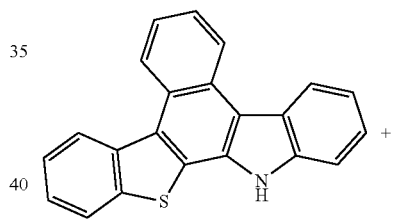

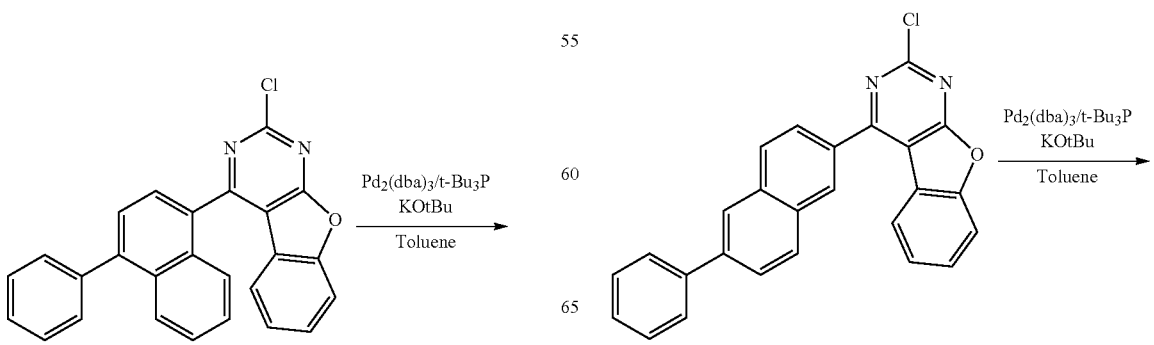

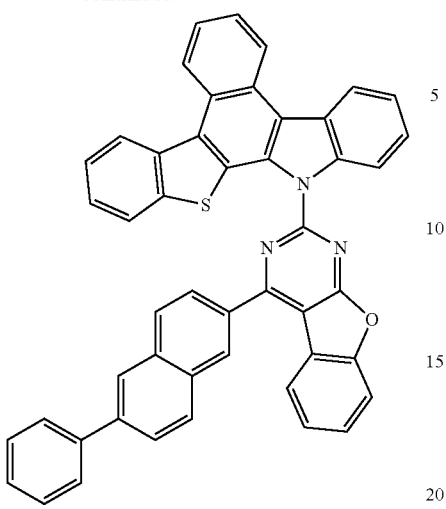

Except for using Sub 1-1 (5 g, 15.46 mmol), Sub 2-2-O-(12) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-O-(12) (7.83 g, yield 73%).

(13) 1-1-2-O-(13) Synthesis

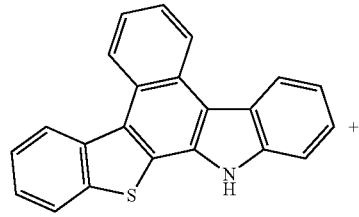

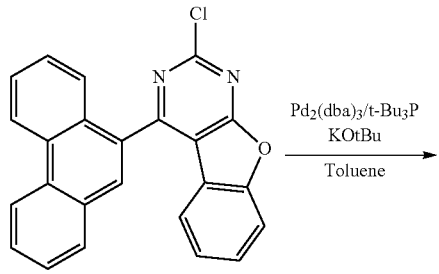

Except for using Sub 1-1 (5 g, 15.46 mmol), Sub 2-2-O-(13) (7.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-O-(13) (7.74 g, yield 75%).

(14) 1-1-2-O-(14) Synthesis

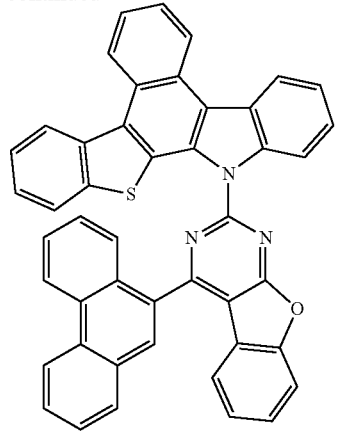

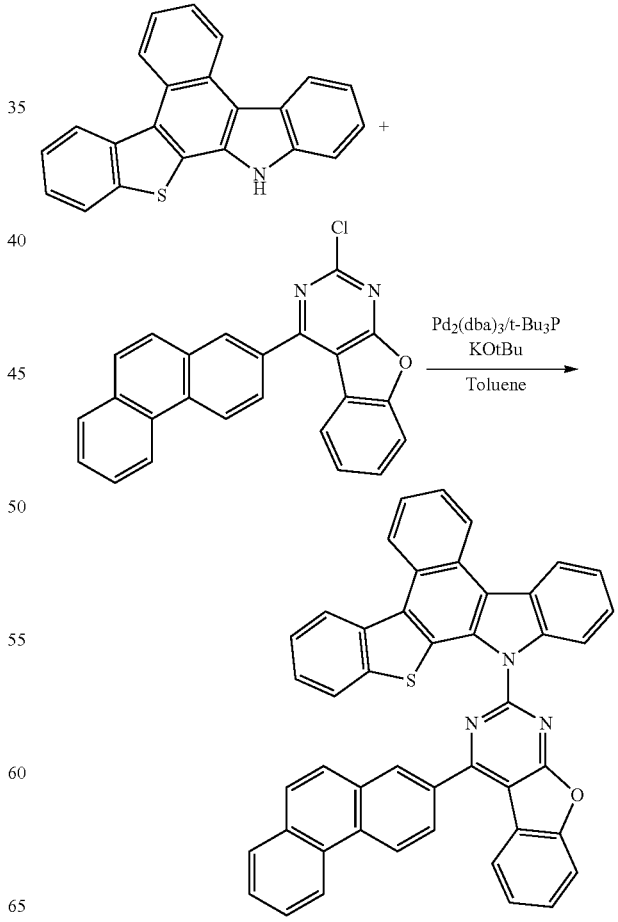

Except for using Sub 1-1 (5 g, 15.46 mmol), Sub 2-2-O-(14) (7.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-O-(14) (8.36 g, yield 81%).

(15) 1-1-2-O-(15) Synthesis

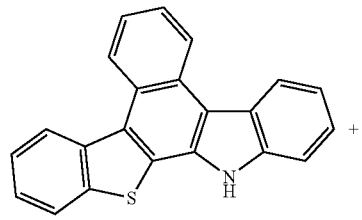

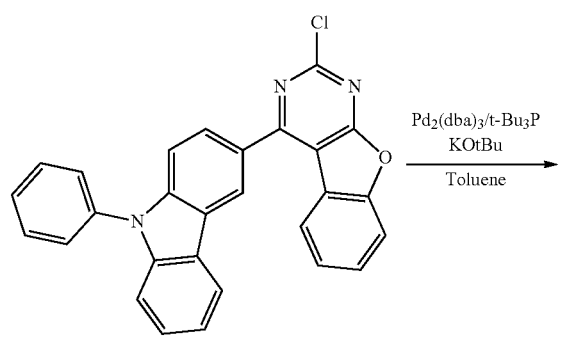

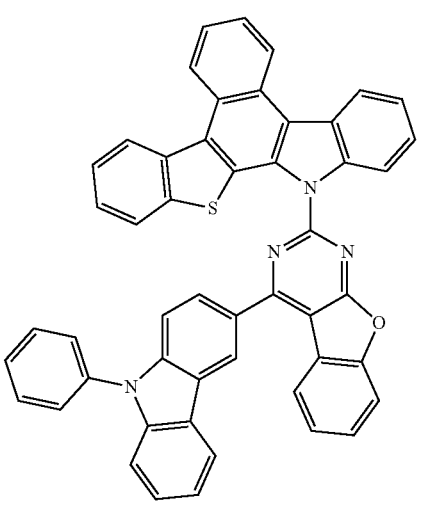

Except for using Sub 1-1 (5 g, 15.46 mmol), Sub 2-2-O-(15) (8.27 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-O-(15) (7.93 g, yield 70%).

(16) 1-1-2-S-(16) Synthesis

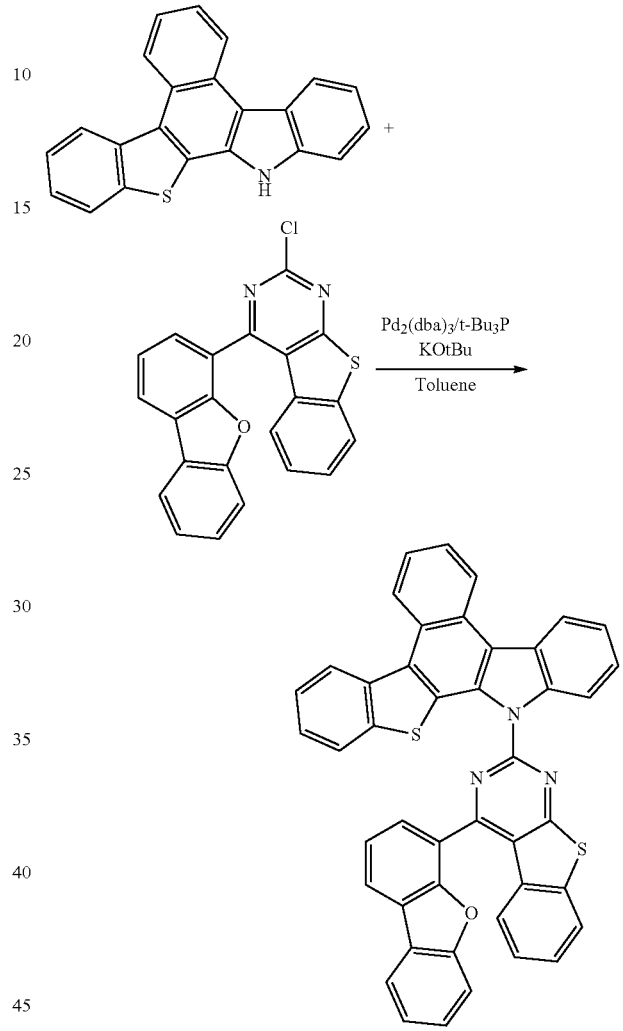

Except for using Sub 1-1 (5 g, 15.46 mmol), Sub 2-2-S-(16) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-S-(16) (7.5 g, yield 72%).

(17) 1-1-2-S-(17) Synthesis

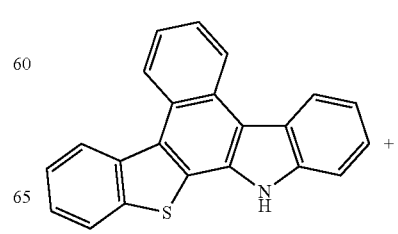

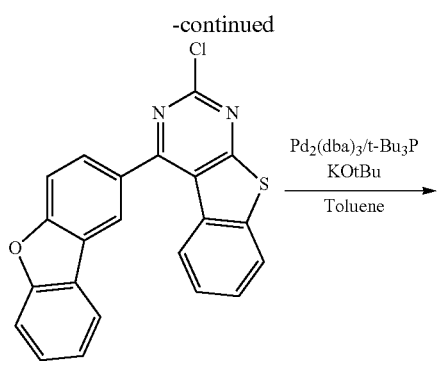

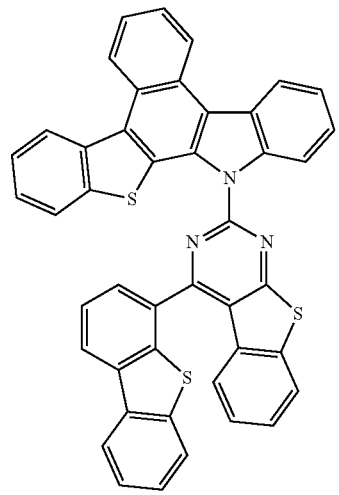

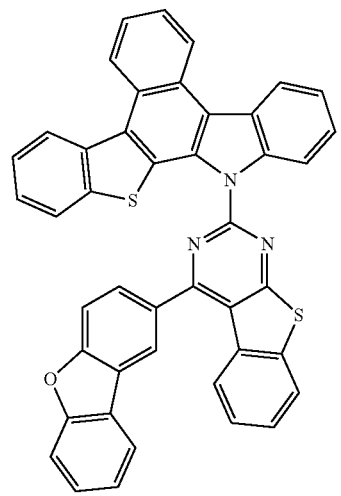

Except for using Sub 1-1 (5 g, 15.46 mmol), Sub 2-2-S-(18) (7.47 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-S-(18) (8.42 g, yield 79%).

(19) 1-1-2-S-(19) Synthesis

Except for using Sub 1-1 (5 g, 15.46 mmol), Sub 2-2-S-(17) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-S-(17) (7.7 g, yield 74%).

(18) 1-1-2-S-(18) Synthesis

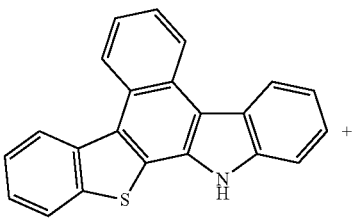

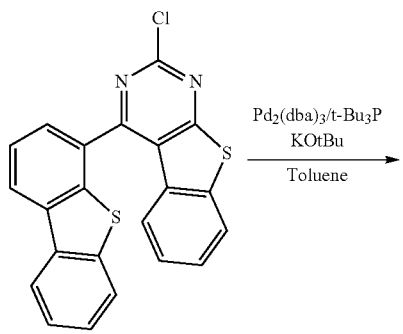

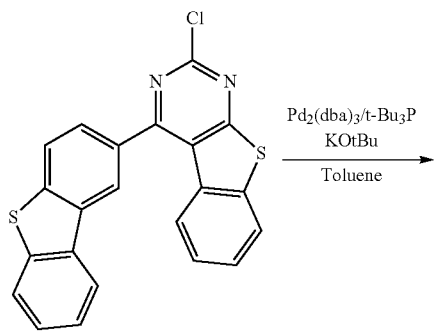

-continued

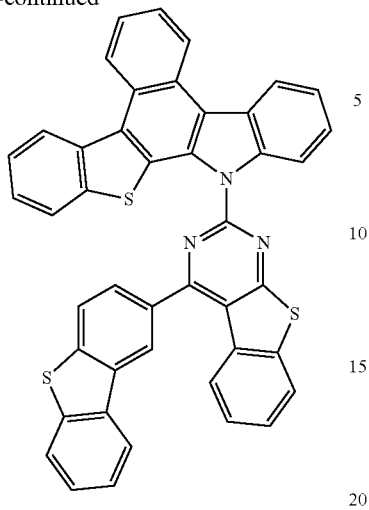

Except for using Sub 1-1 (5 g, 15.46 mmol), Sub 2-2-S-(19) (7.47 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-S-(19) (8.1 g, yield 76%).

(20) 1-1-2-S-(20) Synthesis

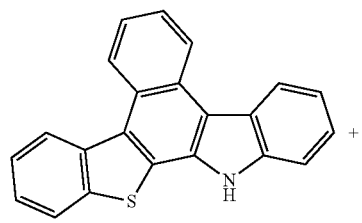

+

-continued

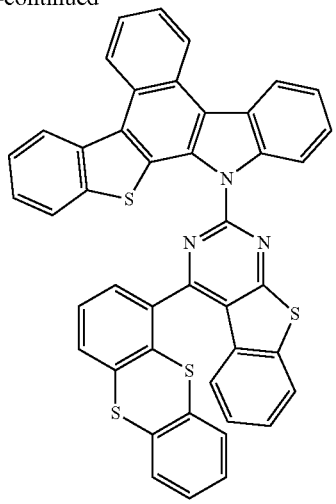

Except for using Sub 1-1 (5 g, 15.46 mmol), Sub 2-2-S-(20) (8.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-1-2-S-(20) (8.92 g, yield 80%).

2. Final Product 2 Synthesis (1) 1-2-1-O-(6) Synthesis

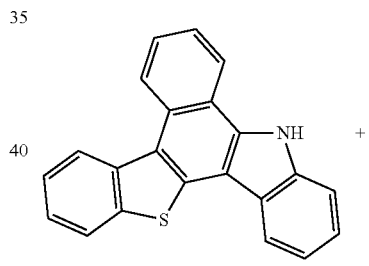

+

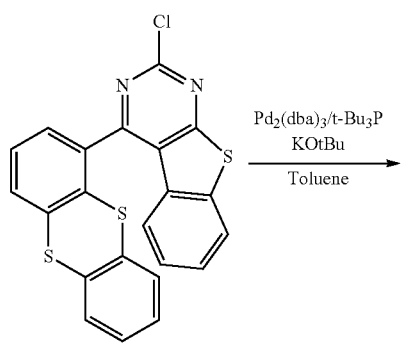

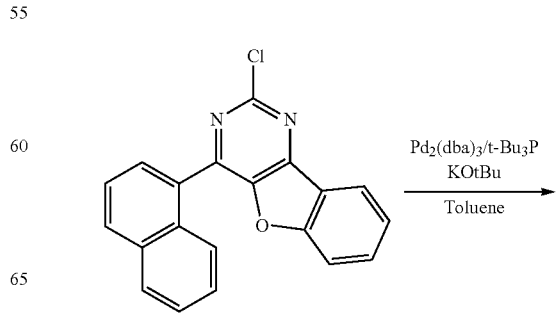

-continued

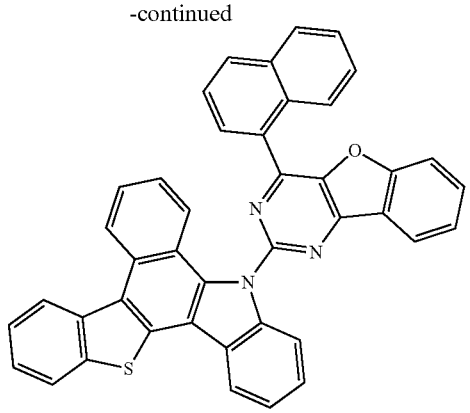

Except for using Sub 1-2 (5 g, 15.46 mmol), Sub 2-2-S-(20) (8.06 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-O-(6) (7.06 g, yield 74%).

(2) 1-2-1-O-(7) Synthesis

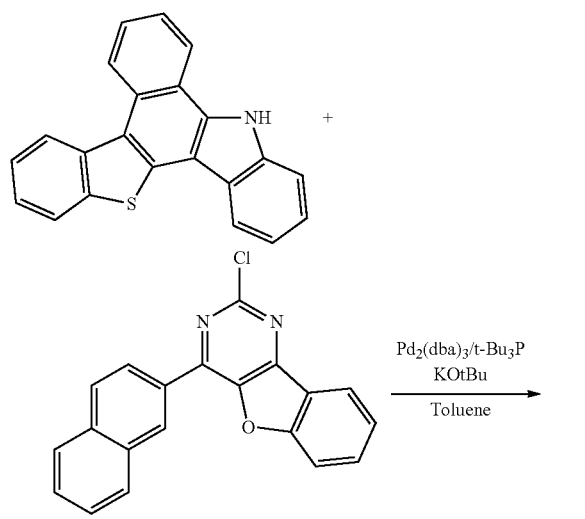

Except for using Sub 1-2 (5 g, 15.46 mmol), Sub 2-1-O-(7) (6.13 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-O-(7) (6.78 g, yield 71%).

(3) 1-2-1-O-(8) Synthesis

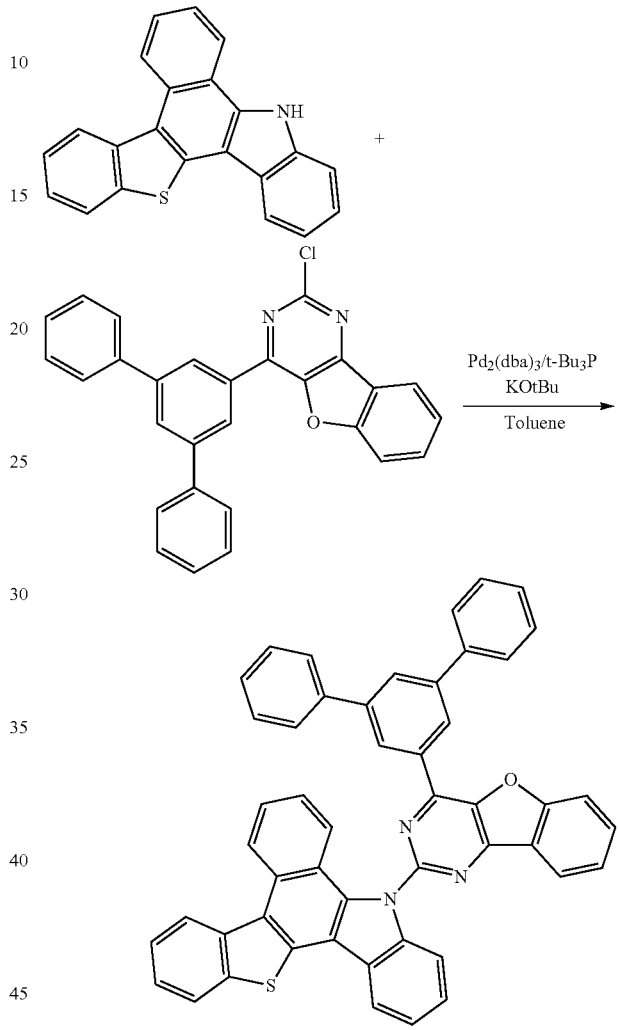

Except for using Sub 1-2 (5 g, 15.46 mmol), Sub 2-1-O-(8) (8.03 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-O-(8) (7.79 g, yield 70%).

(4) 1-2-1-O-(9) Synthesis

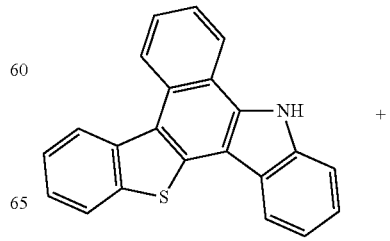

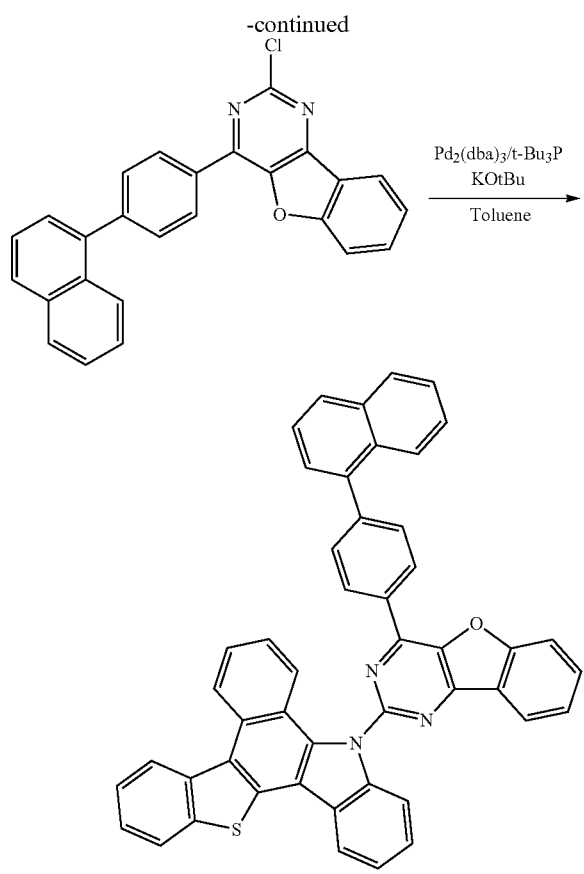

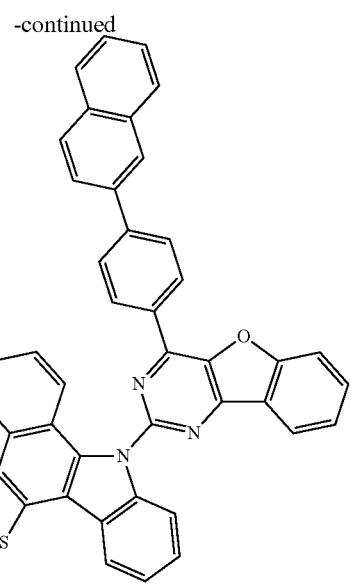

Except for using Sub 1-2 (5 g, 15.46 mmol), Sub 2-1-O-(9) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-O-(9) (8.25 g, yield 77%).

(5) 1-2-1-O-(10) Synthesis

Except for using Sub 1-2 (5 g, 15.46 mmol), Sub 2-1-O-(10) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-O-(10) (8.36 g, yield 78%).

(6) 1-2-1-S-(11) Synthesis

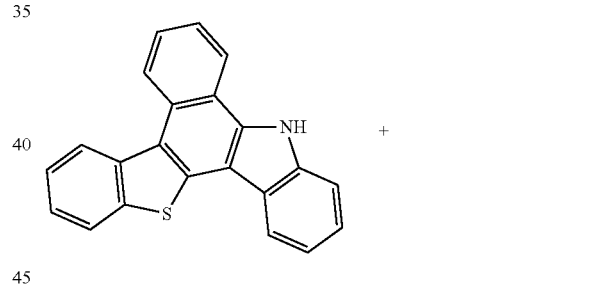

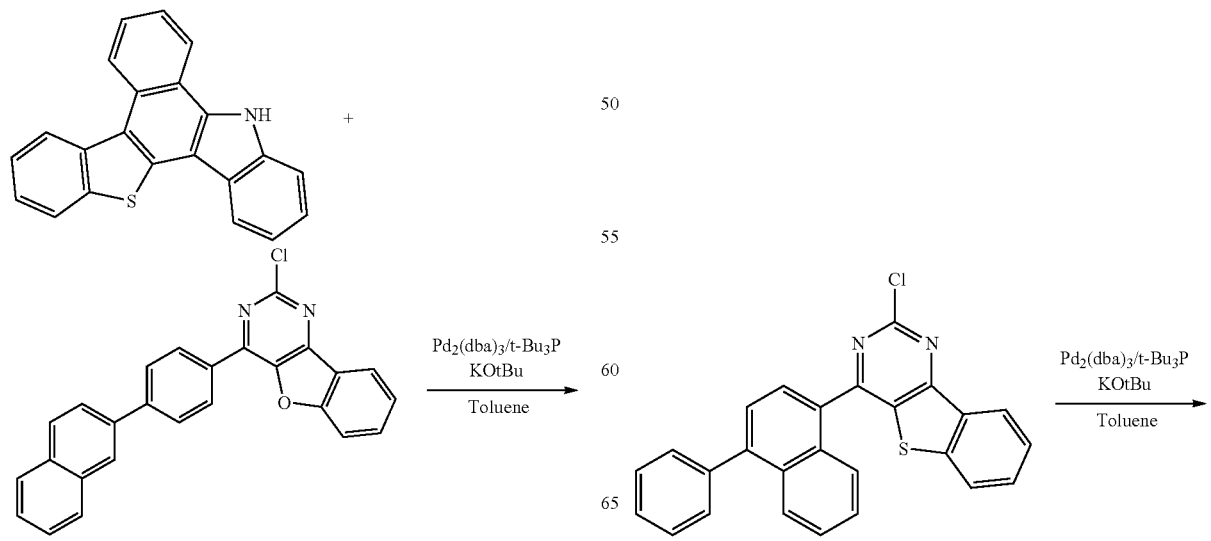

-continued

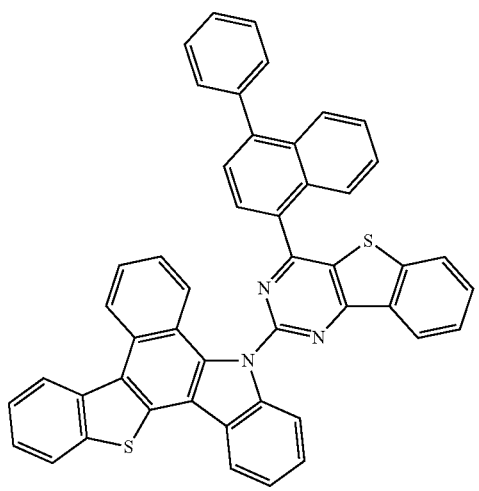

Except for using Sub 1-2 (5 g, 15.46 mmol), Sub 2-1-S-(11) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-S-(11) (8.88 g, yield 81%).

(7) 1-2-1-S-(12) Synthesis

-continued

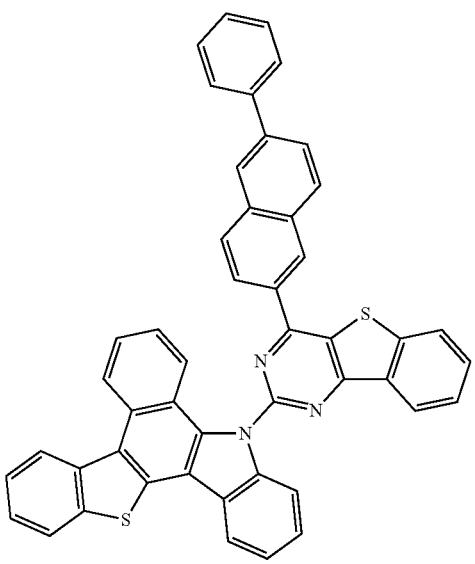

Except for using Sub 1-2 (5 g, 15.46 mmol), Sub 2-1-S-(12) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-S-(12) (7.79 g, yield 71%).

(8) 1-2-1-S-(13) Synthesis

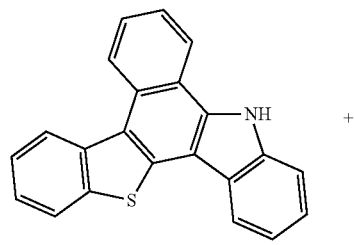

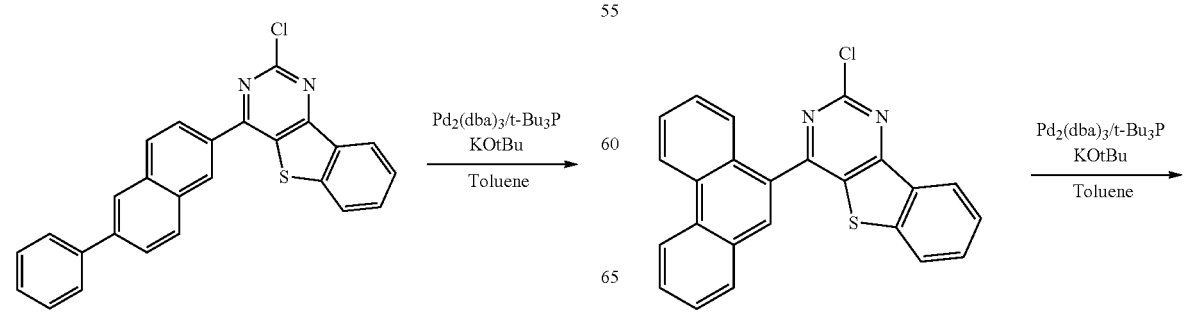

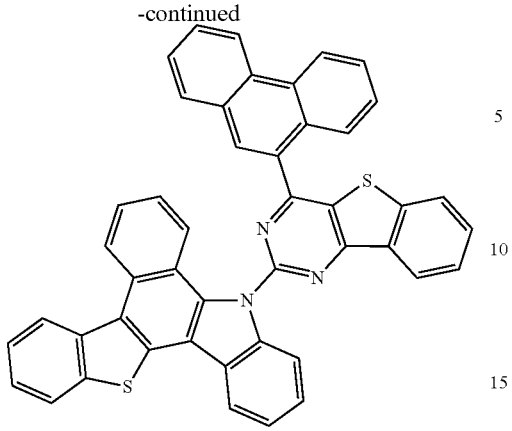

Except for using Sub 1-2 (5 g, 15.46 mmol), Sub 2-1-S-(13) (7.36 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-S-(13) (7.29 g, yield 69%).

(9) 1-2-1-S-(14) Synthesis

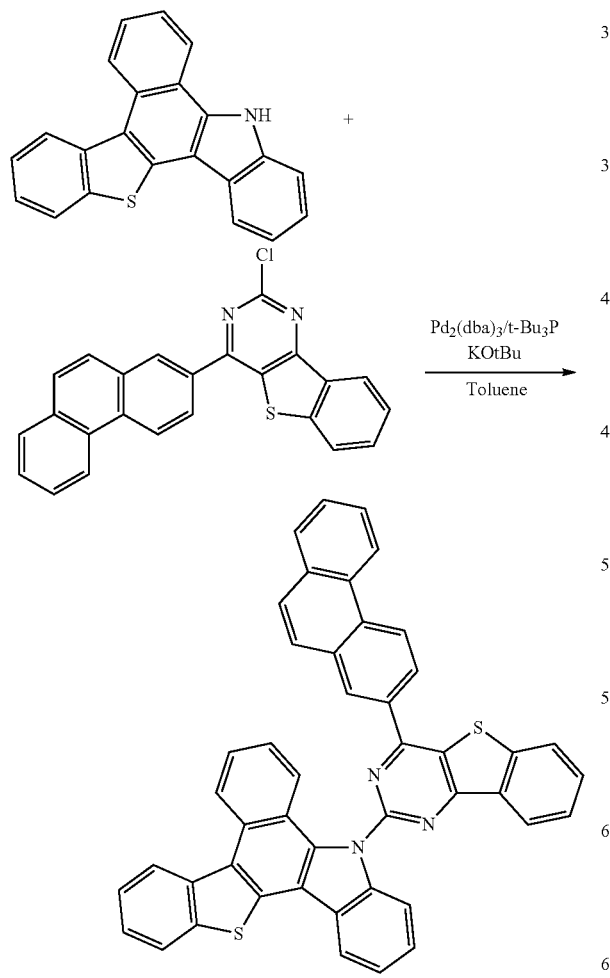

Except for using Sub 1-2 (5 g, 15.46 mmol), Sub 2-1-S-(14) (7.36 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-S-(14) (7.82 g, yield 74%).

(10) 1-2-1-S-(15) Synthesis

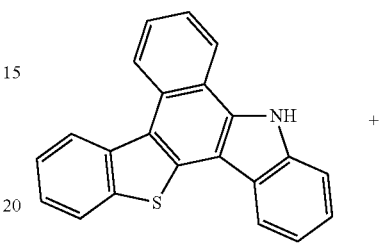

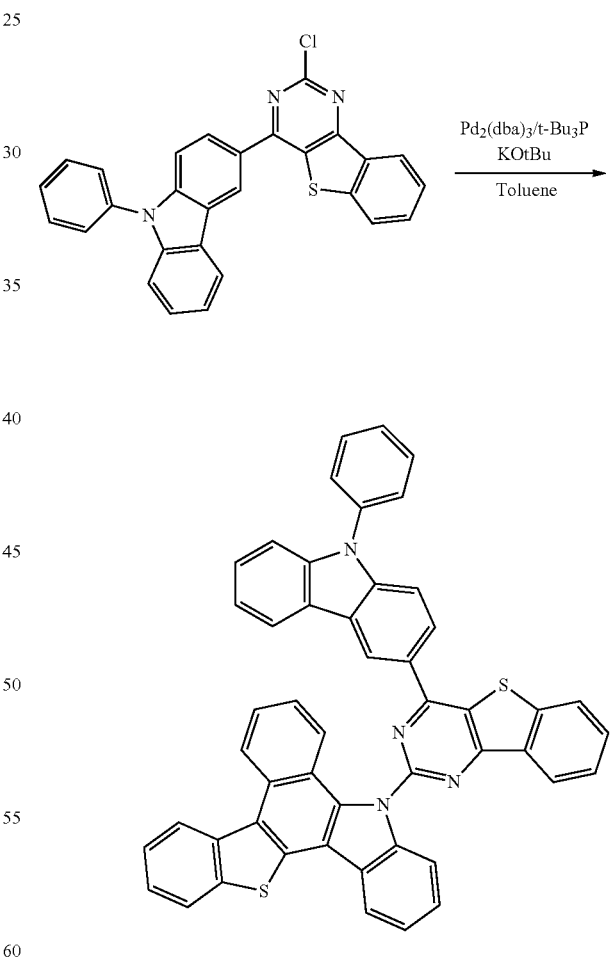

Except for using Sub 1-2 (5 g, 15.46 mmol), Sub 2-1-S-(15) (8.57 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-1-S-(15) (7.98 g, yield 69%).

(11) 1-2-2-O-(16) Synthesis

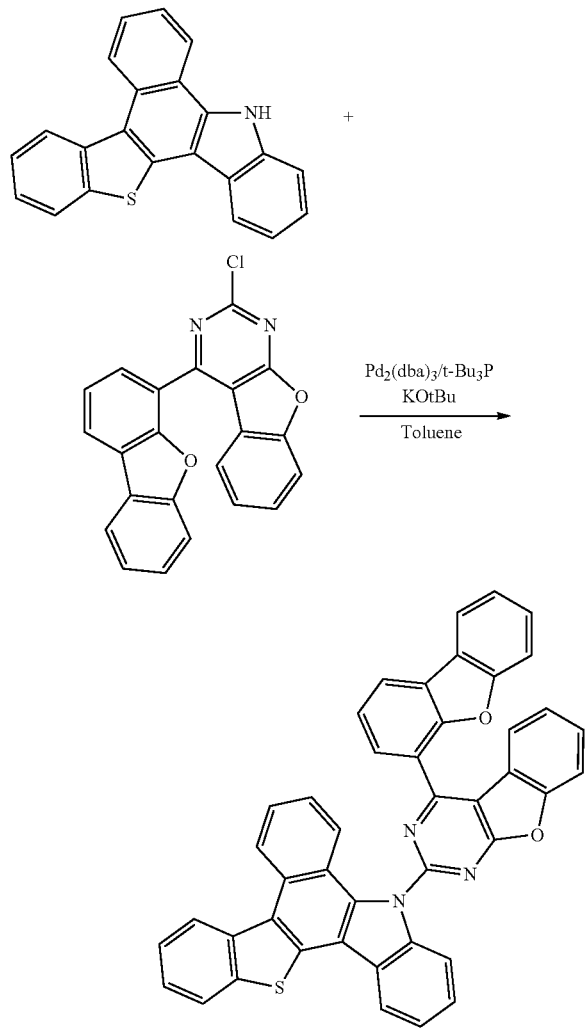

Except for using Sub 1-2 (5 g, 15.46 mmol), Sub 2-2-O-(16) (6.87 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-O-(16) (7.42 g, yield 73%).

(12) 1-2-2-O-(17) Synthesis

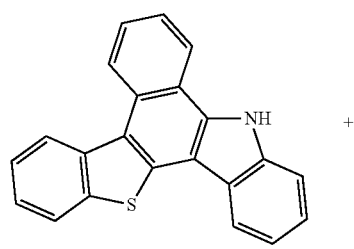

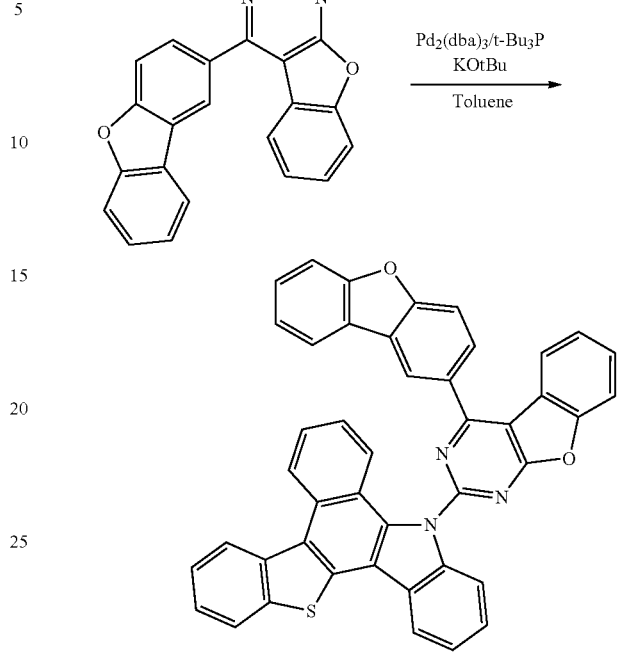

Except for using Sub 1-2 (5 g, 15.46 mmol), Sub 2-2-O-(17) (6.87 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-O-(17) (7.01 g, yield 69%).

(13) 1-2-2-O-(18) Synthesis

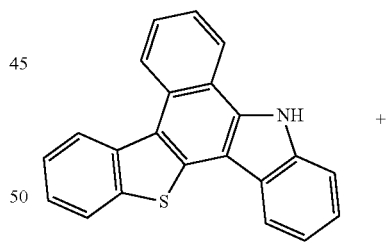

-continued

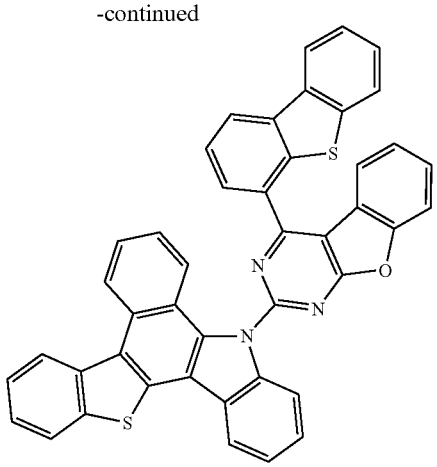

Except for using Sub 1-2 (5 g, 15.46 mmol), Sub 2-2-O-(18) (7.17 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-O-(18) (7.70 g, yield 74%).

(14) 1-2-2-O-(19) Synthesis

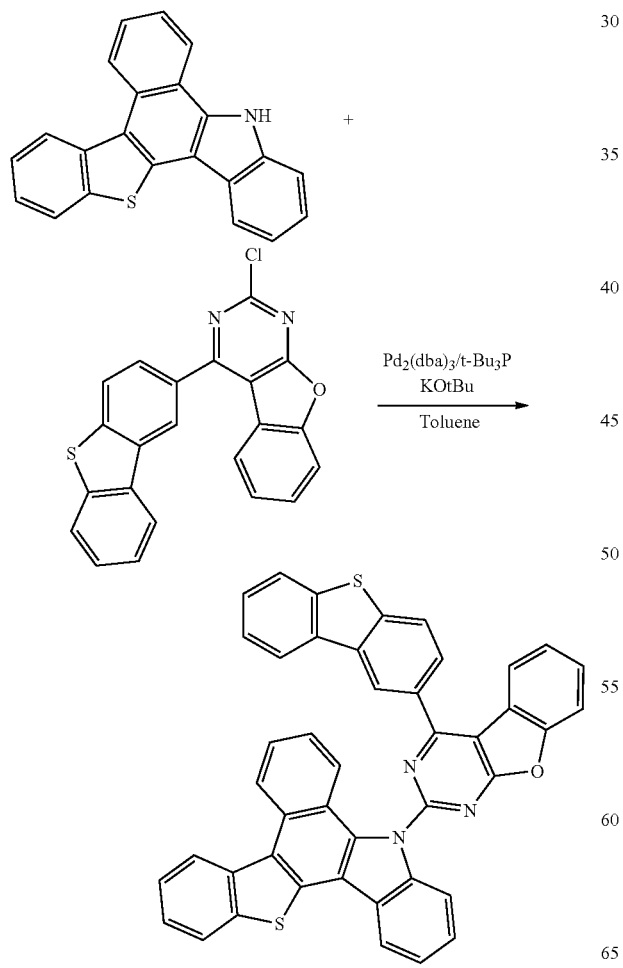

Except for using Sub 1-2 (5 g, 15.46 mmol), Sub 2-2-O-(19) (7.17 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-O-(19) (7.5 g, yield 72%).

(15) 1-2-2-O-(20) Synthesis

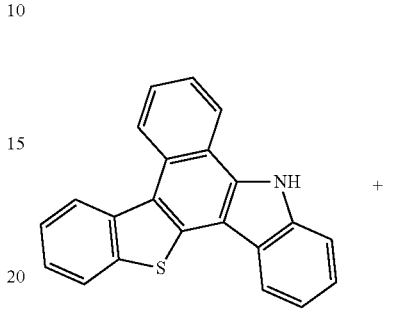

Except for using Sub 1-2 (5 g, 15.46 mmol), Sub 2-2-O-(20) (7.77 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-O-(20) (8.73 g, yield 80%).

(16) 1-2-2-S-(1) Synthesis

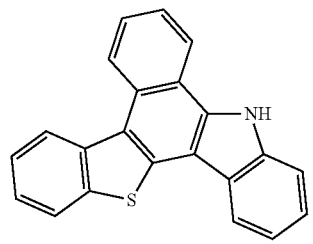
+

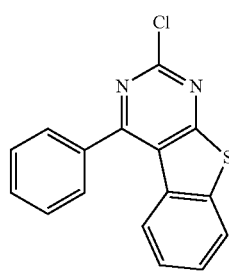

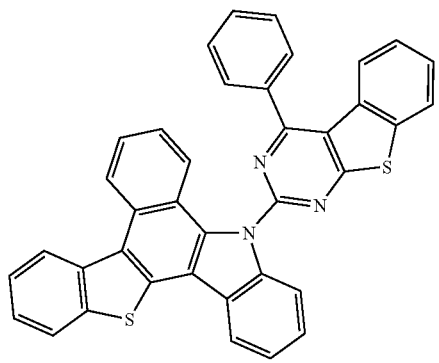

Except for using Sub 1-2 (5 g, 15.46 mmol), Sub 2-2-S-(1) (5.5 g 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-S-(1) (6.49 g, yield 72%).

(17) 1-2-2-S-(2) Synthesis

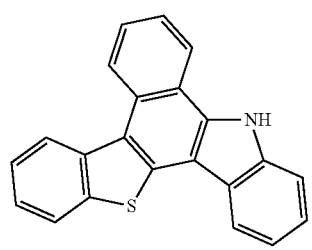
+

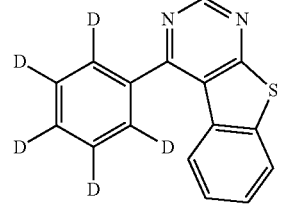

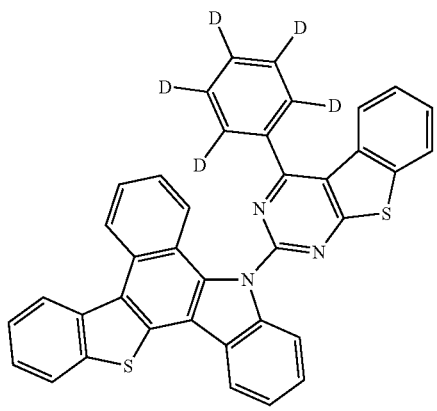

Except for using Sub 1-2 (5 g, 15.46 mmol), Sub 2-2-S-(2) (5.59 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-S-(2) (6.28 g, yield 69%).

(18) 1-2-2-S-(3) Synthesis

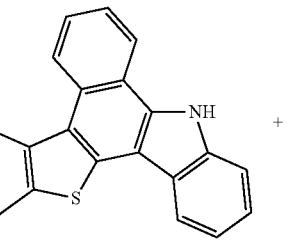
+

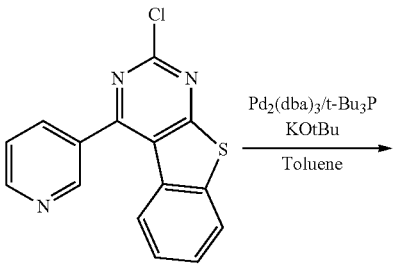

-continued

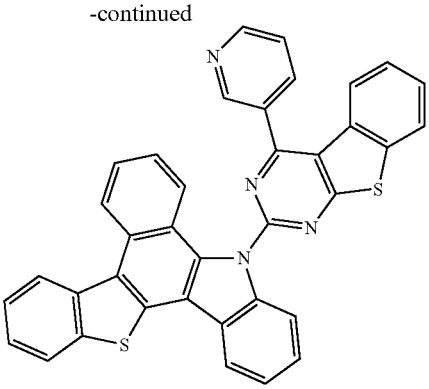

Except for using Sub 1-2 (5 g, 15.46 mmol), Sub 2-2-S-(3) (5.52 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-S-(3) (6.87 g, yield 76%).

(19) 1-2-2-S-(4) Synthesis

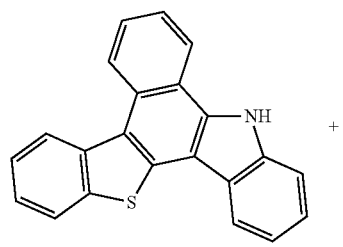

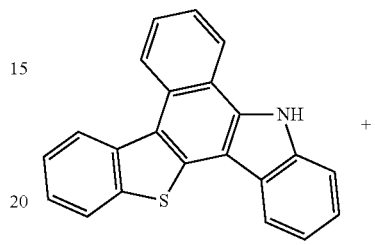

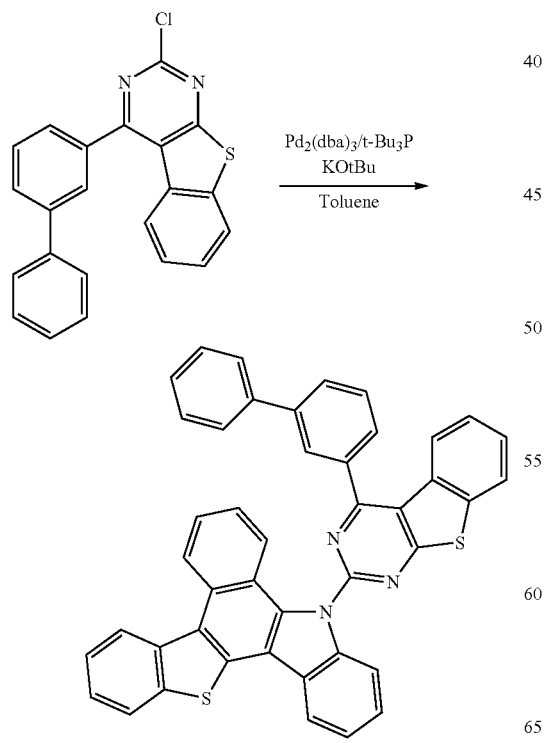

Except for using Sub 1-2 (5 g, 15.46 mmol), Sub 2-2-S-(4) (6.91 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-S-(4) (7.85 g, yield 77%).

(20) 1-2-2-S-(5) Synthesis

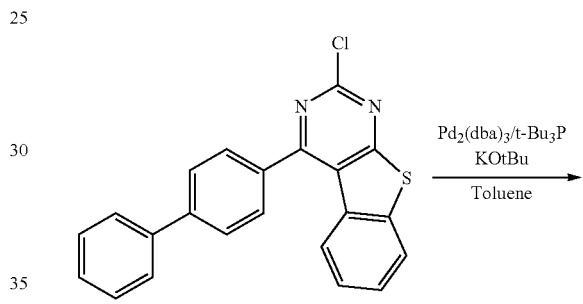

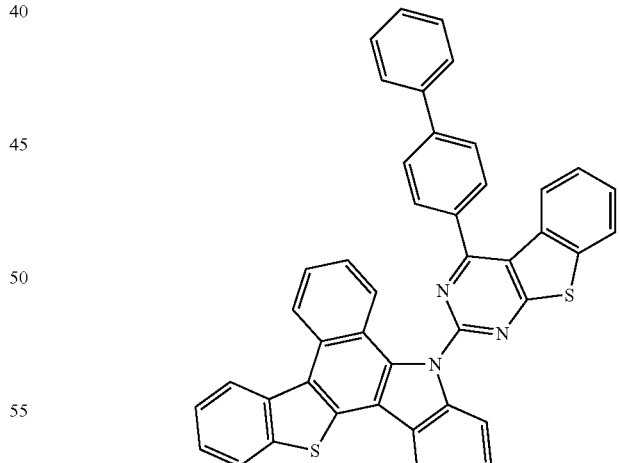

Except for using Sub 1-2 (5 g, 15.46 mmol), Sub 2-2-S-(5) (6.91 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-2-2-S-(5) (7.44 g, yield 73%).

3. Final Product 3 Synthesis

(1) 1-3-1-O-(11) Synthesis

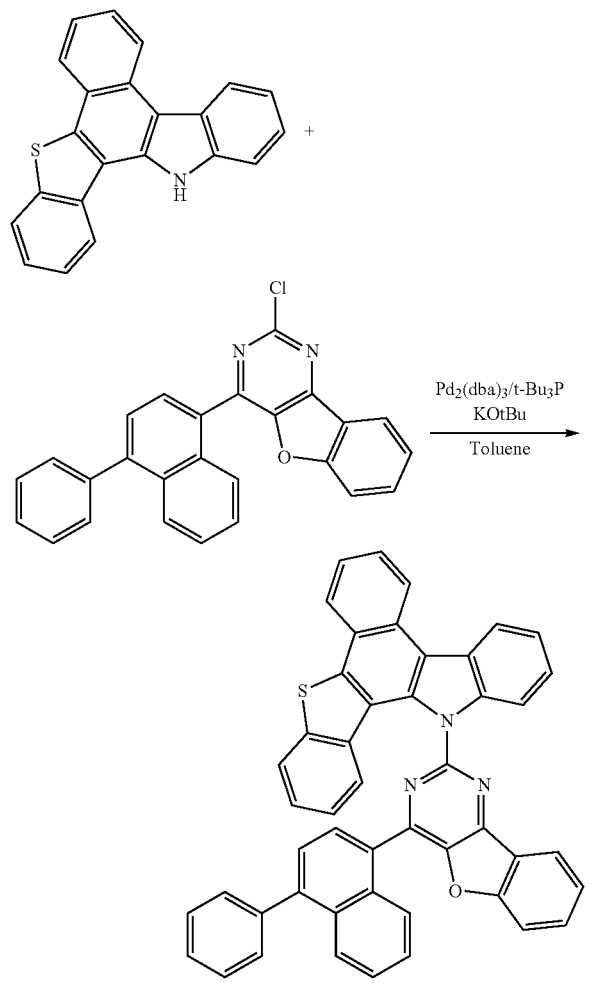

Except for using Sub 1-3 (5 g, 15.46 mmol), Sub 2-1-O-(11) (7.54 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-O-(11) (8.04 g, yield 75%).

(2) 1-3-1-O-(12) Synthesis

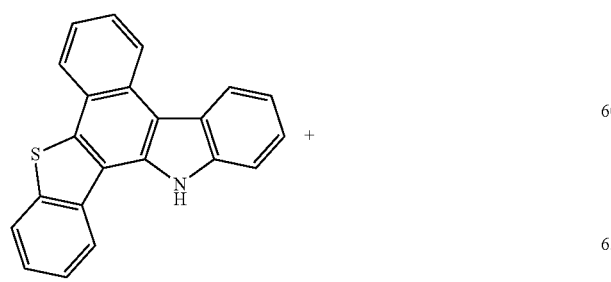

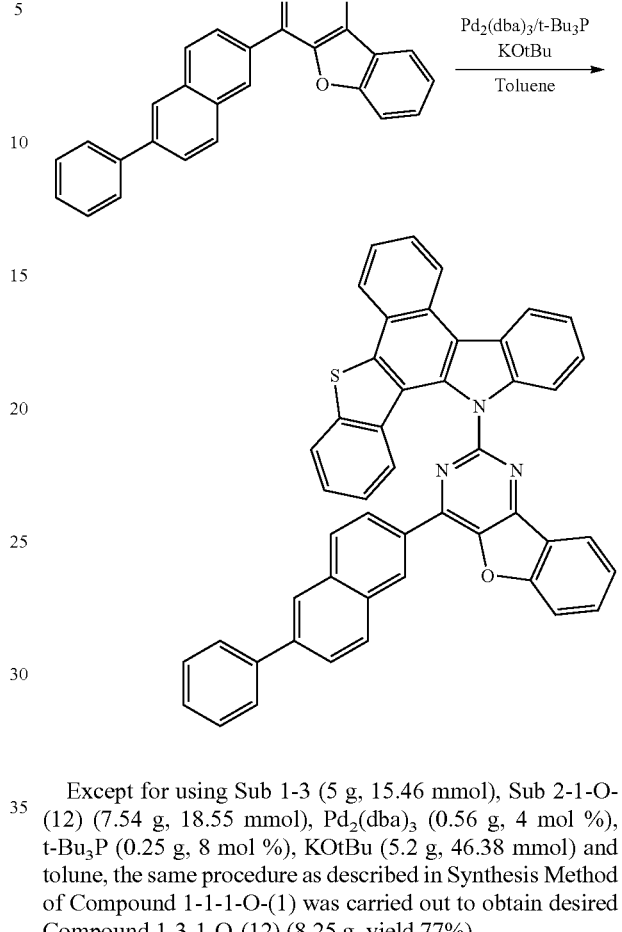

Except for using Sub 1-3 (5 g, 15.46 mmol), Sub 2-1-O-(12) (7.54 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-O-(12) (8.25 g, yield 77%).

(3) 1-3-1-O-(13) Synthesis

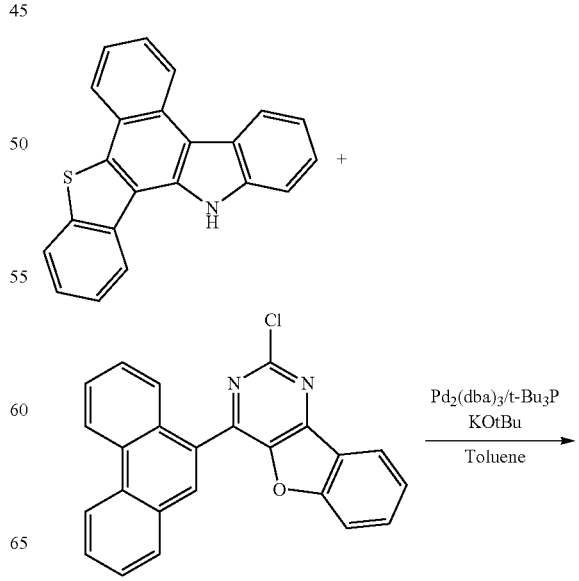

219
-continued

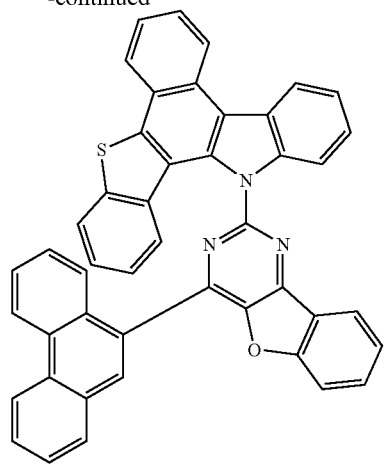

Except for using Sub 1-3 (5 g, 15.46 mmol), Sub 2-1-O-(13) (7.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-O-(13) (7.53 g, yield 73%).

(4) 1-3-1-O-(14) Synthesis

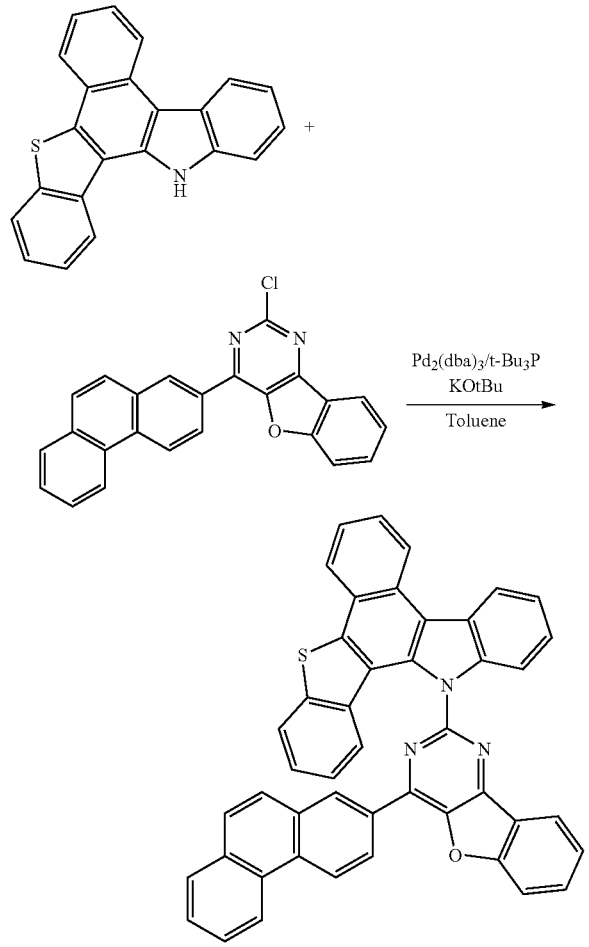

Except for using Sub 1-3 (5 g, 15.46 mmol), Sub 2-1-O-(14) (7.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-O-(14) (8.46 g, yield 82%).

(5) 1-3-1-O-(15) Synthesis

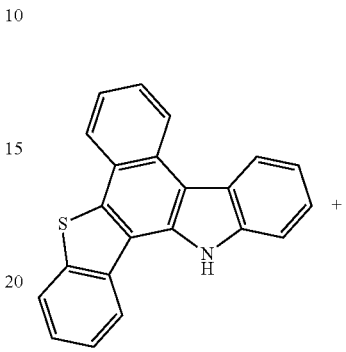

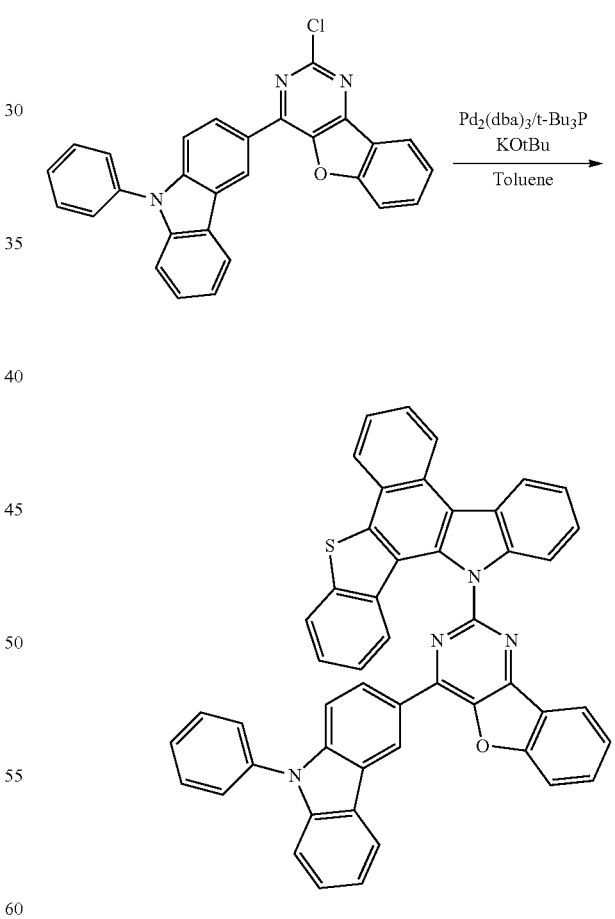

Except for using Sub 1-3 (5 g, 15.46 mmol), Sub 2-1-O-(15) (8.27 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-O-(15) (8.95 g, yield 79%).

(6) 1-3-1-S-(16) Synthesis

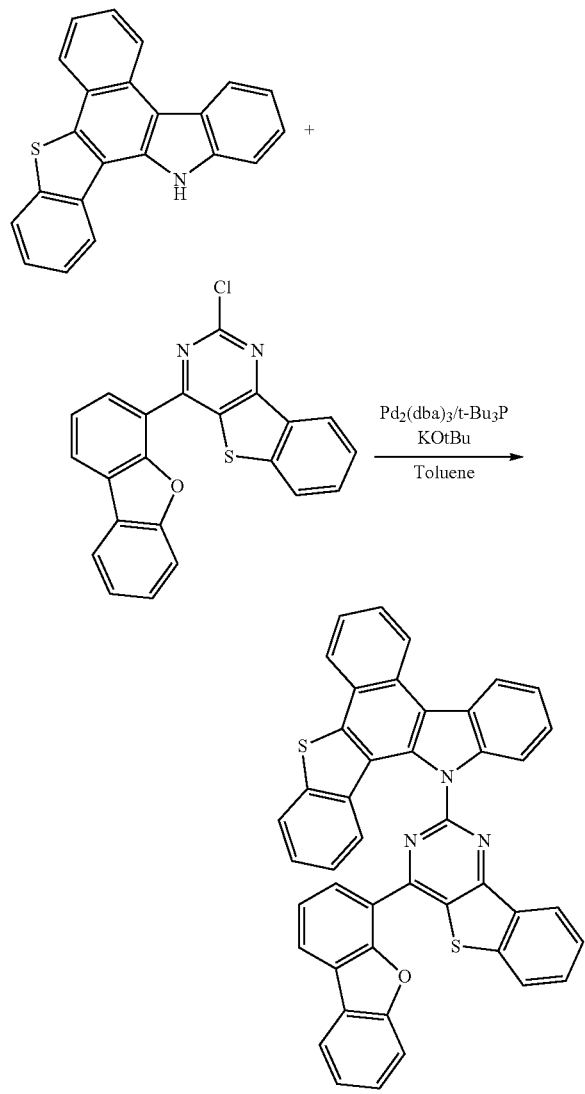

Except for using Sub 1-3 (5 g, 15.46 mmol), Sub 2-1-S-(16) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-S-(16) (7.91 g, yield 76%).

(7) 1-3-1-S-(17) Synthesis

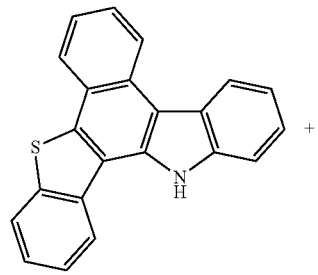

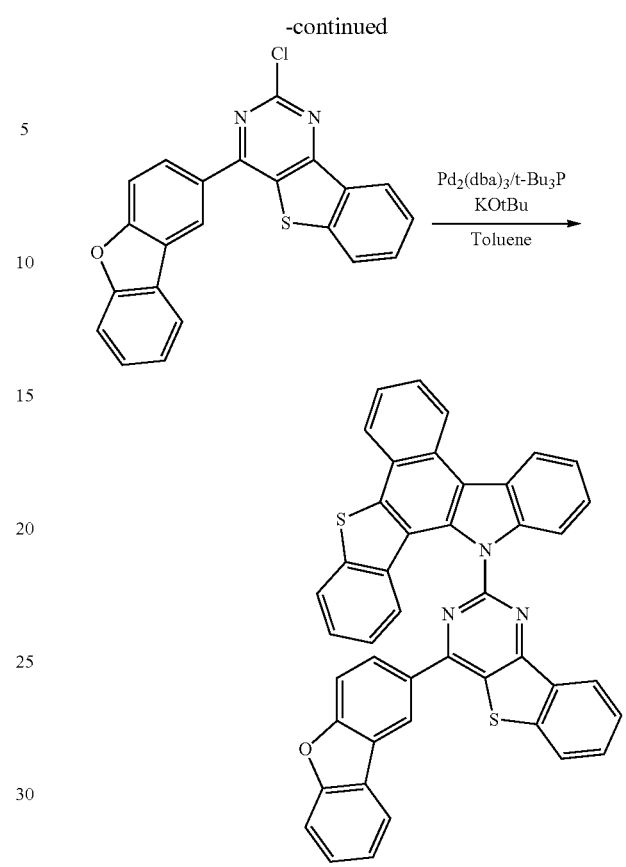

Except for using Sub 1-3 (5 g, 15.46 mmol), Sub 2-1-S-(17) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-S-(17) (7.39 g, yield 71%).

(8) 1-3-1-S-(18) Synthesis

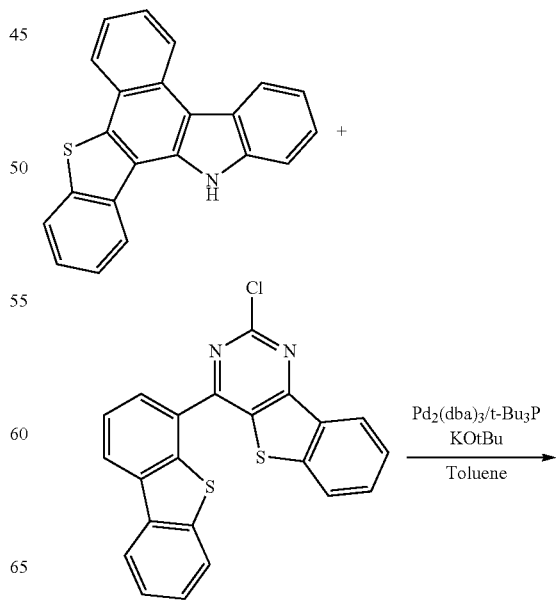

223
-continued

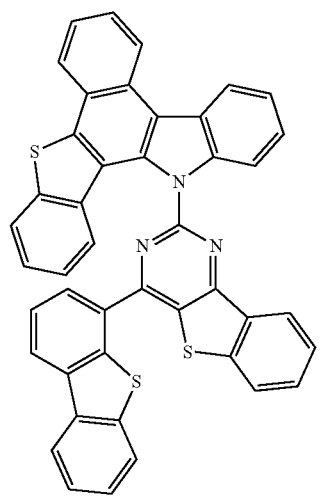

224
-continued

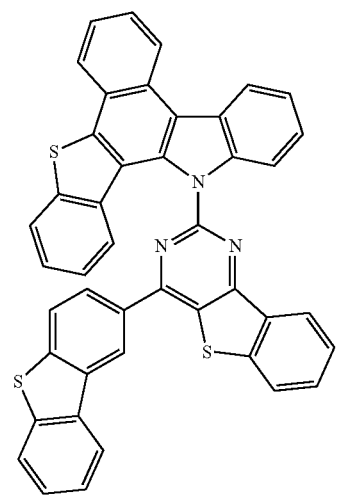

Except for using Sub 1-3 (5 g, 15.46 mmol), Sub 2-1-S-(18) (7.47 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-S-(18) (7.89 g, yield 74%).

(9) 1-3-1-S-(19) Synthesis

Except for using Sub 1-3 (5 g, 15.46 mmol), Sub 2-1-S-(19) (7.47 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-S-(19) (8.21 g, yield 77%).

(10) 1-3-1-S-(20) Synthesis

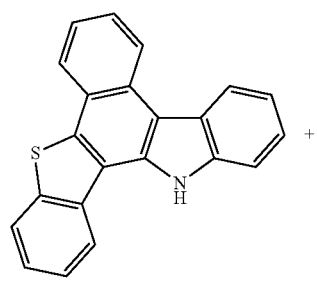

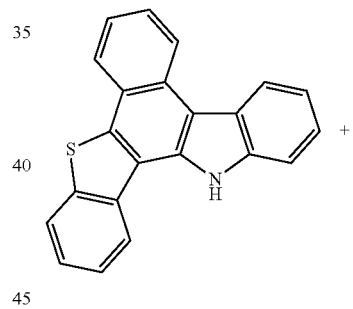

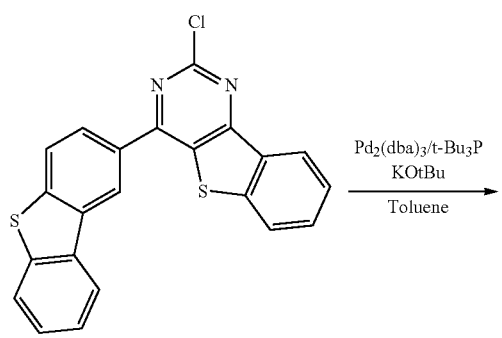

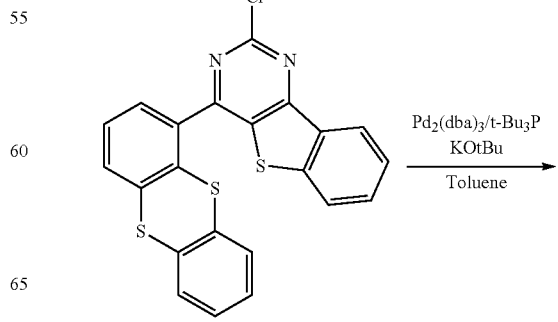

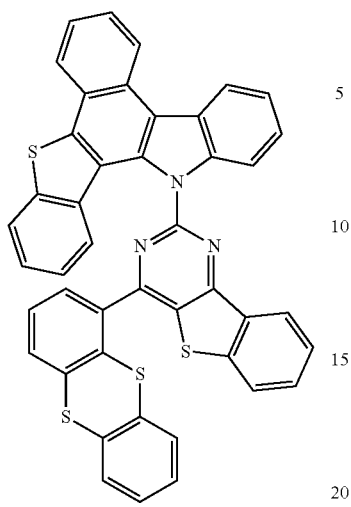

Except for using Sub 1-3 (5 g, 15.46 mmol), Sub 2-1-S-(20) (8.06 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-1-S-(20) (8.59 g, yield 77%).

(11) 1-3-2-O-(1) Synthesis

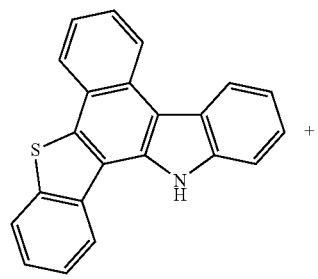

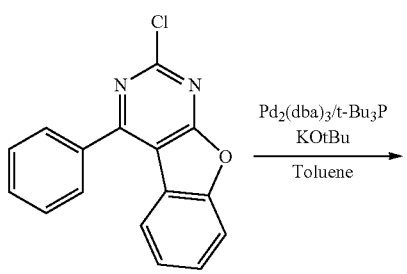

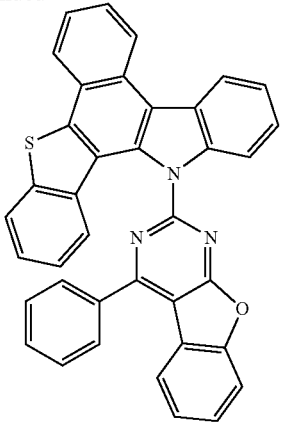

Except for using Sub 1-3 (5 g, 15.46 mmol), Sub 2-2-O-(1) (5.20 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-O-(1) (6.49 g, 74%), yield 74%).

(12) 1-3-2-O-(2) Synthesis

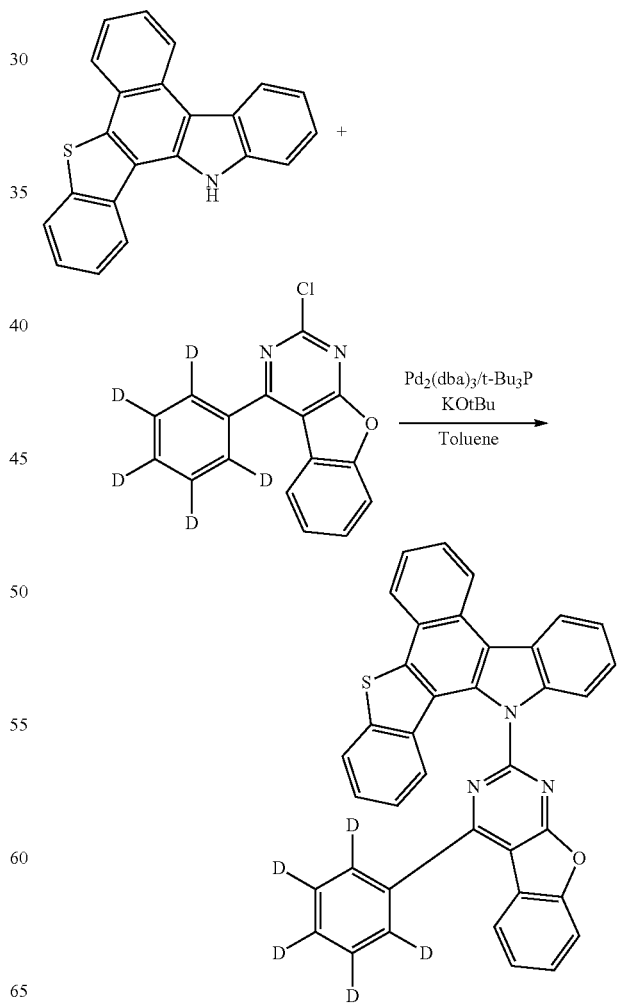

Except for using Sub 1-3 (5 g, 15.46 mmol), Sub 2-2-O-(2) (5.30 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-O-(2) (7.08 g, yield 80%).

(13) 1-3-2-O-(3) Synthesis

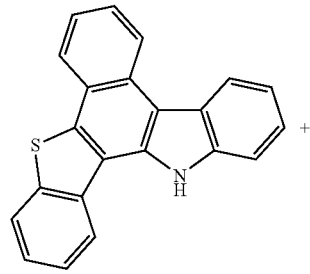

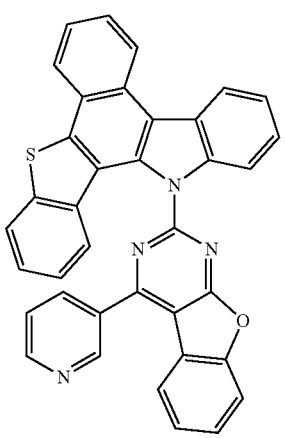

Except for using Sub 1-3 (5 g, 15.46 mmol), Sub 2-2-O-(3) (5.22 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-O-(3) (7.03 g, yield 80%).

(14) 1-3-2-O-(4) Synthesis

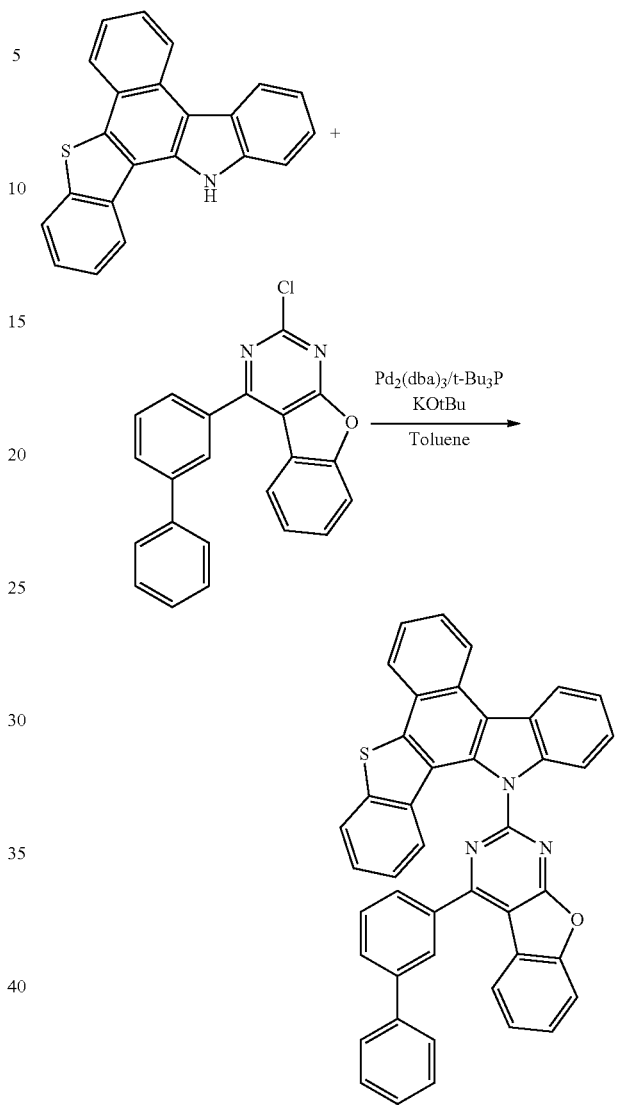

Except for using Sub 1-3 (5 g, 15.46 mmol), Sub 2-2-O-(4) (6.61 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-O-(4) (7.86 g, yield 79%).

(15) 1-3-2-O-(5) Synthesis

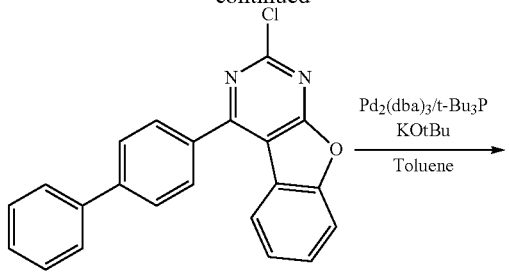

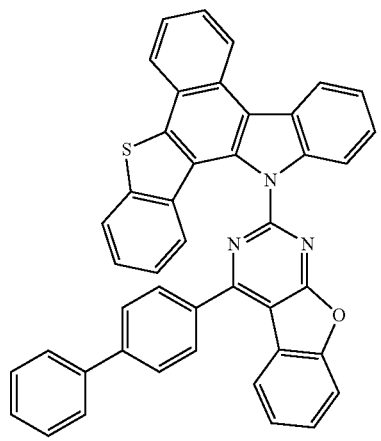

Except for using Sub 1-3 (5 g, 15.46 mmol), Sub 2-2-O-(5) (6.61 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-O-(5) (7.66 g, yield 77%).

(16) 1-3-2-S-(6) Synthesis

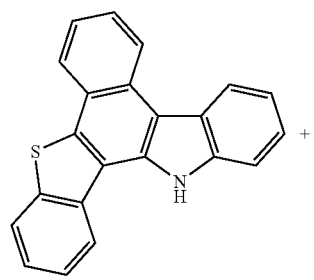

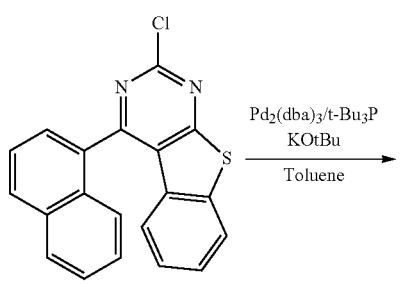

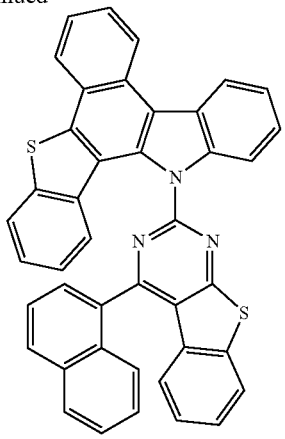

Except for using Sub 1-3 (5 g, 15.46 mmol), Sub 2-2-S-(6) (6.43 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-S-(6) (7.34 g, yield 75%).

(17) 1-3-2-S-(7) Synthesis

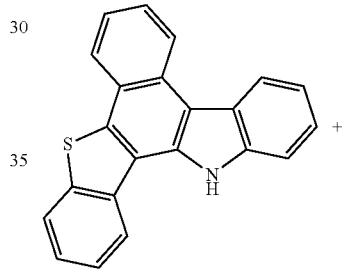

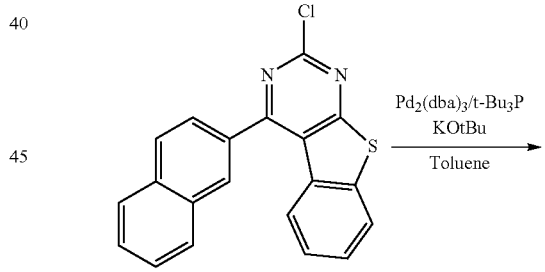

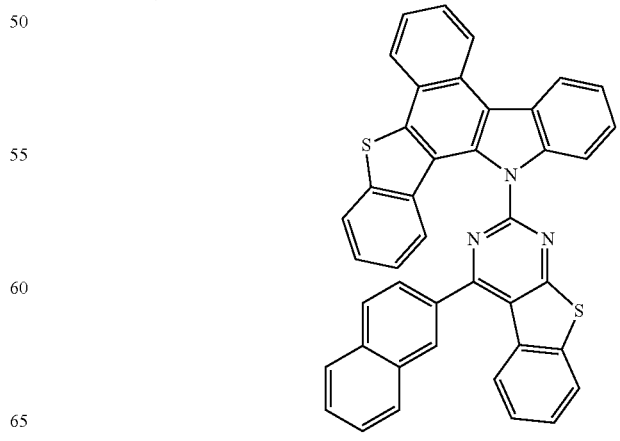

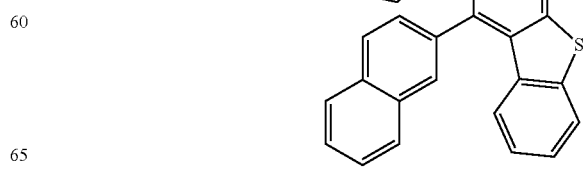

Except for using Sub 1-3 (5 g, 15.46 mmol), Sub 2-2-S-(7) (6.43 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-S-(7) (6.85 g, yield 70%).

(18) 1-3-2-S-(8) Synthesis

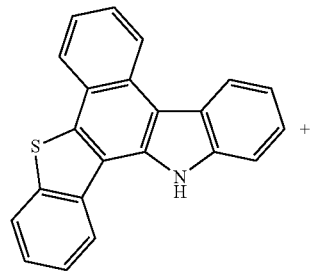
+

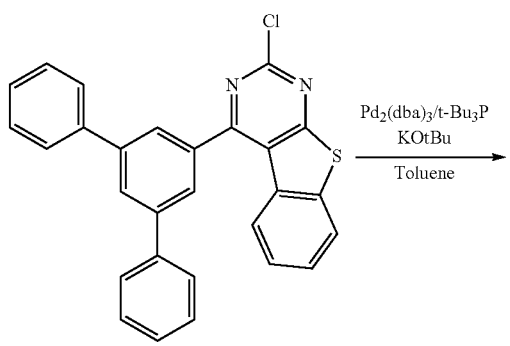

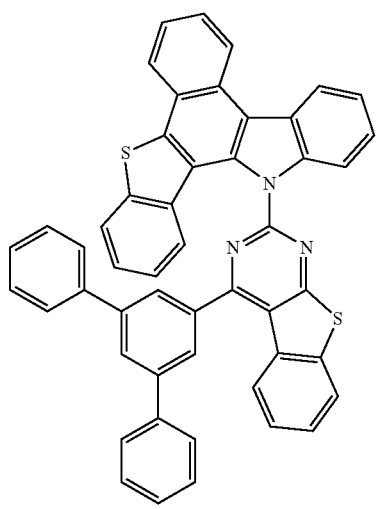

Except for using Sub 1-3 (5 g, 15.46 mmol), Sub 2-2-S-(8) (8.32 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-S-(8) (8.64 g, yield 76%).

(19) 1-3-2-S-(9) Synthesis

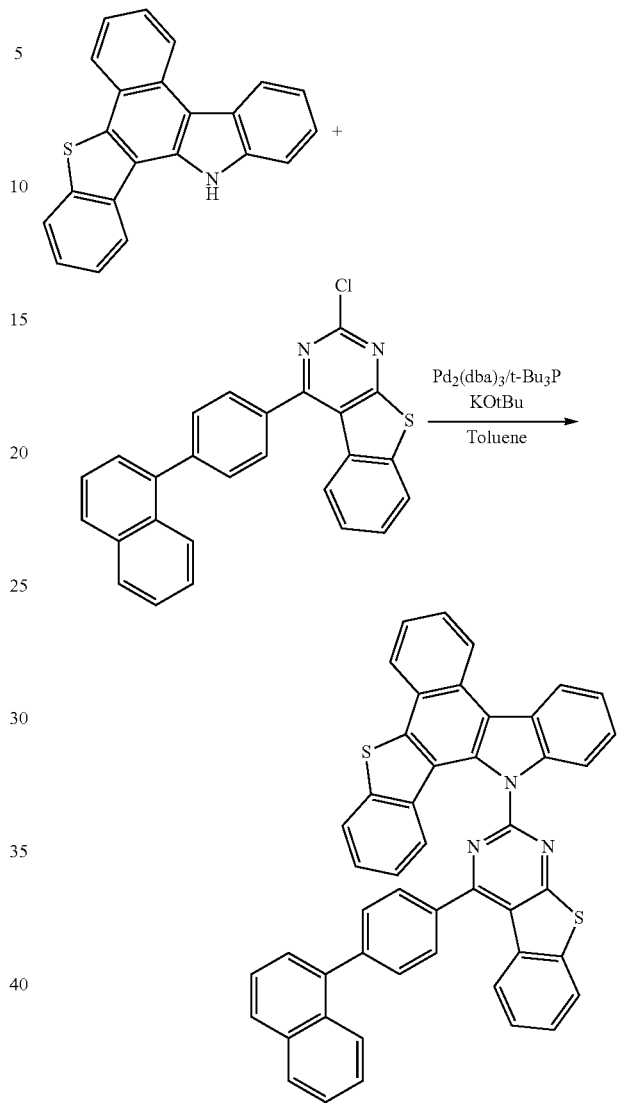

Except for using Sub 1-3 (5 g, 15.46 mmol), Sub 2-2-S-(9) (7.84 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-S-(9) (8.34 g, yield 76%).

(20) 1-3-2-S-(10) Synthesis

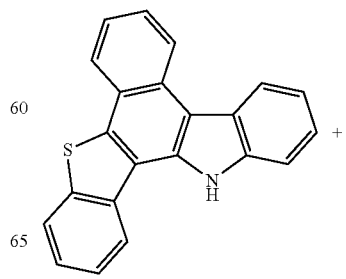
+

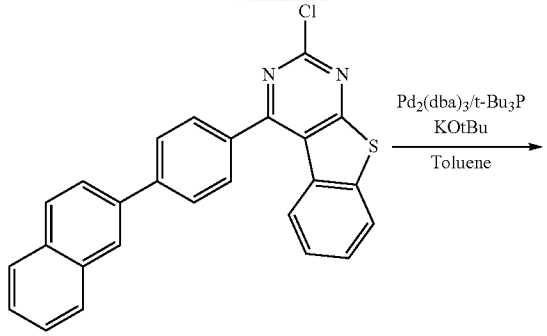
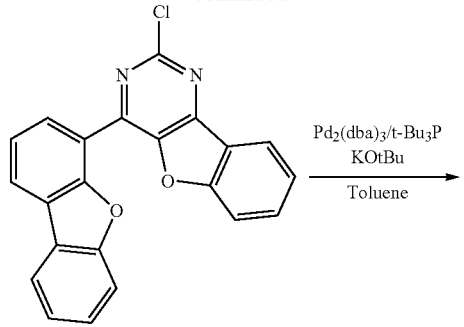

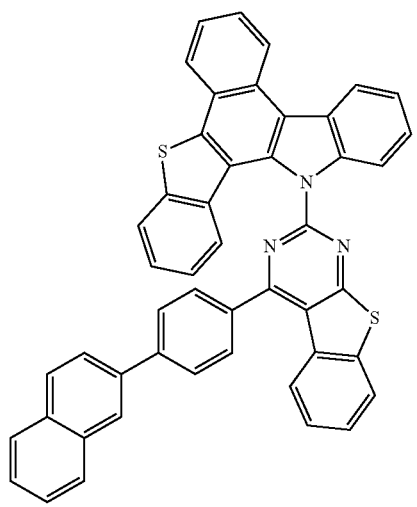

Except for using Sub 1-3 (5 g, 15.46 mmol), Sub 2-2-S-(10) (7.84 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-3-2-S-(10) (8.77 g, yield 80%).

4. Final Product 4 Synthesis (1) 1-4-1-O-(16) Synthesis

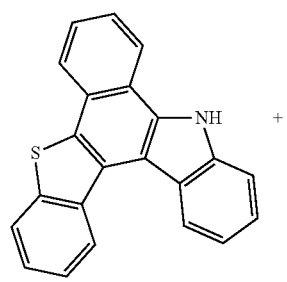  +

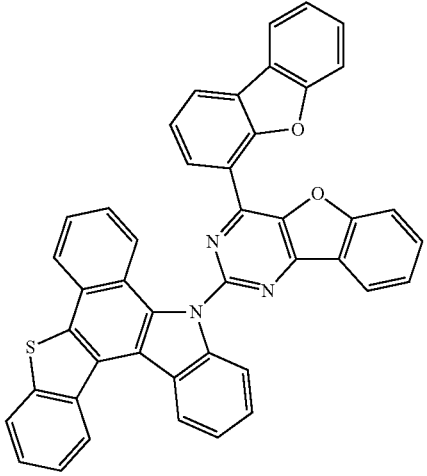

Except for using Sub 1-4 (5 g, 15.46 mmol), Sub 2-1-O-(16) (6.87 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-O-(16) (6.81 g, yield 67%).

(2) 1-4-1-O-(17) Synthesis

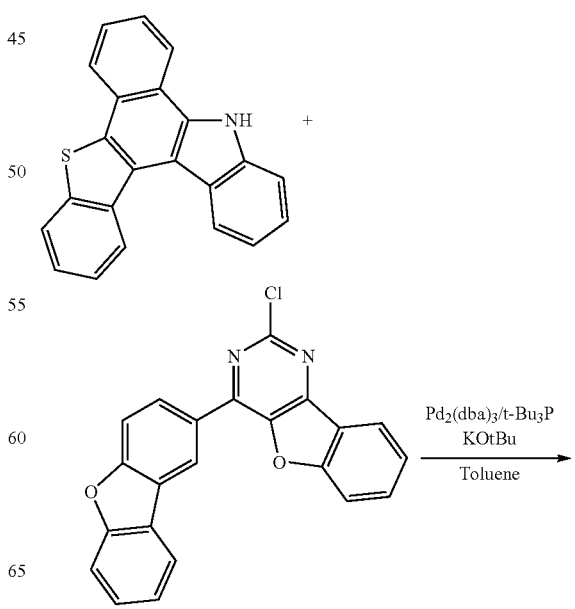

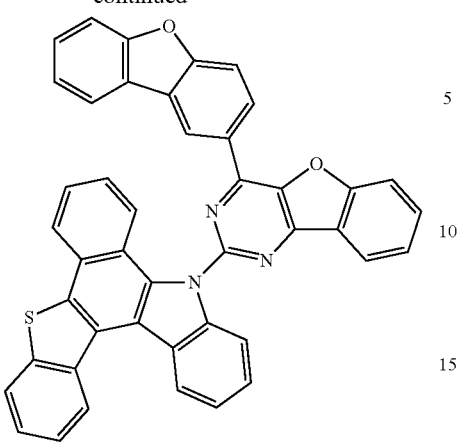

Except for using Sub 1-4 (5 g, 15.46 mmol), Sub 2-1-O-(17) (6.87 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-O-(17) (7.01 g, yield 69%).

(3) 1-4-1-O-(18) Synthesis

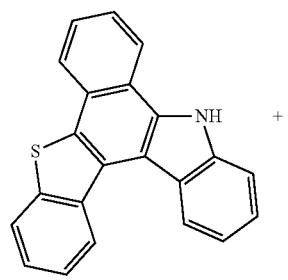

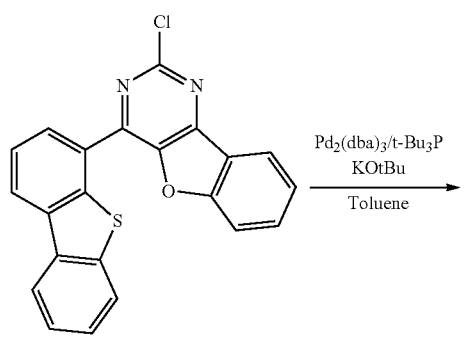

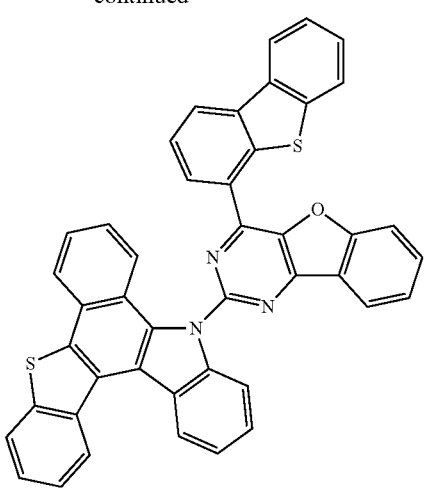

Except for using Sub 1-4 (5 g, 15.46 mmol), Sub 2-1-O-(18) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-O-(18) (7.18 g, yield 69%).

(4) 1-4-1-O-(19) Synthesis

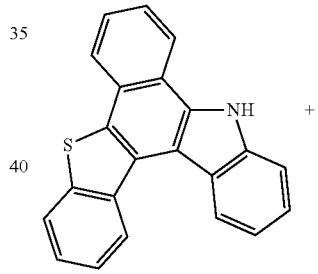

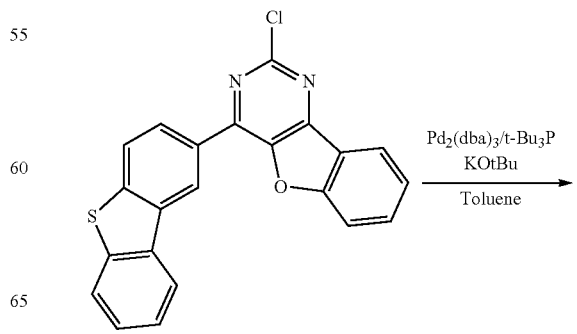

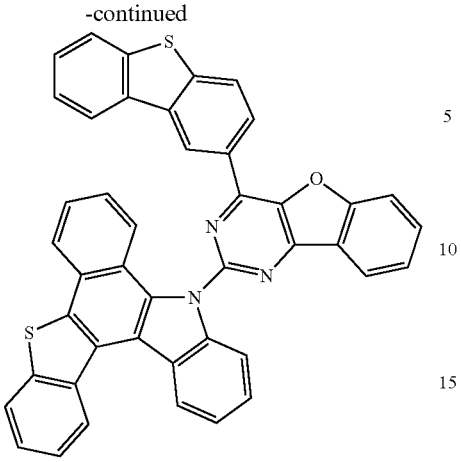

Except for using Sub 1-4 (5 g, 15.46 mmol), Sub 2-1-O-(19) (7.17 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-O-(19) (7.7 g, yield 74%).

(5) 1-4-1-O-(20) Synthesis

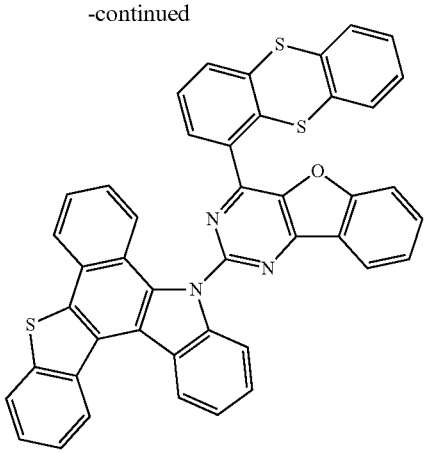

Except for using Sub 1-4 (5 g, 15.46 mmol), Sub 2-1-O-(20) (7.77 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-O-(20) (7.85 g, yield 72%).

(6) 1-4-1-S-(1) Synthesis

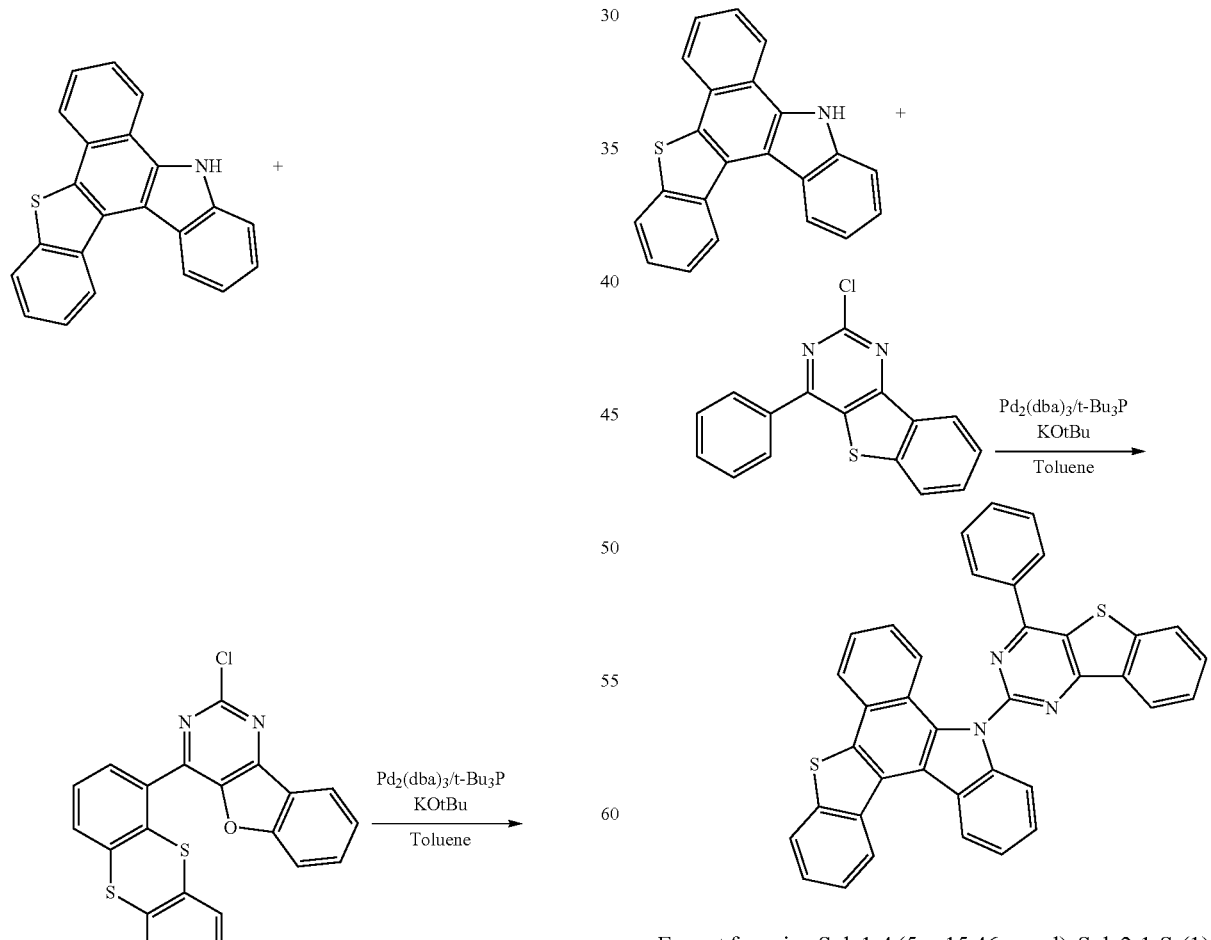

Except for using Sub 1-4 (5 g, 15.46 mmol), Sub 2-1-S-(1) (5.5 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-S-(1) (6.04 g, yield 67%).

(7) 1-4-1-S-(2) Synthesis

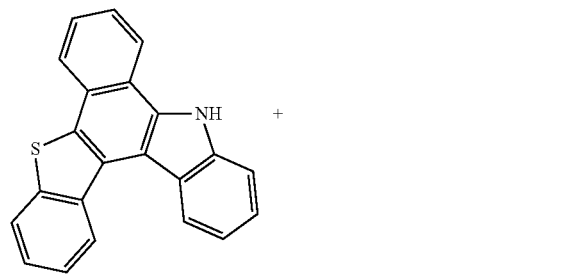

+

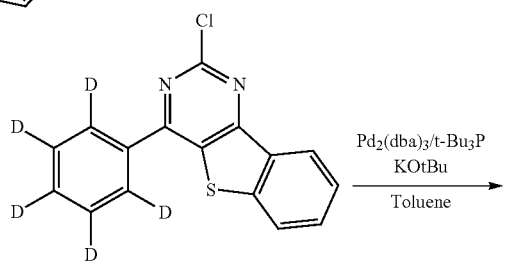

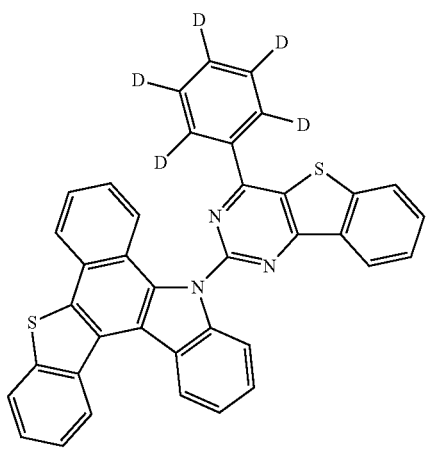

Except for using Sub 1-4 (5 g, 15.46 mmol), Sub 2-1-S-(2) (5.59 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-S-(2) (6.37 g, yield 70%).

(8) 1-4-1-S-(3) Synthesis

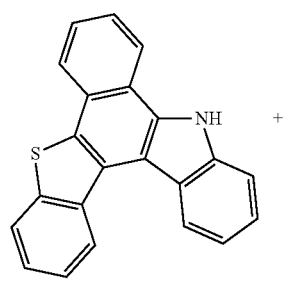

+

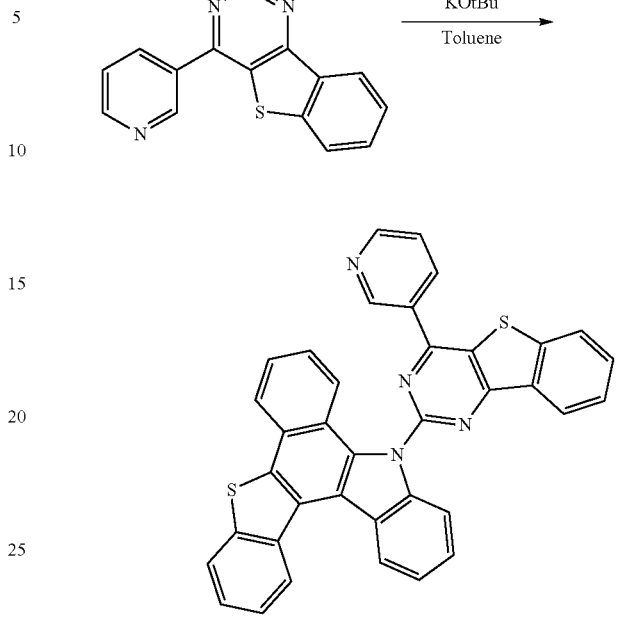

Except for using Sub 1-4 (5 g, 15.46 mmol), Sub 2-1-S-(3) (5.52 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-S-(3) (7.14 g, yield 79%).

(9) 1-4-1-S-(4) Synthesis

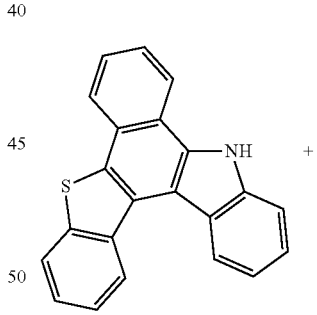

+

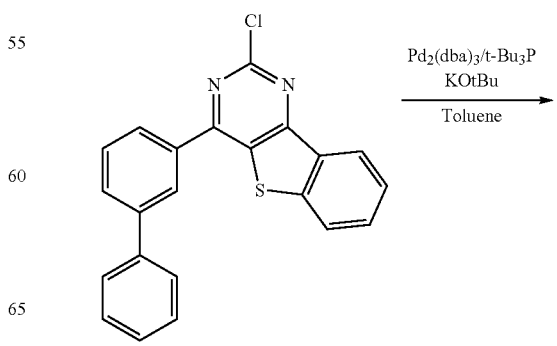

-continued

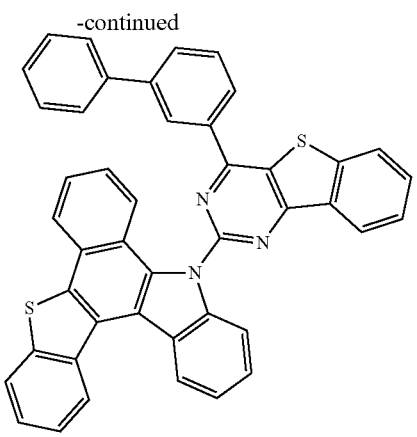

Except for using Sub 1-4 (5 g, 15.46 mmol), Sub 2-1-S-(4) (6.91 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-S-(4) (7.34 g, yield 72%).

(10) 1-4-1-S-(5) Synthesis

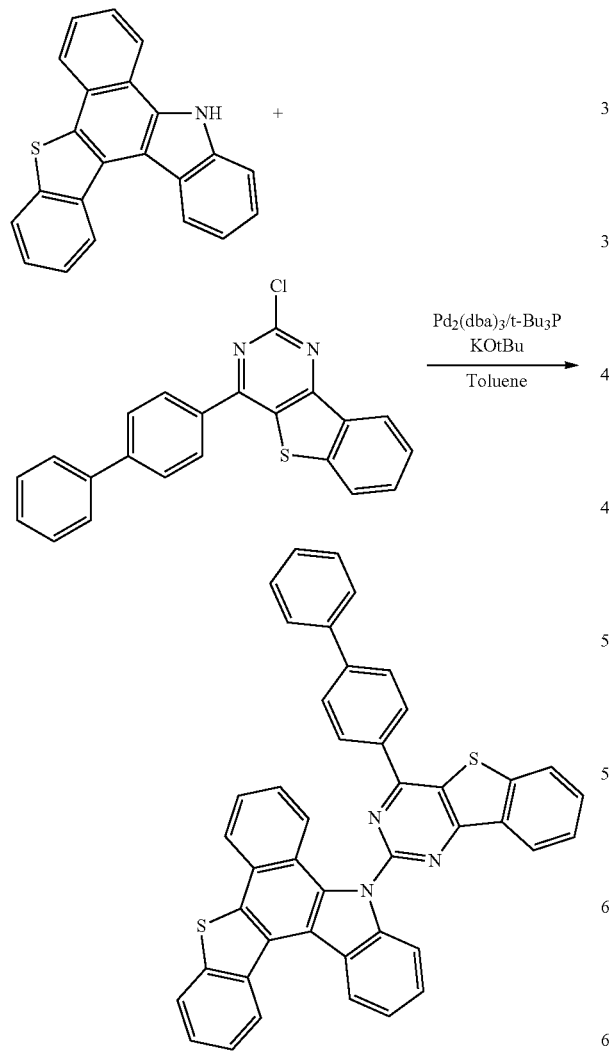

Except for using Sub 1-4 (5 g, 15.46 mmol), Sub 2-1-S-(5) (6.91 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-1-S-(5) (6.93 g, yield 68%).

(11) 1-4-2-O-(6) Synthesis

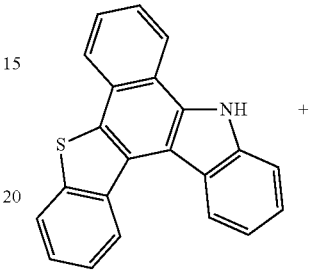

Except for using Sub 1-4 (5 g, 15.46 mmol), Sub 2-2-O-(6) (6.13 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-O-(6) (6.11 g, yield 64%).

(12) 1-4-2-O-(7) Synthesis

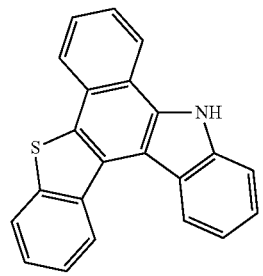

+

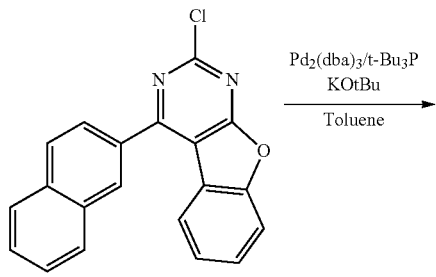

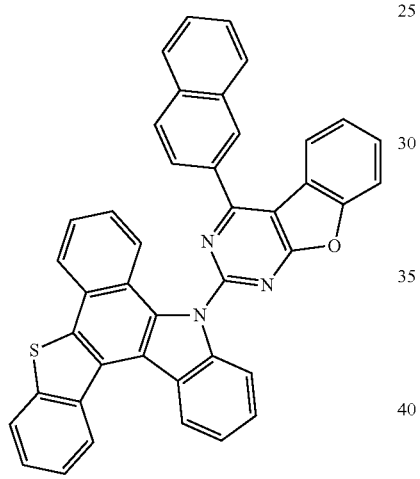

Except for using Sub 1-4 (5 g, 15.46 mmol), Sub 2-2-O-(7) (6.13 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-O-(7) (5.82 g, yield 61%).

(13) 1-4-2-O-(8) Synthesis

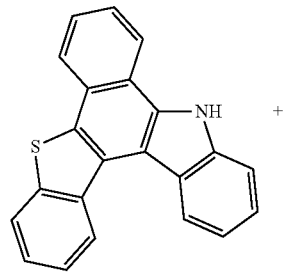

+

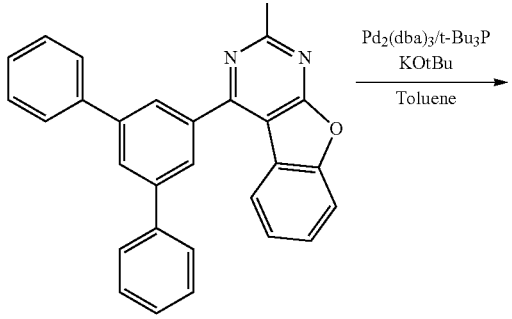

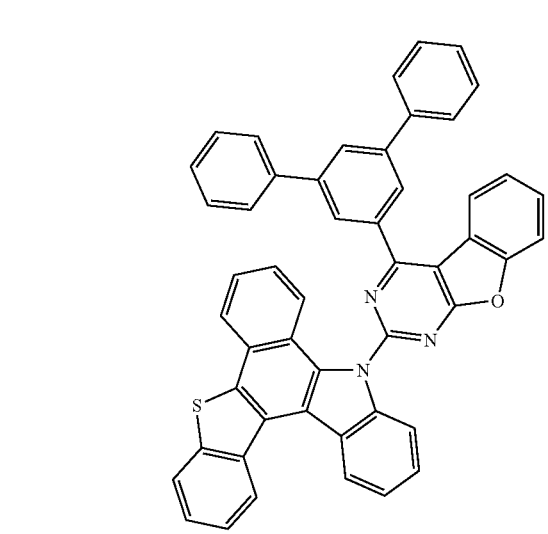

Except for using Sub 1-4 (5 g, 15.46 mmol), Sub 2-2-O-(8) (8.03 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-O-(8) (6.67 g, yield 60%).

(14) 1-4-2-O-(9) Synthesis

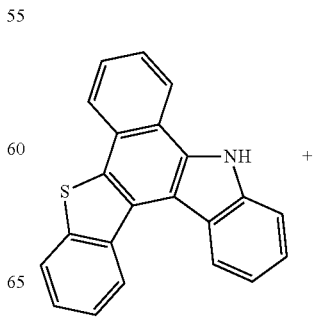

+

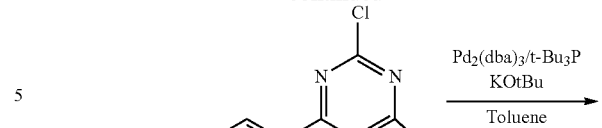

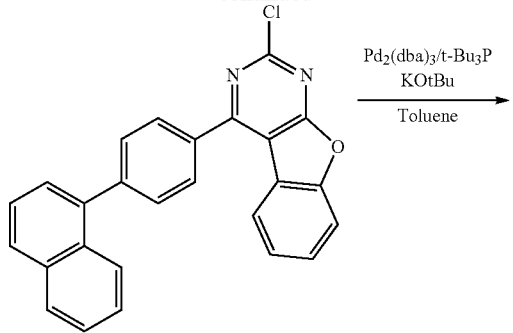

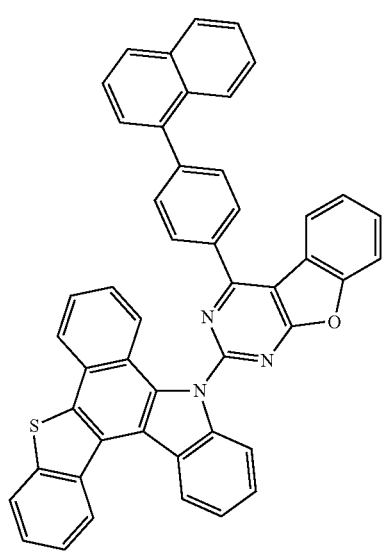

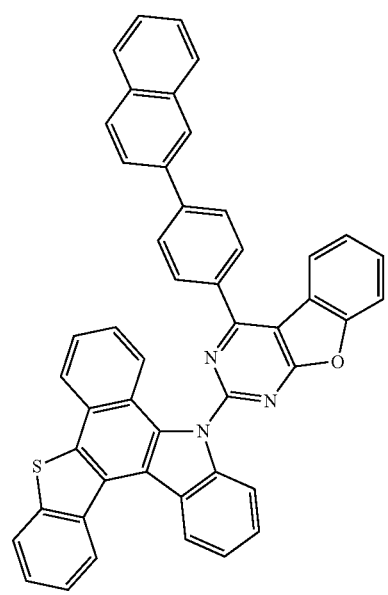

Except for using Sub 1-4 (5 g, 15.46 mmol), Sub 2-2-O-(9) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-O-(9) (7.18 g, yield 67%).

(15) 1-4-2-O-(10) Synthesis

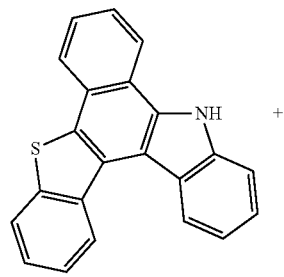

Except for using Sub 1-4 (5 g, 15.46 mmol), Sub 2-2-O-(10) (7.54 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-O-(10) (6.97 g, yield 65%).

(16) 1-4-2-S-(11) Synthesis

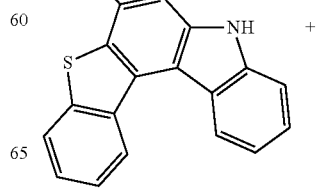

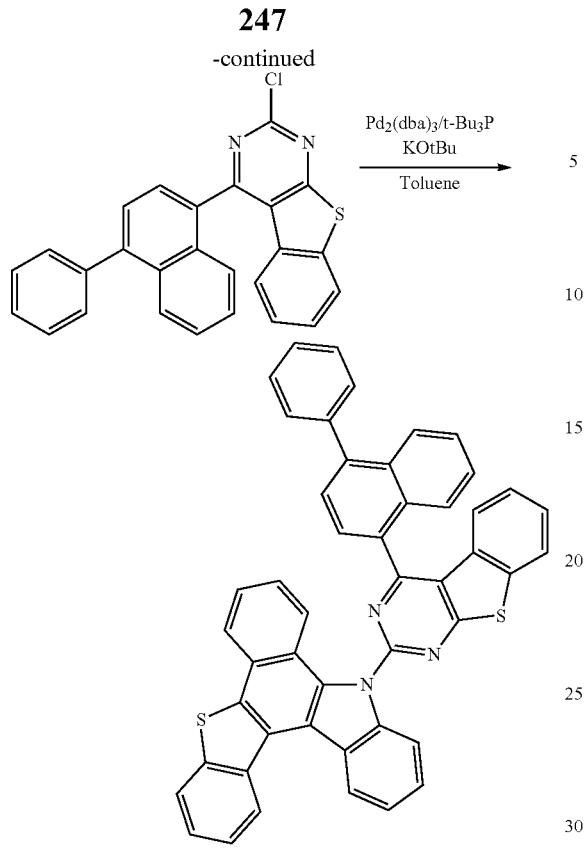

Except for using Sub 1-4 (5 g, 15.46 mmol), Sub 2-2-S-(11) (7.84 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-S-(11) (7.68 g, yield 70%).

(17) 1-4-2-S-(12) Synthesis

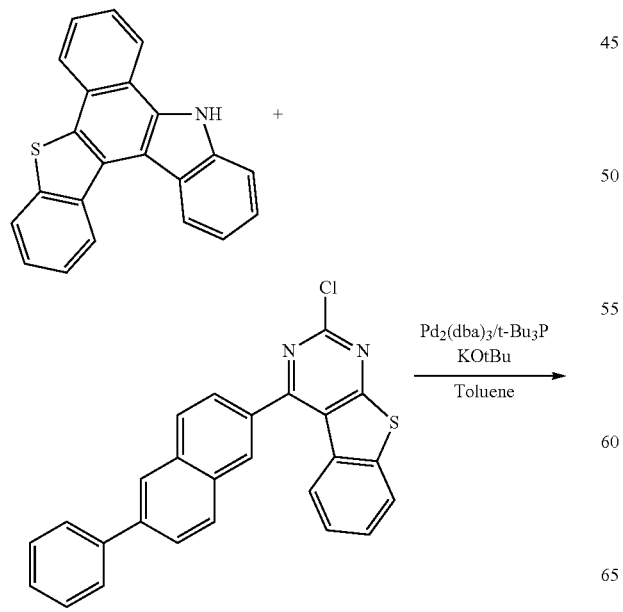

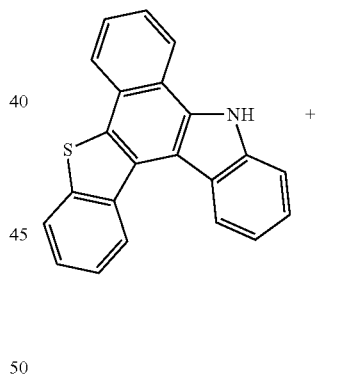

Except for using Sub 1-4 (5 g, 15.46 mmol), Sub 2-2-S-(12) (7.84 g, 18.55 mmol), Pd₂(dba)₃ (0.56 g, 4 mol %), t-Bu₃P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-S-(12) (6.58 g, yield 60%).

(18) 1-4-2-S-(13) Synthesis

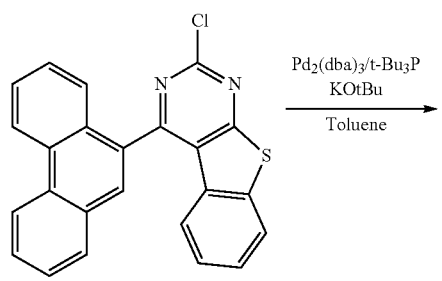

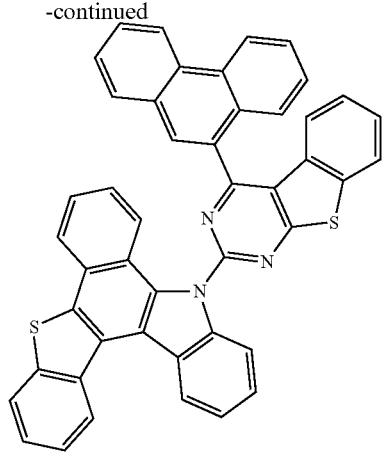

Except for using Sub 1-4 (5 g, 15.46 mmol), Sub 2-2-S-(13) (7.36 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-S-(13) (6.34 g, yield 60%).

(19) 1-4-2-S-(14) Synthesis

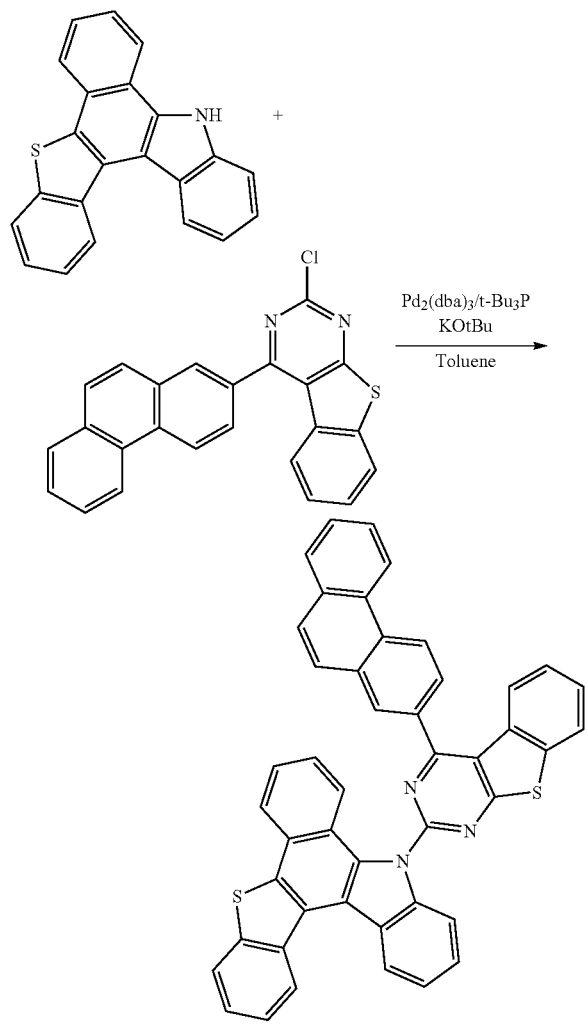

Except for using Sub 1-4 (5 g, 15.46 mmol), Sub 2-2-S-(14) (7.36 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-S-(14) (6.66 g, yield 66%).

(20) 1-4-2-S-(15) Synthesis

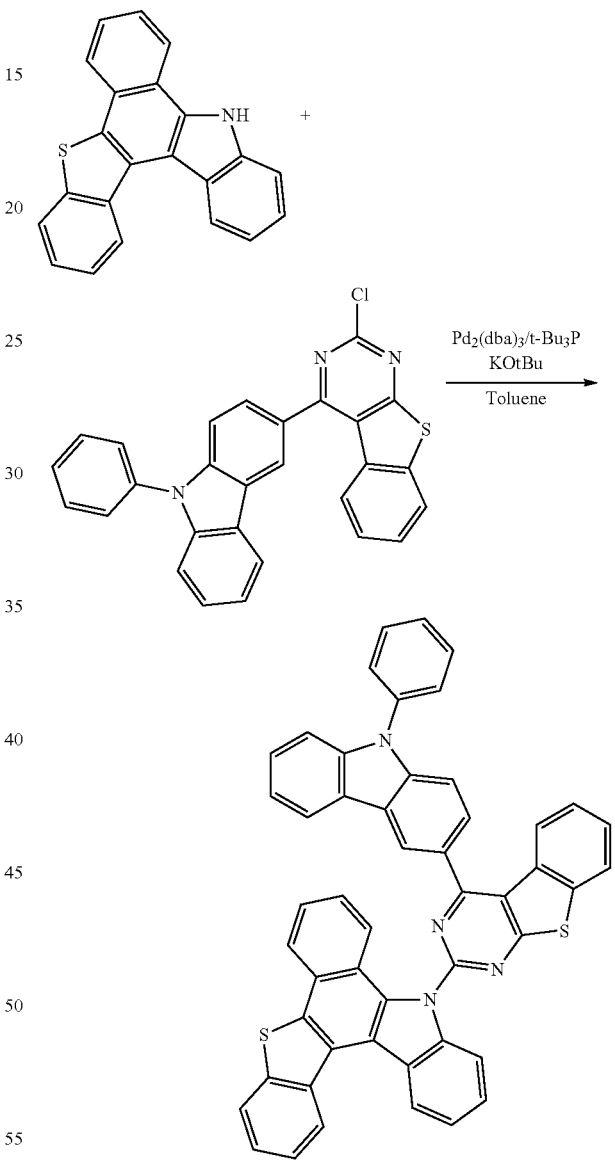

Except for using Sub 1-4 (5 g, 15.46 mmol), Sub 2-2-S-(15) (8.57 g, 18.55 mmol), Pd$_2$(dba)$_3$ (0.56 g, 4 mol %), t-Bu$_3$P (0.25 g, 8 mol %), KOtBu (5.2 g, 46.38 mmol) and tolune, the same procedure as described in Synthesis Method of Compound 1-1-1-O-(1) was carried out to obtain desired Compound 1-4-2-S-(15) (6.94 g, yield 60%).

In Table 3 below, FD-MS data of the compounds 1-1-1-O-(1) to 1-4-2-S-(23) prepared in the Synthesis Examples of the present invention are given.

TABLE 3

| Compound | FD-MS | Compound | FD-MS |
|---|---|---|---|
| 1-1-1-O-(1) | m/z = 567.14 ($C_{38}H_{21}N_3OS$ = 567.66) | 1-1-1-O-(2) | m/z = 572.17 ($C_{38}H_{16}D_5N_3OS$ = 572.69) |
| 1-1-1-O-(3) | m/z = 568.14 ($C_{37}H_{20}N_4OS$ = 568.65) | 1-1-1-O-(4) | m/z = 643.17 ($C_{44}H_{25}N_3OS$ = 643.75) |
| 1-1-1-O-(5) | m/z = 643.17 ($C_{44}H_{25}N_3OS$ = 643.75) | 1-1-1-O-(6) | m/z = 617.16 ($C_{42}H_{23}N_3OS$ = 617.72) |
| 1-1-1-O-(7) | m/z = 617.16 ($C_{42}H_{23}N_3OS$ = 617.72) | 1-1-1-O-(8) | m/z = 719.20 ($C_{50}H_{29}N_3OS$ = 719.85) |
| 1-1-1-O-(9) | m/z = 693.19 ($C_{48}H_{27}N_3OS$ = 693.81) | 1-1-1-O-(10) | m/z = 693.19 ($C_{48}H_{27}N_3OS$ = 693.81) |
| 1-1-1-O-(11) | m/z = 693.19 ($C_{48}H_{27}N_3OS$ = 693.81) | 1-1-1-O-(12) | m/z = 693.19 ($C_{48}H_{27}N_3OS$ = 693.81) |
| 1-1-1-O-(13) | m/z = 667.17 ($C_{46}H_{25}N_3OS$ = 667.78) | 1-1-1-O-(14) | m/z = 667.17 ($C_{46}H_{25}N_3OS$ = 667.78) |
| 1-1-1-O-(15) | m/z = 732.20 ($C_{50}H_{28}N_4OS$ = 732.85) | 1-1-1-O-(16) | m/z = 657.15 ($C_{44}H_{23}N_3O_2S$ = 657.74) |
| 1-1-1-O-(17) | m/z = 657.15 ($C_{44}H_{23}N_3O_2S$ = 657.74) | 1-1-1-O-(18) | m/z = 673.13 ($C_{44}H_{23}N_3OS_2$ = 673.80) |
| 1-1-1-O-(19) | m/z = 673.13 ($C_{44}H_{23}N_3OS_2$ = 673.80) | 1-1-1-O-(20) | m/z = 705.10 ($C_{44}H_{23}N_3OS_3$ = 705.87) |
| 1-1-1-O-(21) | m/z = 617.16 ($C_{42}H_{23}N_3OS$ = 617.72) | 1-1-1-O-(22) | m/z = 693.19 ($C_{48}H_{27}N_3OS$ = 693.81) |
| 1-1-1-S-(1) | m/z = 583.12 ($C_{38}H_{21}N_3S_2$ = 583.72) | 1-1-1-S-(2) | m/z = 588.15 ($C_{38}H_{16}D_5N_3S_2$ = 588.75) |
| 1-1-1-S-(3) | m/z = 584.11 ($C_{37}H_{20}N_4S_2$ = 584.71) | 1-1-1-S-(4) | m/z = 659.15 ($C_{44}H_{25}N_3S_2$ 659.82) |
| 1-1-1-S-(5) | m/z = 659.15 ($C_{44}H_{25}N_3S_2$ = 659.82) | 1-1-1-S-(6) | m/z = 633.13 ($C_{42}H_{23}N_3S_2$ 633.78) |
| 1-1-1-S-(7) | m/z = 633.13 ($C_{42}H_{23}N_3S_2$ = 633.78) | 1-1-1-S-(8) | m/z = 735.18 ($C_{50}H_{29}N_3S_2$ = 735.92) |
| 1-1-1-S-(9) | m/z = 709.16 ($C_{48}H_{27}N_3S_2$ = 709.88) | 1-1-1-S-(10) | m/z = 709.16 ($C_{48}H_{27}N_3S_2$ = 709.88) |
| 1-1-1-S-(11) | m/z = 709.16 ($C_{48}H_{27}N_3S_2$ = 709.88) | 1-1-1-S-(12) | m/z = 709.16 ($C_{48}H_{27}N_3S_2$ = 709.88) |
| 1-1-1-S-(13) | m/z = 683.15 ($C_{46}H_{25}N_3S_2$ = 683.84) | 1-1-1-S-(14) | m/z = 683.15 ($C_{46}H_{25}N_3S_2$ = 683.84) |
| 1-1-1-S-(15) | m/z = 748.18 ($C_{50}H_{28}N_4S_2$ = 748.91) | 1-1-1-S-(16) | m/z = 673.13 ($C_{44}H_{23}N_3OS_2$ = 673.80) |
| 1-1-1-S-(17) | m/z = 673.13 ($C_{44}H_{23}N_3OS_2$ = 673.80) | 1-1-1-S-(18) | m/z = 689.11 ($C_{44}H_{23}N_3S_3$ = 689.87) |
| 1-1-1-S-(19) | m/z = 689.11 ($C_{44}H_{23}N_3S_3$ = 689.87) | 1-1-1-S-(20) | m/z = 721.08 ($C_{44}H_{23}N_3S_4$ = 721.93) |
| 1-1-1-S-(21) | m/z = 683.15 ($C_{46}H_{25}N_3S_2$ = 683.84) | 1-1-1-S-(22) | m/z = 785.20 ($C_{54}H_{31}N_3S_2$ = 785.97) |
| 1-1-1-S-(23) | m/z = 739.12 ($C_{48}H_{25}N_3S_3$ = 739.93) | | |
| 1-1-2-O-(1) | m/z = 567.14 ($C_{38}H_{21}N_3OS$ = 567.66) | 1-1-2-O-(2) | m/z = 572.17 ($C_{38}H_{16}D_5N_3OS$ = 572.69) |
| 1-1-2-O-(3) | m/z = 568.14 ($C_{37}H_{20}N_4OS$ = 568.65) | 1-1-2-O-(4) | m/z = 643.17 ($C_{44}H_{25}N_3OS$ = 643.75) |
| 1-1-2-O-(5) | m/z = 643.17 ($C_{44}H_{25}N_3OS$ = 643.75) | 1-1-2-O-(6) | m/z = 617.16 ($C_{42}H_{23}N_3OS$ = 617.72) |
| 1-1-2-O-(7) | m/z = 617.16 ($C_{42}H_{23}N_3OS$ = 617.72) | 1-1-2-O-(8) | m/z = 719.20 ($C_{50}H_{29}N_3OS$ = 719.85) |
| 1-1-2-O-(9) | m/z = 693.19 ($C_{48}H_{27}N_3OS$ = 693.81) | 1-1-2-O-(10) | m/z = 693.19 ($C_{48}H_{27}N_3OS$ = 693.81) |
| 1-1-2-O-(11) | m/z = 693.19 ($C_{48}H_{27}N_3OS$ = 693.81) | 1-1-2-O-(12) | m/z = 693.19 ($C_{48}H_{27}N_3OS$ = 693.81) |
| 1-1-2-O-(13) | m/z = 667.17 ($C_{46}H_{25}N_3OS$ = 667.78) | 1-1-2-O-(14) | m/z = 667.17 ($C_{46}H_{25}N_3OS$ = 667.78) |
| 1-1-2-O-(15) | m/z = 732.20 ($C_{50}H_{28}N_4OS$ = 732.85) | 1-1-2-O-(16) | m/z = 657.15 ($C_{44}H_{23}N_3O_2S$ = 657.74) |
| 1-1-2-O-(17) | m/z = 657.15 ($C_{44}H_{23}N_3O_2S$ = 657.74) | 1-1-2-O-(18) | m/z = 673.13 ($C_{44}H_{23}N_3OS_2$ = 673.80) |
| 1-1-2-O-(19) | m/z = 673.13 ($C_{44}H_{23}N_3OS_2$ = 673.80) | 1-1-2-O-(20) | m/z = 705.10 ($C_{44}H_{23}N_3OS_3$ = 705.87) |
| 1-1-2-O-(21) | m/z = 667.17 ($C_{46}H_{25}N_3OS$ = 667.78) | 1-1-2-O-(22) | m/z = 667.17 ($C_{46}H_{25}N_3OS$ = 667.78) |
| 1-1-2-S-(1) | m/z = 583.12 ($C_{38}H_{21}N_3S_2$ = 583.72) | 1-1-2-S-(2) | m/z = 588.15 ($C_{38}H_{16}D_5N_3S_2$ = 588.75) |
| 1-1-2-S-(3) | m/z = 584.11 ($C_{37}H_{20}N_4S_2$ = 584.71) | 1-1-2-S-(4) | m/z = 659.15 ($C_{44}H_{25}N_3S_2$ = 659.82) |
| 1-1-2-S-(5) | m/z = 659.15 ($C_{44}H_{25}N_3S_2$ = 659.82) | 1-1-2-S-(6) | m/z = 633.13 ($C_{42}H_{23}N_3S_2$ = 633.78) |
| 1-1-2-S-(7) | m/z = 633.13 ($C_{42}H_{23}N_3S_2$ = 633.78) | 1-1-2-S-(8) | m/z = 735.18 ($C_{50}H_{29}N_3S_2$ = 735.92) |
| 1-1-2-S-(9) | m/z = 709.16 ($C_{48}H_{27}N_3S_2$ = 709.88) | 1-1-2-S-(10) | m/z = 709.16 ($C_{48}H_{27}N_3S_2$ = 709.88) |
| 1-1-2-S-(11) | m/z = 709.16 ($C_{48}H_{27}N_3S_2$ = 709.88) | 1-1-2-S-(12) | m/z = 709.16 ($C_{48}H_{27}N_3S_2$ = 709.88) |
| 1-1-2-S-(13) | m/z = 683.15 ($C_{46}H_{25}N_3S_2$ = 683.84) | 1-1-2-S-(14) | m/z = 683.15 ($C_{46}H_{25}N_3S_2$ = 683.84) |
| 1-1-2-S-(15) | m/z = 748.18 ($C_{50}H_{28}N_4S_2$ = 748.91) | 1-1-2-S-(16) | m/z = 673.13 ($C_{44}H_{23}N_3OS_2$ = 673.80) |
| 1-1-2-S-(17) | m/z = 673.13 ($C_{44}H_{23}N_3OS_2$ = 673.80) | 1-1-2-S-(18) | m/z = 689.11 ($C_{44}H_{23}N_3S_3$ = 489.87) |
| 1-1-2-S-(19) | m/z = 689.11 ($C_{44}H_{23}N_3S_3$ = 689.87) | 1-1-2-S-(20) | m/z = 721.08 ($C_{44}H_{23}N_3S_4$ = 721.93) |
| 1-1-2-S-(21) | m/z = 683.15 ($C_{46}H_{25}N_3S_2$ = 683.84) | 1-1-2-S-(22) | m/z = 709.16 ($C_{48}H_{27}N_3S_2$ = 709.88) |
| 1-1-2-S-(23) | m/z = 826.22 ($C_{56}H_{34}N_4S_2$ = 827.03) | | |
| 1-2-1-O-(1) | m/z = 567.14 ($C_{38}H_{21}N_3OS$ = 567.66) | 1-2-1-O-(2) | m/z = 572.17 ($C_{38}H_{16}D_5N_3OS$ = 572.69) |
| 1-2-1-O-(3) | m/z = 568.14 ($C_{37}H_{20}N_4OS$ = 568.65) | 1-2-1-O-(4) | m/z = 643.17 ($C_{44}H_{25}N_3OS$ = 643.75) |
| 1-2-1-O-(5) | m/z = 643.17 ($C_{44}H_{25}N_3OS$ = 643.75) | 1-2-1-O-(6) | m/z = 617.16 ($C_{42}H_{23}N_3OS$ = 617.72) |
| 1-2-1-O-(7) | m/z = 617.16 ($C_{42}H_{23}N_3OS$ = 617.72) | 1-2-1-O-(8) | m/z = 719.20 ($C_{50}H_{29}N_3OS$ = 719.85) |
| 1-2-1-O-(9) | m/z = 693.19 ($C_{48}H_{27}N_3OS$ = 693.81) | 1-2-1-O-(10) | m/z = 693.19 ($C_{48}H_{27}N_3OS$ = 693.81) |
| 1-2-1-O-(11) | m/z = 693.19 ($C_{48}H_{27}N_3OS$ = 693.81) | 1-2-1-O-(12) | m/z = 693.19 ($C_{48}H_{27}N_3OS$ = 693.81) |
| 1-2-1-O-(13) | m/z = 667.17 ($C_{46}H_{25}N_3OS$ = 667.78) | 1-2-1-O-(14) | m/z = 667.17 ($C_{46}H_{25}N_3OS$ = 667.78) |
| 1-2-1-O-(15) | m/z = 732.20 ($C_{50}H_{28}N_4OS$ = 732.85) | 1-2-1-O-(16) | m/z = 657.15 ($C_{44}H_{23}N_3O_2S$ = 657.74) |
| 1-2-1-O-(17) | m/z = 657.15 ($C_{44}H_{23}N_3O_2S$ = 657.74) | 1-2-1-O-(18) | m/z = 673.13 ($C_{44}H_{23}N_3OS_2$ = 673.80) |
| 1-2-1-O-(19) | m/z = 673.13 ($C_{44}H_{23}N_3OS_2$ = 673.80) | 1-2-1-O-(20) | m/z = 705.10 ($C_{44}H_{23}N_3OS_3$ = 705.87) |
| 1-2-1-O-(21) | m/z = 617.16 ($C_{42}H_{23}N_3OS$ = 617.72) | 1-2-1-O-(22) | m/z = 693.19 ($C_{48}H_{27}N_3OS$ = 693.81) |
| 1-2-1-S-(1) | m/z = 583.12 ($C_{38}H_{21}N_3S_2$ = 583.72) | 1-2-1-S-(2) | m/z = 588.15 ($C_{38}H_{16}D_5N_3S_2$ = 588.75) |
| 1-2-1-S-(3) | m/z = 584.11 ($C_{37}H_{20}N_4S_2$ = 584.71) | 1-2-1-S-(4) | m/z = 659.15 ($C_{44}H_{25}N_3S_2$ = 659.82) |
| 1-2-1-S-(5) | m/z = 659.15 ($C_{44}H_{25}N_3S_2$ = 659.82) | 1-2-1-S-(6) | m/z = 633.13 ($C_{42}H_{23}N_3S_2$ = 633.78) |
| 1-2-1-S-(7) | m/z = 633.13 ($C_{42}H_{23}N_3S_2$ = 633.78) | 1-2-1-S-(8) | m/z = 735.18 ($C_{50}H_{29}N_3S_2$ = 735.92) |
| 1-2-1-S-(9) | m/z = 709.16 ($C_{48}H_{27}N_3S_2$ = 709.88) | 1-2-1-S-(10) | m/z = 709.16 ($C_{48}H_{27}N_3S_2$ = 709.88) |
| 1-2-1-S-(11) | m/z = 709.16 ($C_{48}H_{27}N_3S_2$ = 709.88) | 1-2-1-S-(12) | m/z = 709.16 ($C_{48}H_{27}N_3S_2$ = 709.88) |
| 1-2-1-S-(13) | m/z = 683.15 ($C_{46}H_{25}N_3S_2$ = 683.84) | 1-2-1-S-(14) | m/z = 683.15 ($C_{46}H_{25}N_3S_2$ = 683.84) |
| 1-2-1-S-(15) | m/z = 748.18 ($C_{50}H_{28}N_4S_2$ = 748.91) | 1-2-1-S-(16) | m/z = 673.13 ($C_{44}H_{23}N_3OS_2$ = 673.80) |
| 1-2-1-S-(17) | m/z = 673.13 ($C_{44}H_{23}N_3OS_2$ = 673.80) | 1-2-1-S-(18) | m/z = 689.11 ($C_{44}H_{23}N_3S_3$ = 689.87) |
| 1-2-1-S-(19) | m/z = 689.11 ($C_{44}H_{23}N_3S_3$ = 689.87) | 1-2-1-S-(20) | m/z = 721.08 ($C_{44}H_{23}N_3S_4$ = 721.93) |
| 1-2-1-S-(21) | m/z = 759.18 ($C_{52}H_{29}N_3S_2$ = 759.94) | 1-2-1-S-(22) | m/z = 633.13 ($C_{42}H_{23}N_3S_2$ = 633.78) |
| 1-2-1-S-(23) | m/z = 739.12 ($C_{48}H_{25}N_3S_3$ = 739.93) | | |
| 1-2-2-O-(1) | m/z = 567.14 ($C_{38}H_{21}N_3OS$ = 567.66) | 1-2-2-O-(2) | m/z = 572.17 ($C_{38}H_{16}D_5N_3OS$ = 572.69) |
| 1-2-2-O-(3) | m/z = 568.14 ($C_{37}H_{20}N_4OS$ = 568.65) | 1-2-2-O-(4) | m/z = 643.17 ($C_{44}H_{25}N_3OS$ = 643.75) |
| 1-2-2-O-(5) | m/z = 643.17 ($C_{44}H_{25}N_3OS$ = 643.75) | 1-2-2-O-(6) | m/z = 617.16 ($C_{42}H_{23}N_3OS$ = 617.72) |
| 1-2-2-O-(7) | m/z = 617.16 ($C_{42}H_{23}N_3OS$ = 617.72) | 1-2-2-O-(8) | m/z = 719.20 ($C_{50}H_{29}N_3OS$ = 719.85) |
| 1-2-2-O-(9) | m/z = 693.19 ($C_{48}H_{27}N_3OS$ = 693.81) | 1-2-2-O-(10) | m/z = 693.19 ($C_{48}H_{27}N_3OS$ = 693.81) |
| 1-2-2-O-(11) | m/z = 693.19 ($C_{48}H_{27}N_3OS$ = 693.81) | 1-2-2-O-(12) | m/z = 693.19 ($C_{48}H_{27}N_3OS$ = 693.81) |
| 1-2-2-O-(13) | m/z = 667.17 ($C_{46}H_{25}N_3OS$ = 667.78) | 1-2-2-O-(14) | m/z = 667.17 ($C_{46}H_{25}N_3OS$ = 667.78) |
| 1-2-2-O-(15) | m/z = 732.20 ($C_{50}H_{28}N_4OS$ = 732.85) | 1-2-2-O-(16) | m/z = 657.15 ($C_{44}H_{23}N_3O_2S$ = 657.74) |
| 1-2-2-O-(17) | m/z = 657.15 ($C_{44}H_{23}N_3O_2S$ = 657.74) | 1-2-2-O-(18) | m/z = 673.13 ($C_{44}H_{23}N_3OS_2$ = 673.80) |

TABLE 3-continued

| Compound | FD-MS | Compound | FD-MS |
|---|---|---|---|
| 1-2-2-O-(19) | m/z = 673.13 ($C_{44}H_{23}N_3OS_2$ = 673.80) | 1-2-2-O-(20) | m/z = 705.10 ($C_{44}H_{23}N_3OS_3$ = 705.87) |
| 1-2-2-O-(21) | m/z = 667.17 ($C_{46}H_{25}N_3OS$ = 667.78) | 1-2-2-O-(22) | m/z = 667.17 ($C_{46}H_{25}N_3OS$ = 667.78) |
| 1-2-2-S-(1) | m/z = 583.12 ($C_{38}H_{21}N_3S_2$ = 583.72) | 1-2-2-S-(2) | m/z = 588.15 ($C_{38}H_{16}D_5N_3S_2$ = 588.75) |
| 1-2-2-S-(3) | m/z = 584.11 ($C_{37}H_{20}N_4S_2$ = 584.71) | 1-2-2-S-(4) | m/z = 659.15 ($C_{44}H_{25}N_3S_2$ = 659.82) |
| 1-2-2-S-(5) | m/z = 659.15 ($C_{44}H_{25}N_3S_2$ = 659.82) | 1-2-2-S-(6) | m/z = 633.13 ($C_{42}H_{23}N_3S_2$ = 633.78) |
| 1-2-2-S-(7) | m/z = 633.13 ($C_{42}H_{23}N_3S_2$ = 633.78) | 1-2-2-S-(8) | m/z = 735.18 ($C_{50}H_{29}N_3S_2$ = 735.92) |
| 1-2-2-S-(9) | m/z = 709.16 ($C_{48}H_{27}N_3S_2$ = 709.88) | 1-2-2-S-(10) | m/z = 709.16 ($C_{48}H_{27}N_3S_2$ = 709.88) |
| 1-2-2-S-(11) | m/z = 709.16 ($C_{48}H_{27}N_3S_2$ = 709.88) | 1-2-2-S-(12) | m/z = 709.16 ($C_{48}H_{27}N_3S_2$ = 709.88) |
| 1-2-2-S-(13) | m/z = 683.15 ($C_{46}H_{25}N_3S_2$ = 683.84) | 1-2-2-S-(14) | m/z = 683.15 ($C_{46}H_{25}N_3S_2$ = 683.84) |
| 1-2-2-S-(15) | m/z = 748.18 ($C_{50}H_{28}N_4S_2$ = 748.91) | 1-2-2-S-(16) | m/z = 673.13 ($C_{44}H_{23}N_3OS_2$ = 673.80) |
| 1-2-2-S-(17) | m/z = 673.13 ($C_{44}H_{23}N_3OS_2$ = 673.80) | 1-2-2-S-(18) | m/z = 689.11 ($C_{44}H_{23}N_3S_3$ = 689.87) |
| 1-2-2-S-(19) | m/z = 689.11 ($C_{44}H_{23}N_3S_3$ = 689.87) | 1-2-2-S-(20) | m/z = 721.08 ($C_{44}H_{23}N_3S_4$ = 721.93) |
| 1-2-2-S-(21) | m/z = 683.15 ($C_{46}H_{25}N_3S_2$ = 683.84) | 1-2-2-S-(22) | m/z = 709.16 ($C_{48}H_{27}N_3S_2$ = 709.88) |
| 1-2-1-S-(23) | m/z = 739.12 ($C_{48}H_{25}N_3S_3$ = 739.93) | | |
| 1-3-1-O-(1) | m/z = 567.14 ($C_{38}H_{21}N_3OS$ = 567.66) | 1-3-1-O-(2) | m/z = 572.17 ($C_{38}H_{16}D_5N_3OS$ = 572.69) |
| 1-3-1-O-(3) | m/z = 568.14 ($C_{37}H_{20}N_4OS$ = 568.65) | 1-3-1-O-(4) | m/z = 643.17 ($C_{44}H_{25}N_3OS$ = 643.75) |
| 1-3-1-O-(5) | m/z = 643.17 ($C_{44}H_{25}N_3OS$ = 643.75) | 1-3-1-O-(6) | m/z = 617.16 ($C_{42}H_{23}N_3OS$ = 617.72) |
| 1-3-1-O-(7) | m/z = 617.16 ($C_{42}H_{23}N_3OS$ = 617.72) | 1-3-1-O-(8) | m/z = 719.20 ($C_{50}H_{29}N_3OS$ = 719.85) |
| 1-3-1-O-(9) | m/z = 693.19 ($C_{48}H_{27}N_3OS$ = 693.81) | 1-3-1-O-(10) | m/z = 693.19 ($C_{48}H_{27}N_3OS$ = 693.81) |
| 1-3-1-O-(11) | m/z = 693.19 ($C_{48}H_{27}N_3OS$ = 693.81) | 1-3-1-O-(12) | m/z = 693.19 ($C_{48}H_{27}N_3OS$ = 693.81) |
| 1-3-1-O-(13) | m/z = 667.17 ($C_{46}H_{25}N_3OS$ = 667.78) | 1-3-1-O-(14) | m/z = 667.17 ($C_{46}H_{25}N_3OS$ = 667.78) |
| 1-3-1-O-(15) | m/z = 732.20 ($C_{50}H_{28}N_4OS$ = 732.85) | 1-3-1-O-(16) | m/z = 657.15 ($C_{44}H_{23}N_3O_2S$ = 657.74) |
| 1-3-1-O-(17) | m/z = 657.15 ($C_{44}H_{23}N_3O_2S$ = 657.74) | 1-3-1-O-(18) | m/z = 673.13 ($C_{44}H_{23}N_3OS_2$ = 673.80) |
| 1-3-1-O-(19) | m/z = 673.13 ($C_{44}H_{23}N_3OS_2$ = 673.80) | 1-3-1-O-(20) | m/z = 705.10 ($C_{44}H_{23}N_3OS_3$ = 705.87) |
| 1-3-1-O-(21) | m/z = 617.16 ($C_{42}H_{23}N_3OS$ = 617.72) | 1-3-1-O-(22) | m/z = 693.19 ($C_{48}H_{27}N_3OS$ = 693.81) |
| 1-3-1-S-(1) | m/z = 583.12 ($C_{38}H_{21}N_3S_2$ = 583.72) | 1-3-1-S-(2) | m/z = 588.15 ($C_{38}H_{16}D_5N_3S_2$ = 588.75) |
| 1-3-1-S-(3) | m/z = 584.11 ($C_{37}H_{20}N_4S_2$ = 584.71) | 1-3-1-S-(4) | m/z = 659.15 ($C_{44}H_{25}N_3S_2$ = 659.82) |
| 1-3-1-S-(5) | m/z = 659.15 ($C_{44}H_{25}N_3S_2$ = 659.82) | 1-3-1-S-(6) | m/z = 633.13 ($C_{42}H_{23}N_3S_2$ = 633.78) |
| 1-3-1-S-(7) | m/z = 633.13 ($C_{42}H_{23}N_3S_2$ = 633.78) | 1-3-1-S-(8) | m/z = 735.18 ($C_{50}H_{29}N_3S_2$ = 735.92) |
| 1-3-1-S-(9) | m/z = 709.16 ($C_{48}H_{27}N_3S_2$ = 709.88) | 1-3-1-S-(10) | m/z = 709.16 ($C_{48}H_{27}N_3S_2$ = 709.88) |
| 1-3-1-S-(11) | m/z = 709.16 ($C_{48}H_{27}N_3S_2$ = 709.88) | 1-3-1-S-(12) | m/z = 709.16 ($C_{48}H_{27}N_3S_2$ = 709.88) |
| 1-3-1-S-(13) | m/z = 683.15 ($C_{46}H_{25}N_3S_2$ = 683.84) | 1-3-1-S-(14) | m/z = 683.15 ($C_{46}H_{25}N_3S_2$ = 683.84) |
| 1-3-1-S-(15) | m/z = 748.18 ($C_{50}H_{28}N_4S_2$ = 748.91) | 1-3-1-S-(16) | m/z = 673.13 ($C_{44}H_{23}N_3OS_2$ = 673.80) |
| 1-3-1-S-(17) | m/z = 673.13 ($C_{44}H_{23}N_3OS_2$ = 673.80) | 1-3-1-S-(18) | m/z = 689.11 ($C_{44}H_{23}N_3S_3$ = 689.87) |
| 1-3-1-S-(19) | m/z = 689.11 ($C_{44}H_{23}N_3S_3$ = 689.87) | 1-3-1-S-(20) | m/z = 721.08 ($C_{44}H_{23}N_3S_4$ = 721.93) |
| 1-3-1-S-(21) | m/z = 683.15 ($C_{46}H_{25}N_3S_2$ = 683.84) | 1-3-1-S-(22) | m/z = 709.16 ($C_{48}H_{27}N_3S_2$ = 709.88) |
| 1-3-1-S-(23) | m/z = 739.12 ($C_{48}H_{25}N_3S_3$ = 739.93) | | |
| 1-3-2-O-(1) | m/z = 567.14 ($C_{38}H_{21}N_3OS$ = 567.66) | 1-3-2-O-(2) | m/z = 572.17 ($C_{38}H_{16}D_5N_3OS$ = 572.69) |
| 1-3-2-O-(3) | m/z = 568.14 ($C_{37}H_{20}N_4OS$ = 568.65) | 1-3-2-O-(4) | m/z = 643.17 ($C_{44}H_{25}N_3OS$ = 643.75) |
| 1-3-2-O-(5) | m/z = 643.17 ($C_{44}H_{25}N_3OS$ = 643.75) | 1-3-2-O-(6) | m/z = 617.16 ($C_{42}H_{23}N_3OS$ = 617.72) |
| 1-3-2-O-(7) | m/z = 617.16 ($C_{42}H_{23}N_3OS$ = 617.72) | 1-3-2-O-(8) | m/z = 719.20 ($C_{50}H_{29}N_3OS$ = 719.85) |
| 1-3-2-O-(9) | m/z = 693.19 ($C_{48}H_{27}N_3OS$ = 693.81) | 1-3-2-O-(10) | m/z = 693.19 ($C_{48}H_{27}N_3OS$ = 693.81) |
| 1-3-2-O-(11) | m/z = 693.19 ($C_{48}H_{27}N_3OS$ = 693.81) | 1-3-2-O-(12) | m/z = 693.19 ($C_{48}H_{27}N_3OS$ = 693.81) |
| 1-3-2-O-(13) | m/z = 667.17 ($C_{46}H_{25}N_3OS$ = 667.78) | 1-3-2-O-(14) | m/z = 667.17 ($C_{46}H_{25}N_3OS$ = 667.78) |
| 1-3-2-O-(15) | m/z = 732.20 ($C_{50}H_{28}N_4OS$ = 732.85) | 1-3-2-O-(16) | m/z = 657.15 ($C_{44}H_{23}N_3O_2S$ = 657.74) |
| 1-3-2-O-(17) | m/z = 657.15 ($C_{44}H_{23}N_3O_2S$ = 657.74) | 1-3-2-O-(18) | m/z = 673.13 ($C_{44}H_{23}N_3OS_2$ = 673.80) |
| 1-3-2-O-(19) | m/z = 673.13 ($C_{44}H_{23}N_3OS_2$ = 673.80) | 1-3-2-O-(20) | m/z = 705.10 ($C_{44}H_{23}N_3OS_3$ = 705.87) |
| 1-3-2-O-(21) | m/z = 667.17 ($C_{46}H_{25}N_3OS$ = 667.78) | 1-3-2-O-(22) | m/z = 572.17 ($C_{38}H_{16}D_5N_3OS$ = 572.69) |
| 1-3-2-S-(1) | m/z = 583.12 ($C_{38}H_{21}N_3S_2$ = 583.72) | 1-3-2-S-(2) | m/z = 588.15 ($C_{38}H_{16}D_5N_3S_2$ = 588.75) |
| 1-3-2-S-(3) | m/z = 584.11 ($C_{37}H_{20}N_4S_2$ = 584.71) | 1-3-2-S-(4) | m/z = 659.15 ($C_{44}H_{25}N_3S_2$ = 659.82) |
| 1-3-2-S-(5) | m/z = 659.15 ($C_{44}H_{25}N_3S_2$ = 659.82) | 1-3-2-S-(6) | m/z = 633.13 ($C_{42}H_{23}N_3S_2$ = 633.78) |
| 1-3-2-S-(7) | m/z = 633.13 ($C_{42}H_{23}N_3S_2$ = 633.78) | 1-3-2-S-(8) | m/z = 735.18 ($C_{50}H_{29}N_3S_2$ = 735.92) |
| 1-3-2-S-(9) | m/z = 709.16 ($C_{48}H_{27}N_3S_2$ = 709.88) | 1-3-2-S-(10) | m/z = 709.16 ($C_{48}H_{27}N_3S_2$ = 709.88) |
| 1-3-2-S-(11) | m/z = 709.16 ($C_{48}H_{27}N_3S_2$ = 709.88) | 1-3-2-S-(12) | m/z = 709.16 ($C_{48}H_{27}N_3S_2$ = 709.88) |
| 1-3-2-S-(13) | m/z = 683.15 ($C_{46}H_{25}N_3S_2$ = 683.84) | 1-3-2-S-(14) | m/z = 683.15 ($C_{46}H_{25}N_3S_2$ = 683.84) |
| 1-3-2-S-(15) | m/z = 748.18 ($C_{50}H_{28}N_4S_2$ = 748.91) | 1-3-2-S-(16) | m/z = 673.13 ($C_{44}H_{23}N_3OS_2$ = 673.80) |
| 1-3-2-S-(17) | m/z = 673.13 ($C_{44}H_{23}N_3OS_2$ = 673.80) | 1-3-2-S-(18) | m/z = 689.11 ($C_{44}H_{23}N_3S_3$ = 689.87) |
| 1-3-2-S-(19) | m/z = 689.11 ($C_{44}H_{23}N_3S_3$ = 689.87) | 1-3-2-S-(20) | m/z = 721.08 ($C_{44}H_{23}N_3S_4$ = 721.93) |
| 1-3-2-S-(21) | m/z = 683.15 ($C_{46}H_{25}N_3S_2$ = 683.84) | 1-3-2-S-(22) | m/z = 709.16 ($C_{48}H_{27}N_3S_2$ = 709.88) |
| 1-3-2-S-(23) | m/z = 826.22 ($C_{56}H_{34}N_4S_2$ = 827.03) | | |
| 1-4-1-O-(1) | m/z = 567.14 ($C_{38}H_{21}N_3OS$ = 567.66) | 1-4-1-O-(2) | m/z = 572.17 ($C_{38}H_{16}D_5N_3OS$ = 572.69) |
| 1-4-1-O-(3) | m/z = 568.14 ($C_{37}H_{20}N_4OS$ = 568.65) | 1-4-1-O-(4) | m/z = 643.17 ($C_{44}H_{25}N_3OS$ = 643.75) |
| 1-4-1-O-(5) | m/z = 643.17 ($C_{44}H_{25}N_3OS$ = 643.75) | 1-4-1-O-(6) | m/z = 617.16 ($C_{42}H_{23}N_3OS$ = 617.72) |
| 1-4-1-O-(7) | m/z = 617.16 ($C_{42}H_{23}N_3OS$ = 617.72) | 1-4-1-O-(8) | m/z = 719.20 ($C_{50}H_{29}N_3OS$ = 719.85) |
| 1-4-1-O-(9) | m/z = 693.19 ($C_{48}H_{27}N_3OS$ = 693.81) | 1-4-1-O-(10) | m/z = 693.19 ($C_{48}H_{27}N_3OS$ = 693.81) |
| 1-4-1-O-(11) | m/z = 693.19 ($C_{48}H_{27}N_3OS$ = 693.81) | 1-4-1-O-(12) | m/z = 693.19 ($C_{48}H_{27}N_3OS$ = 693.81) |
| 1-4-1-O-(13) | m/z = 667.17 ($C_{46}H_{25}N_3OS$ = 667.78) | 1-4-1-O-(14) | m/z = 667.17 ($C_{46}H_{25}N_3OS$ = 667.78) |
| 1-4-1-O-(15) | m/z = 732.20 ($C_{50}H_{28}N_4OS$ = 732.85) | 1-4-1-O-(16) | m/z = 657.15 ($C_{44}H_{23}N_3O_2S$ = 657.74) |
| 1-4-1-O-(17) | m/z = 657.15 ($C_{44}H_{23}N_3O_2S$ = 657.74) | 1-4-1-O-(18) | m/z = 673.13 ($C_{44}H_{23}N_3OS_2$ = 673.80) |
| 1-4-1-O-(19) | m/z = 673.13 ($C_{44}H_{23}N_3OS_2$ = 673.80) | 1-4-1-O-(20) | m/z = 705.10 ($C_{44}H_{23}N_3OS_3$ = 705.87) |
| 1-4-1-O-(21) | m/z = 617.16 ($C_{42}H_{23}N_3OS$ = 617.72) | 1-4-1-O-(22) | m/z = 693.19 ($C_{48}H_{27}N_3OS$ = 693.81) |
| 1-4-1-S-(1) | m/z = 583.12 ($C_{38}H_{21}N_3S_2$ = 583.72) | 1-4-1-S-(2) | m/z = 588.15 ($C_{38}H_{16}D_5N_3S_2$ = 588.75) |
| 1-4-1-S-(3) | m/z = 584.11 ($C_{37}H_{20}N_4S_2$ = 584.71) | 1-4-1-S-(4) | m/z = 659.15 ($C_{44}H_{25}N_3S_2$ = 659.82) |
| 1-4-1-S-(5) | m/z = 659.15 ($C_{44}H_{25}N_3S_2$ = 659.82) | 1-4-1-S-(6) | m/z = 633.13 ($C_{42}H_{23}N_3S_2$ = 633.78) |
| 1-4-1-S-(7) | m/z = 633.13 ($C_{42}H_{23}N_3S_2$ = 633.78) | 1-4-1-S-(8) | m/z = 735.18 ($C_{50}H_{29}N_3S_2$ = 735.92) |
| 1-4-1-S-(9) | m/z = 709.16 ($C_{48}H_{27}N_3S_2$ = 709.88) | 1-4-1-S-(10) | m/z = 709.16 ($C_{48}H_{27}N_3S_2$ = 709.88) |
| 1-4-1-S-(11) | m/z = 709.16 ($C_{48}H_{27}N_3S_2$ = 709.88) | 1-4-1-S-(12) | m/z = 709.16 ($C_{48}H_{27}N_3S_2$ = 709.88) |
| 1-4-1-S-(13) | m/z = 683.15 ($C_{46}H_{25}N_3S_2$ = 683.84) | 1-4-1-S-(14) | m/z = 683.15 ($C_{46}H_{25}N_3S_2$ = 683.84) |

TABLE 3-continued

| Compound | FD-MS | Compound | FD-MS |
|---|---|---|---|
| 1-4-1-S-(15) | m/z = 748.18 ($C_{50}H_{28}N_4S_2$ = 748.91) | 1-4-1-S-(16) | m/z = 673.13 ($C_{44}H_{23}N_3OS_2$ = 673.80) |
| 1-4-1-S-(17) | m/z = 673.13 ($C_{44}H_{23}N_3OS_2$ = 673.80) | 1-4-1-S-(18) | m/z = 689.11 ($C_{44}H_{23}N_3S_3$ = 689.87) |
| 1-4-1-S-(19) | m/z = 689.11 ($C_{44}H_{23}N_3S_3$ = 689.87) | 1-4-1-S-(20) | m/z = 721.08 ($C_{44}H_{23}N_3S_4$ = 721.93) |
| 1-4-1-S-(21) | m/z = 709.16 ($C_{48}H_{27}N_3S_2$ = 709.88) | 1-4-1-S-(22) | m/z = 633.13 ($C_{42}H_{23}N_3S_2$ = 633.78) |
| 1-4-1-S-(23) | m/z = 739.12 ($C_{48}H_{25}N_3S_3$ = 739.93) | | |
| 1-4-2-O-(1) | m/z = 567.14 ($C_{38}H_{21}N_3OS$ = 567.66) | 1-4-2-O-(2) | m/z = 572.17 ($C_{38}H_{16}D_5N_3OS$ = 572.69) |
| 1-4-2-O-(3) | m/z = 568.14 ($C_{37}H_{20}N_4OS$ = 568.65) | 1-4-2-O-(4) | m/z = 643.17 ($C_{44}H_{25}N_3OS$ = 643.75) |
| 1-4-2-O-(5) | m/z = 643.17 ($C_{44}H_{25}N_3OS$ = 643.75) | 1-4-2-O-(6) | m/z = 617.16 ($C_{42}H_{23}N_3OS$ = 617.72) |
| 1-4-2-O-(7) | m/z = 617.16 ($C_{42}H_{23}N_3OS$ = 617.72) | 1-4-2-O-(8) | m/z = 719.20 ($C_{50}H_{29}N_3OS$ = 719.85) |
| 1-4-2-O-(9) | m/z = 693.19 ($C_{48}H_{27}N_3OS$ = 693.81) | 1-4-2-O-(10) | m/z = 693.19 ($C_{48}H_{27}N_3OS$ = 693.81) |
| 1-4-2-O-(11) | m/z = 693.19 ($C_{48}H_{27}N_3OS$ = 693.81) | 1-4-2-O-(12) | m/z = 693.19 ($C_{48}H_{27}N_3OS$ = 693.81) |
| 1-4-2-O-(13) | m/z = 667.17 ($C_{46}H_{25}N_3OS$ = 667.78) | 1-4-2-O-(14) | m/z = 667.17 ($C_{46}H_{25}N_3OS$ = 667.78) |
| 1-4-2-O-(15) | m/z = 732.20 ($C_{50}H_{28}N_4OS$ = 732.85) | 1-4-2-O-(16) | m/z = 657.15 ($C_{44}H_{23}N_3O_2S$ = 657.74) |
| 1-4-2-O-(17) | m/z = 657.15 ($C_{44}H_{23}N_3O_2S$ = 657.74) | 1-4-2-O-(18) | m/z = 657.13 ($C_{44}H_{23}N_3OS_2$ = 673.80) |
| 1-4-2-O-(19) | m/z = 673.13 ($C_{44}H_{23}N_3OS_2$ = 673.80) | 1-4-2-O-(20) | m/z = 705.10 ($C_{44}H_{23}N_3OS_3$ = 705.87) |
| 1-4-2-O-(21) | m/z = 667.17 ($C_{46}H_{25}N_3OS$ = 667.78) | 1-4-2-O-(22) | m/z = 667.17 ($C_{46}H_{25}N_3OS$ = 667.78) |
| 1-4-2-S-(1) | m/z = 583.12 ($C_{38}H_{21}N_3S_2$ = 583.72) | 1-4-2-S-(2) | m/z = 588.15 ($C_{38}H_{16}D_5N_3S_2$ = 588.75) |
| 1-4-2-S-(3) | m/z = 584.11 ($C_{37}H_{20}N_4S_2$ = 584.71) | 1-4-2-S-(4) | m/z = 659.15 ($C_{44}H_{25}N_3S_2$ = 659.82) |
| 1-4-2-S-(5) | m/z = 659.15 ($C_{44}H_{25}N_3S_2$ = 659.82) | 1-4-2-S-(6) | m/z = 633.13 ($C_{42}H_{23}N_3S_2$ = 633.78) |
| 1-4-2-S-(7) | m/z = 633.13 ($C_{42}H_{23}N_3S_2$ = 633.78) | 1-4-2-S-(8) | m/z = 735.18 ($C_{50}H_{29}N_3S_2$ = 735.92) |
| 1-4-2-S-(9) | m/z = 709.16 ($C_{48}H_{27}N_3S_2$ = 709.88) | 1-4-2-S-(10) | m/z = 709.16 ($C_{48}H_{27}N_3S_2$ = 709.88) |
| 1-4-2-S-(11) | m/z = 709.16 ($C_{48}H_{27}N_3S_2$ = 709.88) | 1-4-2-S-(12) | m/z = 709.16 ($C_{48}H_{27}N_3S_2$ = 709.88) |
| 1-4-2-S-(13) | m/z = 683.15 ($C_{46}H_{25}N_3S_2$ = 683.84) | 1-4-2-S-(14) | m/z = 683.15 ($C_{46}H_{25}N_3S_2$ = 683.84) |
| 1-4-2-S-(15) | m/z = 748.18 ($C_{50}H_{28}N_4S_2$ = 748.91) | 1-4-2-S-(16) | m/z = 673.13 ($C_{44}H_{23}N_3OS_2$ = 673.80) |
| 1-4-2-S-(17) | m/z = 673.13 ($C_{44}H_{23}N_3OS_2$ = 673.80) | 1-4-2-S-(18) | m/z = 689.11 ($C_{44}H_{23}N_3S_3$ = 689.87) |
| 1-4-2-S-(19) | m/z = 689.11 ($C_{44}H_{23}N_3S_3$ = 689.87) | 1-4-2-S-(20) | m/z = 721.08 ($C_{44}H_{23}N_3S_4$ = 721.93) |
| 1-4-2-S-(21) | m/z = 683.15 ($C_{46}H_{25}N_3S_2$ = 683.84) | 1-4-2-S-(22) | m/z = 709.16 ($C_{48}H_{27}N_3S_2$ = 709.88) |
| 1-4-2-S-(23) | m/z = 839.24 ($C_{58}H_{37}N_3S_2$ = 840.06) | | |

Fabrication and Evaluation of Organic Electronic Element

Test Example I-1

Red Organic Light Emitting Diode (a Phosphorescent Host)

Organic light emitting diodes (OLEDs) were fabricated according to a conventional method by using a compound of the present invention as a phosphorescent host material. First, an ITO layer (anode) was formed on a glass substrate, and a film of 4,4',4''-Tris[2-naphthyl(phenyl)amino]triphenylamine (hereinafter abbreviated as "2-TNATA") was vacuum-deposited on the ITO layer to form a hole injection layer with a thickness of 60 nm. Subsequently, 4,4-bis[N-(1-naphthyl)-N-phenylamino]biphenyl (hereinafter abbreviated as "NPD") was vacuum-deposited with a thickness of 60 nm on the hole injection layer to form a hole transport layer. Subsequently, a light emitting layer with a thickness of 30 nm was deposited on the hole transport layer by doping the hole transport layer with the compound 1-1-1-O-(1) of the present invention as a host material and the compound A below as a dopant material in a weight ratio of 95:5. Next, a film of ((1,1'-bisphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, and a film of tris(8-quinolinolato)aluminum (hereinafter abbreviated as "$Alq_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

<Compound A>

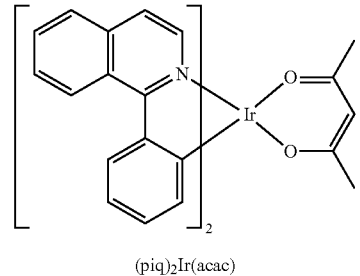

(piq)$_2$Ir(acac)

[Test Example I-2] to Test Example [□-320]

Red Organic Light Emitting Diode (a Phosphorescent Host)

The OLED was manufactured in the same manner as described in Test Example I-1, except that any one of the compounds 1-1-1-O-(2) to 1-4-2-S-(23) of the present invention in the Table 4 below was used as the host material of the light emitting layer, instead of the inventive compound 1-1-1-O-(1).

[Comparative Example I-1] to [Comparative Example 1-17]

An OLED was manufactured in the same manner as described in Test Example I-1, except that any one of the Comparative Compounds 1 to 17 represented below was used as the host material of the light emitting layer, instead of the inventive compound 1-1-1-O-(1).

-continued
<comp.Com 1>
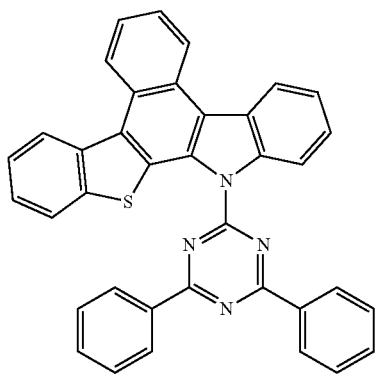
<comp.Com 2>
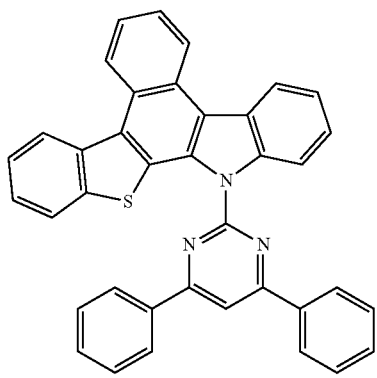
<comp.Com 3>
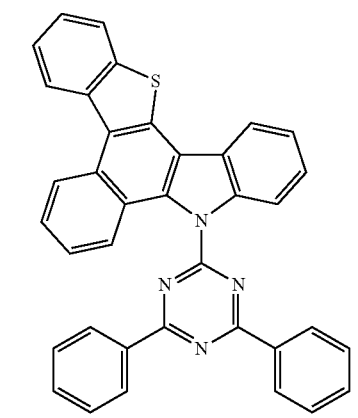
<comp.Com 4>
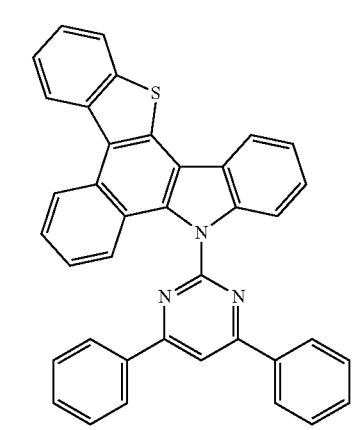
<comp.Com 5>
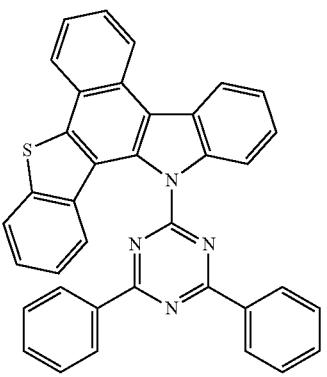
<comp.Com 6>
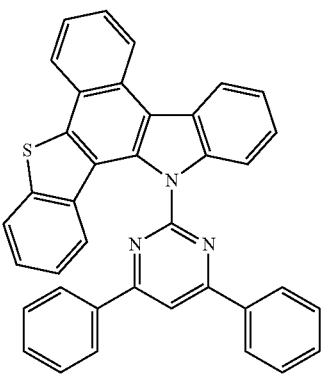
<comp.Com 7>
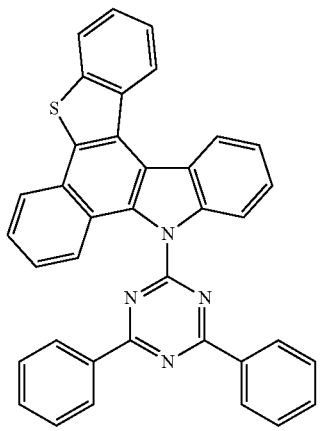

<comp.Com 8>
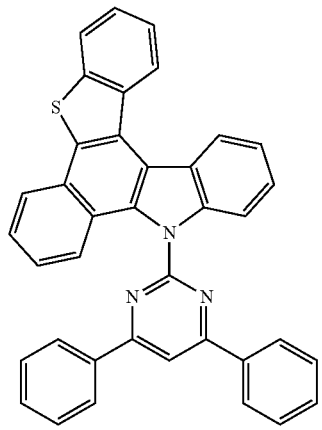
<comp.Com 9>
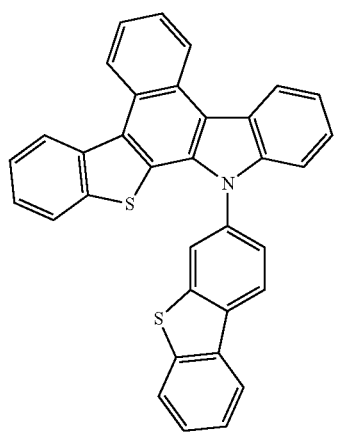
<comp.Com 10>
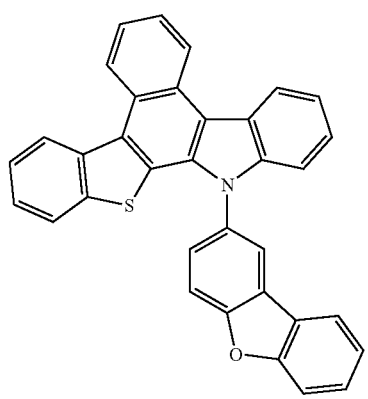
<comp.Com 11>
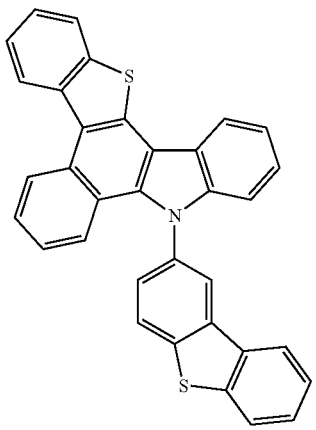
<comp.Com 12>
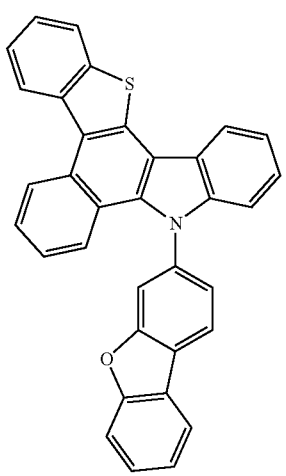
<comp.Com 13>
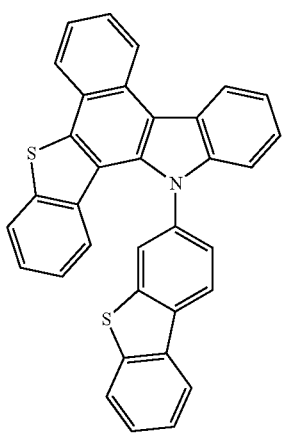

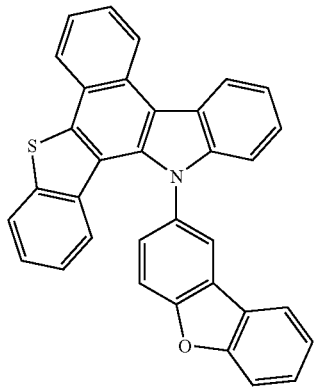

<comp.Com 14>

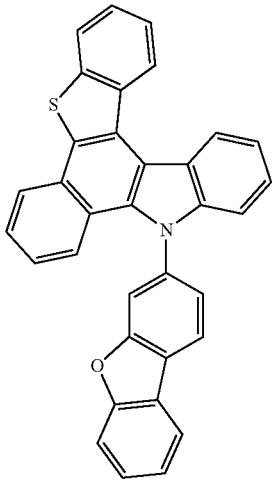

<comp.Com 16>

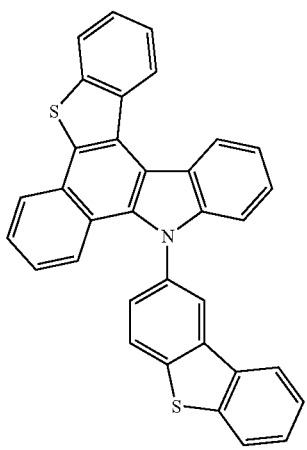

<comp.Com 15>

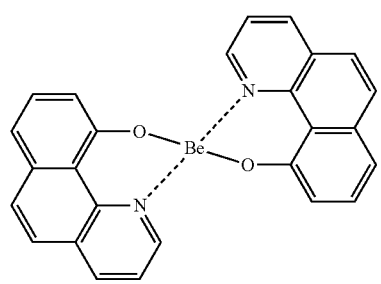

<comp.Com 17>

BeBq$_2$

A forward bias DC voltage was applied to each of the OLEDs manufactured through Test Examples (I-1) to (I-320) and Comparative Example (I-1) to (I-17), and electroluminescence (EL) characteristics of the OLED were measured by PR-650 (Photoresearch). Also, T95 life span was measured by life span measuring equipment (Mcscience) at a reference brightness of 2500 cd/m$^2$. Table 4 below shows evaluation results of OLEDs manufactured Test Examples and Comparative Examples.

TABLE 4

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(I-1) | comp. Com 1 | 6.3 | 26.0 | 2500 | 9.6 | 101.0 | 0.66 | 0.32 |
| comp. Ex(I-2) | comp. Com 2 | 6.2 | 25.8 | 2500 | 9.7 | 103.7 | 0.66 | 0.32 |
| comp. Ex(I-3) | comp. Com 3 | 6.3 | 27.0 | 2500 | 9.3 | 82.1 | 0.66 | 0.33 |
| comp. Ex(I-4) | comp. Com 4 | 6.3 | 27.2 | 2500 | 9.2 | 88.3 | 0.66 | 0.33 |
| comp. Ex(I-5) | comp. Com 5 | 6.4 | 27.1 | 2500 | 9.2 | 86.9 | 0.66 | 0.33 |
| comp. Ex(I-6) | comp. Com 6 | 6.3 | 27.0 | 2500 | 9.3 | 89.6 | 0.66 | 0.33 |
| comp. Ex(I-7) | comp. Com 7 | 6.4 | 26.4 | 2500 | 9.5 | 94.0 | 0.66 | 0.32 |
| comp. Ex(I-8) | comp. Com 8 | 6.2 | 26.5 | 2500 | 9.4 | 91.5 | 0.66 | 0.32 |
| comp. Ex(I-9) | comp. Com 9 | 6.4 | 27.1 | 2500 | 9.2 | 80.1 | 0.66 | 0.32 |
| comp. Ex(I-10) | comp. Com 10 | 6.3 | 26.9 | 2500 | 9.3 | 86.2 | 0.66 | 0.32 |
| comp. Ex(I-11) | comp. Com 11 | 6.4 | 27.8 | 2500 | 9.0 | 87.0 | 0.66 | 0.32 |
| comp. Ex(I-12) | comp. Com 12 | 6.4 | 27.9 | 2500 | 8.9 | 83.9 | 0.66 | 0.32 |
| comp. Ex(I-13) | comp. Com 13 | 6.5 | 27.7 | 2500 | 9.0 | 83.9 | 0.66 | 0.32 |
| comp. Ex(I-14) | comp. Com 14 | 6.4 | 27.6 | 2500 | 9.1 | 80.2 | 0.66 | 0.33 |
| comp. Ex(I-15) | comp. Com 15 | 6.4 | 27.8 | 2500 | 9.0 | 83.9 | 0.66 | 0.33 |
| comp. Ex(I-16) | comp. Com 16 | 6.5 | 28.1 | 2500 | 8.9 | 89.4 | 0.66 | 0.32 |
| comp. Ex(I-17) | comp. Com 17 | 6.5 | 30.1 | 2500 | 8.3 | 61.5 | 0.66 | 0.33 |
| Ex. (I-1) | Com. 1-1-1-O-(1) | 5.9 | 16.4 | 2500 | 15.2 | 161.7 | 0.66 | 0.33 |
| Ex. (I-2) | Com. 1-1-1-O-(2) | 5.9 | 16.5 | 2500 | 15.2 | 163.2 | 0.66 | 0.33 |
| Ex. (I-3) | Com. 1-1-1-O-(3) | 5.8 | 20.7 | 2500 | 12.1 | 139.6 | 0.66 | 0.32 |
| Ex. (I-4) | Com. 1-1-1-O-(4) | 6.0 | 17.4 | 2500 | 14.4 | 151.6 | 0.66 | 0.32 |

TABLE 4-continued

| Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|
| Ex. (I-5) | Com. 1-1-1-O-(5) | 5.9 | 16.8 | 2500 | 14.9 | 151.3 | 0.66 | 0.33 |
| Ex. (I-6) | Com. 1-1-1-O-(6) | 6.0 | 18.9 | 2500 | 13.2 | 147.7 | 0.66 | 0.32 |
| Ex. (I-7) | Com. 1-1-1-O-(7) | 6.0 | 17.1 | 2500 | 14.6 | 151.1 | 0.66 | 0.33 |
| Ex. (I-8) | Com. 1-1-1-O-(8) | 5.8 | 19.2 | 2500 | 13.0 | 144.1 | 0.66 | 0.33 |
| Ex. (I-9) | Com. 1-1-1-O-(9) | 5.9 | 18.0 | 2500 | 13.9 | 144.6 | 0.66 | 0.33 |
| Ex. (I-10) | Com. 1-1-1-O-(10) | 6.1 | 18.1 | 2500 | 13.8 | 141.6 | 0.66 | 0.33 |
| Ex. (I-11) | Com. 1-1-1-O-(11) | 6.0 | 18.1 | 2500 | 13.8 | 139.8 | 0.66 | 0.32 |
| Ex. (I-12) | Com. 1-1-1-O-(12) | 5.8 | 18.7 | 2500 | 13.3 | 144.7 | 0.66 | 0.33 |
| Ex. (I-13) | Com. 1-1-1-O-(13) | 5.9 | 18.0 | 2500 | 13.9 | 141.4 | 0.66 | 0.32 |
| Ex. (I-14) | Com. 1-1-1-O-(15) | 6.1 | 19.9 | 2500 | 12.6 | 133.1 | 0.66 | 0.32 |
| Ex. (I-15) | Com. 1-1-1-O-(17) | 6.1 | 18.3 | 2500 | 13.7 | 139.5 | 0.66 | 0.33 |
| Ex. (I-16) | Com. 1-1-1-O-(18) | 6.0 | 16.7 | 2500 | 14.9 | 149.4 | 0.66 | 0.32 |
| Ex. (I-17) | Com. 1-1-1-O-(19) | 5.9 | 17.3 | 2500 | 14.4 | 152.7 | 0.66 | 0.33 |
| Ex. (I-18) | Com. 1-1-1-O-(20) | 6.0 | 20.4 | 2500 | 12.3 | 136.7 | 0.66 | 0.32 |
| Ex. (I-19) | Com. 1-1-1-O-(22) | 5.9 | 17.9 | 2500 | 13.9 | 138.2 | 0.66 | 0.32 |
| Ex. (I-20) | Com. 1-1-1-S-(1) | 5.9 | 15.2 | 2500 | 16.4 | 171.4 | 0.66 | 0.33 |
| Ex. (I-21) | Com. 1-1-1-S-(2) | 5.9 | 15.3 | 2500 | 16.3 | 172.8 | 0.66 | 0.33 |
| Ex. (I-22) | Com. 1-1-1-S-(3) | 6.0 | 17.9 | 2500 | 14.0 | 144.9 | 0.66 | 0.32 |
| Ex. (I-23) | Com. 1-1-1-S-(4) | 5.9 | 16.6 | 2500 | 15.1 | 160.6 | 0.66 | 0.33 |
| Ex. (I-24) | Com. 1-1-1-S-(5) | 6.0 | 16.1 | 2500 | 15.6 | 158.9 | 0.66 | 0.32 |
| Ex. (I-25) | Com. 1-1-1-S-(6) | 6.1 | 16.7 | 2500 | 14.9 | 154.9 | 0.66 | 0.33 |
| Ex. (I-26) | Com. 1-1-1-S-(7) | 5.8 | 16.5 | 2500 | 15.2 | 158.5 | 0.66 | 0.32 |
| Ex. (I-27) | Com. 1-1-1-S-(8) | 5.9 | 17.2 | 2500 | 14.5 | 157.4 | 0.66 | 0.33 |
| Ex. (I-28) | Com. 1-1-1-S-(9) | 5.8 | 17.6 | 2500 | 14.2 | 151.0 | 0.66 | 0.32 |
| Ex. (I-29) | Com. 1-1-1-S-(10) | 5.9 | 17.3 | 2500 | 14.4 | 157.8 | 0.66 | 0.33 |
| Ex. (I-30) | Com. 1-1-1-S-(11) | 6.0 | 16.9 | 2500 | 14.8 | 150.2 | 0.66 | 0.32 |
| Ex. (I-31) | Com. 1-1-1-S-(12) | 6.0 | 16.8 | 2500 | 14.8 | 157.7 | 0.66 | 0.33 |
| Ex. (I-32) | Com. 1-1-1-S-(13) | 6.0 | 17.5 | 2500 | 14.3 | 152.6 | 0.66 | 0.33 |
| Ex. (I-33) | Com. 1-1-1-S-(14) | 6.1 | 17.2 | 2500 | 14.5 | 157.5 | 0.66 | 0.33 |
| Ex. (I-34) | Com. 1-1-1-S-(15) | 5.8 | 18.4 | 2500 | 13.6 | 143.5 | 0.66 | 0.32 |
| Ex. (I-35) | Com. 1-1-1-S-(16) | 6.0 | 17.2 | 2500 | 14.5 | 148.4 | 0.66 | 0.32 |
| Ex. (I-36) | Com. 1-1-1-S-(17) | 5.8 | 16.9 | 2500 | 14.8 | 155.3 | 0.66 | 0.32 |
| Ex. (I-37) | Com. 1-1-1-S-(18) | 5.9 | 16.1 | 2500 | 15.5 | 158.2 | 0.66 | 0.32 |
| Ex. (I-38) | Com. 1-1-1-S-(19) | 5.9 | 15.8 | 2500 | 15.9 | 159.9 | 0.66 | 0.33 |
| Ex. (I-39) | Com. 1-1-1-S-(20) | 5.8 | 18.9 | 2500 | 13.2 | 147.1 | 0.66 | 0.33 |
| Ex. (I-40) | Com. 1-1-1-S-(23) | 6.0 | 17.5 | 2500 | 14.3 | 149.5 | 0.66 | 0.32 |
| Ex. (I-41) | Com. 1-1-2-O-(1) | 6.0 | 16.4 | 2500 | 15.2 | 163.1 | 0.66 | 0.32 |
| Ex. (I-42) | Com. 1-1-2-O-(2) | 5.8 | 16.2 | 2500 | 15.5 | 161.8 | 0.66 | 0.33 |
| Ex. (I-43) | Com. 1-1-2-O-(3) | 6.0 | 19.4 | 2500 | 12.9 | 140.8 | 0.66 | 0.33 |
| Ex. (I-44) | Com. 1-1-2-O-(4) | 5.9 | 17.8 | 2500 | 14.0 | 146.6 | 0.66 | 0.32 |
| Ex. (I-45) | Com. 1-1-2-O-(5) | 5.9 | 16.7 | 2500 | 15.0 | 154.2 | 0.66 | 0.33 |
| Ex. (I-46) | Com. 1-1-2-O-(6) | 5.9 | 18.1 | 2500 | 13.8 | 142.4 | 0.66 | 0.33 |
| Ex. (I-47) | Com. 1-1-2-O-(7) | 5.9 | 16.9 | 2500 | 14.8 | 151.7 | 0.66 | 0.33 |
| Ex. (I-48) | Com. 1-1-2-O-(8) | 5.8 | 18.1 | 2500 | 13.8 | 145.3 | 0.66 | 0.32 |
| Ex. (I-49) | Com. 1-1-2-O-(9) | 6.1 | 18.3 | 2500 | 13.6 | 140.0 | 0.66 | 0.33 |
| Ex. (I-50) | Com. 1-1-2-O-(12) | 5.9 | 18.5 | 2500 | 13.5 | 138.5 | 0.66 | 0.32 |
| Ex. (I-51) | Com. 1-1-2-O-(13) | 5.9 | 18.2 | 2500 | 13.8 | 144.8 | 0.66 | 0.33 |
| Ex. (I-52) | Com. 1-1-2-O-(14) | 5.8 | 18.5 | 2500 | 13.5 | 146.9 | 0.66 | 0.33 |
| Ex. (I-53) | Com. 1-1-2-O-(15) | 5.8 | 19.3 | 2500 | 12.9 | 136.6 | 0.66 | 0.33 |
| Ex. (I-54) | Com. 1-1-2-O-(16) | 5.8 | 18.2 | 2500 | 13.7 | 141.9 | 0.66 | 0.32 |
| Ex. (I-55) | Com. 1-1-2-O-(17) | 5.9 | 18.6 | 2500 | 13.4 | 145.1 | 0.66 | 0.33 |
| Ex. (I-56) | Com. 1-1-2-O-(18) | 5.9 | 17.5 | 2500 | 14.2 | 146.3 | 0.66 | 0.33 |
| Ex. (I-57) | Com. 1-1-2-O-(19) | 5.9 | 17.1 | 2500 | 14.6 | 154.5 | 0.66 | 0.33 |
| Ex. (I-58) | Com. 1-1-2-O-(20) | 5.8 | 19.8 | 2500 | 12.6 | 133.6 | 0.66 | 0.33 |
| Ex. (I-59) | Com. 1-1-2-O-(22) | 5.9 | 18.5 | 2500 | 13.5 | 139.1 | 0.66 | 0.32 |
| Ex. (I-60) | Com. 1-1-2-S-(1) | 5.9 | 15.4 | 2500 | 16.2 | 174.2 | 0.66 | 0.33 |
| Ex. (I-61) | Com. 1-1-2-S-(2) | 6.0 | 15.2 | 2500 | 16.5 | 172.5 | 0.66 | 0.33 |
| Ex. (I-62) | Com. 1-1-2-S-(3) | 5.9 | 19.2 | 2500 | 13.0 | 150.6 | 0.66 | 0.32 |
| Ex. (I-63) | Com. 1-1-2-S-(4) | 5.9 | 16.0 | 2500 | 15.6 | 161.3 | 0.66 | 0.33 |
| Ex. (I-64) | Com. 1-1-2-S-(5) | 5.9 | 16.0 | 2500 | 15.6 | 161.5 | 0.66 | 0.32 |
| Ex. (I-65) | Com. 1-1-2-S-(6) | 5.8 | 17.8 | 2500 | 14.0 | 152.6 | 0.66 | 0.32 |
| Ex. (I-66) | Com. 1-1-2-S-(7) | 6.0 | 15.7 | 2500 | 15.9 | 158.4 | 0.66 | 0.33 |
| Ex. (I-67) | Com. 1-1-2-S-(8) | 5.9 | 16.9 | 2500 | 14.8 | 156.1 | 0.66 | 0.32 |
| Ex. (I-68) | Com. 1-1-2-S-(9) | 6.1 | 16.9 | 2500 | 14.8 | 156.0 | 0.66 | 0.33 |
| Ex. (I-69) | Com. 1-1-2-S-(10) | 5.8 | 16.9 | 2500 | 14.8 | 157.3 | 0.66 | 0.32 |
| Ex. (I-70) | Com. 1-1-2-S-(11) | 6.1 | 16.9 | 2500 | 14.8 | 148.0 | 0.66 | 0.33 |
| Ex. (I-71) | Com. 1-1-2-S-(12) | 6.0 | 16.8 | 2500 | 14.9 | 148.7 | 0.66 | 0.32 |
| Ex. (I-72) | Com. 1-1-2-S-(13) | 6.1 | 17.6 | 2500 | 14.2 | 155.8 | 0.66 | 0.33 |
| Ex. (I-73) | Com. 1-1-2-S-(14) | 5.9 | 16.9 | 2500 | 14.8 | 155.9 | 0.66 | 0.33 |
| Ex. (I-74) | Com. 1-1-2-S-(15) | 6.0 | 18.5 | 2500 | 13.5 | 144.5 | 0.66 | 0.32 |
| Ex. (I-75) | Com. 1-1-2-S-(16) | 6.0 | 17.5 | 2500 | 14.3 | 153.1 | 0.66 | 0.33 |
| Ex. (I-76) | Com. 1-1-2-S-(17) | 6.1 | 16.7 | 2500 | 15.0 | 154.8 | 0.66 | 0.33 |
| Ex. (I-77) | Com. 1-1-2-S-(18) | 5.9 | 16.5 | 2500 | 15.2 | 157.9 | 0.66 | 0.32 |
| Ex. (I-78) | Com. 1-1-2-S-(19) | 5.9 | 16.2 | 2500 | 15.4 | 158.9 | 0.66 | 0.32 |
| Ex. (I-79) | Com. 1-1-2-S-(20) | 5.9 | 19.1 | 2500 | 13.1 | 141.7 | 0.66 | 0.32 |

TABLE 4-continued

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex. (I-80) | Com. 1-1-2-S-(22) | 5.9 | 17.3 | 2500 | 14.5 | 152.4 | 0.66 | 0.32 |
| Ex. (I-81) | Com. 1-2-1-O-(1) | 6.0 | 18.8 | 2500 | 13.3 | 142.4 | 0.66 | 0.32 |
| Ex. (I-82) | Com. 1-2-1-O-(2) | 6.0 | 18.7 | 2500 | 13.4 | 142.1 | 0.66 | 0.32 |
| Ex. (I-83) | Com. 1-2-1-O-(3) | 6.2 | 24.4 | 2500 | 10.2 | 119.2 | 0.66 | 0.33 |
| Ex. (I-84) | Com. 1-2-1-O-(4) | 6.1 | 19.6 | 2500 | 12.8 | 125.8 | 0.66 | 0.32 |
| Ex. (I-85) | Com. 1-2-1-O-(5) | 6.0 | 20.5 | 2500 | 12.2 | 125.2 | 0.66 | 0.33 |
| Ex. (I-86) | Com. 1-2-1-O-(6) | 6.0 | 21.1 | 2500 | 11.8 | 123.3 | 0.66 | 0.32 |
| Ex. (I-87) | Com. 1-2-1-O-(7) | 6.0 | 19.2 | 2500 | 13.0 | 131.7 | 0.66 | 0.32 |
| Ex. (I-88) | Com. 1-2-1-O-(8) | 6.1 | 21.2 | 2500 | 11.8 | 121.2 | 0.66 | 0.32 |
| Ex. (I-89) | Com. 1-2-1-O-(9) | 6.1 | 21.4 | 2500 | 11.7 | 120.8 | 0.66 | 0.32 |
| Ex. (I-90) | Com. 1-2-1-O-(10) | 6.1 | 20.9 | 2500 | 12.0 | 121.8 | 0.66 | 0.33 |
| Ex. (I-91) | Com. 1-2-1-O-(11) | 6.1 | 21.6 | 2500 | 11.6 | 124.8 | 0.66 | 0.33 |
| Ex. (I-92) | Com. 1-2-1-O-(12) | 6.1 | 20.9 | 2500 | 12.0 | 120.8 | 0.66 | 0.33 |
| Ex. (I-93) | Com. 1-2-1-O-(14) | 6.1 | 21.3 | 2500 | 11.7 | 126.8 | 0.66 | 0.33 |
| Ex. (I-94) | Com. 1-2-1-O-(15) | 6.0 | 23.4 | 2500 | 10.7 | 113.2 | 0.66 | 0.33 |
| Ex. (I-95) | Com. 1-2-1-O-(16) | 6.1 | 21.2 | 2500 | 11.8 | 125.5 | 0.66 | 0.32 |
| Ex. (I-96) | Com. 1-2-1-O-(17) | 6.2 | 22.6 | 2500 | 11.1 | 123.5 | 0.66 | 0.32 |
| Ex. (I-97) | Com. 1-2-1-O-(18) | 6.1 | 19.3 | 2500 | 13.0 | 133.8 | 0.66 | 0.33 |
| Ex. (I-98) | Com. 1-2-1-O-(19) | 6.1 | 19.5 | 2500 | 12.8 | 128.1 | 0.66 | 0.33 |
| Ex. (I-99) | Com. 1-2-1-O-(20) | 6.1 | 24.1 | 2500 | 10.4 | 114.5 | 0.66 | 0.33 |
| Ex. (I-100) | Com. 1-2-1-O-(21) | 6.0 | 21.4 | 2500 | 11.7 | 124.2 | 0.66 | 0.33 |
| Ex. (I-101) | Com. 1-2-1-S-(1) | 6.1 | 17.4 | 2500 | 14.4 | 150.7 | 0.66 | 0.33 |
| Ex. (I-102) | Com. 1-2-1-S-(2) | 6.0 | 17.7 | 2500 | 14.1 | 150.8 | 0.66 | 0.32 |
| Ex. (I-103) | Com. 1-2-1-S-(3) | 6.1 | 21.7 | 2500 | 11.5 | 131.0 | 0.66 | 0.32 |
| Ex. (I-104) | Com. 1-2-1-S-(4) | 6.0 | 18.6 | 2500 | 13.4 | 138.9 | 0.66 | 0.32 |
| Ex. (I-105) | Com. 1-2-1-S-(5) | 6.0 | 18.0 | 2500 | 13.9 | 143.5 | 0.66 | 0.32 |
| Ex. (I-106) | Com. 1-2-1-S-(6) | 6.2 | 19.5 | 2500 | 12.8 | 134.0 | 0.66 | 0.33 |
| Ex. (I-107) | Com. 1-2-1-S-(7) | 5.9 | 19.1 | 2500 | 13.1 | 137.3 | 0.66 | 0.33 |
| Ex. (I-108) | Com. 1-2-1-S-(8) | 6.1 | 19.2 | 2500 | 13.0 | 130.0 | 0.66 | 0.33 |
| Ex. (I-109) | Com. 1-2-1-S-(9) | 6.1 | 20.7 | 2500 | 12.1 | 130.4 | 0.66 | 0.32 |
| Ex. (I-110) | Com. 1-2-1-S-(10) | 6.0 | 20.6 | 2500 | 12.2 | 132.8 | 0.66 | 0.33 |
| Ex. (I-111) | Com. 1-2-1-S-(11) | 6.1 | 20.2 | 2500 | 12.3 | 136.0 | 0.66 | 0.33 |
| Ex. (I-112) | Com. 1-2-1-S-(12) | 6.0 | 20.0 | 2500 | 12.5 | 135.5 | 0.66 | 0.32 |
| Ex. (I-113) | Com. 1-2-1-S-(13) | 6.0 | 20.2 | 2500 | 12.4 | 137.5 | 0.66 | 0.33 |
| Ex. (I-114) | Com. 1-2-1-S-(14) | 6.1 | 20.4 | 2500 | 12.3 | 132.3 | 0.66 | 0.32 |
| Ex. (I-115) | Com. 1-2-1-S-(15) | 6.0 | 21.3 | 2500 | 11.7 | 124.6 | 0.66 | 0.32 |
| Ex. (I-116) | Com. 1-2-1-S-(17) | 6.1 | 20.3 | 2500 | 12.3 | 136.4 | 0.66 | 0.32 |
| Ex. (I-117) | Com. 1-2-1-S-(18) | 5.9 | 18.5 | 2500 | 13.5 | 142.4 | 0.66 | 0.33 |
| Ex. (I-118) | Com. 1-2-1-S-(19) | 6.0 | 19.0 | 2500 | 13.1 | 139.8 | 0.66 | 0.33 |
| Ex. (I-119) | Com. 1-2-1-S-(20) | 6.0 | 20.9 | 2500 | 11.9 | 124.1 | 0.66 | 0.33 |
| Ex. (I-120) | Com. 1-2-1-S-(21) | 6.1 | 19.3 | 2500 | 12.9 | 130.6 | 0.66 | 0.33 |
| Ex. (I-121) | Com. 1-2-2-O-(1) | 6.0 | 18.6 | 2500 | 13.4 | 142.6 | 0.66 | 0.32 |
| Ex. (I-122) | Com. 1-2-2-O-(2) | 5.9 | 18.7 | 2500 | 13.4 | 143.1 | 0.66 | 0.32 |
| Ex. (I-123) | Com. 1-2-2-O-(3) | 6.1 | 24.8 | 2500 | 10.1 | 114.9 | 0.66 | 0.33 |
| Ex. (I-124) | Com. 1-2-2-O-(4) | 6.1 | 19.5 | 2500 | 12.8 | 133.5 | 0.66 | 0.32 |
| Ex. (I-125) | Com. 1-2-2-O-(5) | 5.9 | 19.7 | 2500 | 12.7 | 128.7 | 0.66 | 0.32 |
| Ex. (I-126) | Com. 1-2-2-O-(6) | 6.1 | 20.9 | 2500 | 12.0 | 125.9 | 0.66 | 0.33 |
| Ex. (I-127) | Com. 1-2-2-O-(7) | 5.9 | 20.1 | 2500 | 12.5 | 126.0 | 0.66 | 0.33 |
| Ex. (I-128) | Com. 1-2-2-O-(8) | 6.0 | 21.2 | 2500 | 11.8 | 122.6 | 0.66 | 0.32 |
| Ex. (I-129) | Com. 1-2-2-O-(9) | 6.1 | 21.0 | 2500 | 11.9 | 122.2 | 0.66 | 0.33 |
| Ex. (I-130) | Com. 1-2-2-O-(10) | 6.0 | 22.0 | 2500 | 11.4 | 126.5 | 0.66 | 0.33 |
| Ex. (I-131) | Com. 1-2-2-O-(11) | 6.0 | 21.0 | 2500 | 11.9 | 123.8 | 0.66 | 0.33 |
| Ex. (I-132) | Com. 1-2-2-O-(13) | 6.1 | 22.7 | 2500 | 11.0 | 122.1 | 0.66 | 0.33 |
| Ex. (I-133) | Com. 1-2-2-O-(14) | 6.2 | 21.7 | 2500 | 11.5 | 125.2 | 0.66 | 0.33 |
| Ex. (I-134) | Com. 1-2-2-O-(15) | 6.2 | 22.9 | 2500 | 10.9 | 111.0 | 0.66 | 0.33 |
| Ex. (I-135) | Com. 1-2-2-O-(16) | 6.1 | 22.1 | 2500 | 11.3 | 123.3 | 0.66 | 0.32 |
| Ex. (I-136) | Com. 1-2-2-O-(17) | 6.0 | 22.6 | 2500 | 11.1 | 125.6 | 0.66 | 0.32 |
| Ex. (I-137) | Com. 1-2-2-O-(18) | 5.9 | 19.3 | 2500 | 12.9 | 129.3 | 0.66 | 0.33 |
| Ex. (I-138) | Com. 1-2-2-O-(19) | 6.0 | 19.4 | 2500 | 12.9 | 133.3 | 0.66 | 0.32 |
| Ex. (I-139) | Com. 1-2-2-O-(20) | 6.2 | 23.7 | 2500 | 10.6 | 116.1 | 0.66 | 0.32 |
| Ex. (I-140) | Com. 1-2-2-O-(21) | 6.0 | 21.8 | 2500 | 11.5 | 125.2 | 0.66 | 0.33 |
| Ex. (I-141) | Com. 1-2-2-S-(1) | 6.1 | 17.3 | 2500 | 14.4 | 150.4 | 0.66 | 0.32 |
| Ex. (I-142) | Com. 1-2-2-S-(2) | 6.0 | 17.6 | 2500 | 14.2 | 151.8 | 0.66 | 0.33 |
| Ex. (I-143) | Com. 1-2-2-S-(3) | 6.1 | 21.0 | 2500 | 11.9 | 129.9 | 0.66 | 0.33 |
| Ex. (I-144) | Com. 1-2-2-S-(4) | 5.9 | 18.3 | 2500 | 13.6 | 141.7 | 0.66 | 0.33 |
| Ex. (I-145) | Com. 1-2-2-S-(5) | 6.0 | 18.2 | 2500 | 13.7 | 144.7 | 0.66 | 0.32 |
| Ex. (I-146) | Com. 1-2-2-S-(6) | 6.2 | 20.0 | 2500 | 12.5 | 130.9 | 0.66 | 0.33 |
| Ex. (I-147) | Com. 1-2-2-S-(7) | 5.9 | 18.5 | 2500 | 13.5 | 141.7 | 0.66 | 0.33 |
| Ex. (I-148) | Com. 1-2-2-S-(8) | 6.0 | 20.7 | 2500 | 12.1 | 129.3 | 0.66 | 0.33 |
| Ex. (I-149) | Com. 1-2-2-S-(9) | 6.1 | 20.6 | 2500 | 12.1 | 133.4 | 0.66 | 0.33 |
| Ex. (I-150) | Com. 1-2-2-S-(10) | 6.0 | 20.4 | 2500 | 12.2 | 130.4 | 0.66 | 0.32 |
| Ex. (I-151) | Com. 1-2-2-S-(11) | 6.0 | 20.0 | 2500 | 12.5 | 128.7 | 0.66 | 0.33 |
| Ex. (I-152) | Com. 1-2-2-S-(12) | 6.0 | 20.0 | 2500 | 12.5 | 134.8 | 0.66 | 0.32 |
| Ex. (I-153) | Com. 1-2-2-S-(13) | 6.0 | 20.2 | 2500 | 12.4 | 132.0 | 0.66 | 0.33 |
| Ex. (I-154) | Com. 1-2-2-S-(14) | 6.1 | 19.9 | 2500 | 12.6 | 128.1 | 0.66 | 0.33 |

TABLE 4-continued

| Compound | Voltage (V) | Current Density (mA/cm$^2$) | Brightness (cd/m$^2$) | Efficiency (cd/A) | Lifetime T(95) | CIE x | y |
|---|---|---|---|---|---|---|---|
| Ex. (I-155) Com. 1-2-2-S-(15) | 6.0 | 22.5 | 2500 | 11.1 | 123.7 | 0.66 | 0.32 |
| Ex. (I-156) Com. 1-2-2-S-(16) | 6.0 | 19.3 | 2500 | 13.0 | 135.0 | 0.66 | 0.32 |
| Ex. (I-157) Com. 1-2-2-S-(18) | 5.9 | 18.7 | 2500 | 13.4 | 140.0 | 0.66 | 0.32 |
| Ex. (I-158) Com. 1-2-2-S-(19) | 5.9 | 18.0 | 2500 | 13.9 | 135.6 | 0.66 | 0.33 |
| Ex. (I-159) Com. 1-2-2-S-(20) | 6.2 | 21.5 | 2500 | 11.6 | 130.7 | 0.66 | 0.33 |
| Ex. (I-160) Com. 1-2-2-S-(22) | 6.2 | 19.6 | 2500 | 12.7 | 135.6 | 0.66 | 0.33 |
| Ex. (I-161) Com. 1-3-1-O-(1) | 6.0 | 18.6 | 2500 | 13.4 | 144.6 | 0.66 | 0.33 |
| Ex. (I-162) Com. 1-3-1-O-(2) | 5.9 | 19.0 | 2500 | 13.2 | 143.6 | 0.66 | 0.33 |
| Ex. (I-163) Com. 1-3-1-O-(3) | 6.2 | 23.4 | 2500 | 10.7 | 115.5 | 0.66 | 0.33 |
| Ex. (I-164) Com. 1-3-1-O-(4) | 6.0 | 20.7 | 2500 | 12.1 | 128.5 | 0.66 | 0.33 |
| Ex. (I-165) Com. 1-3-1-O-(5) | 6.1 | 19.9 | 2500 | 12.6 | 129.2 | 0.66 | 0.33 |
| Ex. (I-166) Com. 1-3-1-O-(6) | 6.1 | 21.6 | 2500 | 11.6 | 124.0 | 0.66 | 0.33 |
| Ex. (I-167) Com. 1-3-1-O-(7) | 5.9 | 20.8 | 2500 | 12.0 | 128.2 | 0.66 | 0.32 |
| Ex. (I-168) Com. 1-3-1-O-(8) | 6.1 | 22.4 | 2500 | 11.2 | 119.9 | 0.66 | 0.32 |
| Ex. (I-169) Com. 1-3-1-O-(9) | 6.0 | 21.1 | 2500 | 11.8 | 126.9 | 0.66 | 0.33 |
| Ex. (I-170) Com. 1-3-1-O-(10) | 6.1 | 21.4 | 2500 | 11.7 | 122.9 | 0.66 | 0.32 |
| Ex. (I-171) Com. 1-3-1-O-(11) | 6.1 | 21.1 | 2500 | 11.8 | 123.3 | 0.66 | 0.33 |
| Ex. (I-172) Com. 1-3-1-O-(12) | 6.2 | 22.6 | 2500 | 11.0 | 119.6 | 0.66 | 0.32 |
| Ex. (I-173) Com. 1-3-1-O-(13) | 6.1 | 21.5 | 2500 | 11.6 | 119.7 | 0.66 | 0.32 |
| Ex. (I-174) Com. 1-3-1-O-(14) | 6.1 | 21.4 | 2500 | 11.7 | 119.5 | 0.66 | 0.33 |
| Ex. (I-175) Com. 1-3-1-O-(15) | 6.1 | 23.8 | 2500 | 10.5 | 118.1 | 0.66 | 0.33 |
| Ex. (I-176) Com. 1-3-1-O-(17) | 6.0 | 21.6 | 2500 | 11.6 | 121.6 | 0.66 | 0.32 |
| Ex. (I-177) Com. 1-3-1-O-(18) | 6.0 | 19.6 | 2500 | 12.7 | 130.4 | 0.66 | 0.33 |
| Ex. (I-178) Com. 1-3-1-O-(19) | 6.0 | 19.5 | 2500 | 12.8 | 134.9 | 0.66 | 0.32 |
| Ex. (I-179) Com. 1-3-1-O-(20) | 6.0 | 24.4 | 2500 | 10.2 | 115.5 | 0.66 | 0.33 |
| Ex. (I-180) Com. 1-3-1-O-(22) | 6.1 | 21.1 | 2500 | 11.9 | 125.5 | 0.66 | 0.32 |
| Ex. (I-181) Com. 1-3-1-S-(1) | 5.9 | 17.7 | 2500 | 14.2 | 153.7 | 0.66 | 0.32 |
| Ex. (I-182) Com. 1-3-1-S-(2) | 5.9 | 17.3 | 2500 | 14.4 | 153.1 | 0.66 | 0.32 |
| Ex. (I-183) Com. 1-3-1-S-(3) | 6.2 | 21.3 | 2500 | 11.7 | 131.0 | 0.66 | 0.32 |
| Ex. (I-184) Com. 1-3-1-S-(4) | 6.1 | 18.5 | 2500 | 13.5 | 142.1 | 0.66 | 0.33 |
| Ex. (I-185) Com. 1-3-1-S-(5) | 6.0 | 18.6 | 2500 | 13.4 | 142.5 | 0.66 | 0.32 |
| Ex. (I-186) Com. 1-3-1-S-(6) | 6.0 | 20.4 | 2500 | 12.2 | 137.0 | 0.66 | 0.32 |
| Ex. (I-187) Com. 1-3-1-S-(7) | 6.1 | 18.9 | 2500 | 13.3 | 142.6 | 0.66 | 0.33 |
| Ex. (I-188) Com. 1-3-1-S-(8) | 6.2 | 20.1 | 2500 | 12.4 | 135.9 | 0.66 | 0.32 |
| Ex. (I-189) Com. 1-3-1-S-(9) | 6.1 | 20.1 | 2500 | 12.4 | 129.1 | 0.66 | 0.33 |
| Ex. (I-190) Com. 1-3-1-S-(10) | 6.1 | 19.5 | 2500 | 12.8 | 137.0 | 0.66 | 0.33 |
| Ex. (I-191) Com. 1-3-1-S-(11) | 6.0 | 19.3 | 2500 | 13.0 | 132.6 | 0.66 | 0.32 |
| Ex. (I-192) Com. 1-3-1-S-(12) | 6.2 | 19.6 | 2500 | 12.8 | 129.8 | 0.66 | 0.33 |
| Ex. (I-193) Com. 1-3-1-S-(14) | 6.1 | 20.3 | 2500 | 12.3 | 130.2 | 0.66 | 0.32 |
| Ex. (I-194) Com. 1-3-1-S-(15) | 6.2 | 21.8 | 2500 | 11.5 | 127.8 | 0.66 | 0.32 |
| Ex. (I-195) Com. 1-3-1-S-(16) | 6.1 | 19.6 | 2500 | 12.7 | 131.4 | 0.66 | 0.33 |
| Ex. (I-196) Com. 1-3-1-S-(17) | 6.1 | 19.6 | 2500 | 12.8 | 137.4 | 0.66 | 0.32 |
| Ex. (I-197) Com. 1-3-1-S-(18) | 6.0 | 17.9 | 2500 | 14.0 | 142.6 | 0.66 | 0.32 |
| Ex. (I-198) Com. 1-3-1-S-(19) | 6.1 | 18.8 | 2500 | 13.3 | 143.0 | 0.66 | 0.33 |
| Ex. (I-199) Com. 1-3-1-S-(20) | 6.2 | 22.6 | 2500 | 11.0 | 128.7 | 0.66 | 0.32 |
| Ex. (I-200) Com. 1-3-1-S-(23) | 6.2 | 20.1 | 2500 | 12.4 | 129.7 | 0.66 | 0.32 |
| Ex. (I-201) Com. 1-3-2-O-(1) | 6.0 | 18.8 | 2500 | 13.3 | 140.1 | 0.66 | 0.32 |
| Ex. (I-202) Com. 1-3-2-O-(2) | 6.0 | 18.9 | 2500 | 13.2 | 143.7 | 0.66 | 0.32 |
| Ex. (I-203) Com. 1-3-2-O-(3) | 6.1 | 23.9 | 2500 | 10.5 | 120.2 | 0.66 | 0.33 |
| Ex. (I-204) Com. 1-3-2-O-(4) | 6.1 | 19.9 | 2500 | 12.6 | 126.2 | 0.66 | 0.32 |
| Ex. (I-205) Com. 1-3-2-O-(5) | 6.1 | 20.3 | 2500 | 12.3 | 132.8 | 0.66 | 0.32 |
| Ex. (I-206) Com. 1-3-2-O-(6) | 6.0 | 22.5 | 2500 | 11.1 | 121.3 | 0.66 | 0.32 |
| Ex. (I-207) Com. 1-3-2-O-(7) | 5.9 | 20.6 | 2500 | 12.1 | 134.7 | 0.66 | 0.32 |
| Ex. (I-208) Com. 1-3-2-O-(8) | 6.1 | 21.4 | 2500 | 11.7 | 118.4 | 0.66 | 0.32 |
| Ex. (I-209) Com. 1-3-2-O-(10) | 6.0 | 21.3 | 2500 | 11.7 | 125.9 | 0.66 | 0.32 |
| Ex. (I-210) Com. 1-3-2-O-(11) | 6.0 | 21.9 | 2500 | 11.4 | 119.9 | 0.66 | 0.33 |
| Ex. (I-211) Com. 1-3-2-O-(12) | 6.0 | 22.6 | 2500 | 11.1 | 128.0 | 0.66 | 0.32 |
| Ex. (I-212) Com. 1-3-2-O-(13) | 6.2 | 21.8 | 2500 | 11.5 | 120.4 | 0.66 | 0.32 |
| Ex. (I-213) Com. 1-3-2-O-(14) | 6.0 | 20.9 | 2500 | 12.0 | 118.3 | 0.66 | 0.33 |
| Ex. (I-214) Com. 1-3-2-O-(15) | 6.1 | 24.9 | 2500 | 10.1 | 120.3 | 0.66 | 0.33 |
| Ex. (I-215) Com. 1-3-2-O-(16) | 6.1 | 21.1 | 2500 | 11.9 | 120.3 | 0.66 | 0.33 |
| Ex. (I-216) Com. 1-3-2-O-(17) | 6.0 | 22.2 | 2500 | 11.3 | 123.0 | 0.66 | 0.32 |
| Ex. (I-217) Com. 1-3-2-O-(18) | 5.9 | 19.3 | 2500 | 12.9 | 133.9 | 0.66 | 0.33 |
| Ex. (I-218) Com. 1-3-2-O-(19) | 6.0 | 19.7 | 2500 | 12.7 | 131.6 | 0.66 | 0.33 |
| Ex. (I-219) Com. 1-3-2-O-(20) | 6.1 | 23.4 | 2500 | 10.7 | 116.5 | 0.66 | 0.32 |
| Ex. (I-220) Com. 1-3-2-O-(22) | 6.2 | 22.0 | 2500 | 11.4 | 126.1 | 0.66 | 0.32 |
| Ex. (I-221) Com. 1-3-2-S-(1) | 6.1 | 17.5 | 2500 | 14.3 | 152.8 | 0.66 | 0.33 |
| Ex. (I-222) Com. 1-3-2-S-(2) | 6.0 | 17.3 | 2500 | 14.5 | 154.6 | 0.66 | 0.33 |
| Ex. (I-223) Com. 1-3-2-S-(3) | 6.1 | 20.9 | 2500 | 12.0 | 129.7 | 0.66 | 0.32 |
| Ex. (I-224) Com. 1-3-2-S-(4) | 5.9 | 18.1 | 2500 | 13.8 | 144.9 | 0.66 | 0.33 |
| Ex. (I-225) Com. 1-3-2-S-(5) | 6.0 | 18.4 | 2500 | 13.6 | 139.9 | 0.66 | 0.33 |
| Ex. (I-226) Com. 1-3-2-S-(6) | 6.0 | 19.4 | 2500 | 12.9 | 131.8 | 0.66 | 0.32 |
| Ex. (I-227) Com. 1-3-2-S-(7) | 5.9 | 18.5 | 2500 | 13.5 | 141.7 | 0.66 | 0.33 |
| Ex. (I-228) Com. 1-3-2-S-(8) | 6.1 | 20.5 | 2500 | 12.2 | 136.0 | 0.66 | 0.33 |
| Ex. (I-229) Com. 1-3-2-S-(9) | 6.1 | 20.4 | 2500 | 12.2 | 129.0 | 0.66 | 0.32 |

TABLE 4-continued

| Compound | Voltage (V) | Current Density (mA/cm²) | Brightness (cd/m²) | Efficiency (cd/A) | Lifetime T(95) | CIE x | CIE y |
|---|---|---|---|---|---|---|---|
| Ex. (I-230) Com. 1-3-2-S-(10) | 6.1 | 20.2 | 2500 | 12.4 | 135.6 | 0.66 | 0.33 |
| Ex. (I-231) Com. 1-3-2-S-(12) | 6.0 | 20.5 | 2500 | 12.2 | 136.4 | 0.66 | 0.32 |
| Ex. (I-232) Com. 1-3-2-S-(13) | 6.0 | 19.4 | 2500 | 12.9 | 137.6 | 0.66 | 0.33 |
| Ex. (I-233) Com. 1-3-2-S-(14) | 6.0 | 19.8 | 2500 | 12.7 | 134.5 | 0.66 | 0.33 |
| Ex. (I-234) Com. 1-3-2-S-(15) | 6.1 | 21.3 | 2500 | 11.7 | 124.9 | 0.66 | 0.33 |
| Ex. (I-235) Com. 1-3-2-S-(16) | 6.0 | 20.0 | 2500 | 12.5 | 128.6 | 0.66 | 0.33 |
| Ex. (I-236) Com. 1-3-2-S-(17) | 6.2 | 20.2 | 2500 | 12.4 | 130.2 | 0.66 | 0.32 |
| Ex. (I-237) Com. 1-3-2-S-(18) | 6.0 | 18.5 | 2500 | 13.5 | 144.8 | 0.66 | 0.33 |
| Ex. (I-238) Com. 1-3-2-S-(19) | 6.0 | 18.5 | 2500 | 13.5 | 143.3 | 0.66 | 0.33 |
| Ex. (I-239) Com. 1-3-2-S-(20) | 6.1 | 21.2 | 2500 | 11.8 | 127.9 | 0.66 | 0.32 |
| Ex. (I-240) Com. 1-3-2-S-(22) | 6.1 | 20.7 | 2500 | 12.1 | 133.1 | 0.66 | 0.32 |
| Ex. (I-241) Com. 1-4-1-O-(1) | 5.9 | 17.6 | 2500 | 14.2 | 153.9 | 0.66 | 0.33 |
| Ex. (I-242) Com. 1-4-1-O-(2) | 6.0 | 17.3 | 2500 | 14.4 | 150.2 | 0.66 | 0.33 |
| Ex. (I-243) Com. 1-4-1-O-(3) | 6.0 | 21.8 | 2500 | 11.5 | 129.5 | 0.66 | 0.33 |
| Ex. (I-244) Com. 1-4-1-O-(4) | 6.1 | 18.1 | 2500 | 13.8 | 144.0 | 0.66 | 0.32 |
| Ex. (I-245) Com. 1-4-1-O-(5) | 6.0 | 18.8 | 2500 | 13.3 | 141.1 | 0.66 | 0.32 |
| Ex. (I-246) Com. 1-4-1-O-(6) | 6.1 | 20.6 | 2500 | 12.1 | 137.6 | 0.66 | 0.32 |
| Ex. (I-247) Com. 1-4-1-O-(7) | 6.1 | 18.0 | 2500 | 13.9 | 136.1 | 0.66 | 0.32 |
| Ex. (I-248) Com. 1-4-1-O-(8) | 6.1 | 19.7 | 2500 | 12.7 | 135.2 | 0.66 | 0.33 |
| Ex. (I-249) Com. 1-4-1-O-(9) | 6.0 | 20.5 | 2500 | 12.2 | 128.9 | 0.66 | 0.33 |
| Ex. (I-250) Com. 1-4-1-O-(10) | 6.0 | 20.7 | 2500 | 12.1 | 128.4 | 0.66 | 0.33 |
| Ex. (I-251) Com. 1-4-1-O-(11) | 6.1 | 19.4 | 2500 | 12.9 | 134.5 | 0.66 | 0.32 |
| Ex. (I-252) Com. 1-4-1-O-(12) | 6.2 | 19.4 | 2500 | 12.9 | 128.5 | 0.66 | 0.33 |
| Ex. (I-253) Com. 1-4-1-O-(14) | 6.0 | 20.3 | 2500 | 12.3 | 135.6 | 0.66 | 0.33 |
| Ex. (I-254) Com. 1-4-1-O-(15) | 6.0 | 21.1 | 2500 | 11.8 | 129.6 | 0.66 | 0.33 |
| Ex. (I-255) Com. 1-4-1-O-(16) | 6.1 | 20.0 | 2500 | 12.5 | 131.7 | 0.66 | 0.32 |
| Ex. (I-256) Com. 1-4-1-O-(17) | 6.0 | 20.6 | 2500 | 12.2 | 131.0 | 0.66 | 0.32 |
| Ex. (I-257) Com. 1-4-1-O-(18) | 6.0 | 18.6 | 2500 | 13.4 | 141.2 | 0.66 | 0.33 |
| Ex. (I-258) Com. 1-4-1-O-(19) | 5.9 | 18.6 | 2500 | 13.5 | 144.2 | 0.66 | 0.32 |
| Ex. (I-259) Com. 1-4-1-O-(20) | 6.1 | 21.1 | 2500 | 11.8 | 121.3 | 0.66 | 0.32 |
| Ex. (I-260) Com. 1-4-1-O-(22) | 6.2 | 19.6 | 2500 | 12.8 | 135.7 | 0.66 | 0.33 |
| Ex. (I-261) Com. 1-4-1-S-(1) | 5.9 | 16.1 | 2500 | 15.5 | 162.9 | 0.66 | 0.32 |
| Ex. (I-262) Com. 1-4-1-S-(2) | 5.9 | 16.3 | 2500 | 15.3 | 161.4 | 0.66 | 0.32 |
| Ex. (I-263) Com. 1-4-1-S-(3) | 6.0 | 19.4 | 2500 | 12.9 | 135.3 | 0.66 | 0.33 |
| Ex. (I-264) Com. 1-4-1-S-(4) | 6.0 | 17.8 | 2500 | 14.1 | 146.4 | 0.66 | 0.32 |
| Ex. (I-265) Com. 1-4-1-S-(5) | 6.0 | 17.2 | 2500 | 14.5 | 148.7 | 0.66 | 0.32 |
| Ex. (I-266) Com. 1-4-1-S-(6) | 5.9 | 19.2 | 2500 | 13.0 | 140.4 | 0.66 | 0.33 |
| Ex. (I-267) Com. 1-4-1-S-(7) | 5.8 | 17.7 | 2500 | 14.1 | 145.6 | 0.66 | 0.33 |
| Ex. (I-268) Com. 1-4-1-S-(8) | 6.0 | 18.4 | 2500 | 13.6 | 140.2 | 0.66 | 0.32 |
| Ex. (I-269) Com. 1-4-1-S-(9) | 5.8 | 18.9 | 2500 | 13.2 | 139.6 | 0.66 | 0.32 |
| Ex. (I-270) Com. 1-4-1-S-(10) | 6.0 | 17.9 | 2500 | 13.9 | 142.6 | 0.66 | 0.33 |
| Ex. (I-271) Com. 1-4-1-S-(11) | 5.9 | 18.5 | 2500 | 13.5 | 143.0 | 0.66 | 0.33 |
| Ex. (I-272) Com. 1-4-1-S-(12) | 6.1 | 19.0 | 2500 | 13.1 | 139.4 | 0.66 | 0.33 |
| Ex. (I-273) Com. 1-4-1-S-(13) | 6.1 | 18.5 | 2500 | 13.5 | 147.8 | 0.66 | 0.33 |
| Ex. (I-274) Com. 1-4-1-S-(14) | 6.1 | 18.1 | 2500 | 13.8 | 141.0 | 0.66 | 0.32 |
| Ex. (I-275) Com. 1-4-1-S-(15) | 5.9 | 19.9 | 2500 | 12.6 | 134.3 | 0.66 | 0.32 |
| Ex. (I-276) Com. 1-4-1-S-(17) | 6.1 | 18.4 | 2500 | 13.6 | 140.6 | 0.66 | 0.33 |
| Ex. (I-277) Com. 1-4-1-S-(18) | 5.8 | 17.7 | 2500 | 14.1 | 149.4 | 0.66 | 0.33 |
| Ex. (I-278) Com. 1-4-1-S-(19) | 5.8 | 17.7 | 2500 | 14.1 | 148.5 | 0.66 | 0.32 |
| Ex. (I-279) Com. 1-4-1-S-(20) | 5.8 | 19.3 | 2500 | 13.0 | 138.7 | 0.66 | 0.32 |
| Ex. (I-280) Com. 1-4-1-S-(23) | 5.9 | 18.9 | 2500 | 13.2 | 145.9 | 0.66 | 0.33 |
| Ex. (I-281) Com. 1-4-2-O-(1) | 6.0 | 17.5 | 2500 | 14.3 | 150.9 | 0.66 | 0.33 |
| Ex. (I-282) Com. 1-4-2-O-(2) | 6.0 | 17.4 | 2500 | 14.4 | 152.3 | 0.66 | 0.33 |
| Ex. (I-283) Com. 1-4-2-O-(3) | 6.1 | 21.0 | 2500 | 11.9 | 128.1 | 0.66 | 0.32 |
| Ex. (I-284) Com. 1-4-2-O-(4) | 6.0 | 18.2 | 2500 | 13.8 | 138.5 | 0.66 | 0.33 |
| Ex. (I-285) Com. 1-4-2-O-(5) | 6.0 | 19.2 | 2500 | 13.0 | 141.9 | 0.66 | 0.33 |
| Ex. (I-286) Com. 1-4-2-O-(6) | 6.2 | 19.6 | 2500 | 12.8 | 130.2 | 0.66 | 0.32 |
| Ex. (I-287) Com. 1-4-2-O-(7) | 5.9 | 18.5 | 2500 | 13.5 | 135.2 | 0.66 | 0.32 |
| Ex. (I-288) Com. 1-4-2-O-(8) | 6.1 | 19.5 | 2500 | 12.8 | 129.1 | 0.66 | 0.32 |
| Ex. (I-289) Com. 1-4-2-O-(9) | 6.1 | 20.2 | 2500 | 12.4 | 132.5 | 0.66 | 0.33 |
| Ex. (I-290) Com. 1-4-2-O-(10) | 6.1 | 20.5 | 2500 | 12.2 | 133.1 | 0.66 | 0.33 |
| Ex. (I-291) Com. 1-4-2-O-(12) | 6.1 | 19.3 | 2500 | 13.0 | 130.6 | 0.66 | 0.33 |
| Ex. (I-292) Com. 1-4-2-O-(13) | 6.1 | 19.9 | 2500 | 12.6 | 132.4 | 0.66 | 0.33 |
| Ex. (I-293) Com. 1-4-2-O-(14) | 6.1 | 20.0 | 2500 | 12.5 | 134.0 | 0.66 | 0.32 |
| Ex. (I-294) Com. 1-4-2-O-(15) | 6.1 | 22.1 | 2500 | 11.3 | 130.0 | 0.66 | 0.32 |
| Ex. (I-295) Com. 1-4-2-O-(16) | 6.2 | 19.7 | 2500 | 12.7 | 137.6 | 0.66 | 0.33 |
| Ex. (I-296) Com. 1-4-2-O-(17) | 6.2 | 19.8 | 2500 | 12.6 | 135.6 | 0.66 | 0.33 |
| Ex. (I-297) Com. 1-4-2-O-(18) | 5.9 | 18.3 | 2500 | 13.7 | 143.5 | 0.66 | 0.33 |
| Ex. (I-298) Com. 1-4-2-O-(19) | 6.0 | 19.2 | 2500 | 13.0 | 136.4 | 0.66 | 0.32 |
| Ex. (I-299) Com. 1-4-2-O-(20) | 6.1 | 21.7 | 2500 | 11.5 | 124.0 | 0.66 | 0.32 |
| Ex. (I-300) Com. 1-4-2-O-(22) | 6.1 | 19.5 | 2500 | 12.8 | 137.4 | 0.66 | 0.33 |
| Ex. (I-301) Com. 1-4-2-S-(1) | 5.9 | 16.3 | 2500 | 15.3 | 161.2 | 0.66 | 0.32 |
| Ex. (I-302) Com. 1-4-2-S-(2) | 5.9 | 16.2 | 2500 | 15.4 | 160.4 | 0.66 | 0.32 |
| Ex. (I-303) Com. 1-4-2-S-(3) | 5.9 | 20.6 | 2500 | 12.1 | 135.6 | 0.66 | 0.33 |
| Ex. (I-304) Com. 1-4-2-S-(4) | 5.9 | 17.6 | 2500 | 14.2 | 151.0 | 0.66 | 0.33 |

TABLE 4-continued

| Compound | Voltage (V) | Current Density (mA/cm²) | Brightness (cd/m²) | Efficiency (cd/A) | Lifetime T(95) | CIE x | CIE y |
|---|---|---|---|---|---|---|---|
| Ex. (I-305) Com. 1-4-2-S-(5) | 5.8 | 16.7 | 2500 | 15.0 | 151.6 | 0.66 | 0.33 |
| Ex. (I-306) Com. 1-4-2-S-(6) | 5.9 | 18.4 | 2500 | 13.6 | 145.4 | 0.66 | 0.32 |
| Ex. (I-307) Com. 1-4-2-S-(7) | 5.9 | 17.0 | 2500 | 14.7 | 153.1 | 0.66 | 0.32 |
| Ex. (I-308) Com. 1-4-2-S-(8) | 5.9 | 18.7 | 2500 | 13.4 | 138.8 | 0.66 | 0.33 |
| Ex. (I-309) Com. 1-4-2-S-(9) | 6.0 | 18.5 | 2500 | 13.5 | 146.0 | 0.66 | 0.33 |
| Ex. (I-310) Com. 1-4-2-S-(10) | 6.1 | 18.0 | 2500 | 13.9 | 144.9 | 0.66 | 0.33 |
| Ex. (I-311) Com. 1-4-2-S-(11) | 5.9 | 19.1 | 2500 | 13.1 | 138.9 | 0.66 | 0.33 |
| Ex. (I-312) Com. 1-4-2-S-(12) | 5.8 | 18.8 | 2500 | 13.3 | 147.5 | 0.66 | 0.33 |
| Ex. (I-313) Com. 1-4-2-S-(13) | 5.8 | 18.4 | 2500 | 13.6 | 144.3 | 0.66 | 0.33 |
| Ex. (I-314) Com. 1-4-2-S-(14) | 5.9 | 18.9 | 2500 | 13.2 | 140.0 | 0.66 | 0.32 |
| Ex. (I-315) Com. 1-4-2-S-(15) | 6.1 | 20.0 | 2500 | 12.5 | 134.1 | 0.66 | 0.33 |
| Ex. (I-316) Com. 1-4-2-S-(16) | 6.0 | 19.0 | 2500 | 13.2 | 143.2 | 0.66 | 0.33 |
| Ex. (I-317) Com. 1-4-2-S-(18) | 5.8 | 17.8 | 2500 | 14.1 | 147.7 | 0.66 | 0.32 |
| Ex. (I-318) Com. 1-4-2-S-(19) | 5.8 | 16.8 | 2500 | 14.9 | 150.0 | 0.66 | 0.33 |
| Ex. (I-319) Com. 1-4-2-S-(20) | 5.8 | 20.0 | 2500 | 12.5 | 134.7 | 0.66 | 0.33 |
| Ex. (I-320) Com. 1-4-2-S-(22) | 6.0 | 18.9 | 2500 | 13.2 | 139.4 | 0.66 | 0.32 |

Test Example II-1

Yellow Organic Light Emitting Diode (a Phosphorescent Host)

Organic light emitting diodes (OLEDs) were fabricated according to a conventional method by using a compound of the present invention as a phosphorescent host material. First, an ITO layer (anode) was formed on a glass substrate, and a film of 2-TNATA was vacuum-deposited on the ITO layer to form a hole injection layer with a thickness of 60 nm. Subsequently, NPD was vacuum-deposited with a thickness of 60 nm on the hole injection layer to form a hole transport layer. Subsequently, a light emitting layer with a thickness of 30 nm was deposited on the hole transport layer by doping the hole transport layer with the compound 1-1-1-O-(1) of the present invention as a host material and the compound B below as a dopant material in a weight ratio of 95:5. Next, a film of BAlq was vacuum-deposited with a thickness of 10 nm on the light emitting layer to form a hole blocking layer, and a film of Alq₃ was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

<Compound B>

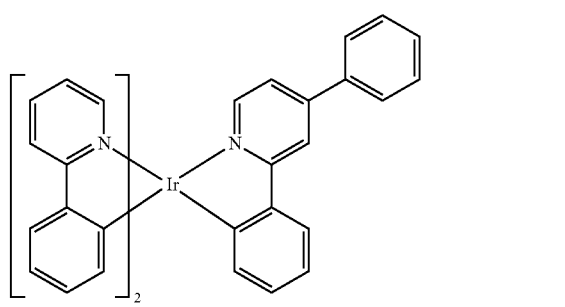

[Test Example 11-2] to [Test Example II-243]

Yellow Organic Light Emitting Diode (a Phosphorescent Host)

The OLED was manufactured in the same manner as described in Test Example II-1, except that any one of the compounds 1-1-1-O-(2) to 1-4-2-S-(23) of the present invention in the Table 5 below was used as the host material of the light emitting layer, instead of the inventive compound 1-1-1-O-(1).

[Comparative Example II-1] to [Comparative Example II-16]

An OLED was manufactured in the same manner as described in Test Example II-1, except that any one of the Comparative Compounds 1 to 16 represented above was used as the host material of the light emitting layer, instead of the inventive compound 1-1-1-O-(1).

A forward bias DC voltage was applied to each of the OLEDs manufactured through Test Examples (II-1) to (II-243) and Comparative Example (II-1) to (II-16), and electroluminescence (EL) characteristics of the OLED were measured by PR-650 (Photoresearch). Also, T95 life span was measured by life span measuring equipment (Mcscience) at a reference brightness of 5000 cd/m². Table 5 below shows evaluation results of OLEDs manufactured Test Examples and Comparative Examples.

TABLE 5

| | Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp. Ex(II-1) | comp. Com 1 | 6.3 | 15.0 | 5000 | 33.4 | 75.3 | 0.44 | 0.52 |
| comp. Ex(II-2) | comp. Com 2 | 6.3 | 15.1 | 5000 | 33.0 | 75.6 | 0.44 | 0.52 |
| comp. Ex(II-3) | comp. Com 3 | 6.3 | 16.8 | 5000 | 29.8 | 63.9 | 0.44 | 0.53 |
| comp. Ex(II-4) | comp. Com 4 | 6.3 | 17.2 | 5000 | 29.1 | 66.3 | 0.44 | 0.53 |
| comp. Ex(II-5) | comp. Com 5 | 6.4 | 17.0 | 5000 | 29.4 | 60.7 | 0.44 | 0.53 |
| comp. Ex(II-6) | comp. Com 6 | 6.3 | 16.7 | 5000 | 30.0 | 68.2 | 0.44 | 0.52 |
| comp. Ex(II-7) | comp. Com 7 | 6.3 | 15.4 | 5000 | 32.4 | 70.9 | 0.44 | 0.52 |
| comp. Ex(II-8) | comp. Com 8 | 6.2 | 15.8 | 5000 | 31.7 | 74.1 | 0.44 | 0.52 |
| comp. Ex(II-9) | comp. Com 9 | 6.3 | 16.2 | 5000 | 30.8 | 64.7 | 0.44 | 0.52 |
| comp. Ex(II-10) | comp. Com 10 | 6.2 | 16.5 | 5000 | 30.3 | 67.1 | 0.44 | 0.52 |
| comp. Ex(II-11) | comp. Com 11 | 6.4 | 18.4 | 5000 | 27.2 | 66.9 | 0.44 | 0.52 |
| comp. Ex(II-12) | comp. Com 12 | 6.3 | 18.4 | 5000 | 27.2 | 68.0 | 0.44 | 0.52 |
| comp. Ex(II-13) | comp. Com 13 | 6.3 | 17.4 | 5000 | 28.7 | 69.7 | 0.44 | 0.53 |
| comp. Ex(II-14) | comp. Com 14 | 6.4 | 17.4 | 5000 | 28.7 | 63.2 | 0.44 | 0.52 |
| comp. Ex(II-15) | comp. Com 15 | 6.4 | 17.9 | 5000 | 27.9 | 64.6 | 0.44 | 0.53 |
| comp. Ex(II-16) | comp. Com 16 | 6.4 | 18.3 | 5000 | 27.4 | 61.4 | 0.44 | 0.52 |
| Ex. (II-1) | Com. 1-1-1-O-(1) | 5.9 | 10.1 | 5000 | 49.7 | 142.7 | 0.44 | 0.53 |
| Ex. (II-2) | Com. 1-1-1-O-(2) | 5.9 | 10.3 | 5000 | 48.7 | 139.9 | 0.44 | 0.53 |
| Ex. (II-3) | Com. 1-1-1-O-(4) | 5.9 | 10.6 | 5000 | 47.2 | 132.3 | 0.44 | 0.53 |
| Ex. (II-4) | Com. 1-1-1-O-(5) | 6.0 | 11.0 | 5000 | 45.5 | 121.2 | 0.44 | 0.52 |
| Ex. (II-5) | Com. 1-1-1-O-(6) | 5.8 | 11.4 | 5000 | 43.9 | 135.9 | 0.44 | 0.52 |
| Ex. (II-6) | Com. 1-1-1-O-(7) | 5.8 | 11.1 | 5000 | 45.2 | 122.6 | 0.44 | 0.52 |
| Ex. (II-7) | Com. 1-1-1-O-(8) | 5.8 | 11.7 | 5000 | 42.8 | 137.8 | 0.44 | 0.53 |
| Ex. (II-8) | Com. 1-1-1-O-(9) | 6.1 | 11.4 | 5000 | 43.9 | 122.4 | 0.44 | 0.53 |
| Ex. (II-9) | Com. 1-1-1-O-(12) | 6.0 | 11.4 | 5000 | 44.0 | 122.7 | 0.44 | 0.53 |
| Ex. (II-10) | Com. 1-1-1-O-(18) | 6.0 | 10.7 | 5000 | 46.8 | 124.4 | 0.44 | 0.53 |
| Ex. (II-11) | Com. 1-1-1-O-(19) | 5.9 | 10.7 | 5000 | 46.9 | 126.5 | 0.44 | 0.53 |
| Ex. (II-12) | Com. 1-1-1-O-(22) | 5.9 | 11.4 | 5000 | 43.8 | 137.1 | 0.44 | 0.52 |
| Ex. (II-13) | Com. 1-1-1-S-(1) | 5.9 | 9.9 | 5000 | 50.5 | 151.3 | 0.44 | 0.53 |
| Ex. (II-14) | Com. 1-1-1-S-(2) | 5.8 | 9.9 | 5000 | 50.3 | 151.4 | 0.44 | 0.52 |
| Ex. (II-15) | Com. 1-1-1-S-(3) | 5.9 | 11.3 | 5000 | 44.3 | 131.3 | 0.44 | 0.52 |
| Ex. (II-16) | Com. 1-1-1-S-(4) | 5.9 | 10.1 | 5000 | 49.5 | 139.2 | 0.44 | 0.52 |
| Ex. (II-17) | Com. 1-1-1-S-(5) | 6.0 | 10.5 | 5000 | 47.5 | 130.7 | 0.44 | 0.52 |
| Ex. (II-18) | Com. 1-1-1-S-(6) | 5.8 | 11.0 | 5000 | 45.4 | 131.7 | 0.44 | 0.53 |
| Ex. (II-19) | Com. 1-1-1-S-(7) | 5.9 | 10.2 | 5000 | 48.8 | 143.2 | 0.44 | 0.52 |
| Ex. (II-20) | Com. 1-1-1-S-(8) | 6.0 | 10.8 | 5000 | 46.1 | 148.4 | 0.44 | 0.52 |
| Ex. (II-21) | Com. 1-1-1-S-(9) | 6.0 | 11.0 | 5000 | 45.6 | 137.6 | 0.44 | 0.53 |
| Ex. (II-22) | Com. 1-1-1-S-(10) | 5.9 | 10.9 | 5000 | 45.8 | 142.4 | 0.44 | 0.52 |
| Ex. (II-23) | Com. 1-1-1-S-(11) | 5.9 | 10.7 | 5000 | 46.5 | 147.6 | 0.44 | 0.53 |
| Ex. (II-24) | Com. 1-1-1-S-(12) | 5.9 | 11.1 | 5000 | 45.1 | 136.8 | 0.44 | 0.53 |
| Ex. (II-25) | Com. 1-1-1-S-(13) | 5.9 | 11.0 | 5000 | 45.4 | 135.3 | 0.44 | 0.52 |
| Ex. (II-26) | Com. 1-1-1-S-(14) | 6.1 | 11.2 | 5000 | 44.8 | 133.8 | 0.44 | 0.53 |
| Ex. (II-27) | Com. 1-1-1-S-(15) | 6.0 | 11.7 | 5000 | 42.9 | 126.9 | 0.44 | 0.53 |
| Ex. (II-28) | Com. 1-1-1-S-(16) | 5.9 | 11.0 | 5000 | 45.4 | 135.3 | 0.44 | 0.53 |
| Ex. (II-29) | Com. 1-1-1-S-(17) | 5.9 | 10.6 | 5000 | 47.0 | 140.2 | 0.44 | 0.52 |
| Ex. (II-30) | Com. 1-1-1-S-(18) | 5.9 | 10.1 | 5000 | 49.3 | 134.2 | 0.44 | 0.53 |
| Ex. (II-31) | Com. 1-1-1-S-(19) | 5.9 | 10.1 | 5000 | 49.6 | 131.8 | 0.44 | 0.53 |
| Ex. (II-32) | Com. 1-1-1-S-(20) | 6.0 | 11.3 | 5000 | 44.4 | 133.8 | 0.44 | 0.53 |
| Ex. (II-33) | Com. 1-1-1-S-(23) | 6.0 | 10.8 | 5000 | 46.2 | 140.8 | 0.44 | 0.53 |
| Ex. (II-34) | Com. 1-1-2-O-(1) | 5.9 | 10.5 | 5000 | 47.6 | 142.3 | 0.44 | 0.52 |
| Ex. (II-35) | Com. 1-1-2-O-(2) | 5.9 | 10.2 | 5000 | 49.0 | 141.2 | 0.44 | 0.52 |
| Ex. (II-36) | Com. 1-1-2-O-(3) | 5.8 | 12.2 | 5000 | 41.1 | 117.3 | 0.44 | 0.52 |
| Ex. (II-37) | Com. 1-1-2-O-(4) | 5.9 | 10.8 | 5000 | 46.5 | 132.9 | 0.44 | 0.53 |
| Ex. (II-38) | Com. 1-1-2-O-(5) | 6.0 | 11.0 | 5000 | 45.5 | 121.5 | 0.44 | 0.53 |
| Ex. (II-39) | Com. 1-1-2-O-(6) | 5.8 | 11.6 | 5000 | 43.1 | 126.2 | 0.44 | 0.53 |
| Ex. (II-40) | Com. 1-1-2-O-(7) | 5.9 | 10.9 | 5000 | 46.0 | 130.4 | 0.44 | 0.53 |
| Ex. (II-41) | Com. 1-1-2-O-(8) | 5.9 | 11.2 | 5000 | 44.6 | 126.0 | 0.44 | 0.52 |
| Ex. (II-42) | Com. 1-1-2-O-(13) | 5.9 | 11.1 | 5000 | 45.0 | 132.5 | 0.44 | 0.53 |
| Ex. (II-43) | Com. 1-1-2-O-(15) | 6.0 | 12.2 | 5000 | 40.8 | 120.2 | 0.44 | 0.52 |
| Ex. (II-44) | Com. 1-1-2-O-(17) | 5.8 | 11.2 | 5000 | 44.8 | 122.1 | 0.44 | 0.52 |
| Ex. (II-45) | Com. 1-1-2-O-(18) | 5.8 | 10.9 | 5000 | 45.7 | 127.5 | 0.44 | 0.52 |
| Ex. (II-46) | Com. 1-1-2-O-(19) | 6.0 | 11.0 | 5000 | 45.6 | 133.9 | 0.44 | 0.52 |
| Ex. (II-47) | Com. 1-1-2-O-(20) | 5.9 | 11.9 | 5000 | 42.2 | 115.2 | 0.44 | 0.53 |
| Ex. (II-48) | Com. 1-1-2-O-(22) | 5.9 | 11.2 | 5000 | 44.7 | 129.1 | 0.44 | 0.52 |
| Ex. (II-49) | Com. 1-1-2-S-(1) | 6.0 | 10.0 | 5000 | 49.8 | 152.5 | 0.44 | 0.53 |
| Ex. (II-50) | Com. 1-1-2-S-(2) | 5.8 | 9.6 | 5000 | 52.0 | 153.1 | 0.44 | 0.52 |
| Ex. (II-51) | Com. 1-1-2-S-(3) | 6.0 | 11.3 | 5000 | 44.4 | 127.3 | 0.44 | 0.53 |
| Ex. (II-52) | Com. 1-1-2-S-(4) | 5.8 | 10.3 | 5000 | 48.5 | 140.4 | 0.44 | 0.53 |
| Ex. (II-53) | Com. 1-1-2-S-(5) | 6.0 | 10.5 | 5000 | 47.7 | 133.6 | 0.44 | 0.52 |
| Ex. (II-54) | Com. 1-1-2-S-(6) | 5.8 | 11.0 | 5000 | 45.4 | 135.7 | 0.44 | 0.53 |
| Ex. (II-55) | Com. 1-1-2-S-(7) | 5.8 | 10.2 | 5000 | 49.1 | 137.6 | 0.44 | 0.52 |
| Ex. (II-56) | Com. 1-1-2-S-(8) | 6.0 | 10.9 | 5000 | 45.9 | 138.7 | 0.44 | 0.52 |
| Ex. (II-57) | Com. 1-1-2-S-(9) | 6.1 | 10.8 | 5000 | 46.4 | 148.5 | 0.44 | 0.53 |
| Ex. (II-58) | Com. 1-1-2-S-(10) | 6.1 | 11.1 | 5000 | 44.9 | 130.5 | 0.44 | 0.52 |
| Ex. (II-59) | Com. 1-1-2-S-(11) | 5.9 | 10.9 | 5000 | 45.7 | 145.3 | 0.44 | 0.53 |

TABLE 5-continued

| Compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|
| Ex. (II-60) Com. 1-1-2-S-(12) | 5.9 | 10.9 | 5000 | 46.1 | 132.5 | 0.44 | 0.52 |
| Ex. (II-61) Com. 1-1-2-S-(13) | 6.0 | 10.6 | 5000 | 47.1 | 141.3 | 0.44 | 0.53 |
| Ex. (II-62) Com. 1-1-2-S-(14) | 6.0 | 11.1 | 5000 | 45.2 | 139.9 | 0.44 | 0.53 |
| Ex. (II-63) Com. 1-1-2-S-(15) | 6.0 | 11.4 | 5000 | 43.8 | 127.0 | 0.44 | 0.52 |
| Ex. (II-64) Com. 1-1-2-S-(16) | 5.8 | 10.8 | 5000 | 46.2 | 137.6 | 0.44 | 0.52 |
| Ex. (II-65) Com. 1-1-2-S-(17) | 6.0 | 11.0 | 5000 | 45.3 | 145.8 | 0.44 | 0.53 |
| Ex. (II-66) Com. 1-1-2-S-(18) | 5.8 | 10.5 | 5000 | 47.7 | 146.1 | 0.44 | 0.52 |
| Ex. (II-67) Com. 1-1-2-S-(19) | 6.0 | 10.2 | 5000 | 48.9 | 130.7 | 0.44 | 0.53 |
| Ex. (II-68) Com. 1-1-2-S-(20) | 6.1 | 11.4 | 5000 | 43.8 | 129.4 | 0.44 | 0.52 |
| Ex. (II-69) Com. 1-1-2-S-(22) | 6.1 | 10.7 | 5000 | 46.7 | 131.9 | 0.44 | 0.53 |
| Ex. (II-70) Com. 1-2-1-O-(1) | 6.1 | 11.5 | 5000 | 43.6 | 122.2 | 0.44 | 0.53 |
| Ex. (II-71) Com. 1-2-1-O-(2) | 5.9 | 11.2 | 5000 | 44.5 | 119.8 | 0.44 | 0.53 |
| Ex. (II-72) Com. 1-2-1-O-(3) | 6.1 | 13.4 | 5000 | 37.3 | 101.8 | 0.44 | 0.52 |
| Ex. (II-73) Com. 1-2-1-O-(4) | 6.1 | 12.0 | 5000 | 41.8 | 115.7 | 0.44 | 0.52 |
| Ex. (II-74) Com. 1-2-1-O-(5) | 6.1 | 12.2 | 5000 | 41.0 | 118.6 | 0.44 | 0.52 |
| Ex. (II-75) Com. 1-2-1-O-(6) | 6.2 | 12.6 | 5000 | 39.7 | 110.7 | 0.44 | 0.53 |
| Ex. (II-76) Com. 1-2-1-O-(7) | 6.1 | 11.9 | 5000 | 42.0 | 115.7 | 0.44 | 0.53 |
| Ex. (II-77) Com. 1-2-1-O-(8) | 6.0 | 12.6 | 5000 | 39.5 | 106.3 | 0.44 | 0.52 |
| Ex. (II-78) Com. 1-2-1-O-(10) | 6.1 | 12.5 | 5000 | 40.0 | 101.0 | 0.44 | 0.53 |
| Ex. (II-79) Com. 1-2-1-O-(11) | 6.0 | 12.7 | 5000 | 39.3 | 102.2 | 0.44 | 0.53 |
| Ex. (II-80) Com. 1-2-1-O-(15) | 6.0 | 13.9 | 5000 | 36.0 | 102.5 | 0.44 | 0.53 |
| Ex. (II-81) Com. 1-2-1-O-(17) | 6.1 | 12.8 | 5000 | 39.0 | 115.9 | 0.44 | 0.52 |
| Ex. (II-82) Com. 1-2-1-O-(18) | 6.0 | 12.2 | 5000 | 41.1 | 110.2 | 0.44 | 0.52 |
| Ex. (II-83) Com. 1-2-1-O-(19) | 5.9 | 12.2 | 5000 | 41.0 | 114.0 | 0.44 | 0.52 |
| Ex. (II-84) Com. 1-2-1-O-(21) | 6.0 | 12.5 | 5000 | 39.9 | 102.1 | 0.44 | 0.52 |
| Ex. (II-85) Com. 1-2-1-S-(1) | 5.9 | 10.6 | 5000 | 47.1 | 134.4 | 0.44 | 0.53 |
| Ex. (II-86) Com. 1-2-1-S-(2) | 6.0 | 10.5 | 5000 | 47.5 | 130.7 | 0.44 | 0.53 |
| Ex. (II-87) Com. 1-2-1-S-(4) | 6.1 | 11.2 | 5000 | 44.4 | 111.5 | 0.44 | 0.52 |
| Ex. (II-88) Com. 1-2-1-S-(5) | 6.0 | 11.5 | 5000 | 43.3 | 123.3 | 0.44 | 0.52 |
| Ex. (II-89) Com. 1-2-1-S-(6) | 6.2 | 11.7 | 5000 | 42.6 | 114.4 | 0.44 | 0.52 |
| Ex. (II-90) Com. 1-2-1-S-(7) | 6.0 | 11.3 | 5000 | 44.4 | 122.3 | 0.44 | 0.52 |
| Ex. (II-91) Com. 1-2-1-S-(8) | 6.2 | 12.3 | 5000 | 40.6 | 124.0 | 0.44 | 0.53 |
| Ex. (II-92) Com. 1-2-1-S-(9) | 6.1 | 12.0 | 5000 | 41.7 | 117.8 | 0.44 | 0.52 |
| Ex. (II-93) Com. 1-2-1-S-(12) | 6.2 | 11.9 | 5000 | 42.1 | 127.8 | 0.44 | 0.53 |
| Ex. (II-94) Com. 1-2-1-S-(14) | 6.2 | 12.3 | 5000 | 40.8 | 117.7 | 0.44 | 0.52 |
| Ex. (II-95) Com. 1-2-1-S-(15) | 6.1 | 12.5 | 5000 | 39.9 | 108.4 | 0.44 | 0.53 |
| Ex. (II-96) Com. 1-2-1-S-(18) | 6.0 | 11.5 | 5000 | 43.6 | 126.1 | 0.44 | 0.53 |
| Ex. (II-97) Com. 1-2-1-S-(19) | 5.9 | 11.2 | 5000 | 44.7 | 116.7 | 0.44 | 0.52 |
| Ex. (II-98) Com. 1-2-1-S-(21) | 6.1 | 12.0 | 5000 | 41.6 | 113.2 | 0.44 | 0.53 |
| Ex. (II-99) Com. 1-2-2-O-(1) | 5.9 | 11.1 | 5000 | 45.0 | 123.2 | 0.44 | 0.52 |
| Ex. (II-100) Com. 1-2-2-O-(2) | 6.1 | 11.3 | 5000 | 44.3 | 125.2 | 0.44 | 0.53 |
| Ex. (II-101) Com. 1-2-2-O-(4) | 6.0 | 11.8 | 5000 | 42.3 | 116.8 | 0.44 | 0.53 |
| Ex. (II-102) Com. 1-2-2-O-(5) | 6.0 | 12.2 | 5000 | 40.9 | 110.9 | 0.44 | 0.52 |
| Ex. (II-103) Com. 1-2-2-O-(6) | 6.2 | 12.5 | 5000 | 40.0 | 117.8 | 0.44 | 0.52 |
| Ex. (II-104) Com. 1-2-2-O-(7) | 5.9 | 11.8 | 5000 | 42.3 | 115.6 | 0.44 | 0.53 |
| Ex. (II-105) Com. 1-2-2-O-(8) | 6.0 | 13.0 | 5000 | 38.3 | 112.7 | 0.44 | 0.53 |
| Ex. (II-106) Com. 1-2-2-O-(9) | 6.1 | 12.4 | 5000 | 40.3 | 103.1 | 0.44 | 0.52 |
| Ex. (II-107) Com. 1-2-2-O-(14) | 6.2 | 12.9 | 5000 | 38.8 | 116.0 | 0.44 | 0.52 |
| Ex. (II-108) Com. 1-2-2-O-(16) | 6.0 | 12.7 | 5000 | 39.3 | 113.1 | 0.44 | 0.53 |
| Ex. (II-109) Com. 1-2-2-O-(18) | 6.1 | 12.2 | 5000 | 41.1 | 116.3 | 0.44 | 0.53 |
| Ex. (II-110) Com. 1-2-2-O-(19) | 6.0 | 11.8 | 5000 | 42.4 | 100.1 | 0.44 | 0.53 |
| Ex. (II-111) Com. 1-2-2-O-(20) | 6.0 | 13.4 | 5000 | 37.3 | 102.5 | 0.44 | 0.53 |
| Ex. (II-112) Com. 1-2-2-O-(21) | 6.2 | 12.6 | 5000 | 39.6 | 108.7 | 0.44 | 0.52 |
| Ex. (II-113) Com. 1-2-2-S-(1) | 5.9 | 10.7 | 5000 | 46.7 | 129.7 | 0.44 | 0.53 |
| Ex. (II-114) Com. 1-2-2-S-(2) | 6.1 | 10.7 | 5000 | 46.9 | 130.0 | 0.44 | 0.53 |
| Ex. (II-115) Com. 1-2-2-S-(3) | 6.0 | 12.8 | 5000 | 39.2 | 114.3 | 0.44 | 0.52 |
| Ex. (II-116) Com. 1-2-2-S-(4) | 6.0 | 11.2 | 5000 | 44.7 | 128.2 | 0.44 | 0.53 |
| Ex. (II-117) Com. 1-2-2-S-(5) | 6.1 | 11.2 | 5000 | 44.6 | 115.9 | 0.44 | 0.53 |
| Ex. (II-118) Com. 1-2-2-S-(6) | 6.1 | 11.7 | 5000 | 42.6 | 121.3 | 0.44 | 0.52 |
| Ex. (II-119) Com. 1-2-2-S-(7) | 6.1 | 11.4 | 5000 | 44.0 | 128.3 | 0.44 | 0.53 |
| Ex. (II-120) Com. 1-2-2-S-(8) | 6.1 | 12.2 | 5000 | 41.1 | 123.0 | 0.44 | 0.52 |
| Ex. (II-121) Com. 1-2-2-S-(10) | 6.0 | 11.8 | 5000 | 42.4 | 110.5 | 0.44 | 0.53 |
| Ex. (II-122) Com. 1-2-2-S-(11) | 6.1 | 12.0 | 5000 | 41.6 | 111.1 | 0.44 | 0.53 |
| Ex. (II-123) Com. 1-2-2-S-(13) | 6.1 | 12.0 | 5000 | 41.5 | 118.8 | 0.44 | 0.53 |
| Ex. (II-124) Com. 1-2-2-S-(18) | 6.0 | 11.2 | 5000 | 44.8 | 117.2 | 0.44 | 0.52 |
| Ex. (II-125) Com. 1-2-2-S-(19) | 5.9 | 11.7 | 5000 | 42.8 | 124.6 | 0.44 | 0.52 |
| Ex. (II-126) Com. 1-2-2-S-(20) | 6.1 | 12.8 | 5000 | 39.0 | 106.1 | 0.44 | 0.53 |
| Ex. (II-127) Com. 1-2-2-S-(22) | 6.2 | 12.4 | 5000 | 40.5 | 114.8 | 0.44 | 0.53 |
| Ex. (II-128) Com. 1-3-1-O-(1) | 5.9 | 11.0 | 5000 | 45.2 | 125.4 | 0.44 | 0.53 |
| Ex. (II-129) Com. 1-3-1-O-(2) | 6.0 | 11.1 | 5000 | 45.1 | 124.4 | 0.44 | 0.53 |
| Ex. (II-130) Com. 1-3-1-O-(3) | 6.2 | 13.3 | 5000 | 37.6 | 103.6 | 0.44 | 0.52 |
| Ex. (II-131) Com. 1-3-1-O-(4) | 6.0 | 11.7 | 5000 | 42.9 | 106.1 | 0.44 | 0.53 |
| Ex. (II-132) Com. 1-3-1-O-(5) | 5.9 | 12.1 | 5000 | 41.3 | 105.7 | 0.44 | 0.53 |
| Ex. (II-133) Com. 1-3-1-O-(6) | 6.0 | 13.0 | 5000 | 38.6 | 107.2 | 0.44 | 0.52 |
| Ex. (II-134) Com. 1-3-1-O-(7) | 6.0 | 11.7 | 5000 | 42.6 | 104.3 | 0.44 | 0.52 |

TABLE 5-continued

| Compound | Voltage (V) | Current Density (mA/cm²) | Brightness (cd/m²) | Efficiency (cd/A) | Lifetime T(95) | CIE x | CIE y |
|---|---|---|---|---|---|---|---|
| Ex. (II-135) | Com. 1-3-1-O-(8) | 6.1 | 12.7 | 5000 | 39.4 | 107.4 | 0.44 | 0.52 |
| Ex. (II-136) | Com. 1-3-1-O-(10) | 6.1 | 12.4 | 5000 | 40.2 | 103.9 | 0.44 | 0.52 |
| Ex. (II-137) | Com. 1-3-1-O-(11) | 6.2 | 13.1 | 5000 | 38.3 | 105.8 | 0.44 | 0.53 |
| Ex. (II-138) | Com. 1-3-1-O-(14) | 6.0 | 12.3 | 5000 | 40.6 | 104.5 | 0.44 | 0.52 |
| Ex. (II-139) | Com. 1-3-1-O-(18) | 6.0 | 12.1 | 5000 | 41.4 | 117.1 | 0.44 | 0.52 |
| Ex. (II-140) | Com. 1-3-1-O-(19) | 5.9 | 12.0 | 5000 | 41.6 | 118.7 | 0.44 | 0.53 |
| Ex. (II-141) | Com. 1-3-1-O-(20) | 6.0 | 13.2 | 5000 | 38.0 | 100.0 | 0.44 | 0.53 |
| Ex. (II-142) | Com. 1-3-1-O-(22) | 6.1 | 12.5 | 5000 | 39.9 | 105.5 | 0.44 | 0.52 |
| Ex. (II-143) | Com. 1-3-1-S-(1) | 6.0 | 10.9 | 5000 | 45.9 | 131.5 | 0.44 | 0.52 |
| Ex. (II-144) | Com. 1-3-1-S-(2) | 6.1 | 10.9 | 5000 | 45.9 | 133.3 | 0.44 | 0.52 |
| Ex. (II-145) | Com. 1-3-1-S-(4) | 6.0 | 11.2 | 5000 | 44.7 | 121.5 | 0.44 | 0.52 |
| Ex. (II-146) | Com. 1-3-1-S-(5) | 6.0 | 11.6 | 5000 | 43.2 | 115.1 | 0.44 | 0.53 |
| Ex. (II-147) | Com. 1-3-1-S-(6) | 6.1 | 11.7 | 5000 | 42.6 | 112.8 | 0.44 | 0.52 |
| Ex. (II-148) | Com. 1-3-1-S-(7) | 6.0 | 11.5 | 5000 | 43.3 | 120.6 | 0.44 | 0.53 |
| Ex. (II-149) | Com. 1-3-1-S-(8) | 6.2 | 12.0 | 5000 | 41.8 | 125.5 | 0.44 | 0.52 |
| Ex. (II-150) | Com. 1-3-1-S-(10) | 6.0 | 11.7 | 5000 | 42.7 | 111.0 | 0.44 | 0.53 |
| Ex. (II-151) | Com. 1-3-1-S-(11) | 6.1 | 12.4 | 5000 | 40.5 | 121.7 | 0.44 | 0.53 |
| Ex. (II-152) | Com. 1-3-1-S-(16) | 6.1 | 12.2 | 5000 | 41.1 | 112.4 | 0.44 | 0.52 |
| Ex. (II-153) | Com. 1-3-1-S-(18) | 5.9 | 11.3 | 5000 | 44.4 | 112.2 | 0.44 | 0.52 |
| Ex. (II-154) | Com. 1-3-1-S-(19) | 5.9 | 11.7 | 5000 | 42.8 | 113.4 | 0.44 | 0.53 |
| Ex. (II-155) | Com. 1-3-1-S-(20) | 6.1 | 12.9 | 5000 | 38.7 | 109.0 | 0.44 | 0.52 |
| Ex. (II-156) | Com. 1-3-1-S-(23) | 6.1 | 12.0 | 5000 | 41.7 | 115.2 | 0.44 | 0.53 |
| Ex. (II-157) | Com. 1-3-2-O-(1) | 6.1 | 11.6 | 5000 | 43.0 | 122.6 | 0.44 | 0.52 |
| Ex. (II-158) | Com. 1-3-2-O-(2) | 6.0 | 11.2 | 5000 | 44.6 | 121.8 | 0.44 | 0.52 |
| Ex. (II-159) | Com. 1-3-2-O-(4) | 6.0 | 11.9 | 5000 | 41.9 | 101.9 | 0.44 | 0.53 |
| Ex. (II-160) | Com. 1-3-2-O-(5) | 6.0 | 11.9 | 5000 | 42.0 | 109.8 | 0.44 | 0.52 |
| Ex. (II-161) | Com. 1-3-2-O-(6) | 6.0 | 12.5 | 5000 | 39.9 | 105.6 | 0.44 | 0.52 |
| Ex. (II-162) | Com. 1-3-2-O-(7) | 6.0 | 11.7 | 5000 | 42.6 | 101.4 | 0.44 | 0.53 |
| Ex. (II-163) | Com. 1-3-2-O-(8) | 6.2 | 12.9 | 5000 | 38.6 | 109.0 | 0.44 | 0.52 |
| Ex. (II-164) | Com. 1-3-2-O-(12) | 6.1 | 12.5 | 5000 | 39.9 | 105.1 | 0.44 | 0.52 |
| Ex. (II-165) | Com. 1-3-2-O-(14) | 6.1 | 13.0 | 5000 | 38.4 | 117.7 | 0.44 | 0.52 |
| Ex. (II-166) | Com. 1-3-2-O-(15) | 6.1 | 13.1 | 5000 | 38.2 | 100.7 | 0.44 | 0.53 |
| Ex. (II-167) | Com. 1-3-2-O-(17) | 6.2 | 12.8 | 5000 | 39.0 | 115.1 | 0.44 | 0.53 |
| Ex. (II-168) | Com. 1-3-2-O-(18) | 6.0 | 11.8 | 5000 | 42.2 | 101.7 | 0.44 | 0.52 |
| Ex. (II-169) | Com. 1-3-2-O-(19) | 6.0 | 12.3 | 5000 | 40.7 | 118.4 | 0.44 | 0.53 |
| Ex. (II-170) | Com. 1-3-2-O-(22) | 6.1 | 12.8 | 5000 | 39.1 | 118.8 | 0.44 | 0.52 |
| Ex. (II-171) | Com. 1-3-2-S-(1) | 6.1 | 10.7 | 5000 | 46.9 | 129.8 | 0.44 | 0.53 |
| Ex. (II-172) | Com. 1-3-2-S-(2) | 6.0 | 10.6 | 5000 | 47.1 | 130.4 | 0.44 | 0.52 |
| Ex. (II-173) | Com. 1-3-2-S-(3) | 6.0 | 12.9 | 5000 | 38.8 | 108.9 | 0.44 | 0.53 |
| Ex. (II-174) | Com. 1-3-2-S-(4) | 6.0 | 11.4 | 5000 | 43.7 | 110.8 | 0.44 | 0.52 |
| Ex. (II-175) | Com. 1-3-2-S-(5) | 6.1 | 11.6 | 5000 | 43.3 | 120.9 | 0.44 | 0.52 |
| Ex. (II-176) | Com. 1-3-2-S-(6) | 6.1 | 12.2 | 5000 | 41.0 | 117.3 | 0.44 | 0.53 |
| Ex. (II-177) | Com. 1-3-2-S-(7) | 6.0 | 11.5 | 5000 | 43.4 | 112.9 | 0.44 | 0.53 |
| Ex. (II-178) | Com. 1-3-2-S-(8) | 6.1 | 11.9 | 5000 | 42.1 | 110.8 | 0.44 | 0.53 |
| Ex. (II-179) | Com. 1-3-2-S-(9) | 6.1 | 12.1 | 5000 | 41.3 | 113.7 | 0.44 | 0.53 |
| Ex. (II-180) | Com. 1-3-2-S-(14) | 6.2 | 12.1 | 5000 | 41.5 | 118.9 | 0.44 | 0.52 |
| Ex. (II-181) | Com. 1-3-2-S-(15) | 6.2 | 12.9 | 5000 | 38.6 | 107.5 | 0.44 | 0.53 |
| Ex. (II-182) | Com. 1-3-2-S-(17) | 6.0 | 12.4 | 5000 | 40.5 | 117.7 | 0.44 | 0.52 |
| Ex. (II-183) | Com. 1-3-2-S-(18) | 6.0 | 11.5 | 5000 | 43.5 | 125.2 | 0.44 | 0.53 |
| Ex. (II-184) | Com. 1-3-2-S-(19) | 5.9 | 11.5 | 5000 | 43.6 | 118.8 | 0.44 | 0.52 |
| Ex. (II-185) | Com. 1-3-2-S-(22) | 6.2 | 12.2 | 5000 | 40.9 | 110.5 | 0.44 | 0.52 |
| Ex. (II-186) | Com. 1-4-1-O-(1) | 6.0 | 10.9 | 5000 | 45.9 | 135.3 | 0.44 | 0.53 |
| Ex. (II-187) | Com. 1-4-1-O-(2) | 5.9 | 11.0 | 5000 | 45.3 | 133.0 | 0.44 | 0.52 |
| Ex. (II-188) | Com. 1-4-1-O-(4) | 6.0 | 11.2 | 5000 | 44.8 | 115.7 | 0.44 | 0.53 |
| Ex. (II-189) | Com. 1-4-1-O-(5) | 6.1 | 11.6 | 5000 | 43.3 | 127.5 | 0.44 | 0.52 |
| Ex. (II-190) | Com. 1-4-1-O-(6) | 6.2 | 11.8 | 5000 | 42.4 | 127.9 | 0.44 | 0.53 |
| Ex. (II-191) | Com. 1-4-1-O-(7) | 6.0 | 11.4 | 5000 | 43.7 | 124.3 | 0.44 | 0.52 |
| Ex. (II-192) | Com. 1-4-1-O-(8) | 6.2 | 11.8 | 5000 | 42.5 | 123.6 | 0.44 | 0.52 |
| Ex. (II-193) | Com. 1-4-1-O-(9) | 6.0 | 12.2 | 5000 | 41.1 | 118.1 | 0.44 | 0.53 |
| Ex. (II-194) | Com. 1-4-1-O-(12) | 6.0 | 12.1 | 5000 | 41.5 | 120.1 | 0.44 | 0.53 |
| Ex. (II-195) | Com. 1-4-1-O-(17) | 6.2 | 11.7 | 5000 | 42.8 | 123.4 | 0.44 | 0.52 |
| Ex. (II-196) | Com. 1-4-1-O-(18) | 6.1 | 11.7 | 5000 | 42.9 | 113.1 | 0.44 | 0.52 |
| Ex. (II-197) | Com. 1-4-1-O-(19) | 5.9 | 11.2 | 5000 | 44.8 | 116.9 | 0.44 | 0.52 |
| Ex. (II-198) | Com. 1-4-1-O-(20) | 6.1 | 13.1 | 5000 | 38.1 | 108.2 | 0.44 | 0.53 |
| Ex. (II-199) | Com. 1-4-1-O-(22) | 6.1 | 11.9 | 5000 | 42.1 | 122.8 | 0.44 | 0.53 |
| Ex. (II-200) | Com. 1-4-1-S-(1) | 5.8 | 10.1 | 5000 | 49.3 | 143.3 | 0.44 | 0.52 |
| Ex. (II-201) | Com. 1-4-1-S-(2) | 6.0 | 10.1 | 5000 | 49.6 | 140.2 | 0.44 | 0.52 |
| Ex. (II-202) | Com. 1-4-1-S-(3) | 5.9 | 11.9 | 5000 | 41.8 | 119.6 | 0.44 | 0.53 |
| Ex. (II-203) | Com. 1-4-1-S-(4) | 5.8 | 11.0 | 5000 | 45.5 | 125.0 | 0.44 | 0.52 |
| Ex. (II-204) | Com. 1-4-1-S-(5) | 6.0 | 10.8 | 5000 | 46.4 | 121.3 | 0.44 | 0.53 |
| Ex. (II-205) | Com. 1-4-1-S-(6) | 6.0 | 11.4 | 5000 | 43.9 | 130.6 | 0.44 | 0.52 |
| Ex. (II-206) | Com. 1-4-1-S-(7) | 5.9 | 10.7 | 5000 | 46.7 | 137.1 | 0.44 | 0.52 |
| Ex. (II-207) | Com. 1-4-1-S-(8) | 5.9 | 11.1 | 5000 | 45.0 | 121.5 | 0.44 | 0.52 |
| Ex. (II-208) | Com. 1-4-1-S-(10) | 5.9 | 11.4 | 5000 | 43.8 | 132.9 | 0.44 | 0.52 |
| Ex. (II-209) | Com. 1-4-1-S-(11) | 6.1 | 11.6 | 5000 | 43.2 | 121.4 | 0.44 | 0.52 |

TABLE 5-continued

| Compound | Voltage (V) | Current Density (mA/cm²) | Brightness (cd/m²) | Efficiency (cd/A) | Lifetime T(95) | CIE x | CIE y |
|---|---|---|---|---|---|---|---|
| Ex. (II-210) Com. 1-4-1-S-(13) | 5.8 | 11.3 | 5000 | 44.1 | 129.4 | 0.44 | 0.53 |
| Ex. (II-211) Com. 1-4-1-S-(15) | 5.8 | 12.3 | 5000 | 40.7 | 120.2 | 0.44 | 0.52 |
| Ex. (II-212) Com. 1-4-1-S-(18) | 5.8 | 10.8 | 5000 | 46.1 | 123.5 | 0.44 | 0.53 |
| Ex. (II-213) Com. 1-4-1-S-(19) | 5.8 | 11.0 | 5000 | 45.4 | 122.9 | 0.44 | 0.52 |
| Ex. (II-214) Com. 1-4-1-S-(23) | 6.0 | 11.7 | 5000 | 42.8 | 124.3 | 0.44 | 0.52 |
| Ex. (II-215) Com. 1-4-2-O-(1) | 6.1 | 11.1 | 5000 | 45.2 | 131.1 | 0.44 | 0.53 |
| Ex. (II-216) Com. 1-4-2-O-(2) | 6.0 | 11.0 | 5000 | 45.7 | 134.2 | 0.44 | 0.53 |
| Ex. (II-217) Com. 1-4-2-O-(3) | 6.2 | 12.6 | 5000 | 39.7 | 110.2 | 0.44 | 0.52 |
| Ex. (II-218) Com. 1-4-2-O-(4) | 6.0 | 11.6 | 5000 | 42.9 | 116.3 | 0.44 | 0.53 |
| Ex. (II-219) Com. 1-4-2-O-(5) | 6.1 | 11.5 | 5000 | 43.3 | 118.0 | 0.44 | 0.52 |
| Ex. (II-220) Com. 1-4-2-O-(6) | 6.1 | 12.0 | 5000 | 41.6 | 120.2 | 0.44 | 0.53 |
| Ex. (II-221) Com. 1-4-2-O-(7) | 6.1 | 11.7 | 5000 | 42.9 | 124.5 | 0.44 | 0.52 |
| Ex. (II-222) Com. 1-4-2-O-(8) | 6.2 | 12.1 | 5000 | 41.2 | 123.7 | 0.44 | 0.53 |
| Ex. (II-223) Com. 1-4-2-O-(10) | 6.1 | 11.9 | 5000 | 42.1 | 124.2 | 0.44 | 0.52 |
| Ex. (II-224) Com. 1-4-2-O-(13) | 6.0 | 12.1 | 5000 | 41.4 | 112.6 | 0.44 | 0.53 |
| Ex. (II-225) Com. 1-4-2-O-(15) | 6.1 | 13.1 | 5000 | 38.2 | 110.5 | 0.44 | 0.52 |
| Ex. (II-226) Com. 1-4-2-O-(16) | 6.1 | 12.0 | 5000 | 41.6 | 113.7 | 0.44 | 0.53 |
| Ex. (II-227) Com. 1-4-2-O-(18) | 6.0 | 11.4 | 5000 | 43.7 | 128.8 | 0.44 | 0.52 |
| Ex. (II-228) Com. 1-4-2-O-(19) | 6.0 | 11.6 | 5000 | 43.0 | 115.6 | 0.44 | 0.52 |
| Ex. (II-229) Com. 1-4-2-O-(22) | 6.1 | 12.0 | 5000 | 41.8 | 128.8 | 0.44 | 0.52 |
| Ex. (II-230) Com. 1-4-2-S-(1) | 5.8 | 10.5 | 5000 | 47.8 | 145.6 | 0.44 | 0.53 |
| Ex. (II-231) Com. 1-4-2-S-(2) | 5.8 | 10.1 | 5000 | 49.5 | 139.3 | 0.44 | 0.53 |
| Ex. (II-232) Com. 1-4-2-S-(4) | 5.8 | 10.6 | 5000 | 47.0 | 136.4 | 0.44 | 0.52 |
| Ex. (II-233) Com. 1-4-2-S-(5) | 6.0 | 10.7 | 5000 | 46.5 | 134.8 | 0.44 | 0.52 |
| Ex. (II-234) Com. 1-4-2-S-(6) | 5.9 | 11.6 | 5000 | 43.0 | 127.3 | 0.44 | 0.53 |
| Ex. (II-235) Com. 1-4-2-S-(7) | 5.8 | 10.6 | 5000 | 47.4 | 134.8 | 0.44 | 0.53 |
| Ex. (II-236) Com. 1-4-2-S-(8) | 6.0 | 11.5 | 5000 | 43.4 | 120.3 | 0.44 | 0.53 |
| Ex. (II-237) Com. 1-4-2-S-(9) | 5.9 | 11.2 | 5000 | 44.6 | 136.4 | 0.44 | 0.53 |
| Ex. (II-238) Com. 1-4-2-S-(12) | 5.8 | 11.3 | 5000 | 44.3 | 126.8 | 0.44 | 0.53 |
| Ex. (II-239) Com. 1-4-2-S-(14) | 6.0 | 11.6 | 5000 | 43.2 | 124.5 | 0.44 | 0.53 |
| Ex. (II-240) Com. 1-4-2-S-(18) | 5.9 | 10.9 | 5000 | 46.0 | 122.9 | 0.44 | 0.53 |
| Ex. (II-241) Com. 1-4-2-S-(19) | 5.8 | 10.6 | 5000 | 47.3 | 135.1 | 0.44 | 0.52 |
| Ex. (II-242) Com. 1-4-2-S-(20) | 6.1 | 12.4 | 5000 | 40.2 | 124.0 | 0.44 | 0.53 |
| Ex. (II-243) Com. 1-4-2-S-(22) | 5.9 | 11.2 | 5000 | 44.8 | 133.0 | 0.44 | 0.52 |

As is apparent from data of Tables 4 and 5 above, Comparative Examples 1-9 to I-16 and Comparative Examples II-9 to II-16 using the Comparative Compound 9 to 16 having a dibenzothienyl group or a dibenzofuryl group as the main substituent were found to be high driving voltage, low luminous efficiency and low life span. Comparative Examples I-1 to I-8 and Comparative Examples II-1 to II-8 using the Comparative Compound 1 to 8 having a triazinyl group or a pyridyl group as the main substituent were found to be improved in luminous efficiency, compared to that of Comparative Examples I-9 to I-16 and Comparative Examples II-9 to II-16. However, those didn't show excellent properties as much as having a significant effect on the organic electric element.

Meanwhile, the Test Examples using the intensive compounds having a dibenzothienyl group or a dibenzofuryl group containing two Ns as the main substituent were found to be low driving voltage, significantly high luminous efficiency and high life span, compared to that of Comparative Examples I-1 to I-17 and Comparative Examples II-1 to II-17. This is found to be attributed to the fact that, the core (dibenzothienyl group, dibenzofuryl group) having highly hole characteristics adopted two nitrogen atoms, and thereby formed appropriate structure to accommodate all of the holes and the electrons, and as a result, the holes and the electrons are easy to achieves the charge balance, and thus the light emission is made efficiently in the light emitting layer. This is found to be attributed to the fact that, the low driving voltage reduced the thermal damage, and the high molecular weight of the core elicited the high Tg value, leading to an improvement in life span.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound represented by Formula 1 below:

[Formula 1]

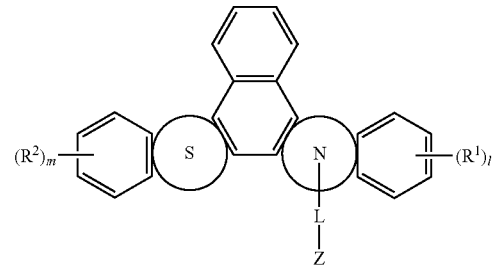

-continued

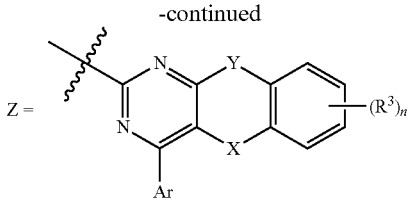

in Formula 1 above,

S ring is a $C_4$-$C_8$ heterocyclic group containing S (sulfer),

N ring is a $C_4$-$C_8$ heterocyclic group containing N (nitrogen), l, m, and n are each an integer from 0 to 4, $R^1$ to $R^3$ are independently selected from the group consisting of halogen, deuterium, a cyano group, a $C_6$-$C_{60}$ aryl group, a $C_2$-$C_{60}$ heterocyclic group containing at least one heteroatom selected from O, N, S, Si, and P, a $C_1$-$C_{30}$ alkoxy group, a $C_1$-$C_{60}$ alkyl group, a $C_2$-$C_{60}$ alkenyl group, and -$L^1$-N(R')(R''), and any two adjacent groups of $R^1$s to $R^3$s are optionally linked together to form a fused ring, L and $L^1$ are independently selected from the group consisting of a single bond, a $C_6$-$C_{60}$ arylene group, and a $C_2$-$C_{60}$ heteroarylene group containing at least one heteroatom selected from O, N, S, Si, and P, wherein the arylene group, and the heteroarylene group are optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{60}$ heterocyclic group containing at least one heteroatom selected from O, N, S, Si, and P, a $C_3$-$C_{20}$ cycloalkyl group, a $C_7$-$C_{20}$ arylalkyl group, and a $C_8$-$C_{20}$ arylalkenyl group, Ar is an unsubstituted $C_6$-$C_{60}$ aryl group, a $C_6$-$C_{60}$ aryl group substituted with deuterium, or a $C_6$-$C_{60}$ aryl group substituted with a C6-C20 aryl group, R' and R'' are independently selected from the group consisting of a $C_6$-$C_{60}$ aryl group, and a $C_2$-$C_{60}$ heterocyclic group containing at least one heteroatom selected from O, N, S, Si, and P, X and Y are independently selected from the group consisting of a single bond, $C(R^4)(R^5)$, $N(R^4)$, O, S, Se, and $Si(R^4)(R^5)$, $R^4$ and $R^5$ are independently selected from the group consisting of hydrogen, deuterium, a $C_6$-$C_{60}$ aryl group, a $C_2$-$C_{60}$ heterocyclic group containing at least one heteroatom selected from O, N, S, Si, and P, a $C_1$-$C_{30}$ alkoxy group, a $C_1$-$C_{60}$ alkyl group, and a $C_2$-$C_{60}$ alkenyl group, when Ar, $R^1$ to $R^5$, R', and R'' are an aryl group, or a heterocyclic group, Ar, $R^1$ to $R^5$, R', and R'' are optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{60}$ heterocyclic group containing at least one heteroatom selected from O, N, S, Si, and P, a $C_3$-$C_{20}$ cycloalkyl group, a $C_7$-$C_{20}$ arylalkyl group, and a $C_8$-$C_{20}$ arylalkenyl group, and when $R^1$ to $R^5$ are an alkyl group, alkenyl group or alkoxy, $R^1$ to $R^5$ are optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{60}$ heterocyclic group containing at least one heteroatom selected from O, N, S, Si, and P, a $C_3$-$C_{20}$ cycloalkyl group, a $C_7$-$C_{20}$ arylalkyl group, and a $C_8$-$C_{20}$ arylalkenyl group.

2. The compound as claimed in claim 1, wherein the compound is represented by one of Formulas below:

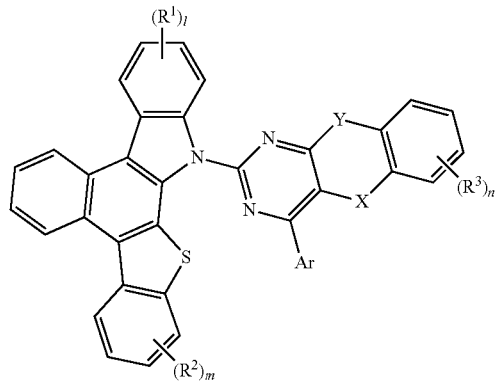

<Formula 1-1>

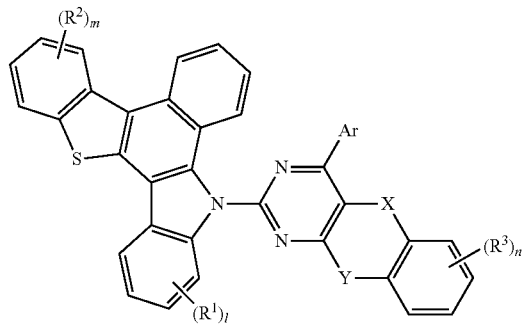

<Formula 1-2>

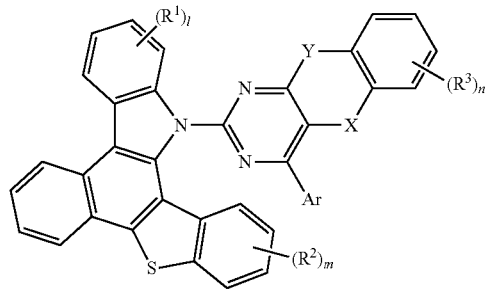

<Formula 1-3>

<Formula 1-4> in Formulas above, Ar, R¹ to R³, l, m, n, X and Y are as defined in Formula 1 of claim 1.

3. The compound as claimed in claim 1, wherein Z is any one of groups below:

Z-1

Z-2

Z-3

Z-4

Z-5

Z-6

Z-7

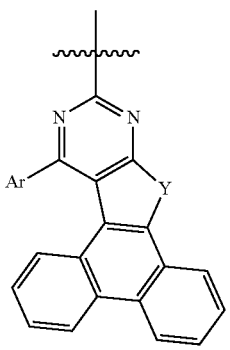
Z-8
in Formulas above, Ar, X and Y are as defined in Formula 1 of claim 1.
4. The compound as claimed in claim 1, wherein the compound is represented by any one of Formulas below:
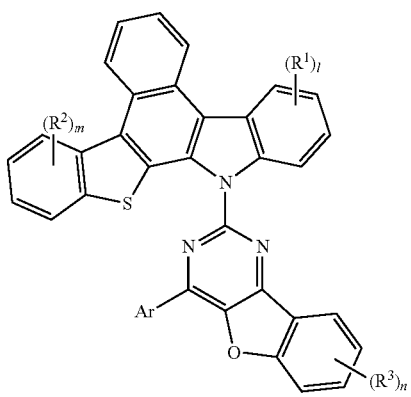
<Formula 1-1-1-O>
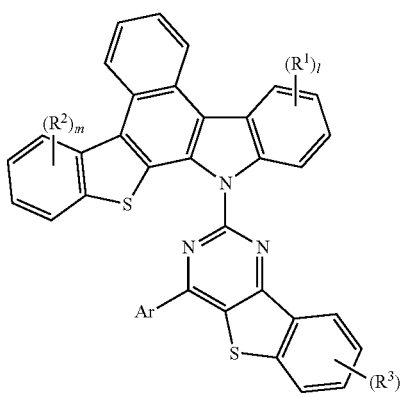
<Formula 1-1-1-S>
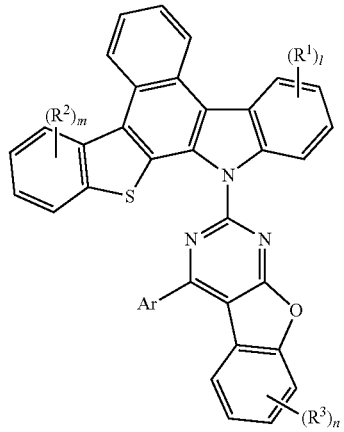
<Formula 1-1-2-O>
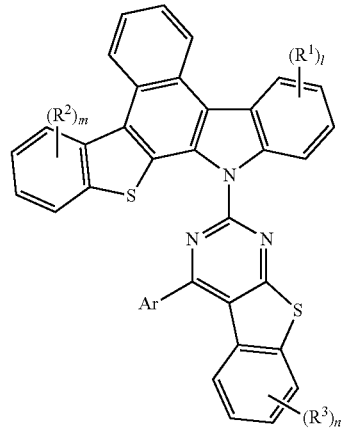
<Formula 1-1-2-S>
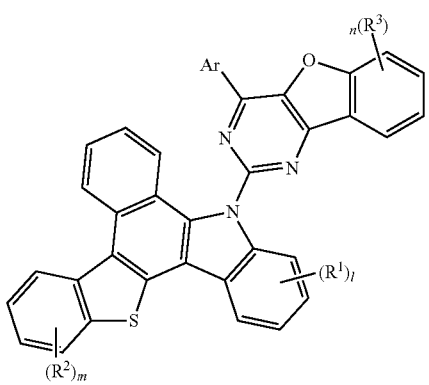
<Formula 1-2-1-O>

<Formula 1-2-1-S>
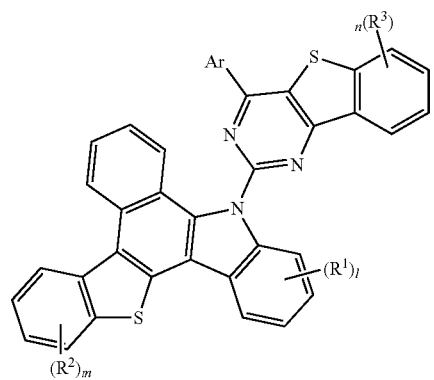
<Formula 1-2-2-O>
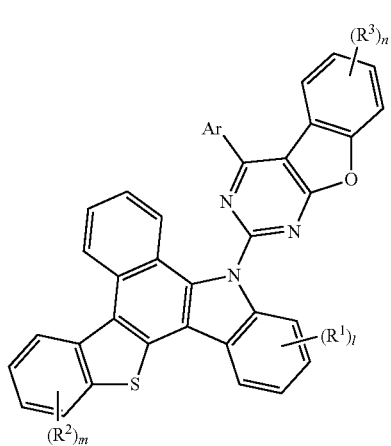
<Formula 1-2-2-S>
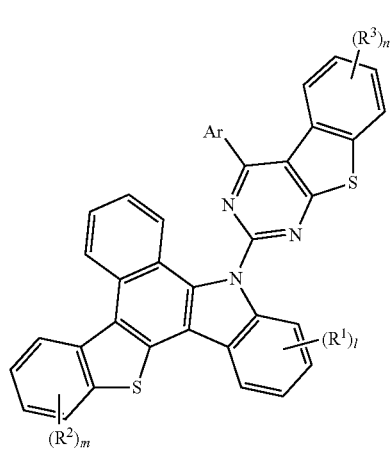
<Formula 1-3-1-O>
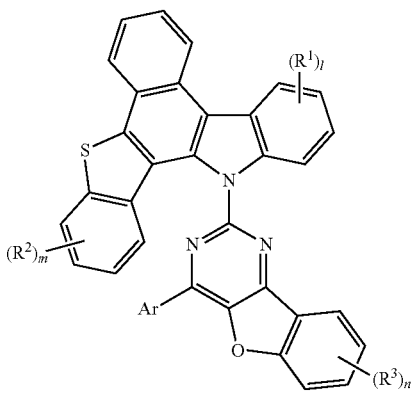
<Formula 1-3-1-S>
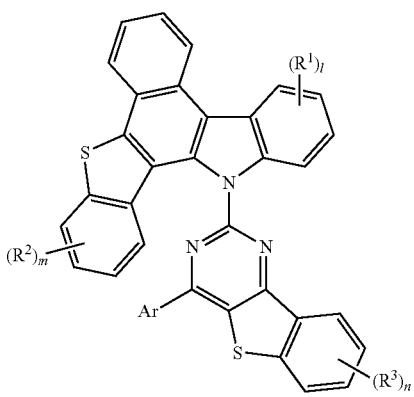
<Formula 1-3-2-O>
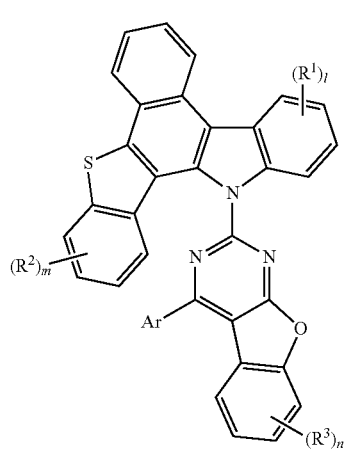

<Formula 1-3-2-S>
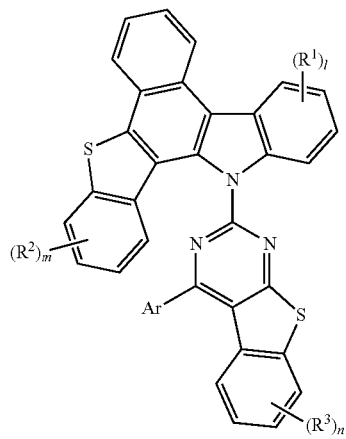
<Formula 1-4-1-O>
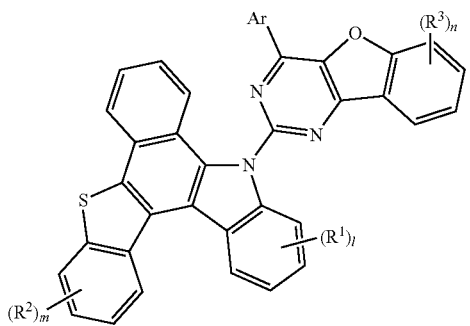
<Formula 1-4-1-S>
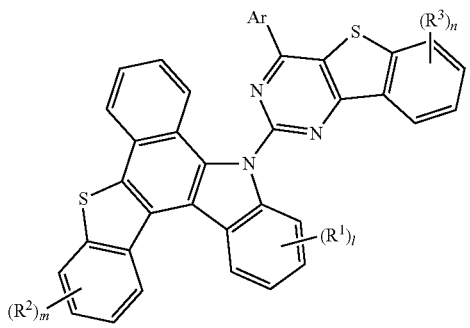
<Formula 1-4-2-O>
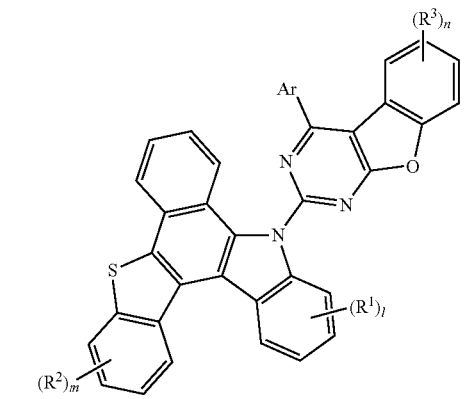
<Formula 1-4-2-S>
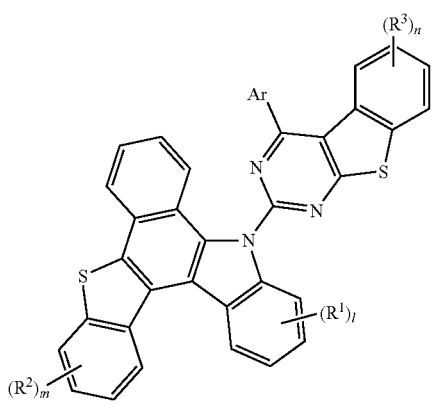
in Formulas above, Ar, $R^1$ to $R^3$, l, m and n are as defined in Formula 1 of claim 1.
5. The compound as claimed in claim 1, wherein Ar is any one of groups below:
Ar-1
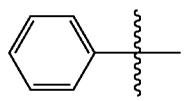
Ar-2
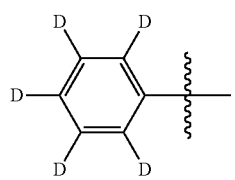
Ar-4
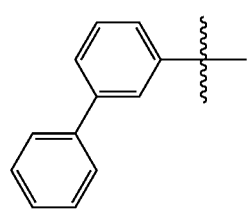
Ar-5
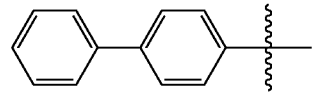
Ar-6
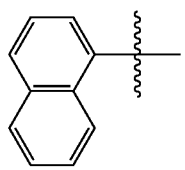
Ar-7
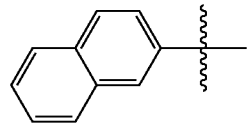

-continued
Ar-8
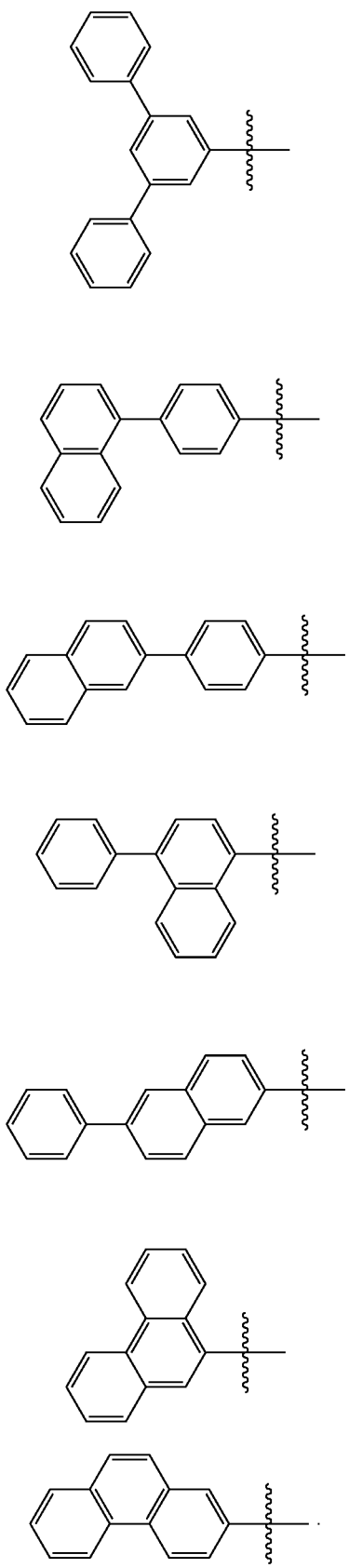
Ar-9
Ar-10
Ar-11
Ar-12
Ar-13
Ar-14
6. The compound as claimed in claim 1, being any one of compounds below:
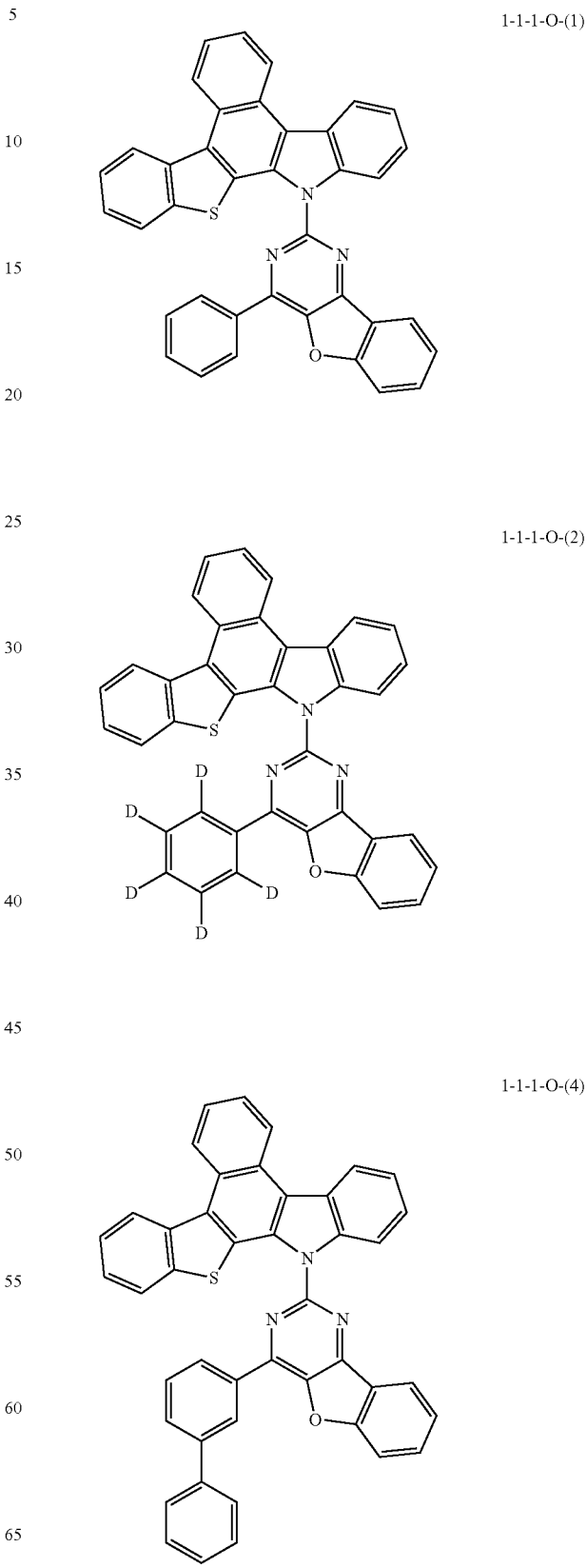
1-1-1-O-(1)
1-1-1-O-(2)
1-1-1-O-(4)

1-1-1-O-(5)
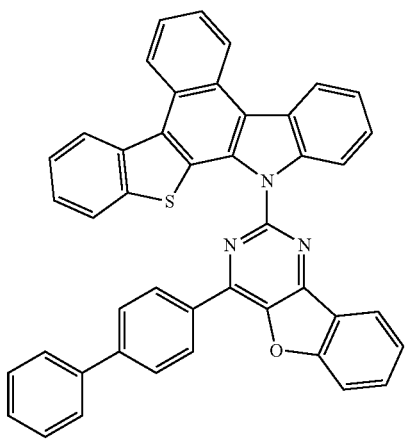
1-1-1-O-(6)
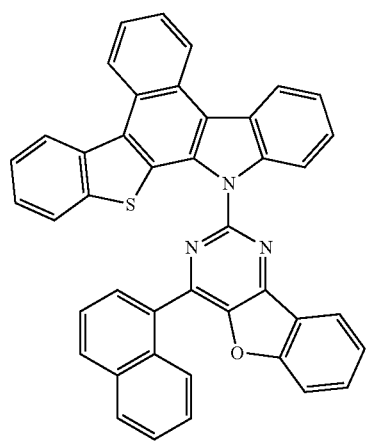
1-1-1-O-(7)
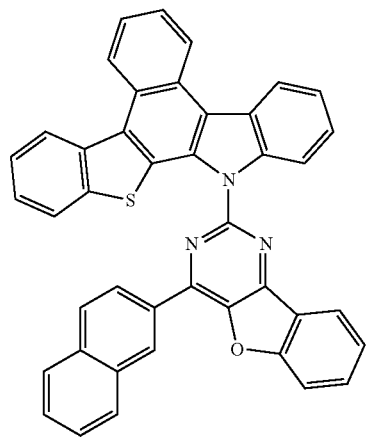
1-1-1-O-(8)
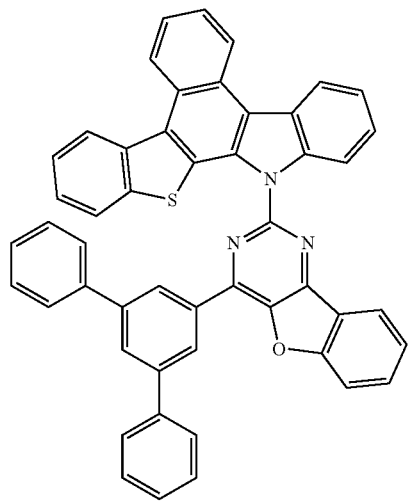
1-1-1-O-(9)
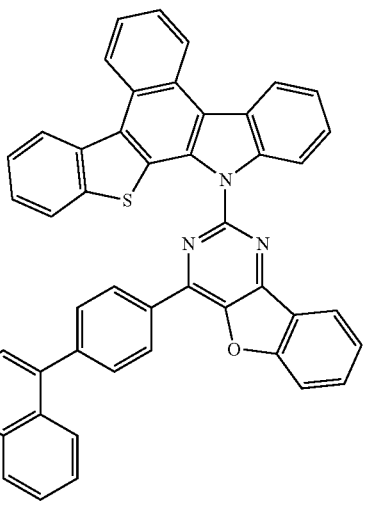
1-1-1-O-(10)
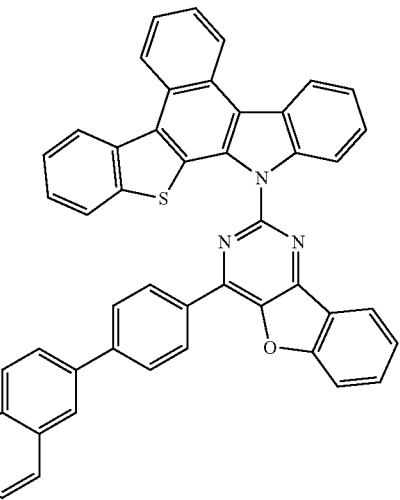

1-1-1-O-(11)
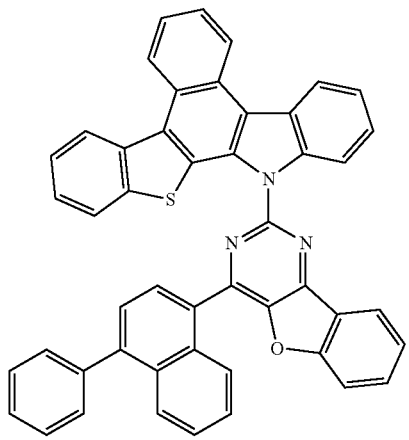
1-1-1-(O)-12
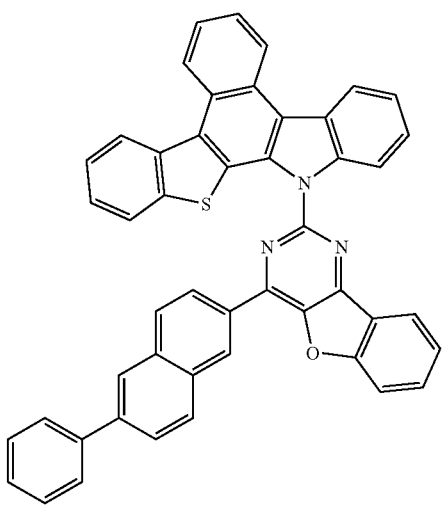
1-1-1-O-(13)
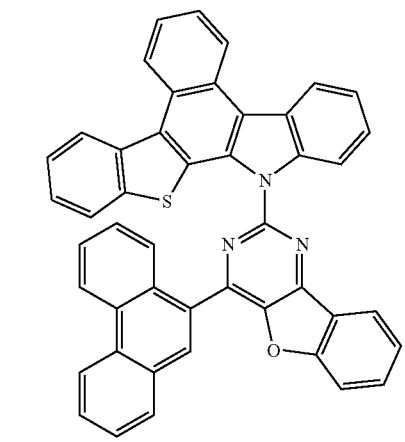
1-1-1-O-(14)
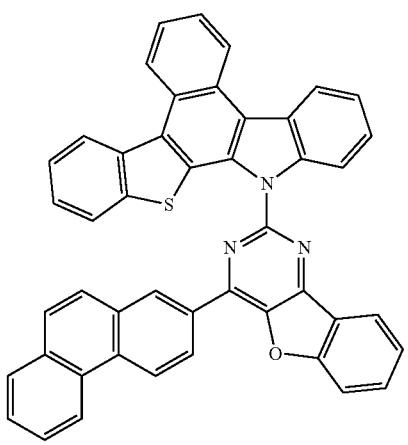
1-1-1-S-(1)
1-1-1-S-(2)
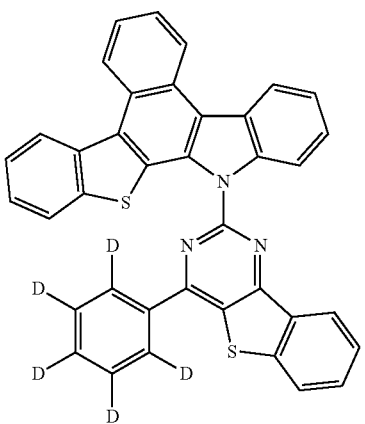

1-1-1-S-(4)
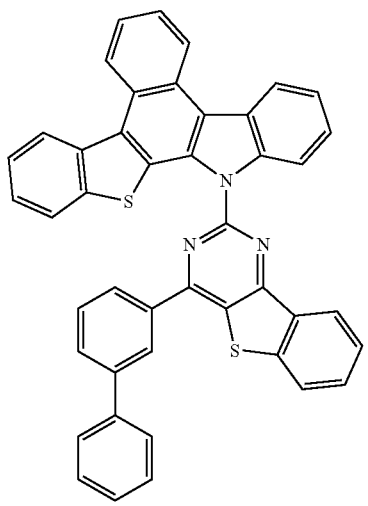
1-1-1-S-(5)
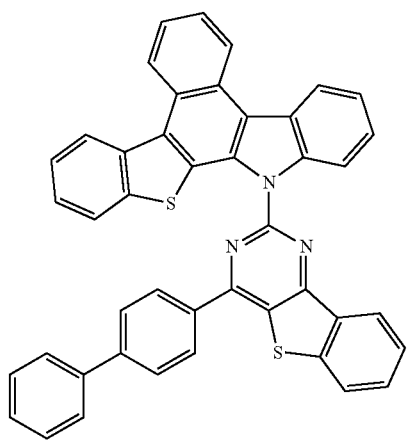
1-1-1-S-(6)
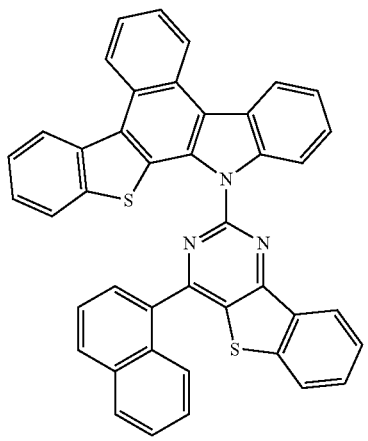
1-1-1-S-(7)
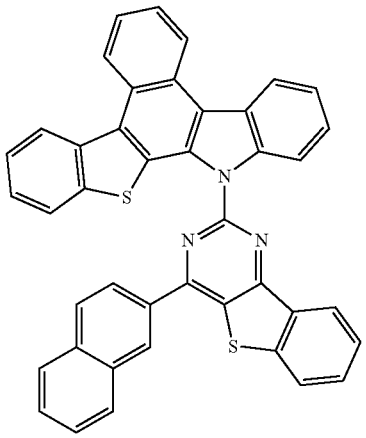
1-1-1-S-(8)
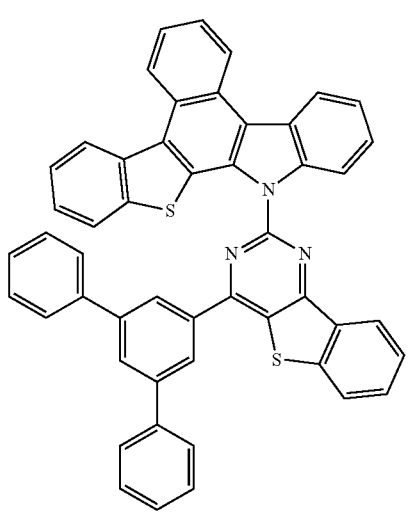
1-1-1-S-(9)
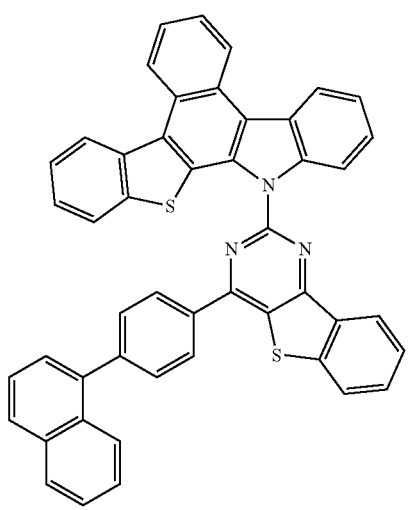

-continued
1-1-1-S-(10)
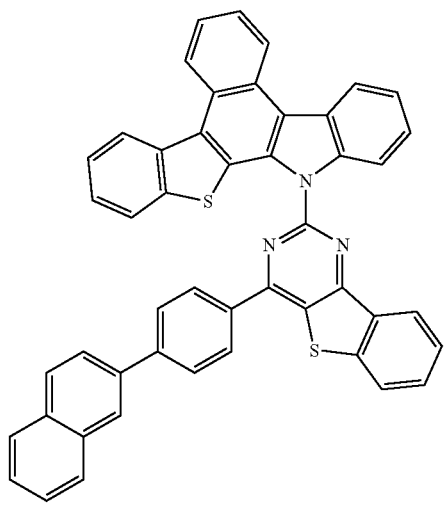
1-1-1-S-(11)
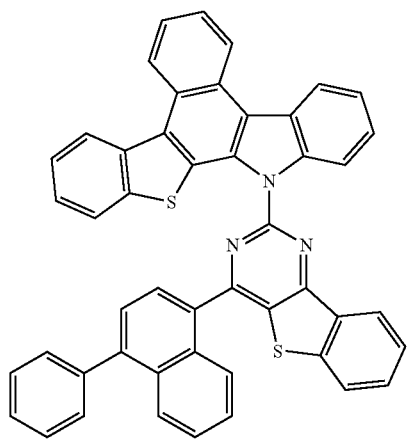
1-1-1-S-(12)
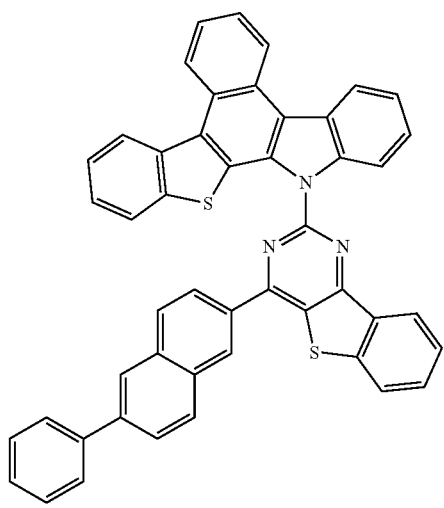
-continued
1-1-1-S-(13)
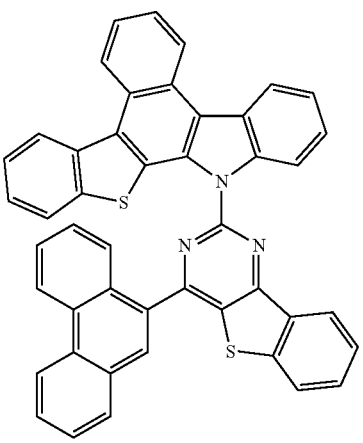
1-1-1-S-(14)
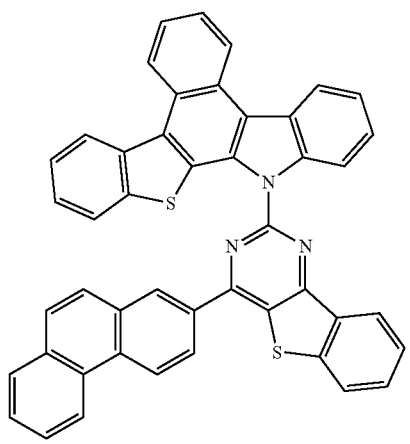
1-1-1-O-(21)
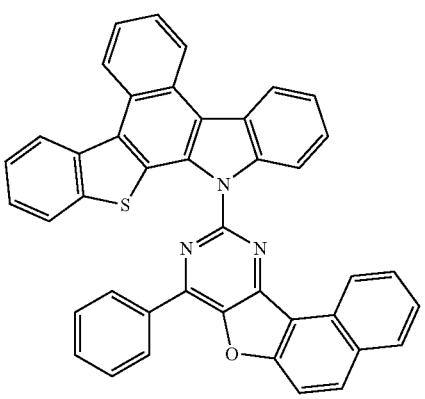

301
-continued
1-1-1-O-(22)
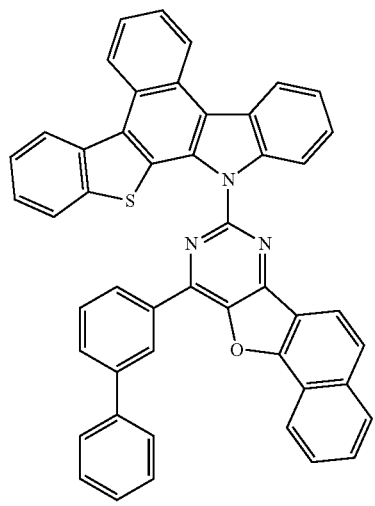
1-1-1-S-(21)
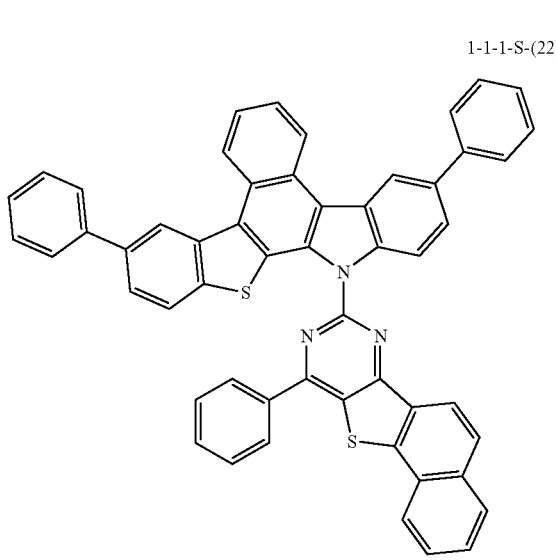
1-1-1-S-(22)
302
-continued
1-1-2-O-(1)
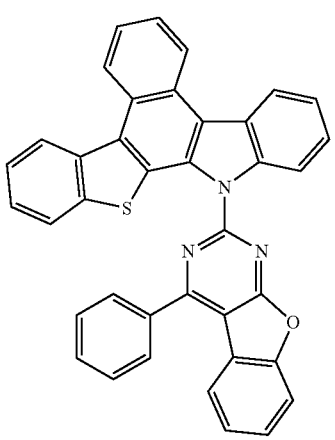
1-1-2-O-(2)
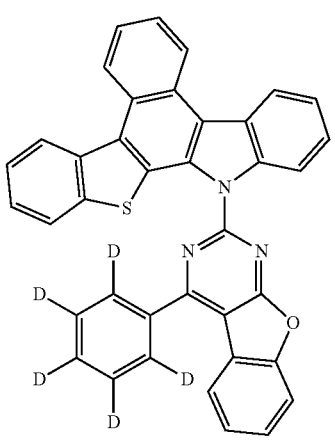
1-1-2-O-(4)
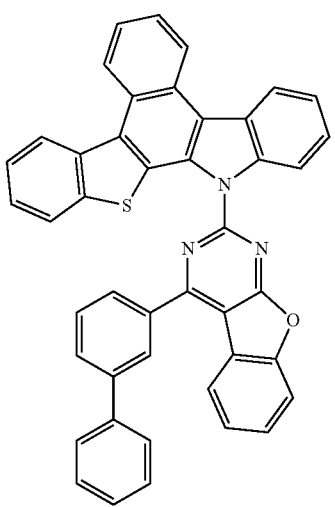

1-1-2-O-(5)
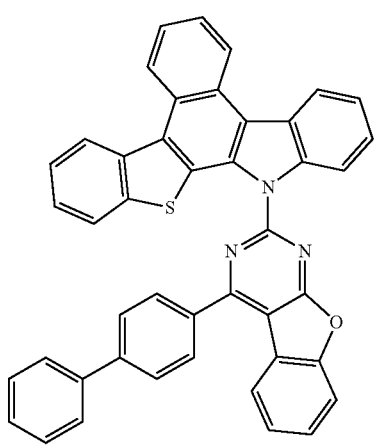
1-1-2-O-(8)
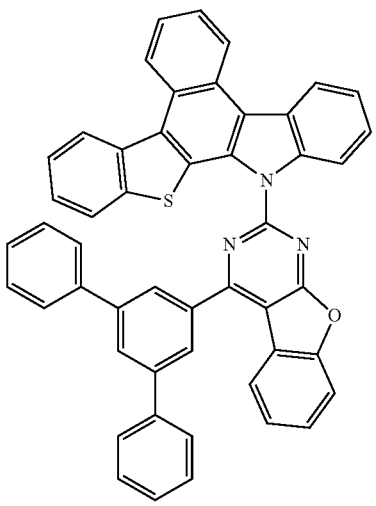
1-1-2-O-(6)
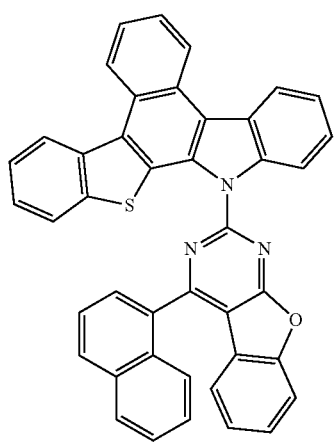
1-1-2-O-(9)
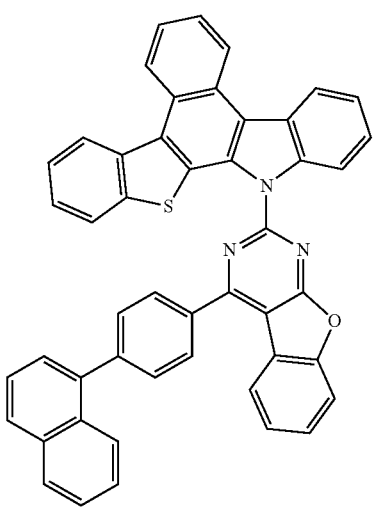
1-1-2-O-(7)
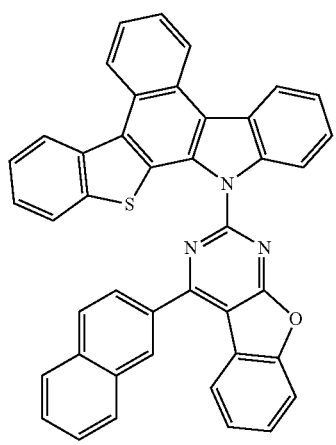
1-1-2-O-(10)
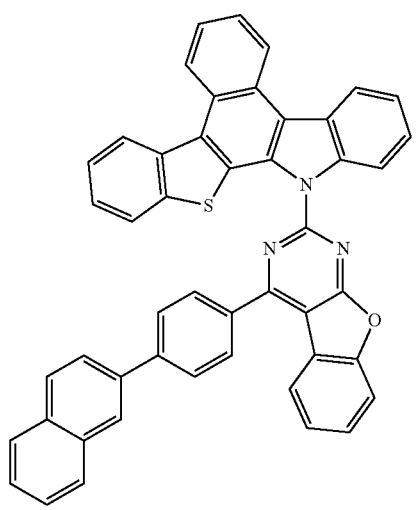

305
-continued
1-1-2-O-(11)
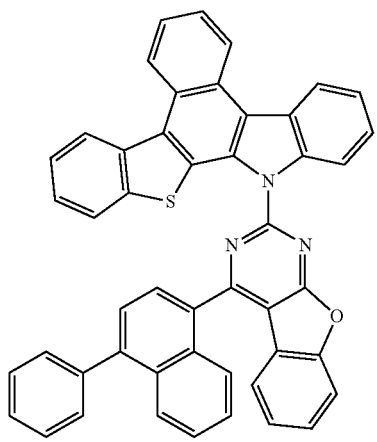
1-1-2-O-(12)
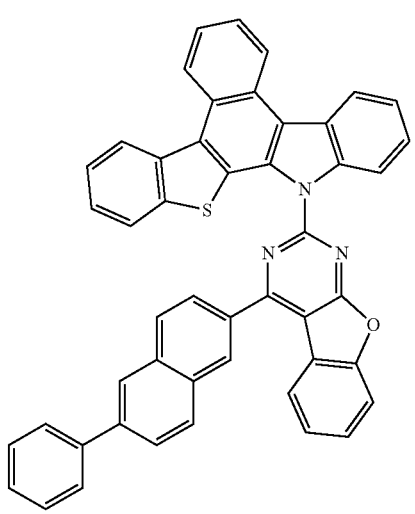
1-1-2-O-(13)
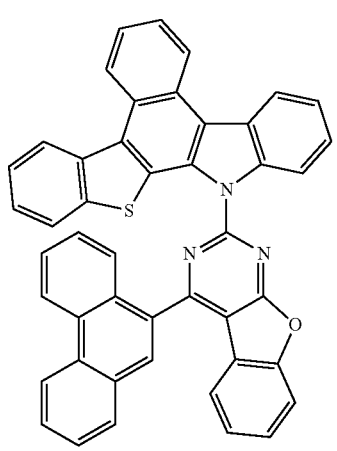
306
-continued
1-1-2-O-(14)
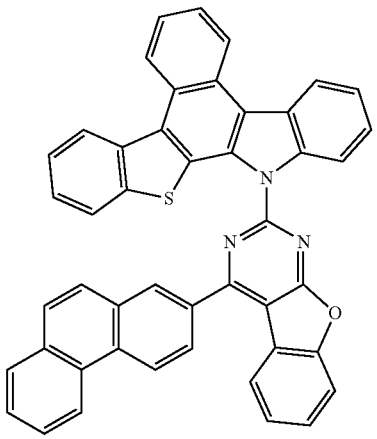
1-1-2-S-(1)
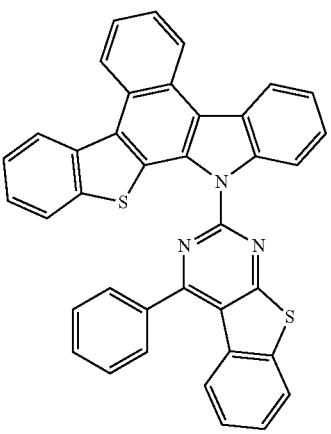
1-1-2-S-(2)
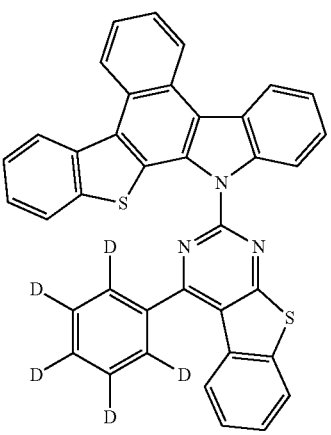

307
-continued
1-1-2-S-(4)
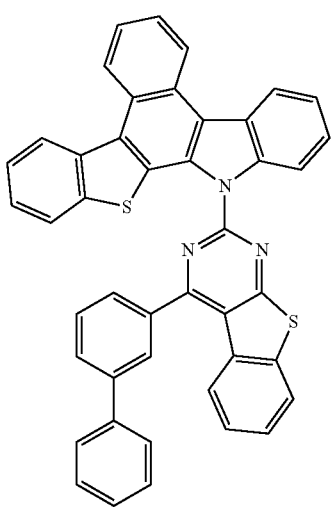
1-1-2-S-(5)
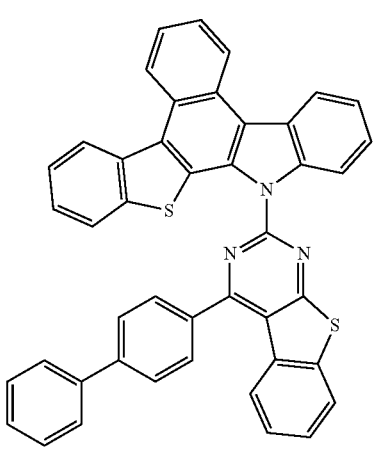
1-1-2-S-(6)
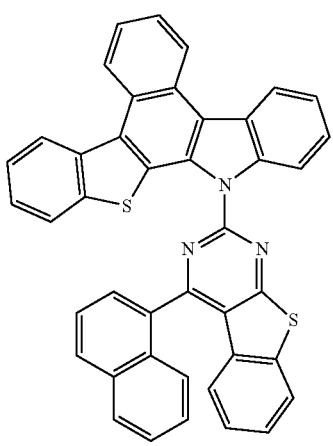
308
-continued
1-1-2-S-(7)
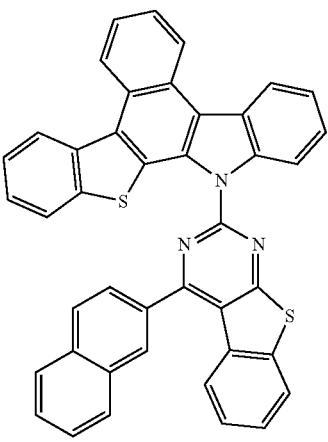
1-1-2-S-(8)
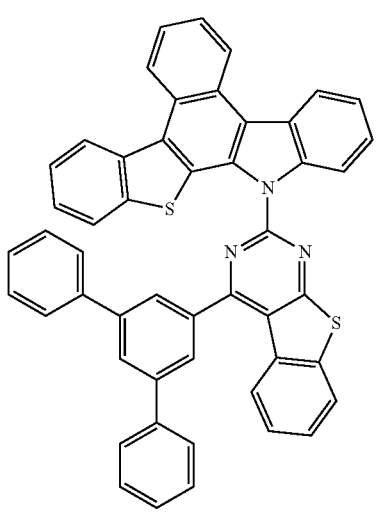
1-1-2-S-(9)
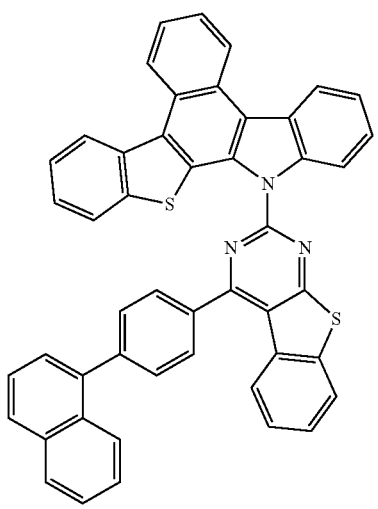

1-1-2-S-(10)
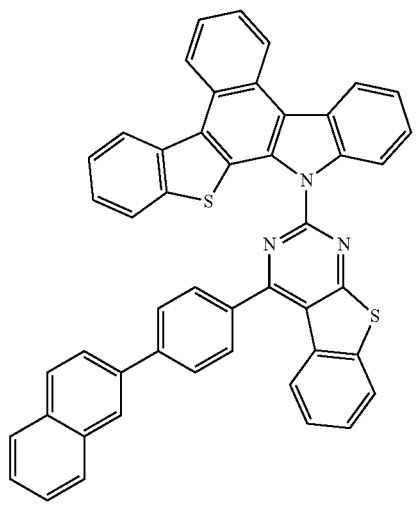
1-1-2-S-(11)
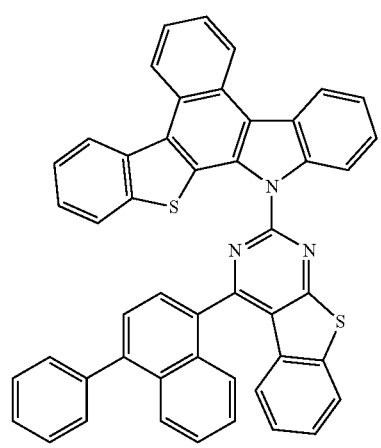
1-1-2-S-(12)
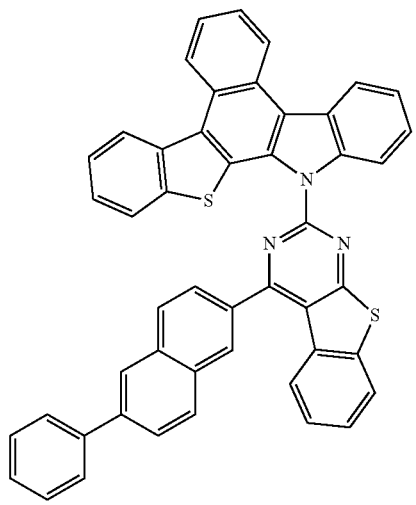
1-1-2-S-(13)
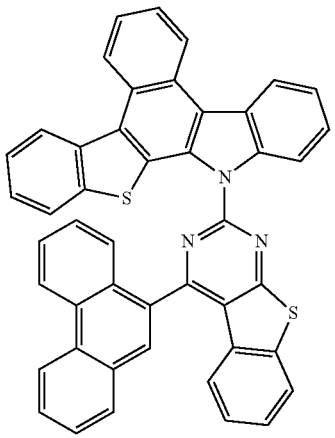
1-1-2-S-(14)
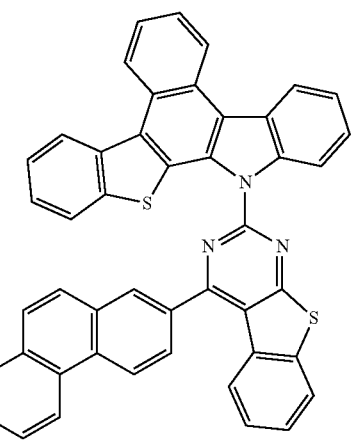
1-1-2-O-(21)

311
-continued
312
-continued
1-1-2-O-(22)
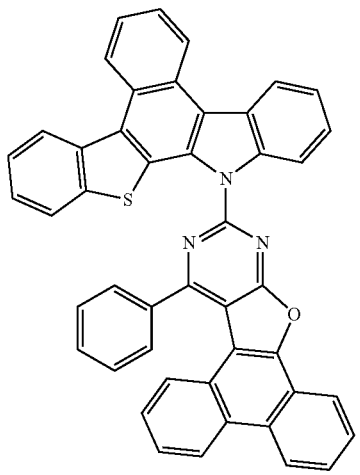
1-1-2-S-(23)
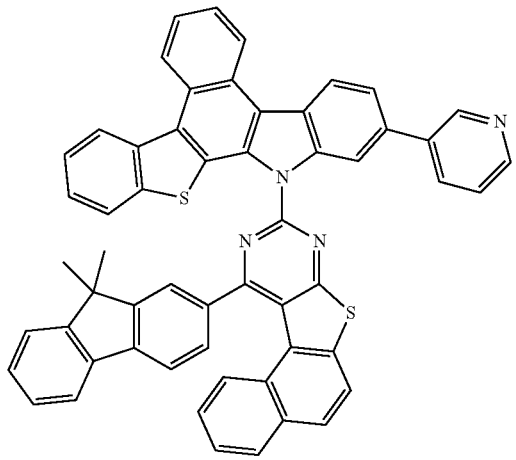
1-1-2-S-(21)
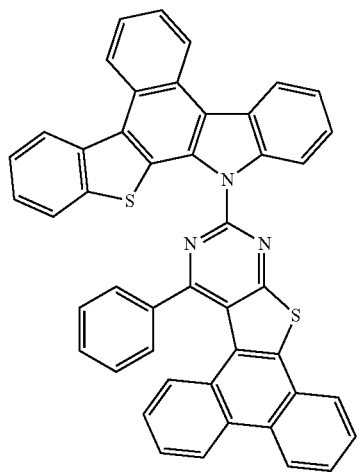
1-2-1-O-(1)
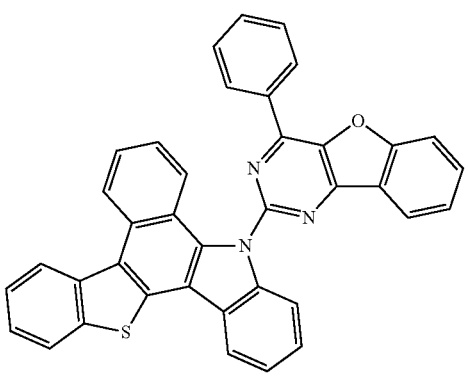
1-1-2-S-(22)
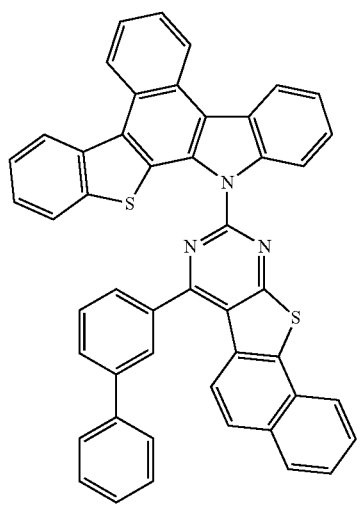
1-2-1-O-(2)
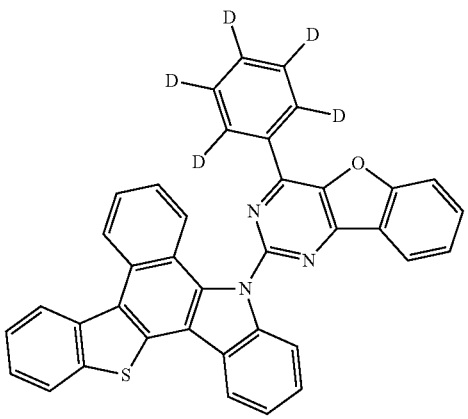

-continued
1-2-1-O-(4)
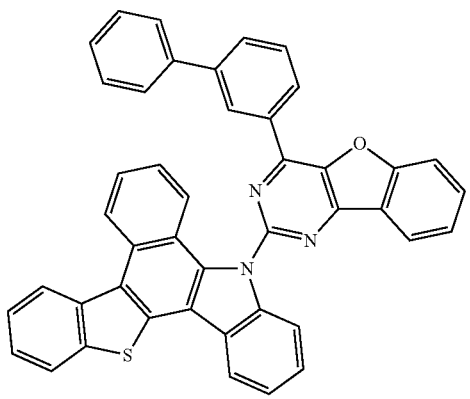
1-2-1-O-(5)
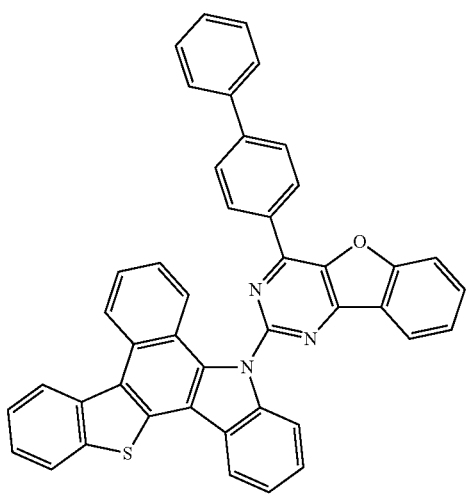
1-2-1-O-(6)
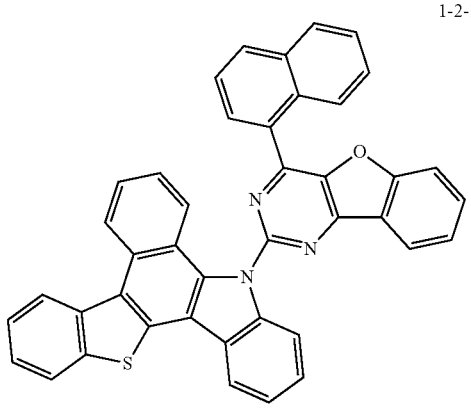
-continued
1-2-1-O-(7)
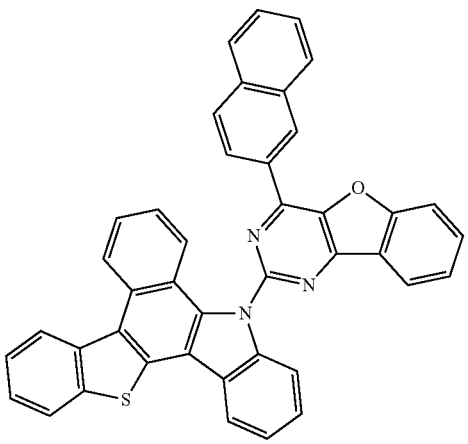
1-2-1-O-(8)
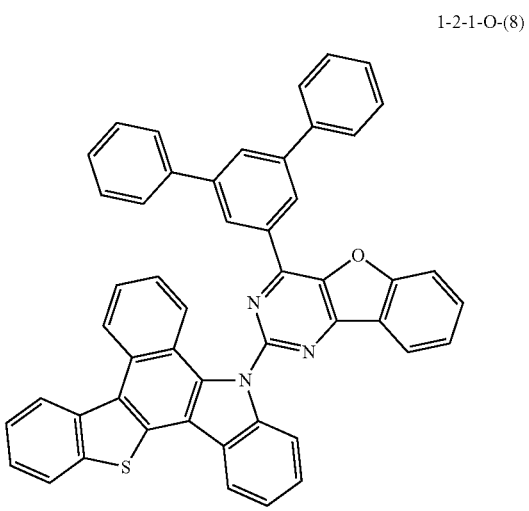
1-2-1-O-(9)
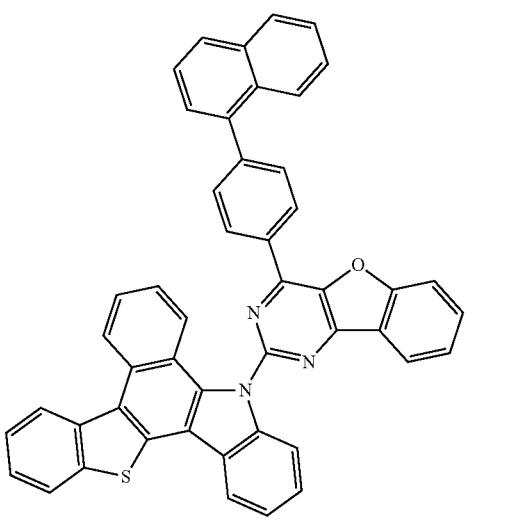

-continued
1-2-1-O-(10)
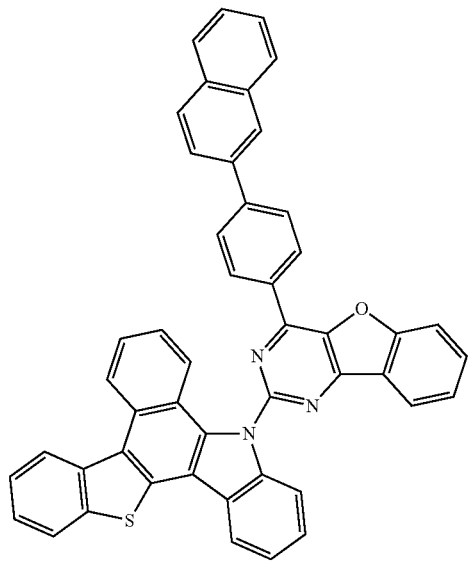
1-2-1-O-(11)
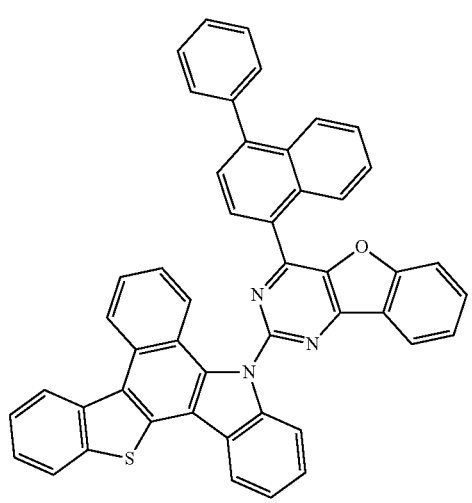
-continued
1-2-1-O-(12)
1-2-1-O-(13)
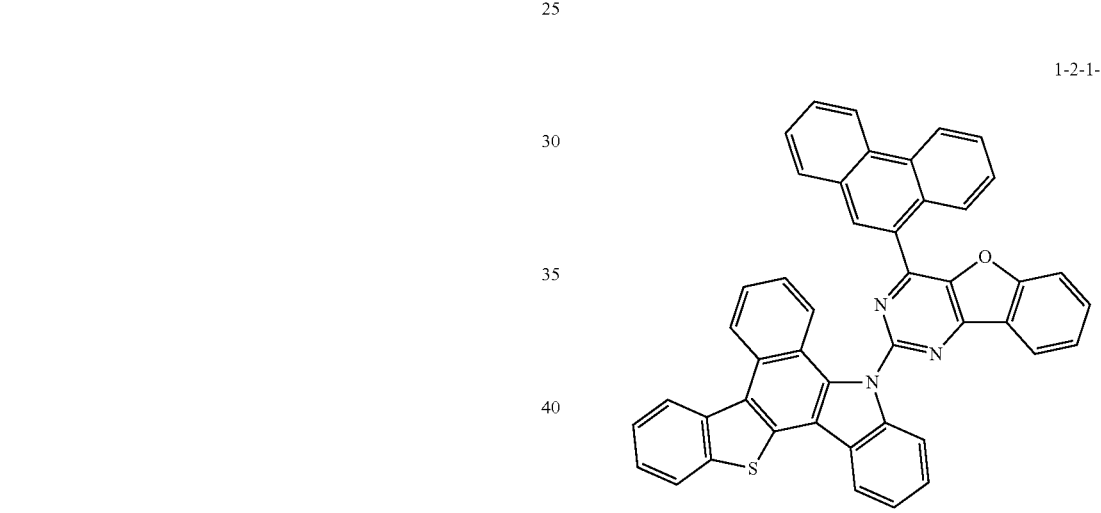
1-2-1-O-(14)
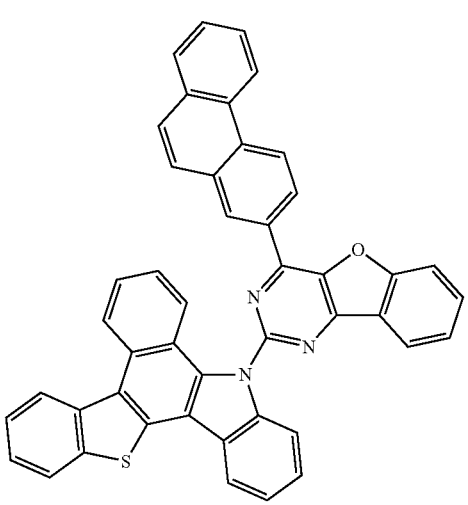

1-2-1-S-(1)
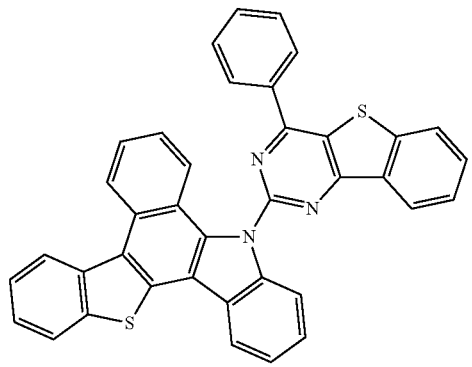
1-2-1-S-(2)
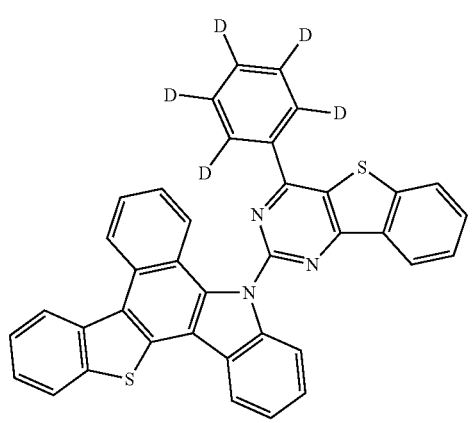
1-2-1-S-(4)
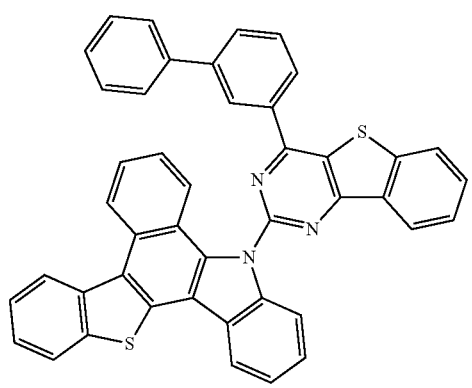
1-2-1-S-(5)
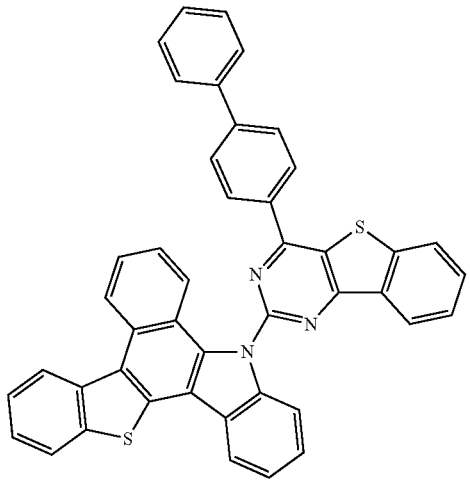
1-2-1-S-(6)
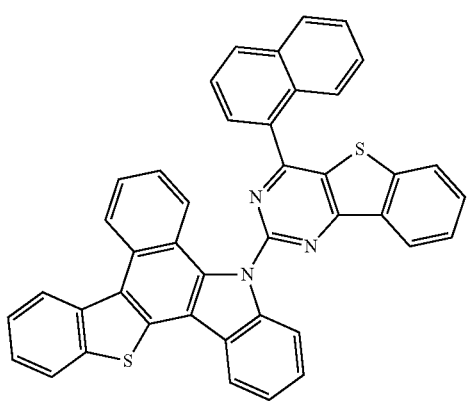
1-2-1-S-(7)
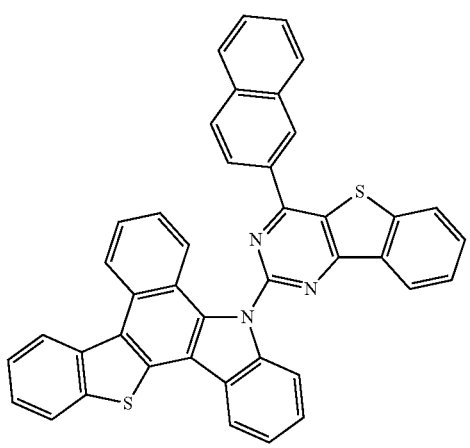

1-2-1-S-(8)
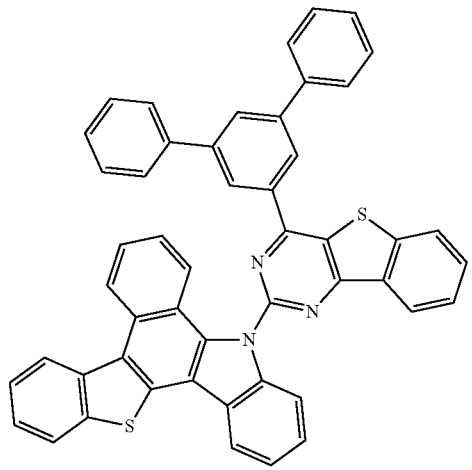
1-2-1-S-(9)
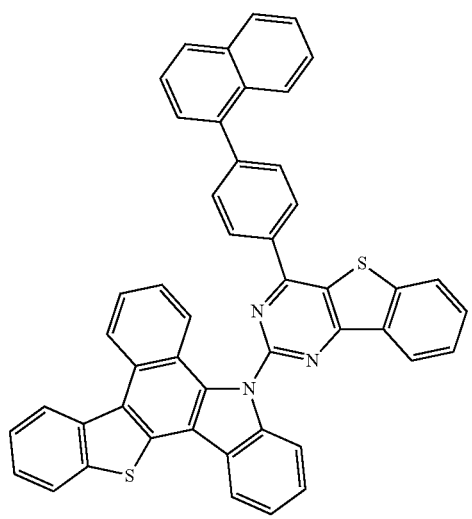
1-2-1-S-(10)
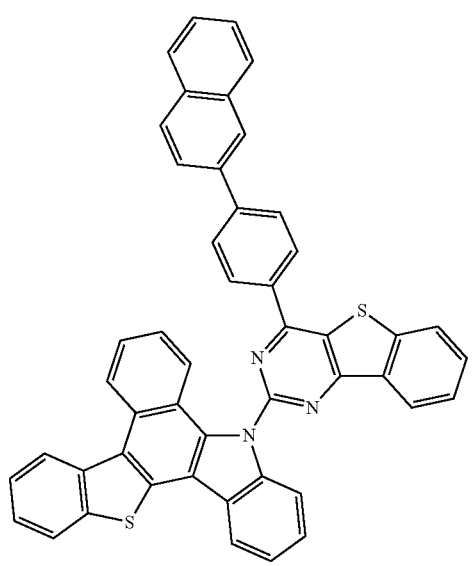
1-2-1-S-(11)
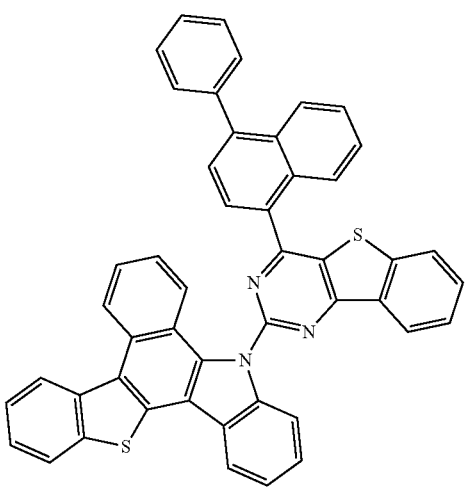
1-2-1-S-(12)
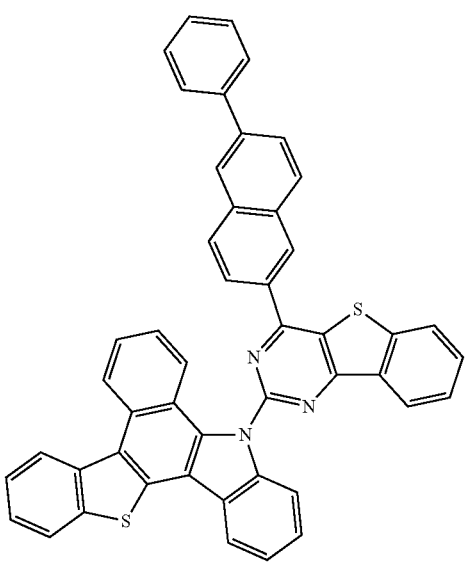
1-2-1-S-(13)
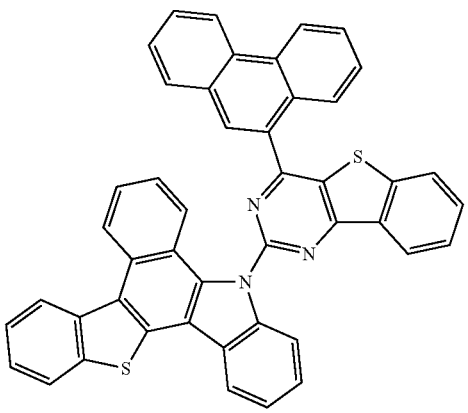

321
-continued
1-2-1-S-(14)
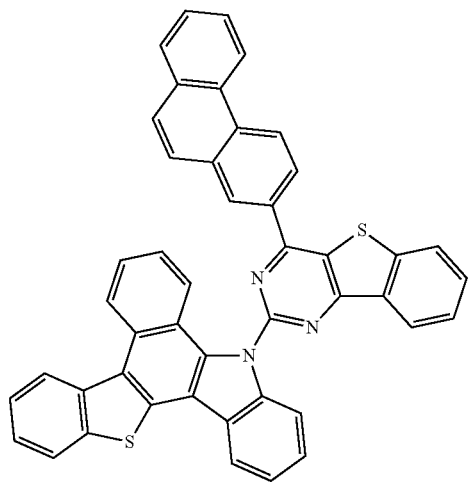
1-2-1-O-(21)
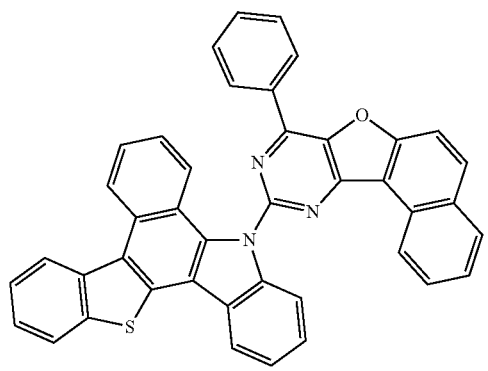
1-2-1-O-(22)
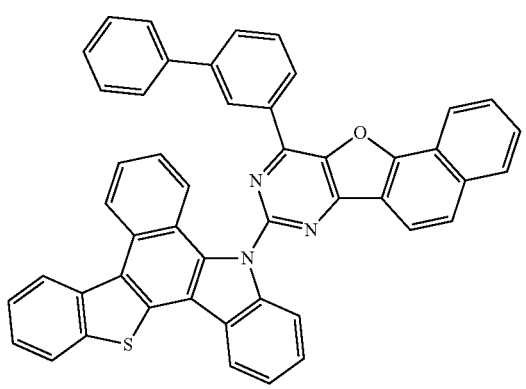
322
-continued
1-2-1-S-(21)
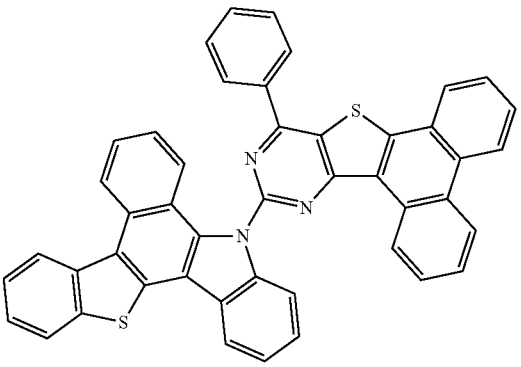
1-2-1-S-(22)
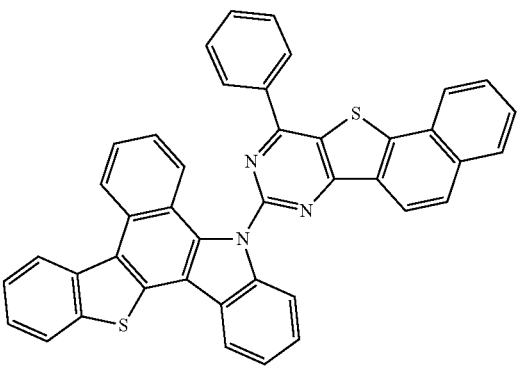
1-2-2-O-(1)
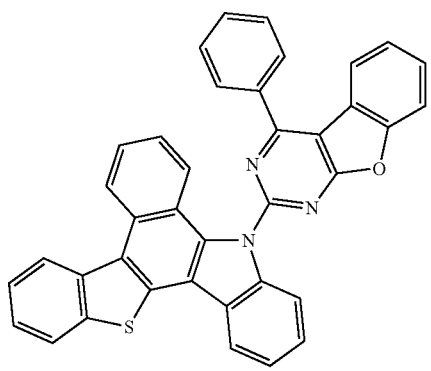
1-2-2-O-(2)
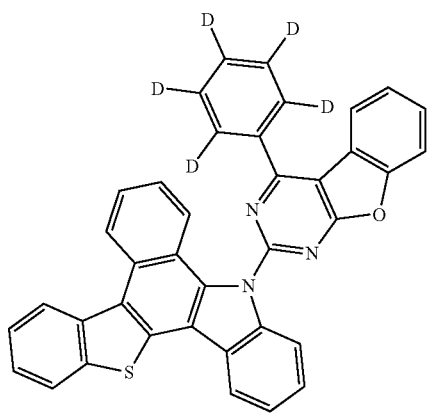

1-2-2-O-(4)
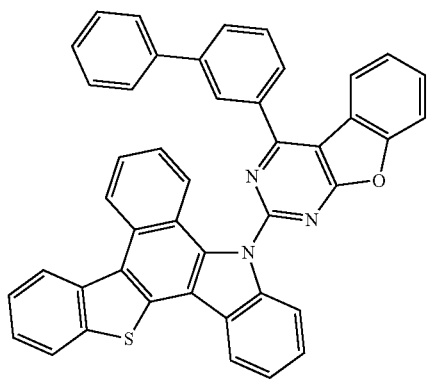
1-2-2-O-(5)
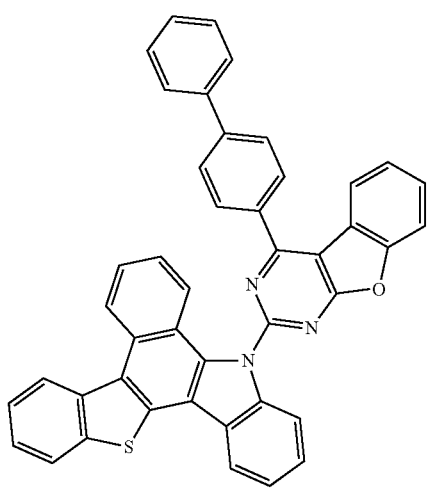
1-2-2-O-(6)
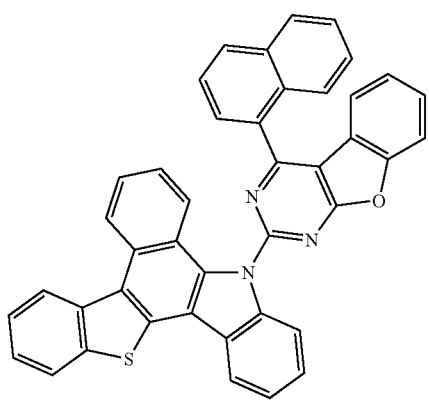
1-2-2-O-(7)
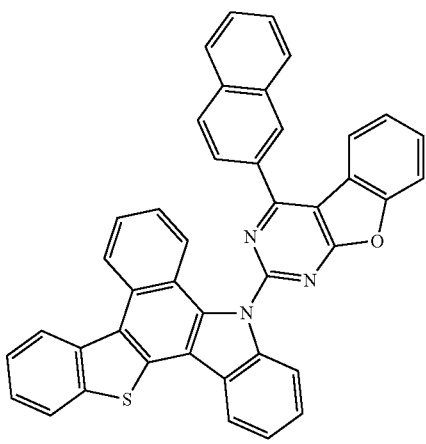
1-2-2-O-(8)
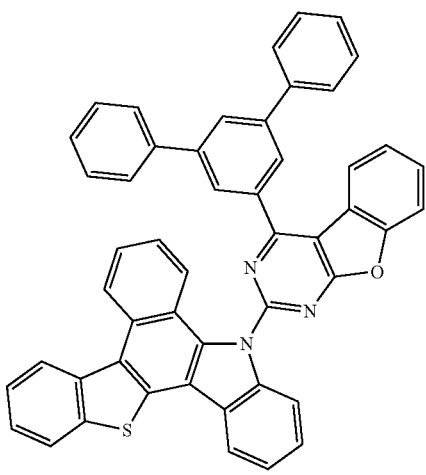
1-2-2-O-(9)
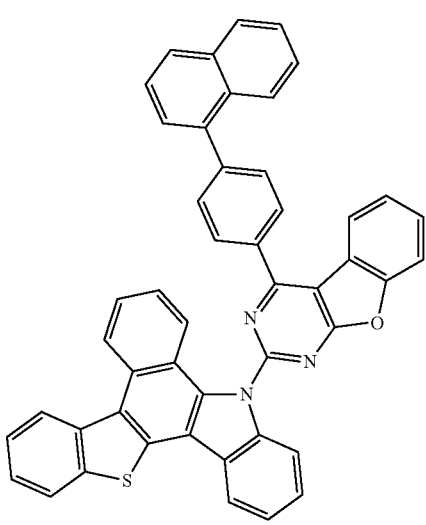

1-2-2-O-(10)
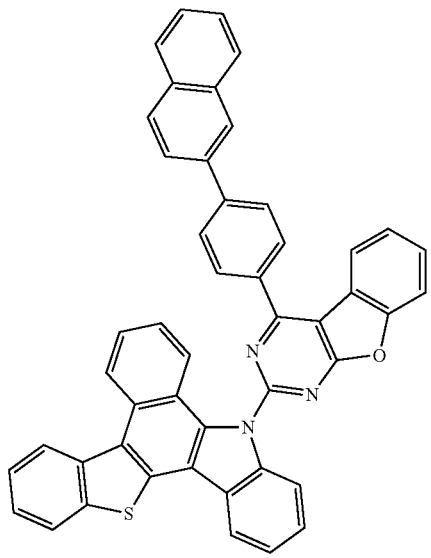
1-2-2-O-(11)
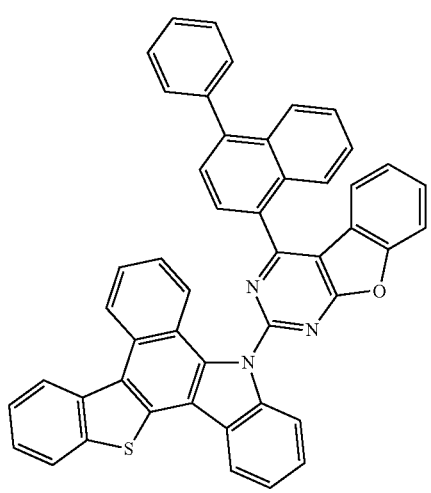
1-2-2-O-(12)
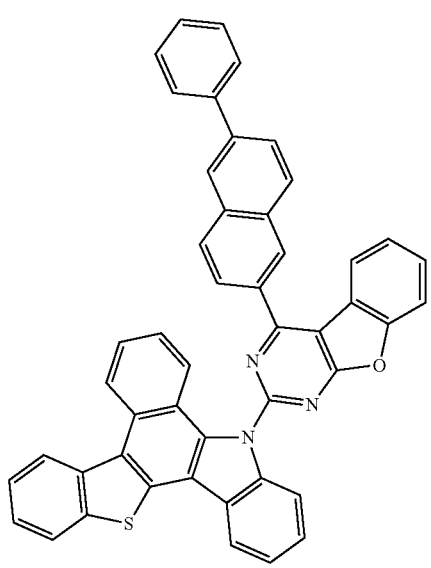
1-2-2-O-(13)
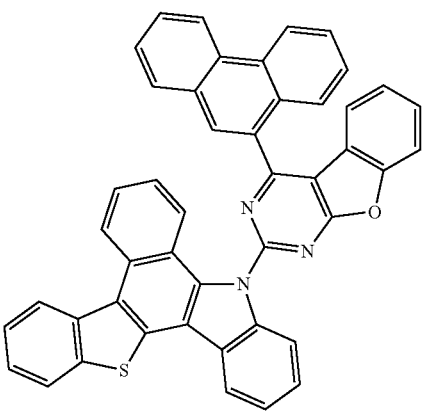
1-2-2-O-(14)
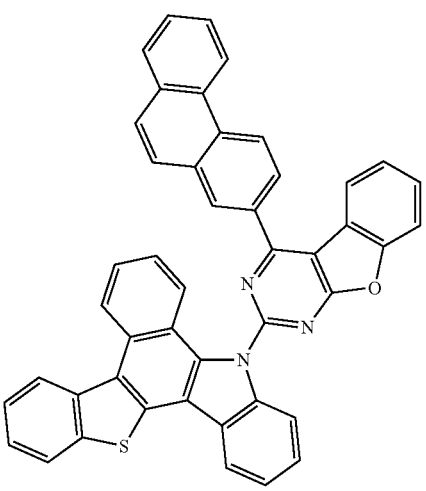
1-2-2-S-(1)
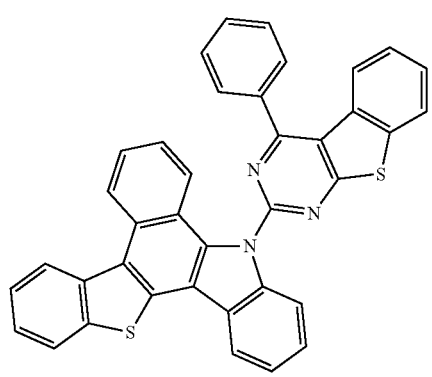

327
-continued
1-2-2-S-(2)
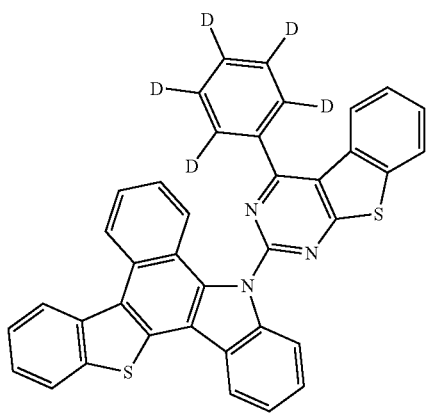
1-2-2-S-(4)
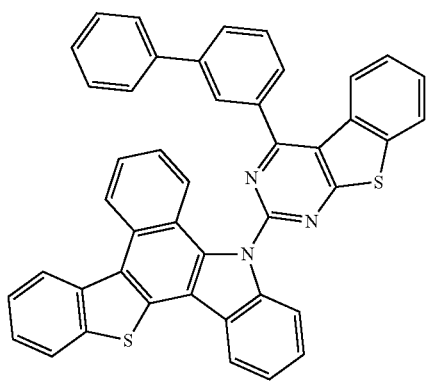
1-2-2-S-(5)
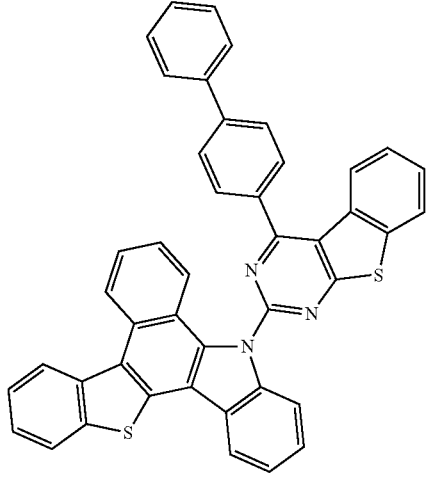
328
-continued
1-2-2-S-(6)
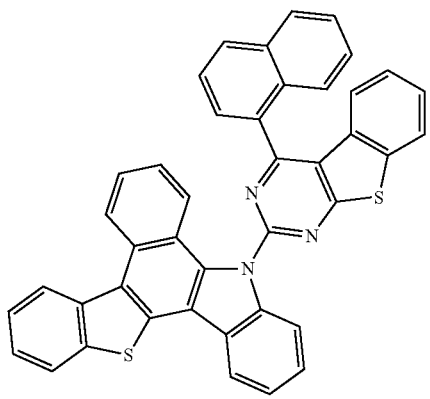
1-2-2-S-(7)
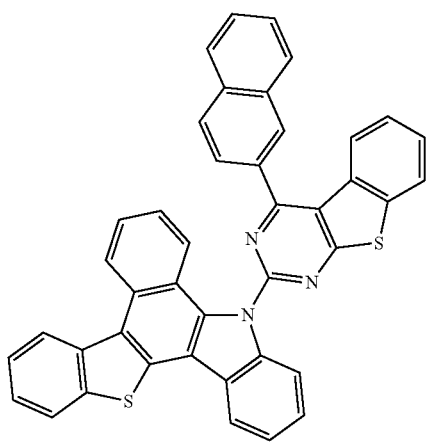
1-2-2-S-(8)
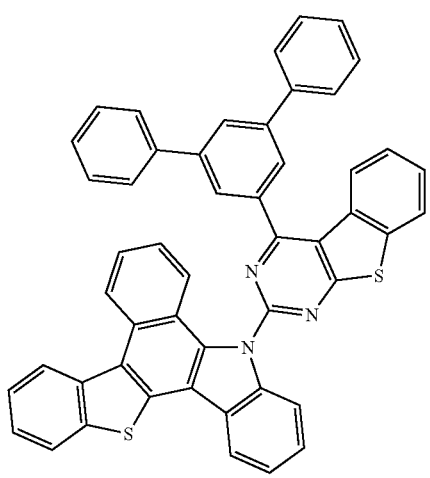

-continued
1-2-2-S-(9)
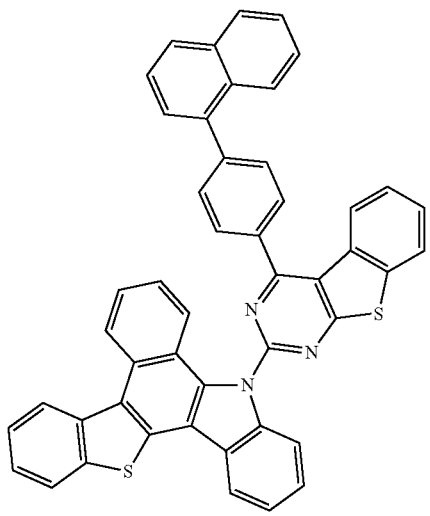
1-2-2-S-(10)
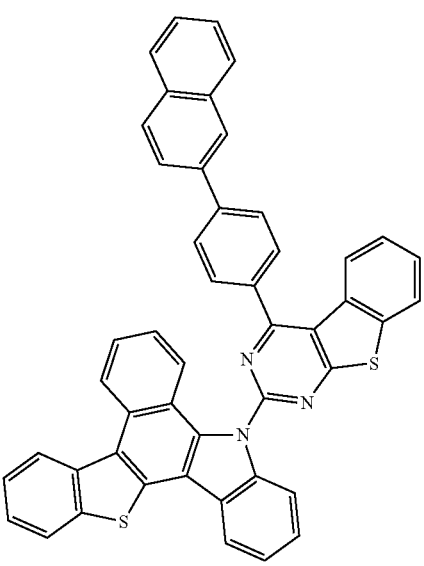
1-2-2-S-(11)
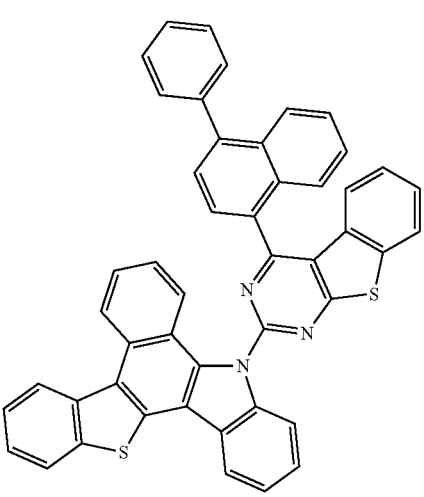
-continued
1-2-2-S-(12)
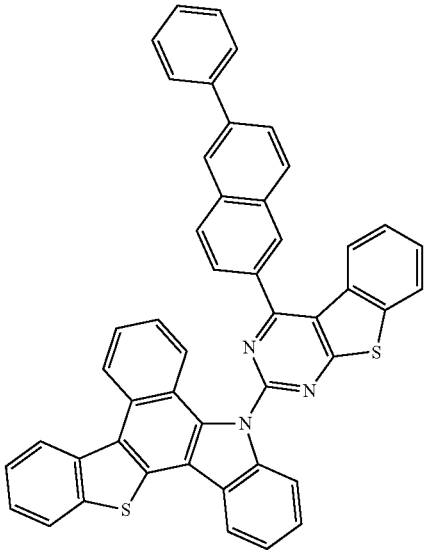
1-2-2-S-(13)
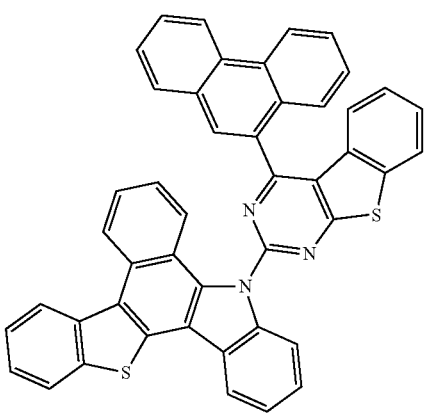
1-2-2-S-(14)
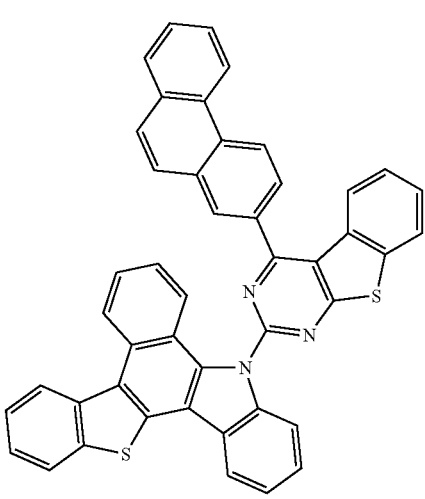

1-2-2-O-(21)
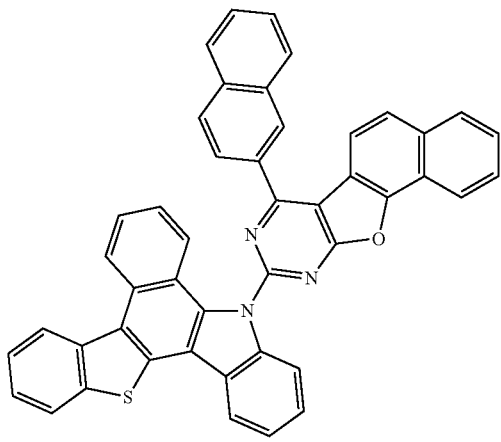
1-2-2-S-(22)
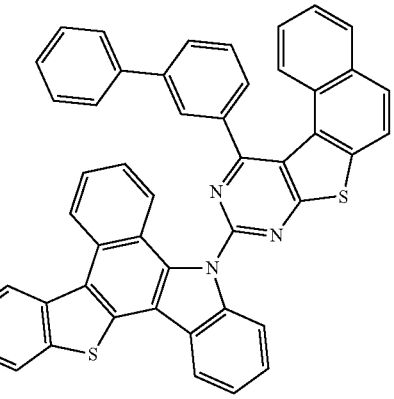
1-2-2-O-(22)
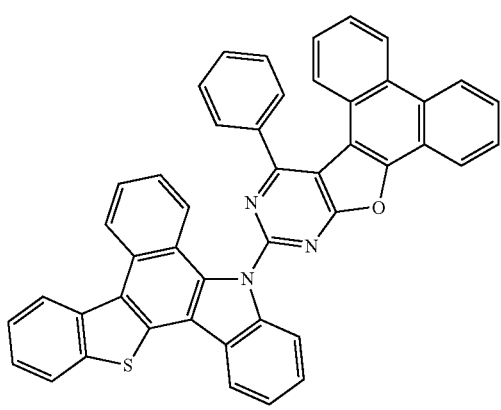
1-2-2-S-(23)
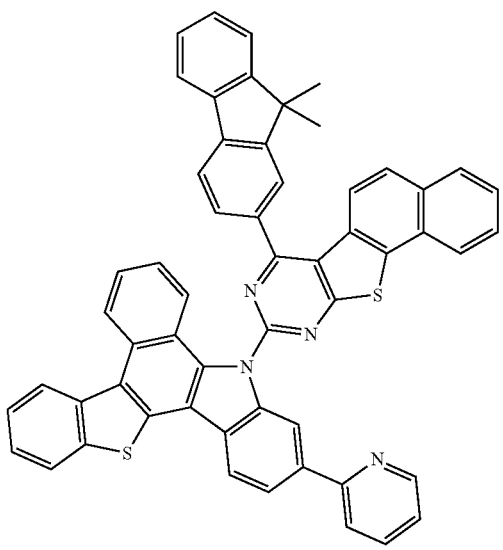
1-2-2-S-(21)
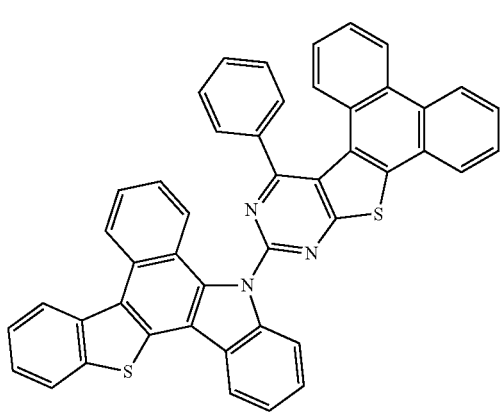
1-3-1-O-(1)
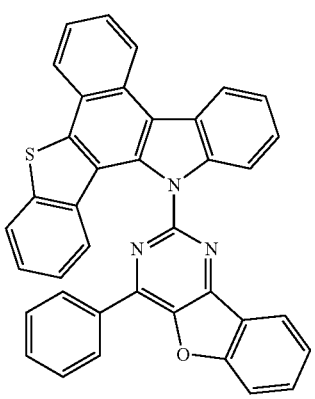

1-3-1-O-(2)
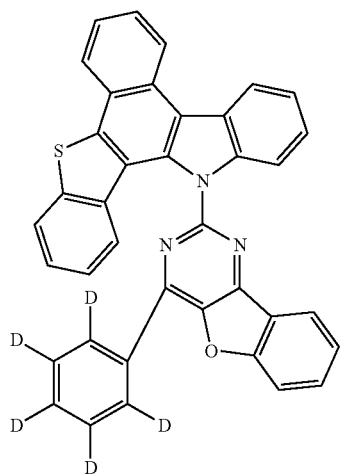
1-3-1-O-(6)
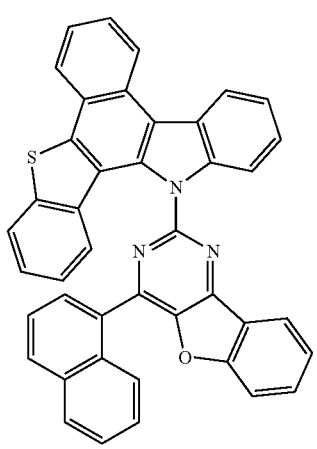
1-3-1-O-(4)
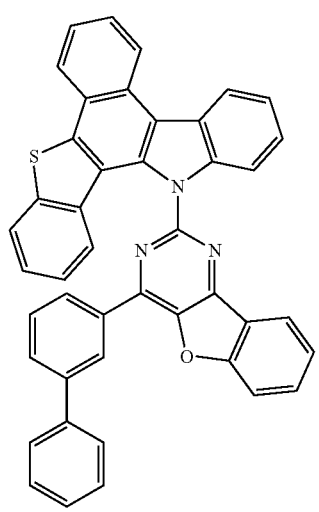
1-3-1-O-(7)
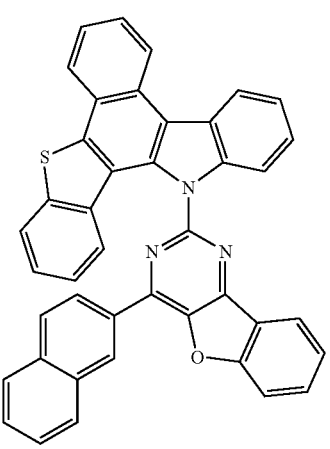
1-3-1-O-(5)
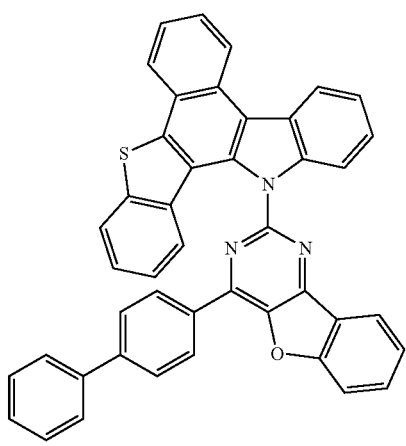
1-3-1-O-(8)
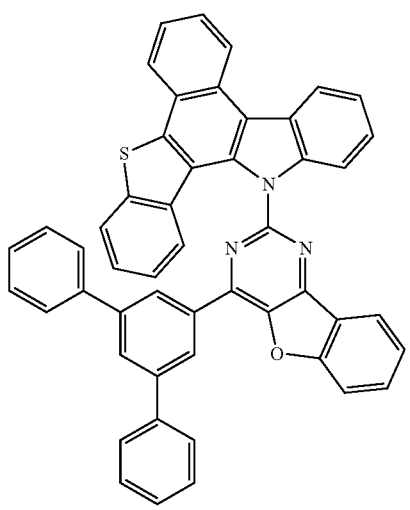

335
-continued
1-3-1-O-(9)
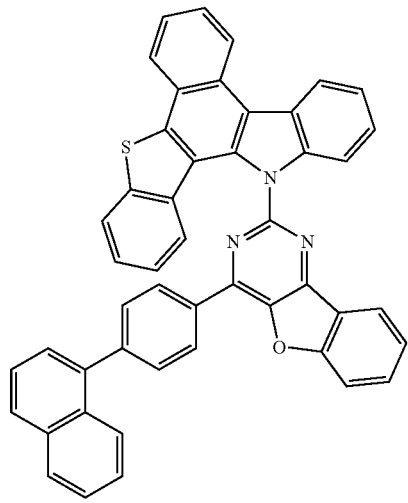
1-3-1-O-(10)
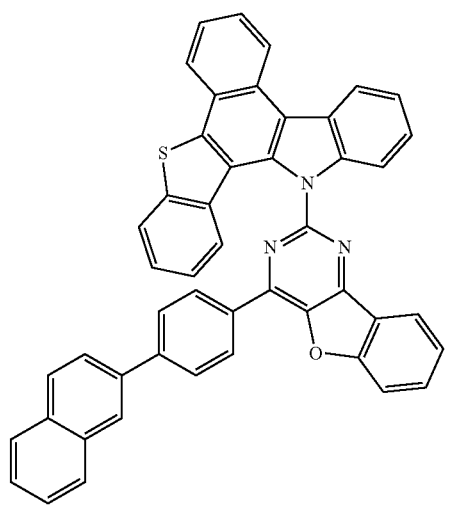
1-3-1-O-(11)
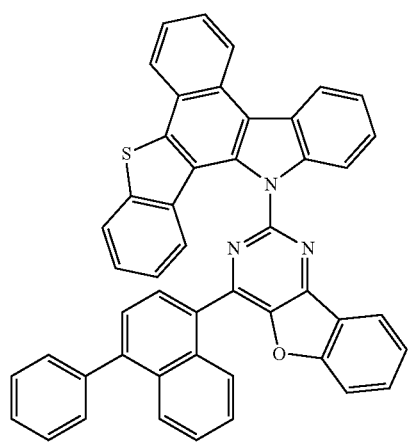
336
-continued
1-3-1-O-(12)
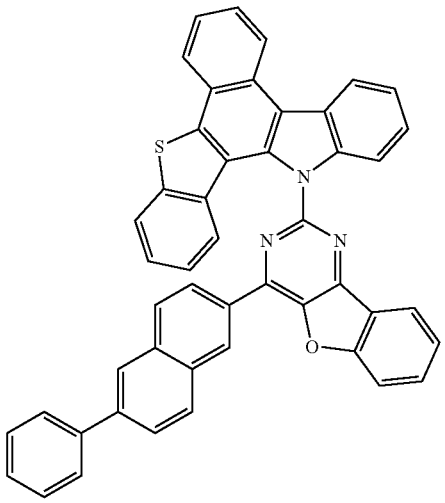
1-3-1-O-(13)
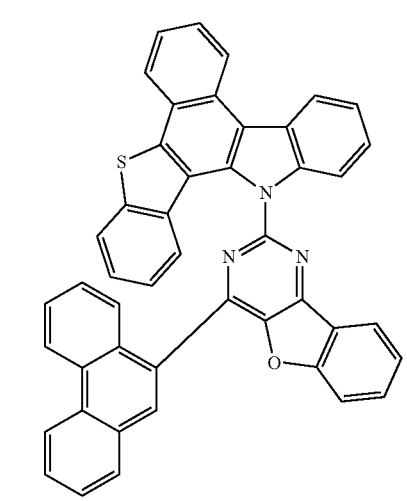
1-3-1-O-(14)
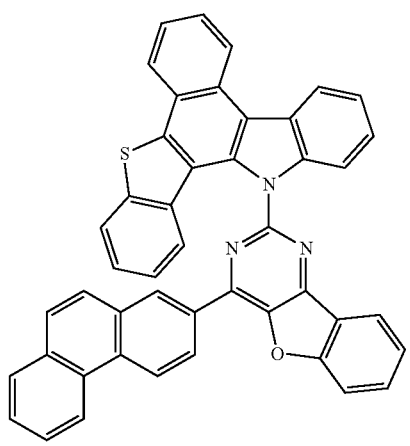

1-3-1-S-(1)
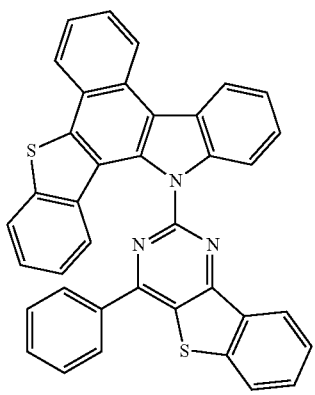
1-3-1-S-(5)
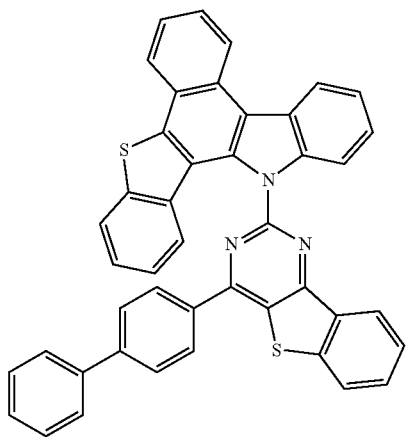
1-3-1-S-(2)
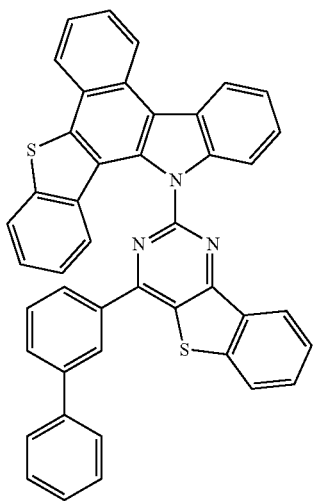
1-3-1-S-(6)
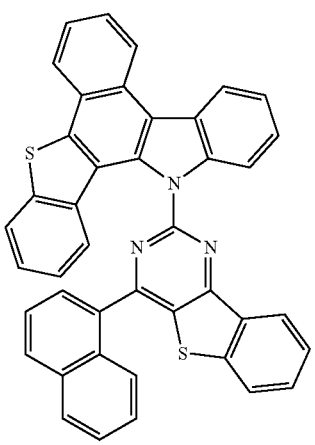
1-3-1-S-(4)
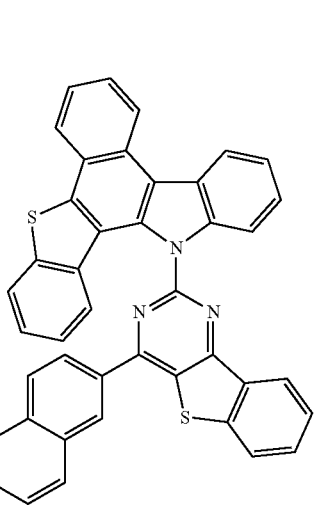
1-3-1-S-(7)

339
-continued
1-3-1-S-(8)
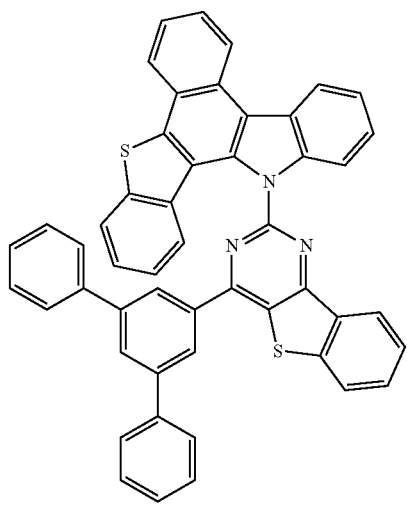
1-3-1-S-(9)
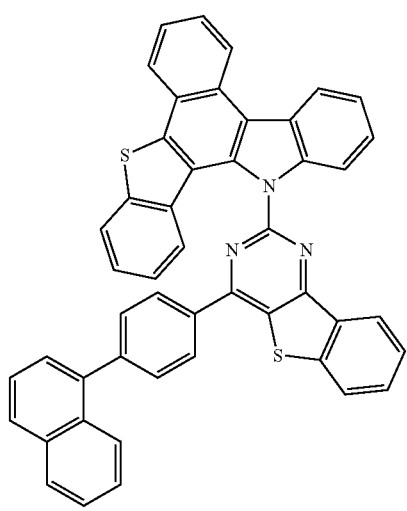
1-3-1-S-(10)
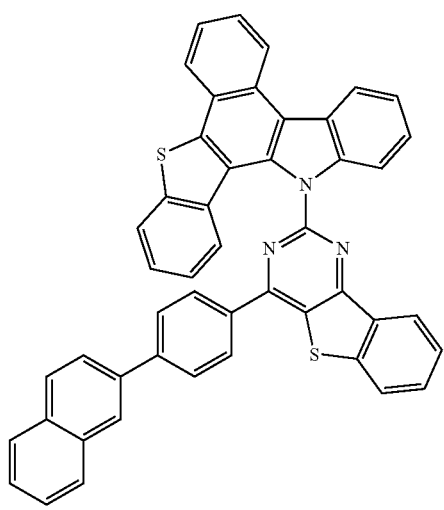
340
-continued
1-3-1-S-(11)
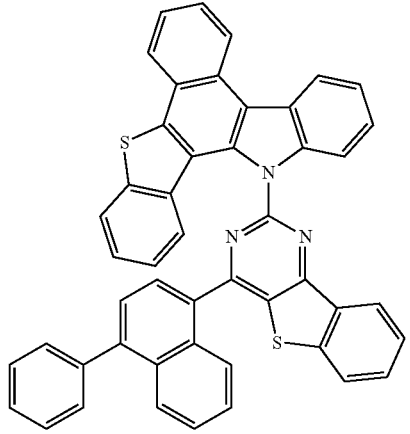
1-3-1-S-(12)
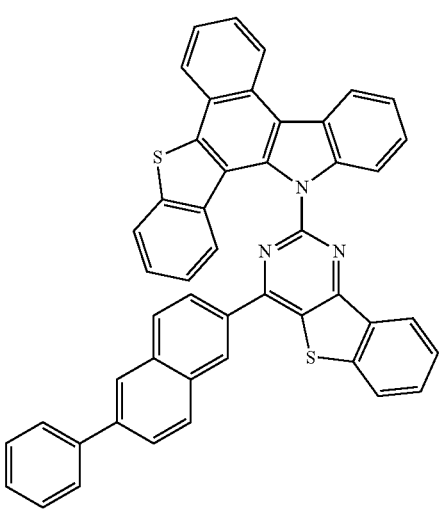
1-3-1-S-(13)
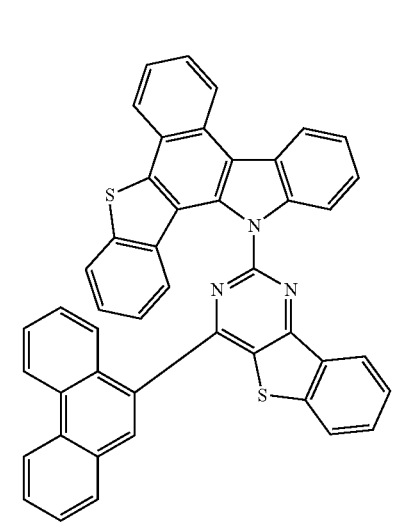

341
-continued
1-3-1-S-(14)
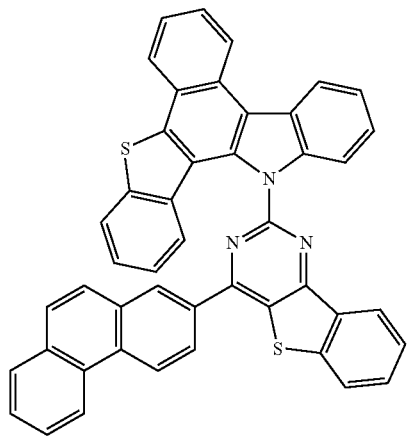
1-3-1-O-(21)
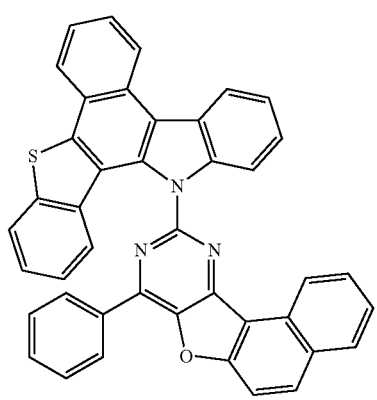
1-3-1-O-(22)
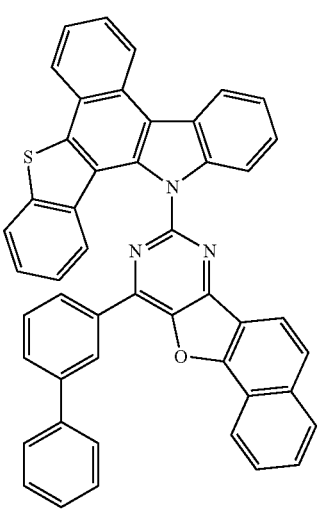
342
-continued
1-3-1-S-(21)
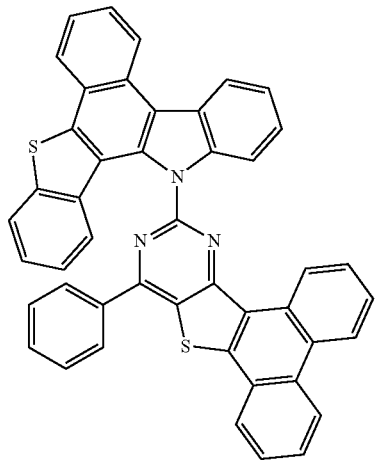
1-3-1-S-(22)
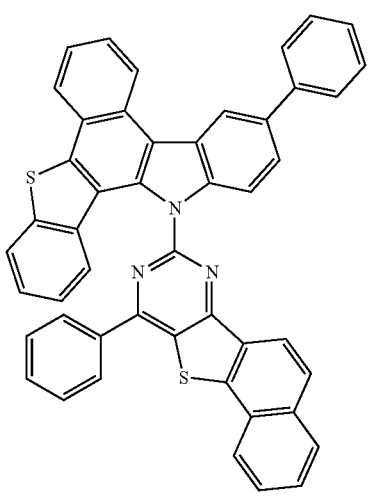
1-3-2-O-(1)
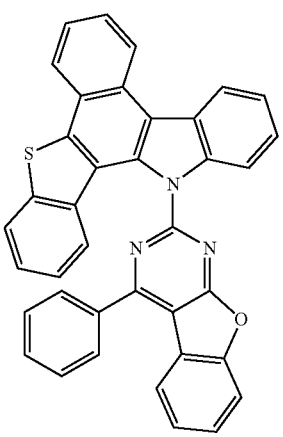

-continued
1-3-2-O-(2)
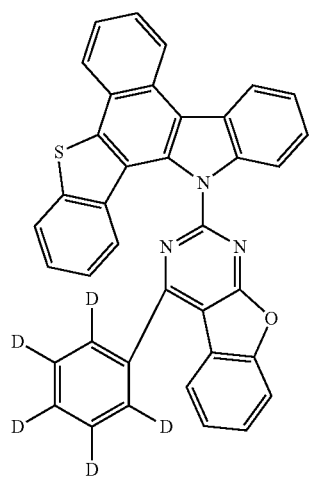
1-3-2-O-(4)
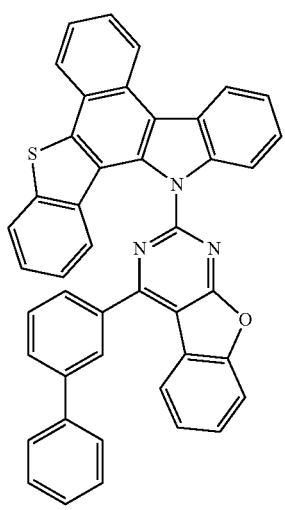
1-3-2-O-(5)
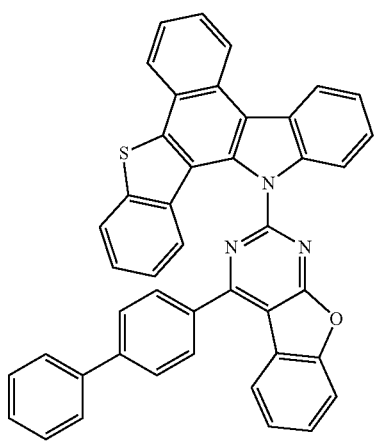
-continued
1-3-2-O-(6)
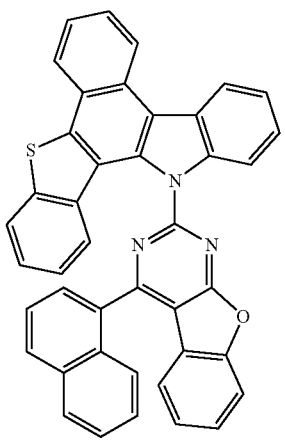
1-3-2-O-(7)
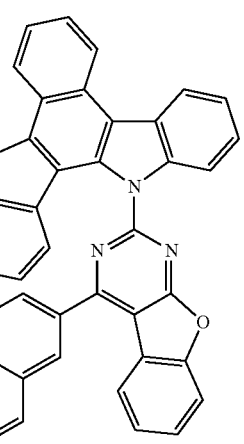
1-3-2-O-(8)
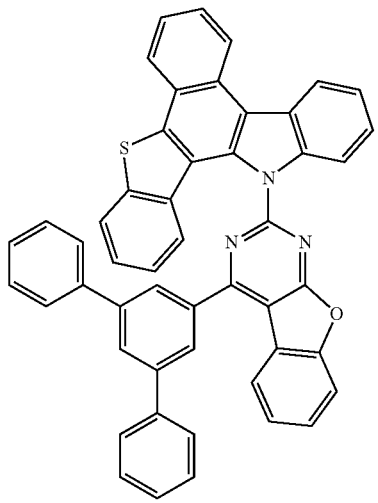

1-3-2-O-(9)
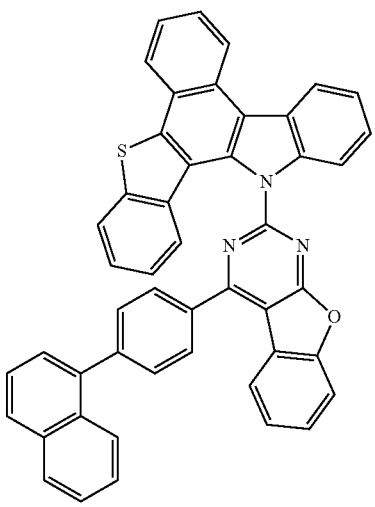
1-3-2-O-(10)
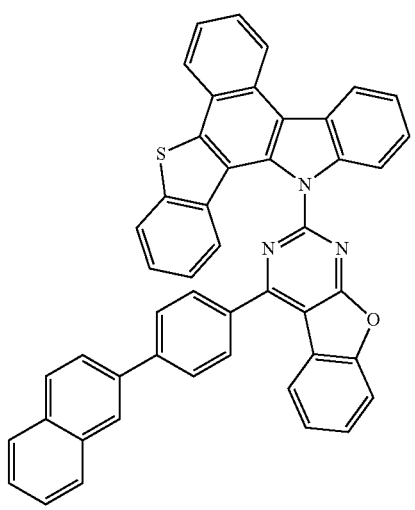
1-3-2-O-(11)
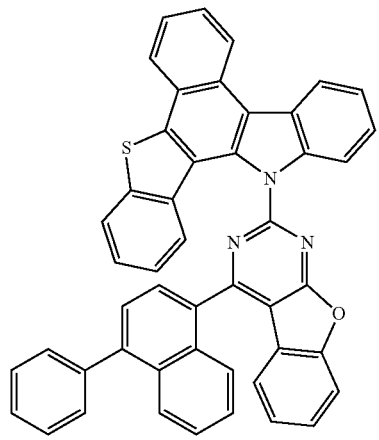
1-3-2-O-(12)
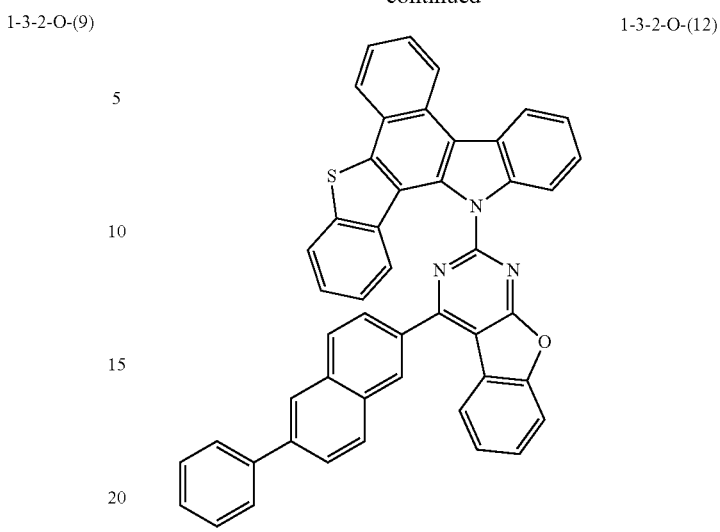
1-3-2-O-(13)
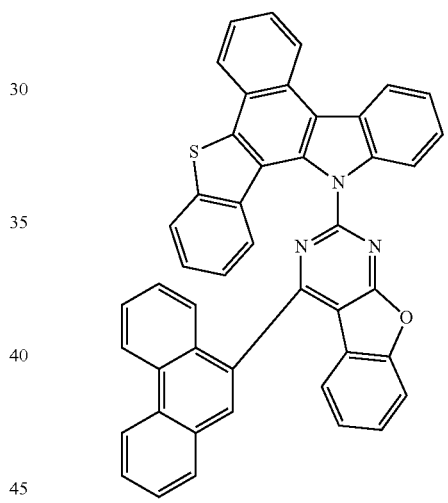
1-3-2-O-(14)
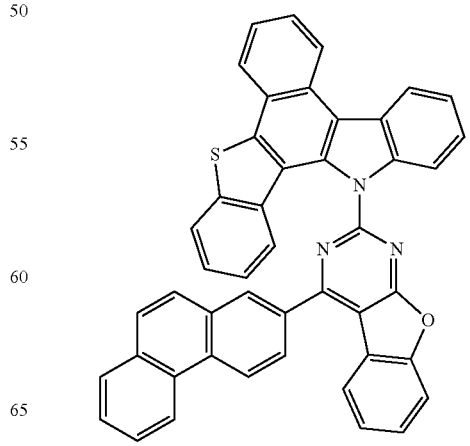

1-3-2-S-(1)
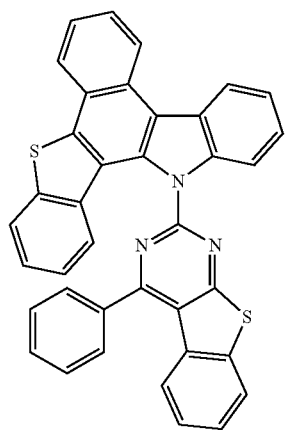
1-3-2-S-(5)
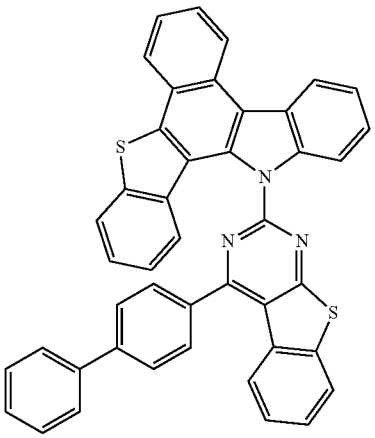
1-3-2-S-(2)
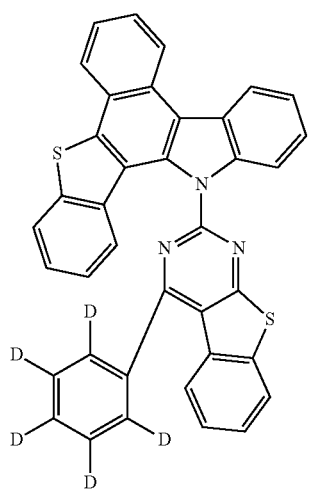
1-3-2-S-(6)
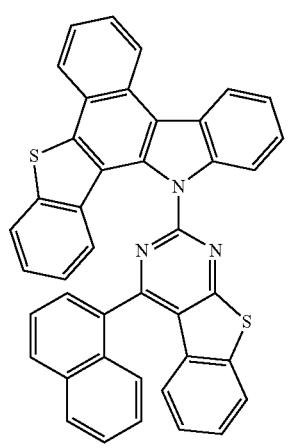
1-3-2-S-(4)
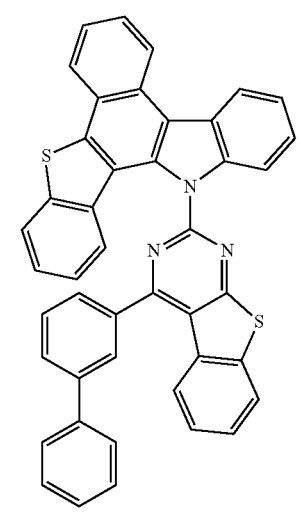
1-3-2-S-(7)
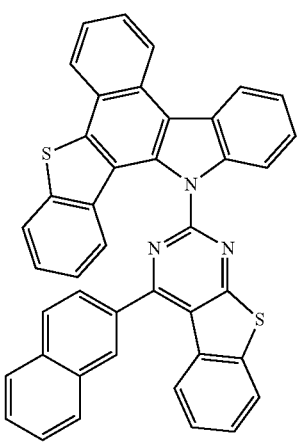

| | |
|---|---|
| 1-3-2-S-(8) 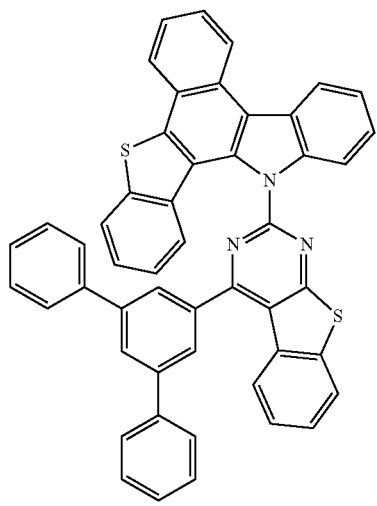 | 1-3-2-S-(11) 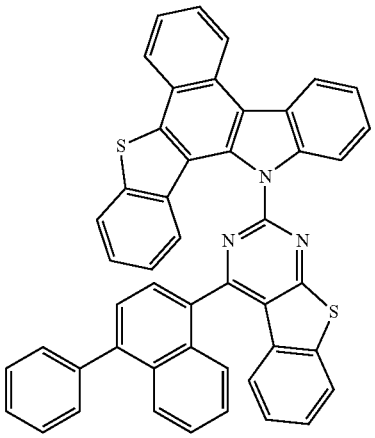 |
| 1-3-2-S-(9) 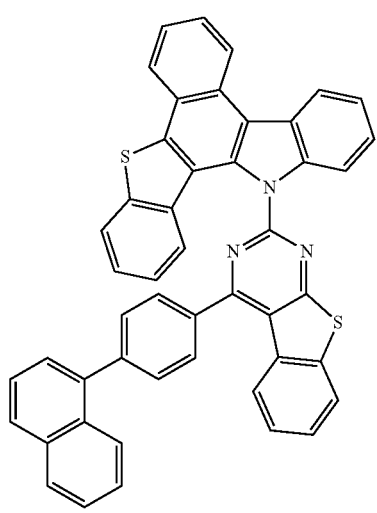 | 1-3-2-S-(12) 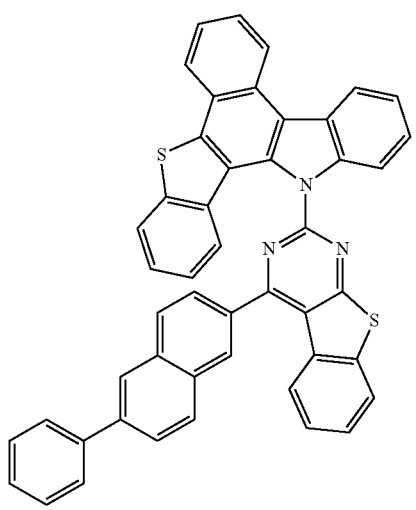 |
| 1-3-2-S-(10) 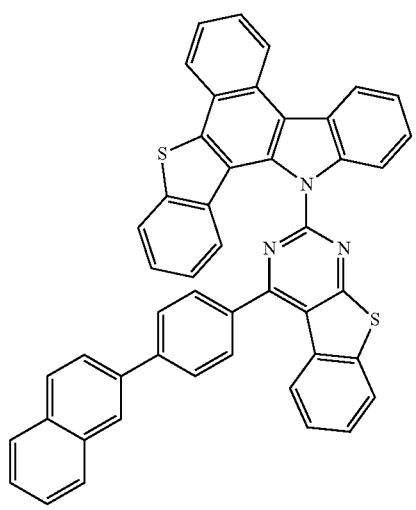 | 1-3-2-S-(13) 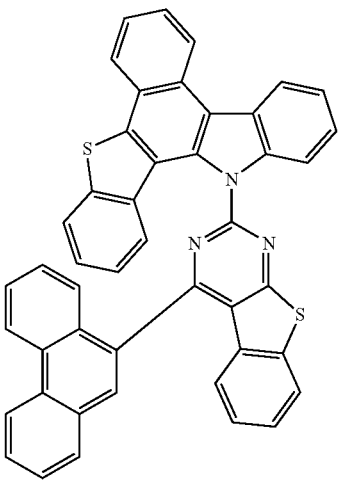 |

1-3-2-S-(14)
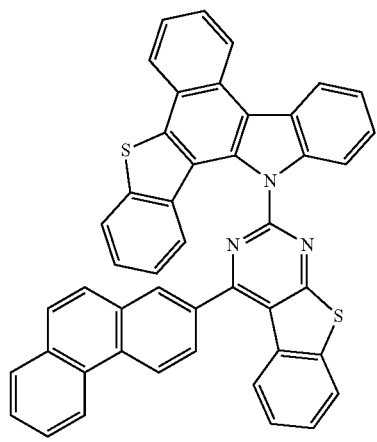
1-3-2-S-(21)
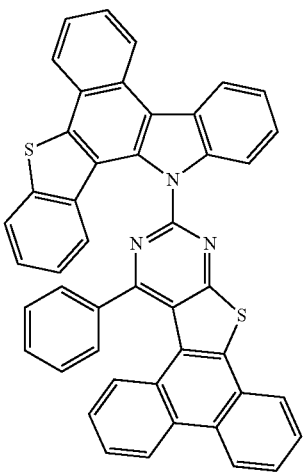
1-3-2-O-(21)
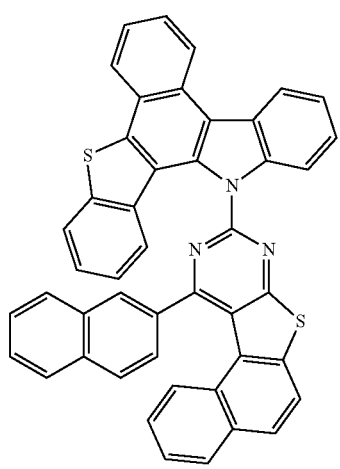
1-3-2-S-(22)
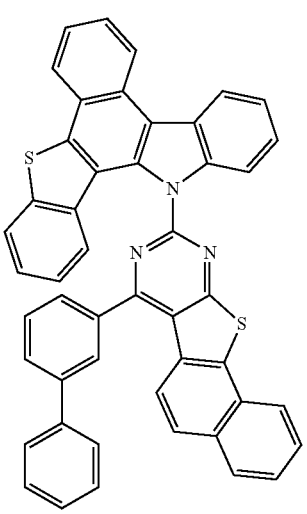
1-3-2-O-(22)
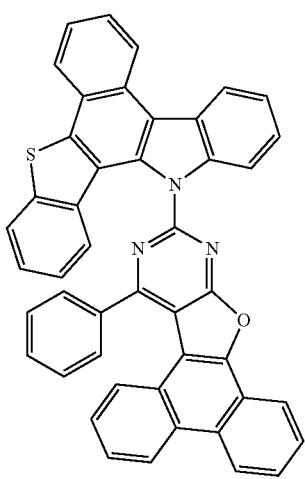
1-3-2-S-(23)
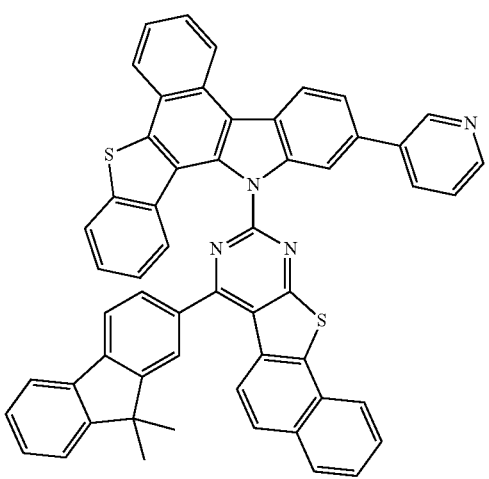

1-4-1-O-(1)
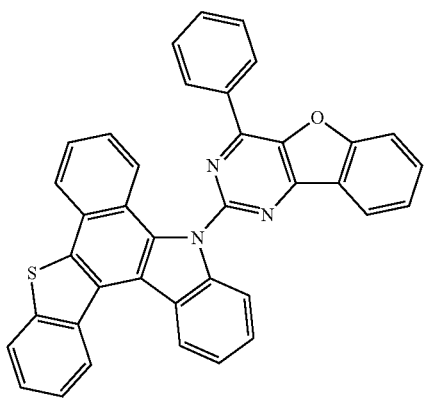
1-4-1-O-(5)
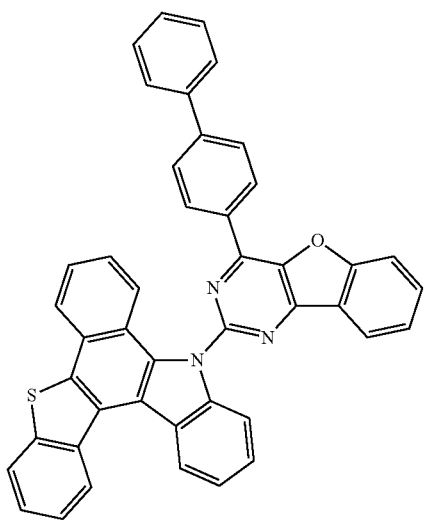
1-4-1-O-(2)
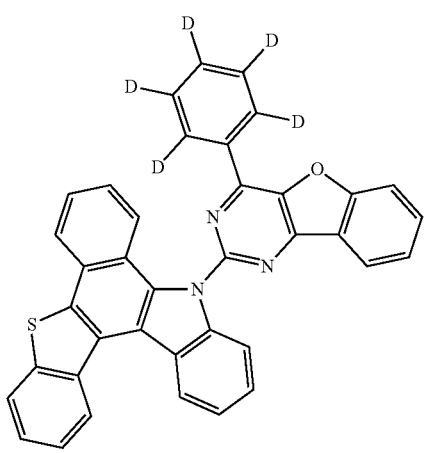
1-4-1-O-(6)
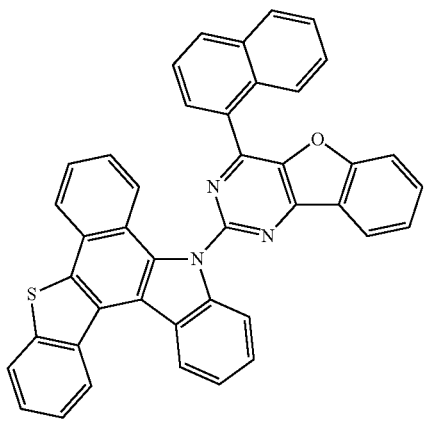
1-4-1-O-(4)
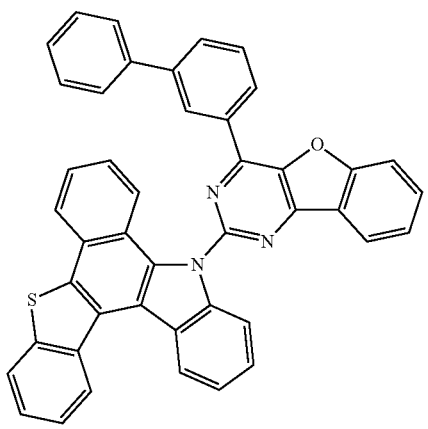
1-4-1-O-(7)
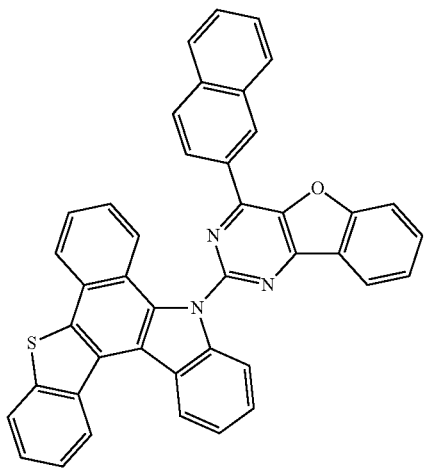

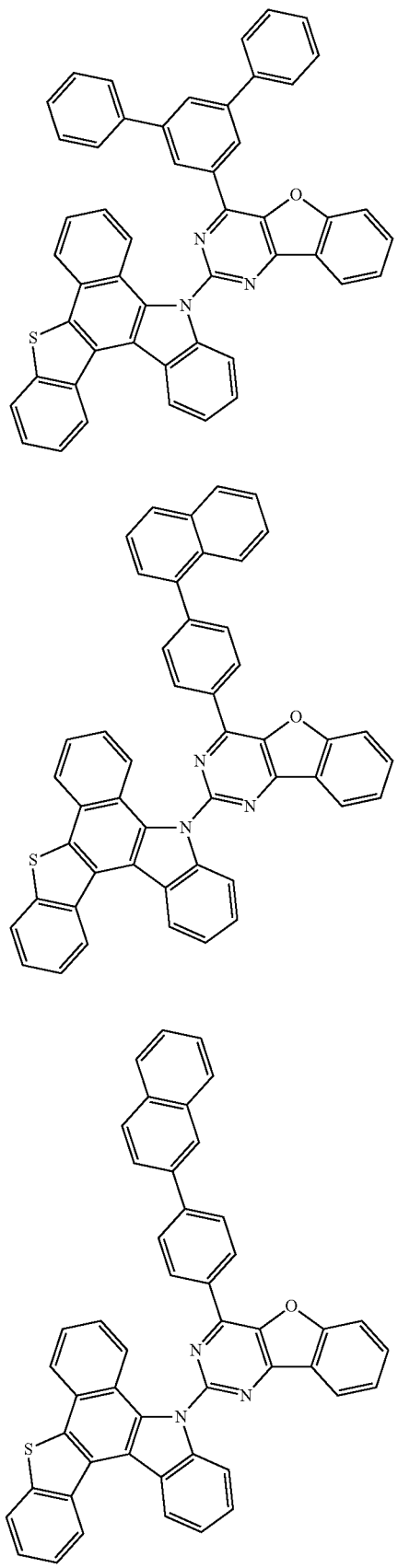
1-4-1-O-(8)
1-4-1-O-(9)
1-4-1-O-(10)
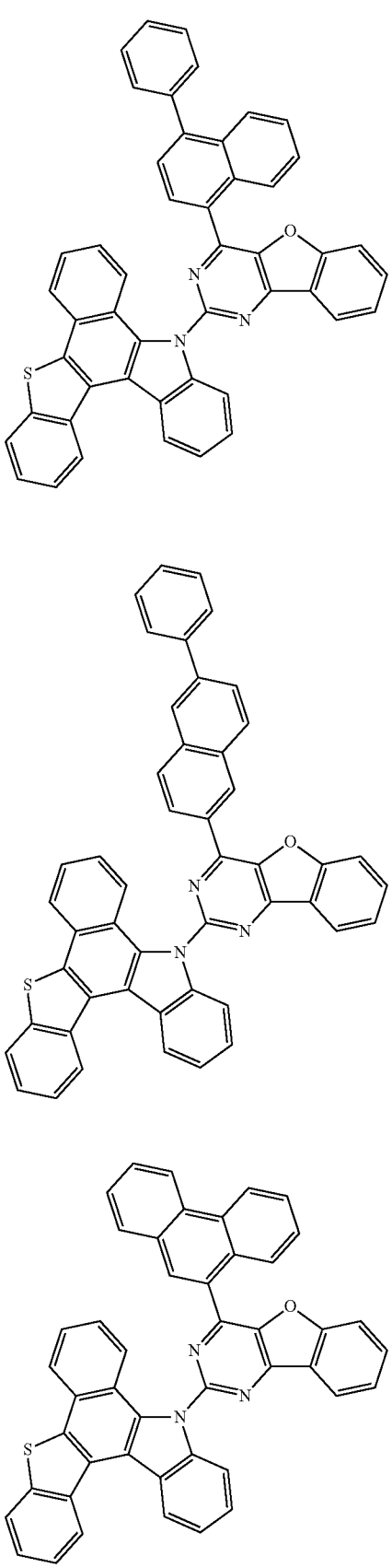
1-4-1-O-(11)
1-4-1-O-(12)
1-4-1-O-(13)

1-4-1-O-(14)
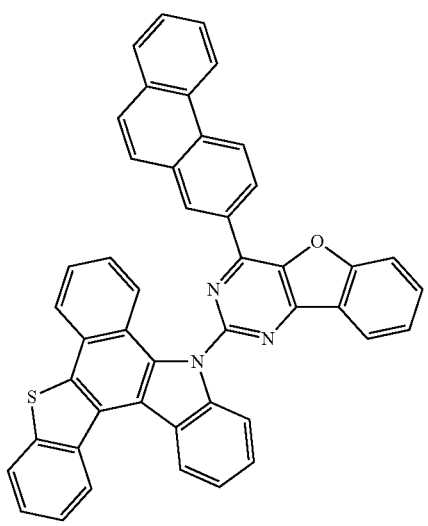
1-4-1-S-(4)
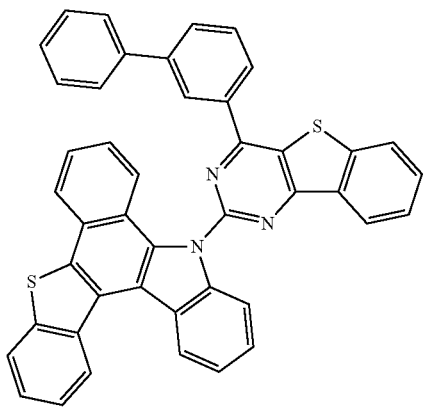
1-4-1-S-(1)
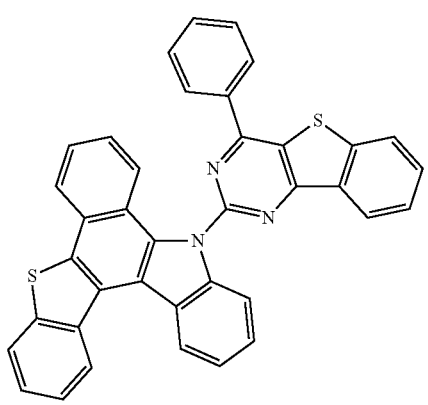
1-4-1-S-(5)
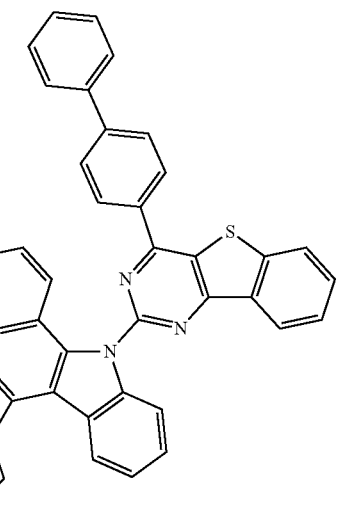
1-4-1-S-(2)
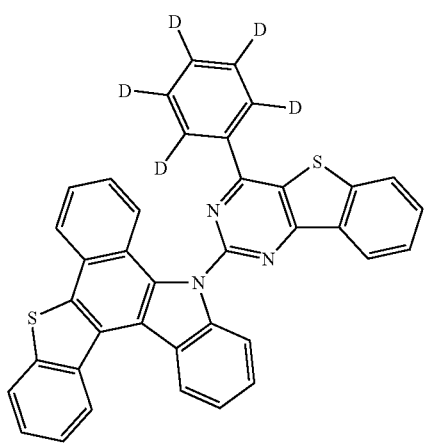
1-4-1-S-(6)
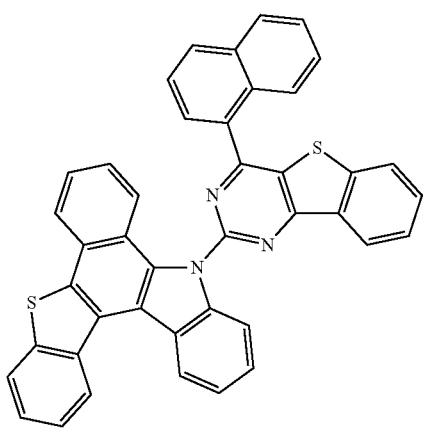

1-4-1-S-(7)
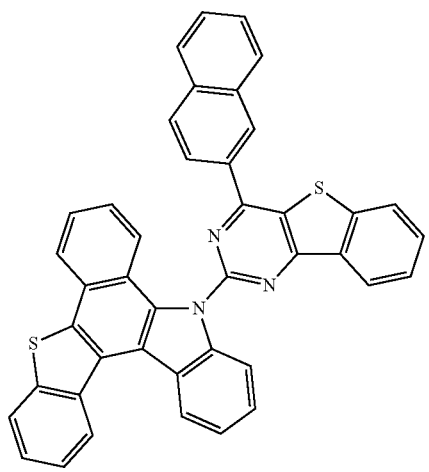
1-4-1-S-(8)
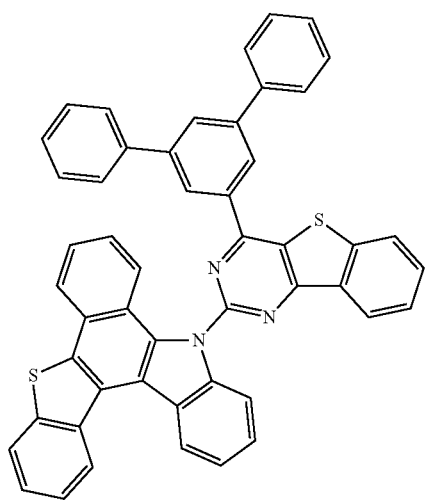
1-4-1-S-(9)
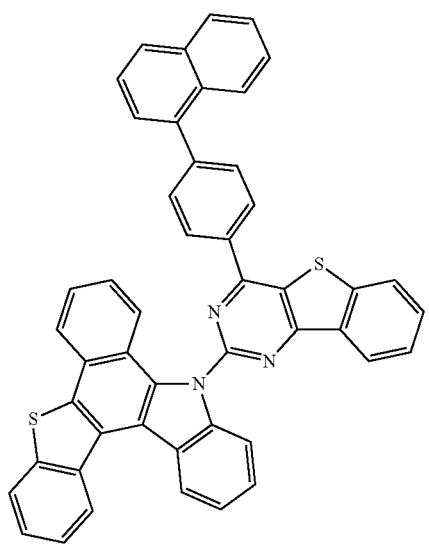
1-4-1-S-(10)
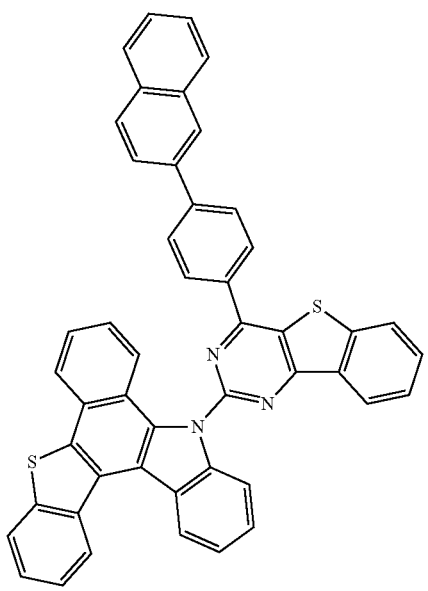
1-4-1-S-(11)
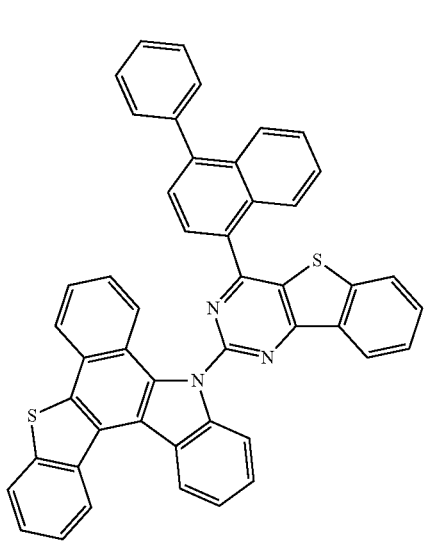

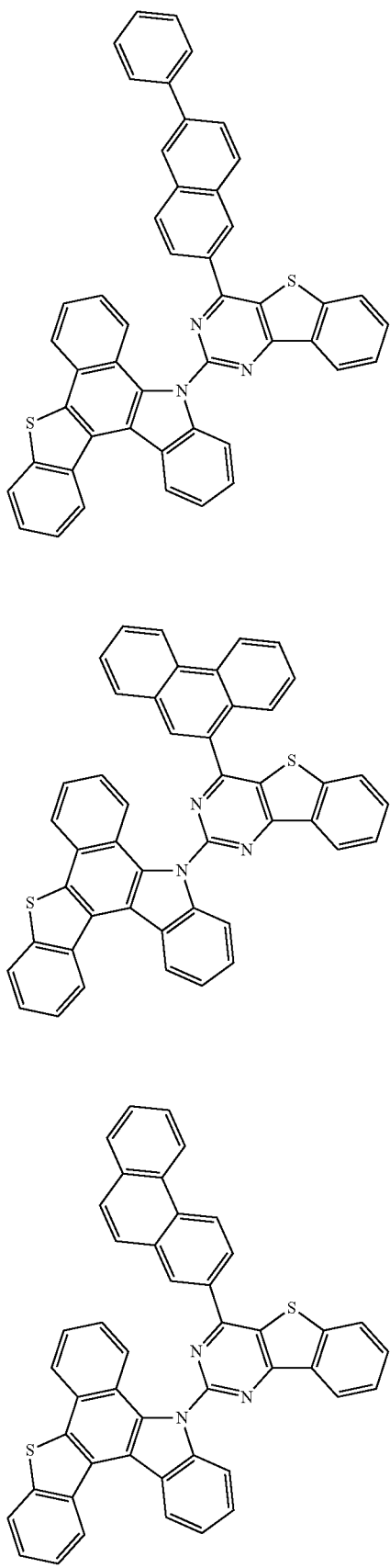
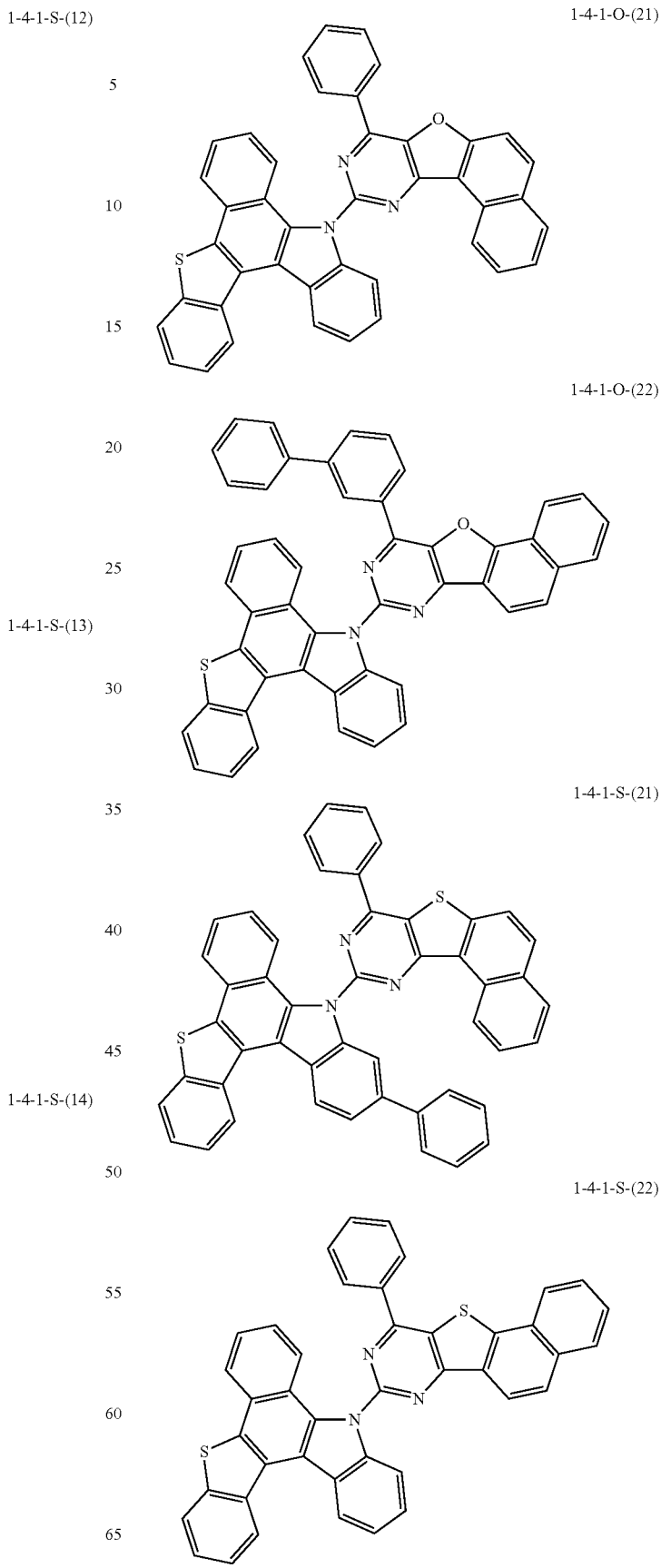

1-4-2-O-(1)
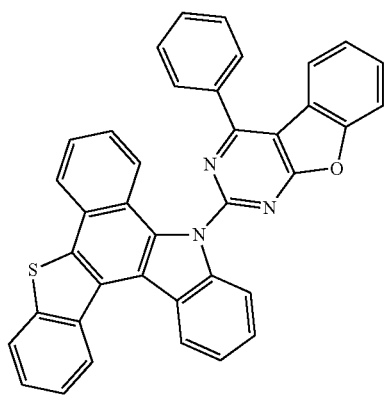
1-4-2-O-(2)
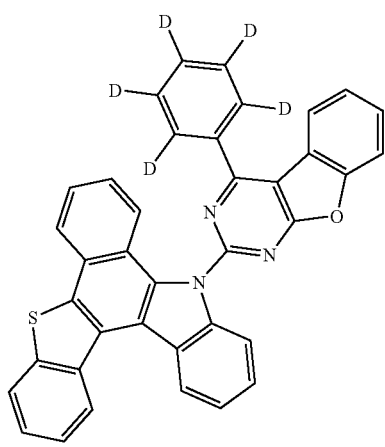
1-4-2-O-(4)
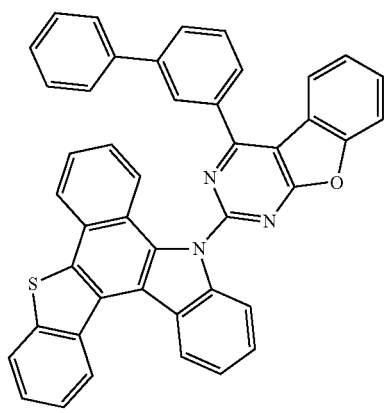
1-4-2-O-(5)
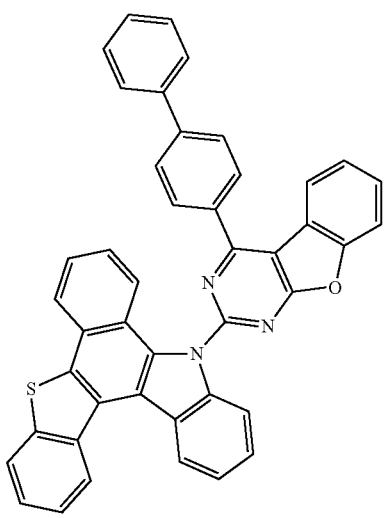
1-4-2-O-(6)
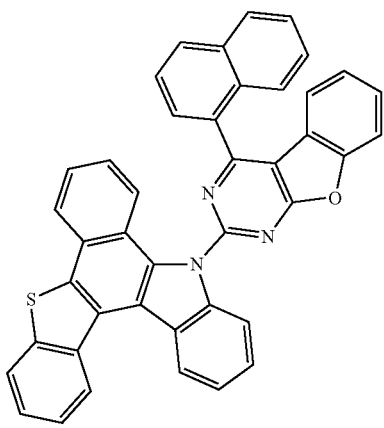
1-4-2-O-(7)
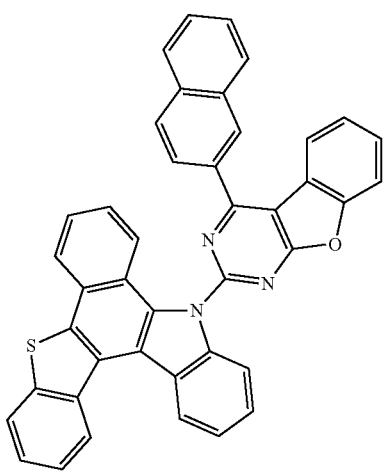

1-4-2-O-(8)
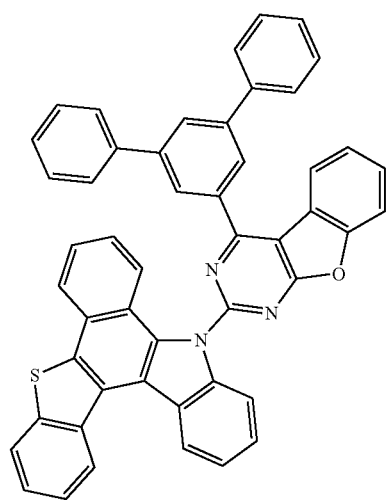
1-4-2-O-(9)
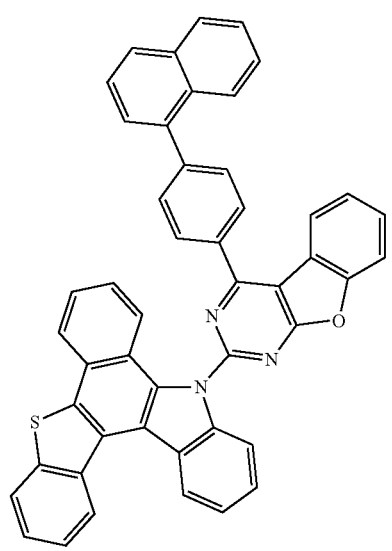
1-4-2-O-(10)
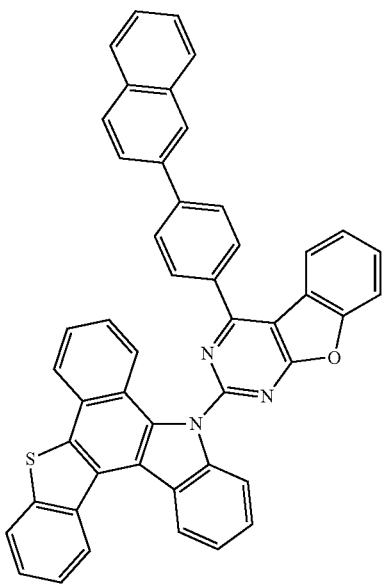
1-4-2-O-(11)
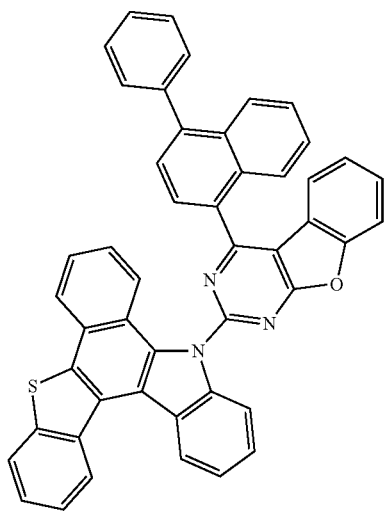
1-4-2-O-(12)
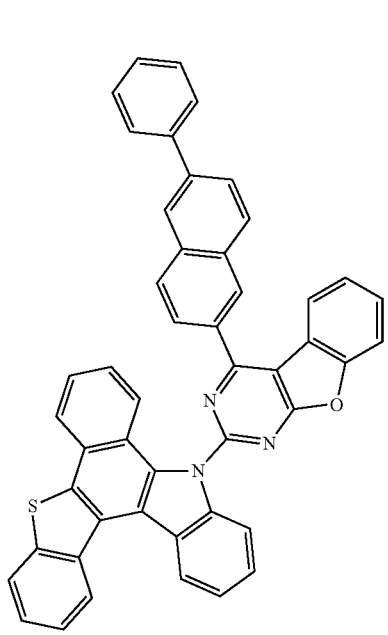
1-4-2-O-(13)
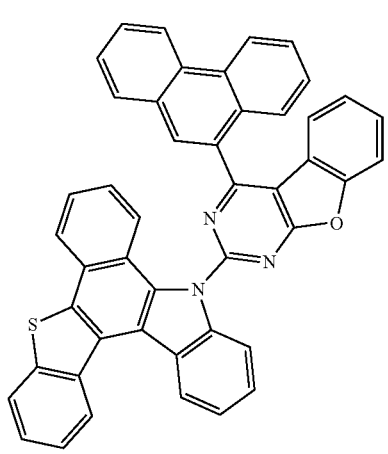

1-4-2-O-(14)
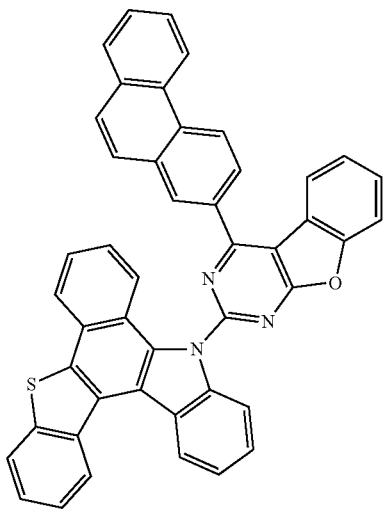
1-4-2-S-(1)
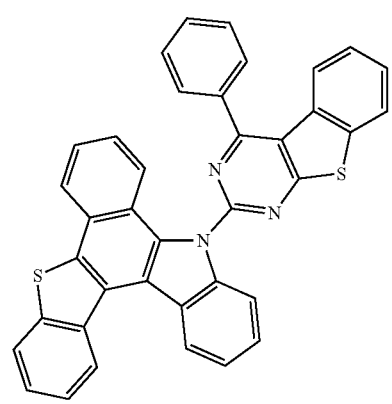
1-4-2-S-(2)
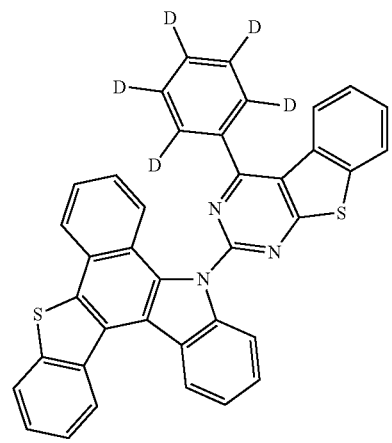
1-4-2-S-(4)
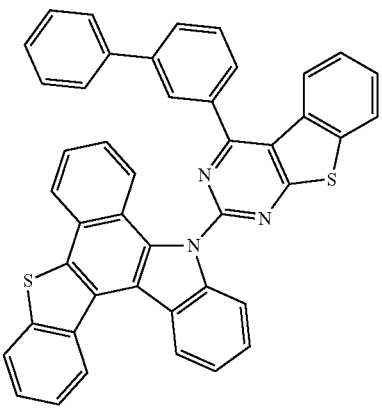
1-4-2-S-(5)
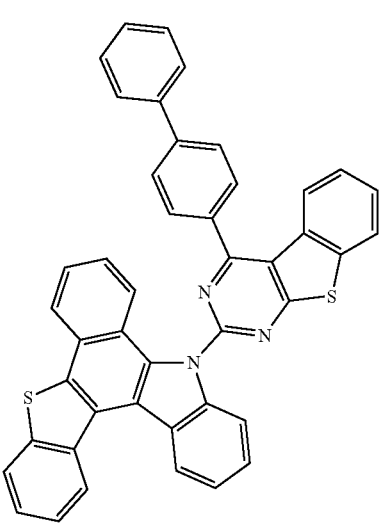
1-4-2-S-(6)
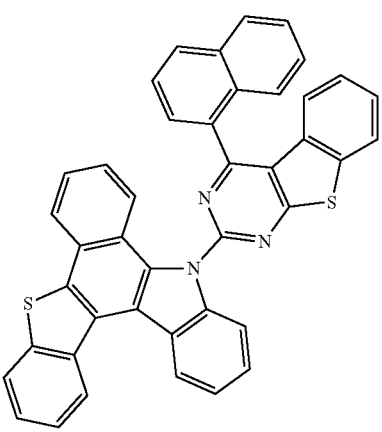

-continued
1-4-2-S-(7)
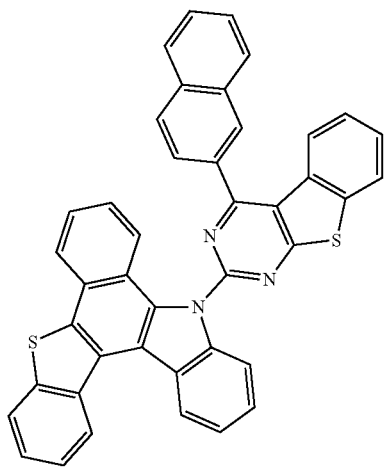
1-4-2-S-(8)
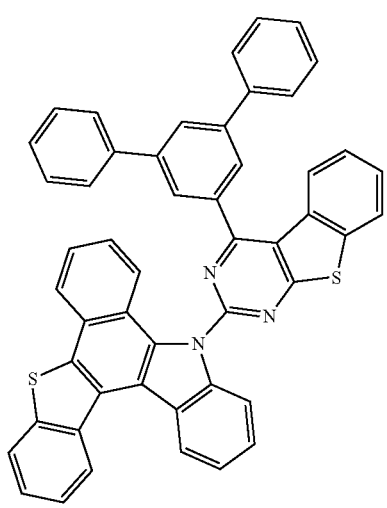
1-4-2-S-(9)
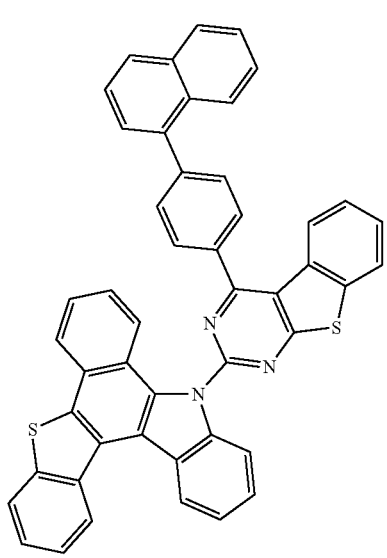
-continued
1-4-2-S-(10)
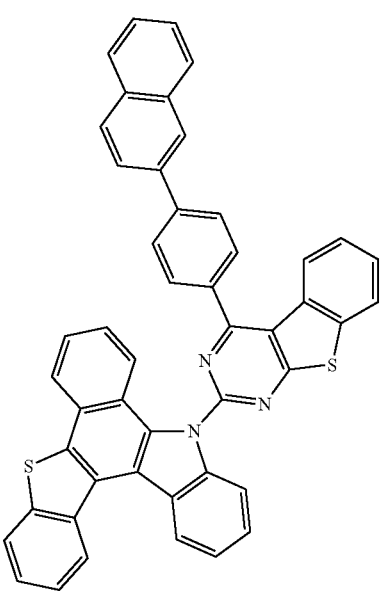
1-4-2-S-(11)
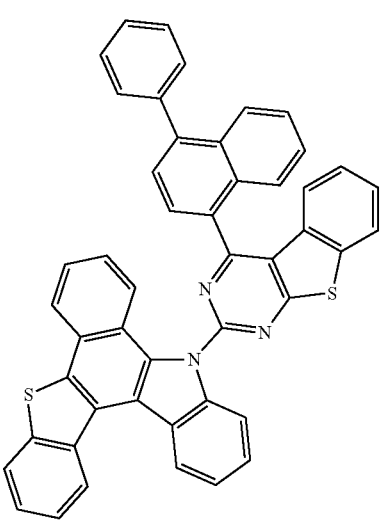

-continued
1-4-2-S-(12)
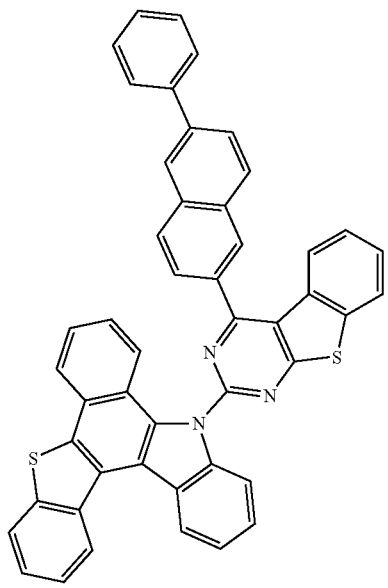
1-4-2-S-(13)
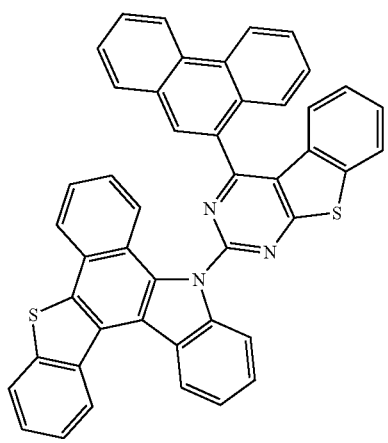
1-4-2-S-(14)
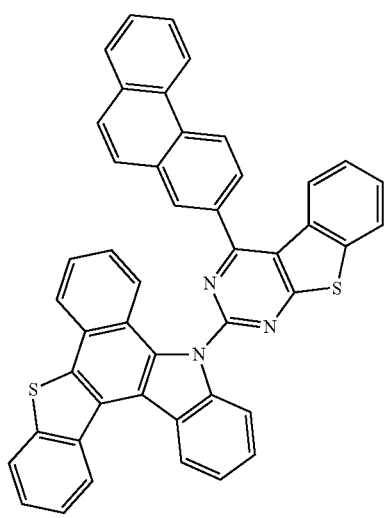
-continued
1-4-2-O-(21)
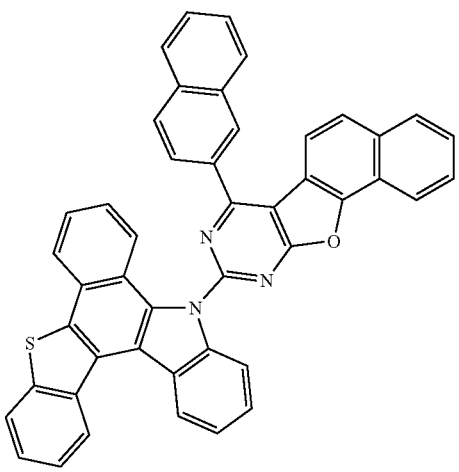
1-4-2-O-(22)
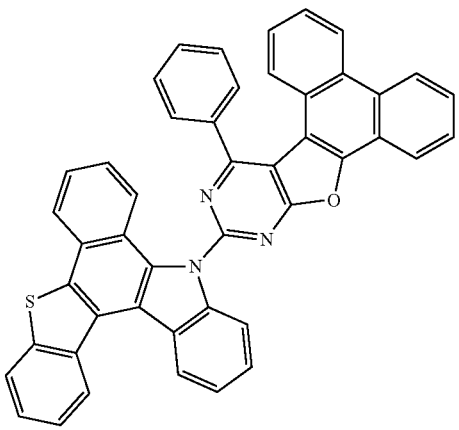
1-4-2-S-(21)
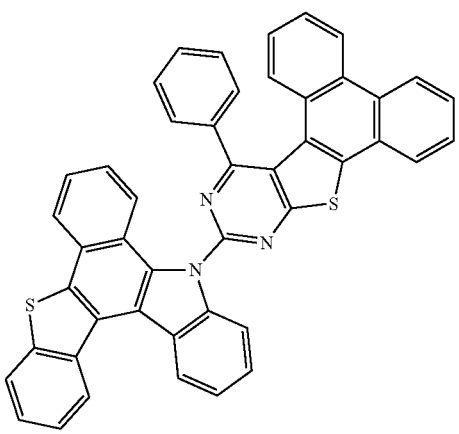

-continued

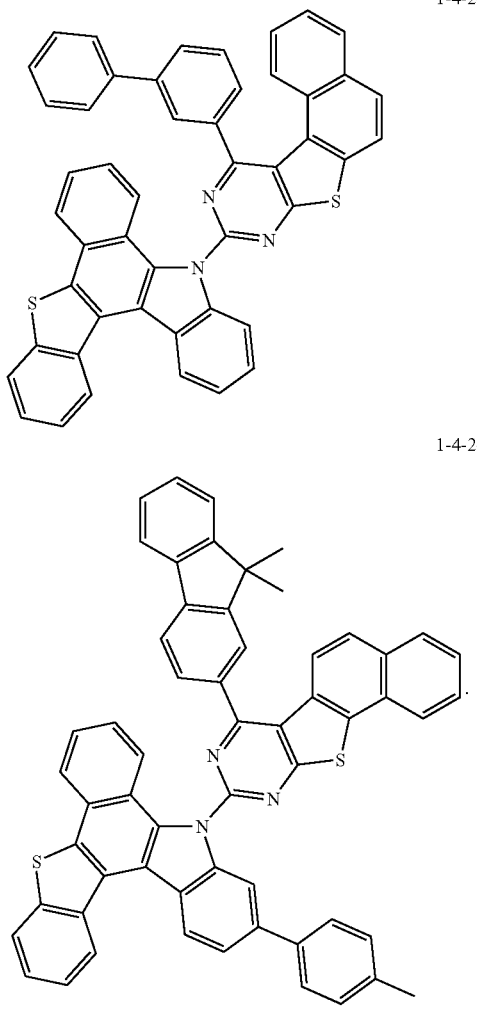

1-4-2-S-(22)

1-4-2-S-(23)

7. An organic electric element comprising a first electrode, a second electrode, and an organic material layer disposed between the first electrode and the second electrode, wherein the organic material layer comprises the compound of claim 1.

8. An organic electric element comprising a first electrode, a second electrode, and an organic material layer disposed between the first electrode and the second electrode, wherein the organic material layer comprises a light emitting layer comprising the compound of claim 1, the compound being the same kind or two or more different kinds.

9. An organic electric element comprising a first electrode, a second electrode, and an organic material layer disposed between the first electrode and the second electrode, wherein the organic material layer comprises a light emitting layer comprising a phosphorescent host material, the phosphorescent host material comprising the compound of claim 1.

10. The organic electric element as claimed in claim 7, wherein the organic electric element further comprises at least one layer to improve luminous efficiency, which is formed on at least one of the sides of the first and second electrodes which are opposite to the organic material layer.

11. The organic electric element as claimed in claim 7, wherein the organic material layer is formed by any one of the processes of spin coating, nozzle printing, inkjet printing, slot coating, dip coating and roll-to-roll.

12. An electronic device comprising a display device, the display device comprising the organic electric element as claimed in claim 7 and a control unit for driving the display device.

13. The electronic device as claimed in claim 12, wherein the organic electric element comprises at least one of an organic light emitting diode (OLED), an organic solar cell, an organic photo conductor (OPC), an organic transistor (organic TFT), and an element for monochromatic or white illumination.

* * * * *